United States Patent
Sharma, Sr. et al.

(10) Patent No.: US 9,308,257 B2
(45) Date of Patent: Apr. 12, 2016

(54) PROTEIN FORMULATION

(75) Inventors: Monika S. Sharma, Sr., Potomac, MD (US); Ambarish Shah, Boyds, MD (US); Scott Hammond, Olney, MD (US)

(73) Assignee: MedImmune, LLC, Gaithursburg, MD (US)

( * ) Notice: Subject to any disclaimer, the term of this patent is extended or adjusted under 35 U.S.C. 154(b) by 171 days.

(21) Appl. No.: 12/744,745

(22) PCT Filed: Nov. 26, 2008

(86) PCT No.: PCT/US2008/084796
§ 371 (c)(1),
(2), (4) Date: May 26, 2010

(87) PCT Pub. No.: WO2009/070642
PCT Pub. Date: Jun. 4, 2009

(65) Prior Publication Data
US 2010/0303827 A1   Dec. 2, 2010

Related U.S. Application Data

(60) Provisional application No. 61/040,384, filed on Mar. 28, 2008, provisional application No. 61/039,985, filed on Mar. 27, 2008, provisional application No. 60/990,772, filed on Nov. 28, 2007.

(51) Int. Cl.
*A61K 39/395* (2006.01)

(52) U.S. Cl.
CPC ....... *A61K 39/39591* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 4,120,649 A | 10/1978 | Schechter | |
| 4,444,887 A | 4/1984 | Hoffmann | |
| 4,474,893 A | 10/1984 | Reading | |
| 4,665,077 A | 5/1987 | Stringfellow et al. | |
| 4,675,187 A | 6/1987 | Konishi et al. | |
| 4,676,980 A | 6/1987 | Segal et al. | |
| 4,714,681 A | 12/1987 | Reading | |
| 4,716,111 A | 12/1987 | Osband et al. | |
| 4,816,567 A | 3/1989 | Cabilly et al. | |
| 4,923,990 A | 5/1990 | Nakano et al. | |
| 4,925,648 A | 5/1990 | Hansen et al. | |
| 5,114,721 A | 5/1992 | Cohen et al. | |
| 5,202,422 A | 4/1993 | Hiatt et al. | |
| 5,223,409 A | 6/1993 | Ladner et al. | |
| 5,225,539 A | 7/1993 | Winter | |
| 5,403,484 A | 4/1995 | Ladner et al. | |
| 5,413,923 A | 5/1995 | Kucherlapati et al. | |
| 5,427,908 A | 6/1995 | Dower et al. | |
| 5,516,637 A | 5/1996 | Huang et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,569,825 A | 10/1996 | Lonberg et al. | |
| 5,571,698 A | 11/1996 | Ladner et al. | |
| 5,573,920 A | 11/1996 | Randle | |
| 5,580,717 A | 12/1996 | Dower et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,639,947 A | 6/1997 | Hiatt et al. | |
| 5,658,727 A | 8/1997 | Barbas et al. | |
| 5,661,016 A | 8/1997 | Lonberg et al. | |
| 5,698,426 A | 12/1997 | Huse | |
| 5,702,892 A | 12/1997 | Mulligan Kehoe | |
| 5,703,080 A | 12/1997 | Nakakura et al. | |
| 5,733,743 A | 3/1998 | Johnson et al. | |
| 5,750,753 A | 5/1998 | Kimae et al. | |
| 5,766,886 A | 6/1998 | Studnicka et al. | |
| 5,780,225 A | 7/1998 | Wigler et al. | |
| 5,807,715 A | 9/1998 | Morrison et al. | |
| 5,814,318 A | 9/1998 | Lonberg et al. | |
| 5,821,047 A | 10/1998 | Garrard et al. | |
| 5,824,520 A | 10/1998 | Mulligan Kehoe | |
| 5,876,969 A | 3/1999 | Fleer et al. | |
| 5,939,598 A | 8/1999 | Kucherlapati et al. | |
| 5,959,177 A | 9/1999 | Hein et al. | |
| 5,969,108 A | 10/1999 | McCafferty et al. | |
| 6,005,079 A | 12/1999 | Casterman et al. | |
| 6,040,498 A | 3/2000 | Stomp et al. | |
| 6,267,958 B1 * | 7/2001 | Andya et al. | 424/130.1 |
| 6,407,213 B1 | 6/2002 | Carter et al. | |
| 6,417,429 B1 | 7/2002 | Hein et al. | |
| 7,112,324 B1 * | 9/2006 | Dorken et al. | 424/133.1 |
| 8,758,747 B2 | 6/2014 | Kallmeyer et al. | |
| 2002/0142964 A1 | 10/2002 | Nissen et al. | |
| 2004/0022792 A1 * | 2/2004 | Klinke et al. | 424/178.1 |
| 2005/0037002 A1 * | 2/2005 | Velardi et al. | 424/143.1 |
| 2007/0014724 A1 | 1/2007 | Witte et al. | |
| 2007/0014794 A1 | 1/2007 | Carter et al. | |
| 2007/0123479 A1 | 5/2007 | Kufer et al. | |

(Continued)

FOREIGN PATENT DOCUMENTS

EP   239400 A2   9/1987
EP   340109 A2   11/1989

(Continued)

OTHER PUBLICATIONS

DeLuca and Boylan, "Formulation of Small Volume Parenterals," in Pharmaceutical Dosage Form: Parenteral Medications, vol. 1, 2$^{nd}$ Edition, Chapter 5, p. 194, Table 5 (2008).

(Continued)

*Primary Examiner* — Yunsoo Kim

(74) *Attorney, Agent, or Firm* — Glance Law Group PC; Melissa J. Pytel

(57) ABSTRACT

The present invention provides stable lyophilized formulations of bispecific antibodies or fragments thereof.

22 Claims, 48 Drawing Sheets

(56) References Cited

U.S. PATENT DOCUMENTS

Figure 2:
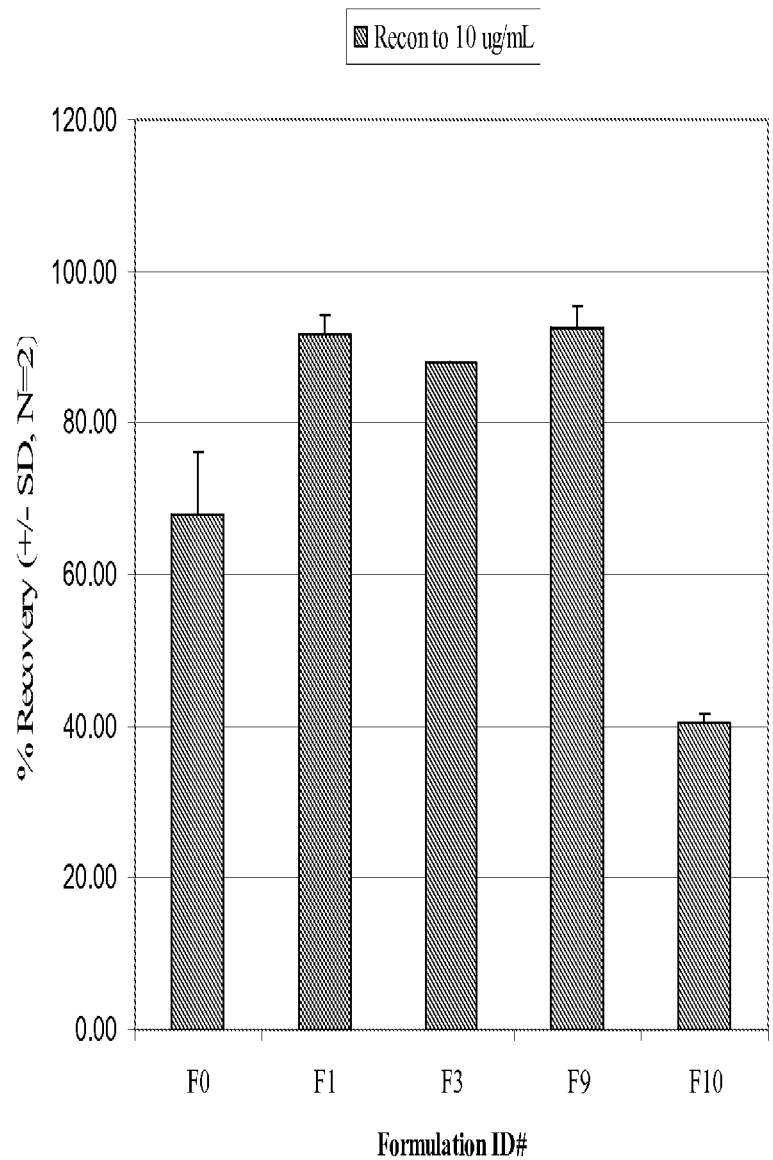

| | | |
|---|---|---|
| 2007/0249529 A1 | 10/2007 | Hofmeister et al. |
| 2008/0004413 A1 | 1/2008 | Schorzman et al. |
| 2009/0226432 A1 | 9/2009 | Lutterbüse et al. |

FOREIGN PATENT DOCUMENTS

| | | |
|---|---|---|
| EP | 413622 A1 | 2/1991 |
| EP | 519596 A1 | 12/1992 |
| EP | 592106 A1 | 4/1994 |
| EP | 1348715 A2 | 10/2003 |
| EP | 1977763 A1 | 10/2008 |
| EP | 2225275 | 9/2010 |
| JP | 2001-503781 | 3/2001 |
| WO | WO9002809 A1 | 3/1990 |
| WO | WO9011294 A1 | 4/1990 |
| WO | WO9008187 A1 | 7/1990 |
| WO | WO9101133 A1 | 7/1991 |
| WO | WO9110737 A1 | 7/1991 |
| WO | WO9110741 A1 | 7/1991 |
| WO | WO9100360 A1 | 10/1991 |
| WO | WO9109967 A1 | 11/1991 |
| WO | WO9201047 A1 | 1/1992 |
| WO | WO9200373 A1 | 5/1992 |
| WO | WO9208802 A1 | 5/1992 |
| WO | WO9218619 A1 | 10/1992 |
| WO | WO9222324 A1 | 12/1992 |
| WO | WO9317105 A1 | 2/1993 |
| WO | WO9315199 A1 | 5/1993 |
| WO | WO9315200 A1 | 5/1993 |
| WO | WO9317715 A1 | 9/1993 |
| WO | WO9311236 A1 | 10/1993 |
| WO | WO9404678 A1 | 3/1994 |
| WO | WO9404690 A1 | 3/1994 |
| WO | 9425591 | 11/1994 |
| WO | WO9520401 A1 | 3/1995 |
| WO | WO9515982 A2 | 6/1995 |
| WO | WO9633735 A1 | 10/1996 |
| WO | WO9634096 A1 | 10/1996 |
| WO | WO9713844 A1 | 4/1997 |
| WO | WO9816654 A1 | 4/1998 |
| WO | WO9846645 A2 | 10/1998 |
| WO | WO9824893 A2 | 11/1998 |
| WO | WO9850433 A2 | 12/1998 |
| WO | WO9907210 A1 | 2/1999 |
| WO | WO0144301 A1 | 6/2001 |
| WO | WO0177137 A1 | 10/2001 |
| WO | WO0210414 A2 | 7/2002 |
| WO | WO2005063291 | 7/2005 |
| WO | WO2007071426 A1 | 6/2007 |
| WO | WO2007073499 | 6/2007 |
| WO | WO2007074880 | 7/2007 |
| WO | WO2009070642 A1 | 6/2009 |

OTHER PUBLICATIONS

"The Pharmacology of Monoclonal Antibodies," vol. 113, Rosenburg, M., et al. eds., Springer-Verlag, New York, pp. 269-315 (1994).
Ames, R.S., et al., "Conversion of murine Fabs isolated from a combinatorial phage display library to full length immunoglobulins," J Immunol Methods, vol. 184, No. 2, pp. 177-186 (1995).
Baca, M., et al., "Antibody humanization using monovalent phage display," J Biol Chem, vol. 272, No. 16, pp. 10678-10684 (1997).
Better, M., et al., "*Escherichia coli* Secretion of an Active Chimeric Antibody Fragment," Science, vol. 240, No. 4855, pp. 1041-1043 (1988).
Bitter, G.A., et al., "Expression and secretion vectors for yeast," Methods Enzymol, vol. 153, pp. 516-544 (1987).
Brinkmann., U., "Phage display of disulfide-stabilized Fv fragments," J Immunol Methods, vol. 182, No. 1, pp. 41-50 (1995).
Brischwein., K., "MT110: a novel bispecific single-chain antibody construct with high efficacy in eradicating established tumors," Mol Immunol., vol. 43, No. 8, pp. 1129-1143 (2005).
Buerke, M. et al., "Novel Small Molecule Inhibitor of Cls Exerts Cardioprotective Effects in Ischemia-Reperfusion Injury in Rabbits," J Immunol., vol. 167, Issue 9, pp. 5375-5380 (2001).
Burton, D.R., "Human Antibodies from Combinatorial Libraries," Advances in Immunology, vol. 57, pp. 191-280 (1994).
Caldas, C., et al., "Design and synthesis of germline-based hemi-humanized single-chain Fv against the CD18 surface antigen," Protein Engineering, vol. 13, No. 5, pp. 353-360 (2000).
Carter, P. et al., "High Level *Escherichia coli* Expression and Production of a Bivalent Humanized Antibody Fragment," Nature Biotechnology, vol. 10, pp. 163-167 (1992).
Chames, Patrick et al, "Bispecific antibodies for cancer therapy", Landes Bioscience, www.landesbioscience.com/journals/mabs/article/10015, Sep. 9, 2009.
Clackson, T., et al., "Making antibody fragments using phage display libraries," Nature, vol. 352, pp. 624-628 (1991).
Cockett, M.I., et al., "High level expression of tissue inhibitor of metalloproteinases in Chinese hamster ovary cells using glutamine synthetase gene amplification," Biotechnology, vol. 8, No. 7, pp. 662-667 (1990).
Colbere-Garapin et al., "A New Dominant Hybrid Selective Marker for Higher Eukaryotic Cells," J. Mol. Biol., vol. 150, No. 1 (1981).
Couto, J.R., et al., "Anti-BA46 Monoclonal Antibody Mc3: Humanization Using a Novel Positional Consensus and in Vivo and in Vitro Characterization," Cancer Research, vol. 55, No. 8, pp. 1717-1722 (1995).
Couto, J.R., et al., "Designing human consensus antibodies with minimal positional templates," Cancer Res., vol. 55, No. 23 Suppl., pp. 5973s-5977s (1995).
Crouse, G.F., et al., "Expression and amplification of engineered mouse dihydrofolate reductase minigenes," Mol. Cell. Biol., vol. 3, pp. 257-266 (1983).
Dreier, T., et al., "Extremely potent, rapid and costimulation-independent cytotoxic T-cell response against lymphoma cells catalyzed by a single-chain bispecific antibody," Int J Cancer, vol. 100, No. 6, pp. 690-697 (2002).
Dreier, T., et al., "T Cell Costimulus-Independent and Very Efficacious Inhibition of Tumor Growth in Mice Bearing Subcutaneous or Leukemic Human B Cell Lymphoma Xenografts by a CD19-/CD3-Bispecific Single-Chain Antibody Construct," The Journal of Immunology, vol. 170, No. 8, pp. 4397-4402 (2003)s.
Foecking, M.K., and Hofstetter, H., "Powerful and versatile enhancer-promoter unit for mammalian expression vectors," Gene, vol. 45, Issue 1, pp. 101-105 (1986).
Freedman et al., "*Non-Hodgkin's Lymphomas*," in Cancer Medicine, vol. 2, 3rd Edition, Holland et al. (eds.), pp. 2028-2068 (Lea & Febiger 1993).
Freireich et al., Quantitative comparison of toxicity of anticancer agents in mouse, rat, monkey, dog, and human, *Cancer Chemotherapy Reports*, NCI 1966 40:219-244.
Gruber, M., et al., "Efficient tumor cell lysis mediated by a bispecific single chain antibody expressed in *Escherichia coli*," The Journal of Immunology, vol. 152, No. 11, pp. 5368-5374 (1994).
Guss, B., et al., "Structure of the IgG-binding regions of streptococcal protein G," EMBO J., vol. 5, No. 7, pp. 1567-1575 (1986).
Hinman, L. M. et al., "Preparation and Characterization of Monoclonal Antibody Conjugates of the Calicheamicins: A Novel and Potent Family of Antitumor Antibiotics," Cancer Research, vol. 53, pp. 3336-3342 (1993).
Hoffmann., P., et al., "Serial killing of tumor cells by cytotoxic T cells redirected with a CD19-/CD3-bispecific single-chain antibody construct," International Journal of Cancer, vol. 115, No. 1, pp. 98-104 (2005).
Holliger, P., ""Diabodies": small bivalent and bispecific antibody fragments," Proc Natl Acad Sci USA., vol. 90, No. 14, pp. 6444-6448 (1993).
Kettleborough , C.A., et al., "Isolation of tumor cell-specific single-chain Fv from immunized mice using phage-antibody libraries and the re-construction of whole antibodies from these antibody fragments," European Journal of Immunilogy, vol. 24, Issue 4, pp. 952-958 (1994).

(56) References Cited

OTHER PUBLICATIONS

Kilpatrick, K.E., et al., "Rapid development of affinity matured monoclonal antibodies using RIMMS," Hybridoma, vol. 16, No. 4, pp. 381-389 (1997).
Köhler, C., and Milstein, C., "Continuous cultures of fused cells secreting antibody of predefined specificity," Nature, vol. 256, pp. 495-497 (1975).
Kostelny, S.A., et al., "Formation of a bispecific antibody by the use of leucine zippers," The Journal of Immunology, vol. 148, No. 5, pp. 1547-1553 (1992).
Kütemeier, G., "Assembly of humanized antibody genes from synthetic oligonucleotides using a single-round PCR," Biotechniques, vol. 17, No. 2, pp. 242-246 (1994).
Lindmark, R. et al., "Binding of immunoglobulins to Protein A and immunoglobulin levels in mammalian sera," J. Immunol. Methods, vol. 62, pp. 1-13 (1983).
Lode, H. N. et al., "Targeted Therapy with a Novel Enediyene Antibiotic Calicheamicin 9 Effectively Suppresses Growth and Dissemination of Liver Metastases in a Syngeneic Model of Murine Neuroblastoma," Cancer Research, vol. 58, pp. 2925-2928 (1998).
Lonberg, N., and Huszar, D., "Human antibodies from transgenic mice," Int Rev Immunol., vol. 13, No. 1, pp. 65-93 (1995).
Marks, J.D., et al., "By-passing immunization. Human antibodies from V-gene libraries displayed on phage," J Mol Biol., vol. 222, No. 3, pp. 581-597 (1991).
Milstein, C., and Cuello, A.C., "Hybrid hybridomas and their use in immunohistochemistry," Nature, vol. 305, pp. 537-540 (1983).
Morea, V., et al., "Antibody Modeling: Implications for Engineering and Design," Methods, vol. 20, No. 3, pp. 267-279 (2000).
Morgan, R.A., and Anderson, W.F., "Human Gene Therapy," Annual Review of Biochemistry, vol. 62, pp. 191-217 (1993).
Mulligan, R.C., "The basic science of gene therapy," Science, vol. 260, No. 5110, pp. 926-932 (1993).
Mulligan, R.C., and Berg, P., "Selection for animal cells that express the *Escherichia coli* gene coding for xanthine-guanine phosphoribosyltransferase," Proc. Nati. Acad. Sci. USA, vol. 78, No. 4, pp. 2072-2076 (1981).
Mullinax, R.L., et al., "Expression of a heterodimeric Fab antibody protein in one cloning step," Biotechniques, vol. 12, No. 6, pp. 864-869 (1992).
Muyldermans, S., "Single domain camel antibodies: current status," J Biotechnol., vol. 74, No. 4, pp. 277-302 (2001).
Nuttall, S.D., et al., "Immunoglobulin VH Domains and Beyond Design and Selection of Single-Domain Binding and Targeting Reagents," Current Pharmaceutical Biotechnology, vol. 1, No. 3, pp. 253-263 (2000).
Offner, H. et al., "T cell receptor peptide therapy triggers autoregulation of experimental encephalomyelitis," Science, vol. 251, pp. 430-432 (1991).
O'Hare, K., et al., "Transformation of mouse fibroblasts to methotrexate resistance by a recombinant plasmid expressing a prokaryotic dihydrofolate reductase," Proc. NatL Acad. Sci. USA, vol. 78, No. 3, pp. 1527-1531 (1981).
Padlan, E.A., "A possible procedure for reducing the immunogenicity of antibody variable domains while preserving their ligand-binding properties," Molecular Immunology, vol. 28, Issue 4-5, pp. 489-498 (1991).
Patti, C. et al., "High-dose cyclophosphamide, etoposide and BCNU (CVB) with autologous stem cell rescue in malignant lymphomas," Eur. J. Haematol, vol. 51, Issue 1, pp. 18-24 (1993).
Pedersen, J.T., et al., "Comparison of surface accessible residues in human and murine immunoglobulin Fv domains. Implication for humanization of murine antibodies," J Mol Biol., vol. 235, No. 3, pp. 959-973 (1994).
Persic. L., "An integrated vector system for the eukaryotic expression of antibodies or their fragments after selection from phage display libraries," Gene, vol. 187, No. 1, pp. 9-18 (1997).
Riechmann, L., and Muvldermans, S., "Single domain antibodies: comparison of camel VH and camelised human VH domains," J Immunol Methods, vol. 231, No. 1-2, pp. 25-38 (1999).

Riechmann, L., et al., "Reshaping human antibodies for therapy," Nature, vol. 332, No. 6162, pp. 323-327 (1988).
Roguska, M.A., et al., "A comparison of two murine monoclonal antibodies humanized by CDR-grafting and variable domain resurfacing," Protein Eng., vol. 9, No. 10, pp. 895-904 (1996).
Roguska, M.A., et al., "Humanization of murine monoclonal antibodies through variable domain resurfacing," Proc Natl Acad Sci USA., vol. 91, No. 3, pp. 969-973 (1994).
Rosen, L., "Antiangiogenic Strategies and Agents in Clinical Trials," The Oncologist, vol. 5, pp. 20-27 (2000).
Ruther, U., and Muler-Hill, B., "Easy identification of cDNA clones," EMBO, vol. 2, No. 10, pp. 1791-1794 (1983).
Sandhu, J.U., "A rapid procedure for the humanization of monoclonal antibodies," Gene, vol. 150, No. 2, pp. 409-410 (1994).
Sato, S. et al., "Quantitative Genetic Variation in CD19 Expression Correlates with Autoimmunity," J Immunology, vol. 165, Issue 11, pp. 6635-6643 (2000).
Sawai, H., et al., "Direct production of the Fab fragment derived from the sperm immobilizing antibody using polymerase chain reaction and cDNA expression vectors," Am J Reprod Immunol., vol. 34, No. 1, pp. 26-34 (1995).
Schlereth, B., et al., "Eradication of tumors from a human colon cancer cell line and from ovarian cancer metastases in immunodeficient mice by a single-chain Ep-CAM-/CD3-bispecific antibody construct," Cancer Res., vol. 65, No. 7, pp. 2882-2889 (2005).
Shaffer, A.L., et al., "Lymphoid malignancies: the dark side of B-cell differentiation," Nat Rev Immunol., vol. 2, No. 12, pp. 920-932 (2002).
Studnicka, G.M., et al. "Human-engineered monoclonal antibodies retain full specific binding activity by preserving non-CDR complementarity-modulating residues," Protein Eng. vol. 7, No. 6, pp. 805-814 (1994).
Suresh, M.R., et al., "Bispecific monoclonal antibodies from hybrid hybridomas," Methods in Enzymology, vol. 121, pp. 210-228 (1986)
Suresh et al., Methods in Enzymology, 121:210 (1986).
Szybalska., E.H., and Szybalski., W., "Genetics of Human Cell Lines, IV. DNA-Mediated Heritable Transformation of a Biochemical Trait," Proc Natl Acad Sci U S A., vol. 48, No. 12, pp. 2026-2034 (1962).
Tan, P., et al., ""Superhumanized" antibodies: reduction of immunogenic potential by complementarity-determining region grafting with human germline sequences: application to an anti-CD28.," J Immunol., vol. 169, No. 2, pp. 1119-1125 (2002).
Tolstoshev, P., "Gene therapy, concepts, current trials and future directions," Annu Rev Pharmacol Toxicol., vol. 33, pp. 573-596 (1993).
Traunecker, A., et al., "Bispecific single chain molecules (Janusins) target cytotoxic lymphocytes on HIV infected cells," The EMBO Journal, vol. 10, No. 12, pp. 3655-3659 (1991).
Van Heeke, G., and Schuster, S.M., "Expression of human asparagine synthetase in *Escherichia coli*," J Biol Chem., vol. 264, No. 10, pp. 5503-5509 (1989).
Wang, Wei et al, Antibody structure, instability, and formulation, www.interscience.wiley.com, Jun. 4, 2006.
Wigler, M., "Transfer of purified herpes virus thymidine kinase gene to cultured mouse cells," Cell, vol. 11, No. 1, pp. 223-232 (1977).
Wigler, M., et al., "Transformation of mammalian cells with an amplifiable dominant-acting gene," Proc Natl Acad Sci U S A, vol. 77, No. 6, pp. 3567-3570 (1980).
Wolf, E., et al., "BiTEs: bispecific antibody constructs with unique anti-tumor activity," Drug Discov Today, vol. 10, No. 18, pp. 1237-1244 (2005).
Wooldridge, J. E. et al., "Immunostimulatory Oligodeoxynucleotides Containing CpG Motifs Enhance the Efficacy of Monoclonal Antibody Therapy of Lymphoma," Blood, vol. 89, No. 8, pp. 2994-2998 (1997).
Wu, G.Y., and Wu, C.H., "Delivery systems for gene therapy," Biotherapy, vol. 3, Issue 1, pp. 87-95 (1991).
"Tumor Necrosis Factor Receptor-IgG1, Fc (Fusion Protein), Recombinant, Human (TNFR)," US Biological Life Sciences, T9160-35F, www.usbio.net/technicalSheet.php?item=T9160-35F, (last accessed May 30, 2014).

(56) References Cited

OTHER PUBLICATIONS

"TNFR Human," GeneDirex, www.genedirecx.com/?p=1165, (Sep. 8, 2011).

Kipriyanov, S.M., et al., "Bispecific CD3 x CD19 diabody for T cell-mediated lysis of malignant human B cells", International Journal of Cancer, John Wiley & Sons, Inc., New York, NY; US, vol. 77, No. 5, Aug. 31, 1998.

Falconer, Robert J. et al, "Stabilization of a monoclonalantibody during purification and formulation by addition of basic amino acid excipients" wileyonlinelibrary.com, Jun. 7, 2011.

Extended European Search Report corresponding to EP 08855346.6 (PCT/US2008/084796) dated Feb. 28, 2013.

International Search Report corresponding to PCT/US2008/84796 Feb. 10, 2009.

Pharmaceutical Excipients Dictionary 2007, International Pharmaceutical Excipients Council Japan (ed.), Yakuji Nippo Corporation, Jul. 25, 2007, 1st edition, p. 322-323 "L-Lysine Hydrochloride".

Griggs et al., "Targeting tumour vasculature: the development of combretastatin A4", Lancet Oncol., 2001, 2(2):82-7 Abstract only.

Inouye et al., "Up-promoter mutations in the Ipp gene of Eschenchia coli", Nucleic Acids Research, 1985, 13 (9):3101-3110.

Logan et al., "Adenovirus tripartite leader sequence enhances translation of mRNAs late after infection", Proc. Natl. Acad. Sci. USA, 1984, 81:3655-3659.

Lowy et al., "Isolation of transforming DNA: cloning the hamster aprt gene", Cell, 1980, 22(3):817-823 Abstract only.

Lueckel et al. "Formulations of Sugars with Amino Acids or Mannitol-Influence of Concentration Ratio on the Properties of the Freeze-Concentrate and the Lyophilizate", Pharmaceutial Development and Technology, 1998, 3 (3):325-336.

Santerre et al., "Expression of prokaryotic genes for hygromycin B and G418 resistance as dominant-selection markers in mouse L cells", Gene, 1984, 30(1-3):147-56 Abstract only.

\* cited by examiner

| ID# | Formulation composition |
|---|---|
| F0 | 25 mM citric acid, 15% trehalose dihydrate, pH 7 |
| F1 | 25 mM citric acid, 15% trehalose dihydrate 0.1% polysorbate 80, pH 7 |
| F3 | 25 mM citric acid, 15% trehalose dihydrate 0.1% polysorbate 80, 500 mM arginine HCl, pH 7 |
| F9 | 25 mM citric acid, 5% trehalose dihydrate, 0.1% polysorbate 80, 500 mM arginine HCl, pH 7 |
| F10 | 25 mM citric acid, 5% Mannitol, pH 7 |

Fig. 1

| ID# | Formulation composition |
|---|---|
| F11 | 25 mM citric acid, 15% trehalose dihydrate, 0.1% polysorbate 80, 100 mM arginine HCl, pH 6 |
| F12 | 25 mM citric acid, 15% trehalose dihydrate, 0.1% polysorbate 80, 100 mM arginine HCl, pH 7 |
| F13 | 25 mM citric acid, 15% trehalose dihydrate, 0.1% polysorbate 80, 500 mM arginine HCl, pH 6 |
| F14 | 25 mM citric acid, 15% trehalose dihydrate 0.1% polysorbate 80, 500 mM arginine HCl, pH 7 |
| F15 | 25 mM citric acid, 15% trehalose dihydrate, 0.1% polysorbate 80, 500 mM lysine HCl, pH 7 |

Fig. 9

| ID# | Formulation composition |
|---|---|
| F26 | 25 mM citric acid, 15% trehalose dihydrate, 0.25% polysorbate 80 pH 7 |
| F27 | 25 mM citric acid, 15% trehalose dihydrate, 0.1% polysorbate 80, 100 mM lysine HCl pH 7 |
| F28 | 25 mM citric acid, 15% trehalose dihydrate, 0.25% polysorbate 80, 100 mM lysine HCl pH 7 |
| F29 | 25 mM citric acid, 15% trehalose dihydrate, 0.1% polysorbate 80, 200 mM lysine HCl pH 7 |
| F30 | 25 mM citric acid, 15% trehalose dihydrate, 0.1% polysorbate 80, 300 mM lysine HCl pH 7 |

Fig. 11

Formulation 25/25:

25mM Citrate, 25mM LysHCl, 6% trehalose, 0.02% Polysorbate 80 at pH 6.0

Formulation 10/50:

10mM Citrate, 50mM LysHCl, 5.5% Trehalose, 0.02% Polysorbate 80 at pH 6.0

Formulation 25/200:

25mM Citrate, 200mM LysHCl, 5.5% Trehalose, 0.02% Polysorbate 80 at pH 6.0

Fig. 27A

Following SC administration in cynomolgus monkeys, MEDI-538 was bioavailable and exhibited serum concentrations that reached a peak at 4 hrs, and had a similar terminal half-life as IV administered drug.

*IN VIVO* MOUSE MODELS FOR ANTI-TUMOR EFFICACY

| Human tumor and T cells | SC Model | IV Model |
|---|---|---|
| MEDI-538 Administration | SC; opposite flank | SC |
| Endpoint | Tumor volume | Paralysis; survival |
| NOD/SCID | | |

Dose-dependent activation (CD69) of splenic T cells in huCD19 transgenic mice following a single SC administration of hys103

PROTEIN FORMULATION

CROSS-REFERENCE TO RELATED APPLICATIONS

This application is a National Phase filing of International Application No. PCT/US2008/084796 filed on Nov. 26, 2008, which claims benefit under 35 U.S.C. §119(e) of U.S. Provisional Application No. 60/990,772, filed on Nov. 28, 2007, U.S. Provisional Application No. 61/039,985, filed on Mar. 27, 2008, and U.S. Provisional Application No. 61/040,384, filed on Mar. 28, 2008, all of which are incorporated by reference in their entireties.

REFERENCE TO THE SEQUENCE LISTING

This application incorporates by reference a Sequence Listing submitted with this application as text file entitled "MT300PCTST25.txt" created on Nov. 25, 2008 and having a size of 12 kilobytes.

1. INTRODUCTION

The present invention provides methods to minimize aggregation of bispecific antibodies or fragments thereof in solution and to minimize antibody loss through absorption to contact surfaces.

The present invention relates to formulations of bispecific antibodies or fragments thereof, which formulations exhibit stability, low to undetectable levels of antibody fragmentation, low to undetectable levels of aggregation, very little to no loss of the biological activities of the bispecific antibodies and very little to no loss of antibody through absorption to contact surfaces during manufacture, preparation, storage and use.

In further embodiments, formulations of the invention comprise BiTE® molecules. In certain embodiments, a formulation of the invention is a lyophilized formulation, which lyophilized formulation maximizes BiTE® molecule recovery from the lyophilized product upon reconstitution. In further embodiments, formulations described herein are injectable formulations suitable for intravenous, subcutaneous, or intramuscular administration. In other embodiments, formulations of the invention comprise a BiTE® molecule having at least a first and a second binding site specific for the CD3 and CD19 antigens, respectively. In one embodiment, treatment is effected by use of a BiTE® molecule specific for CD19. In yet another embodiment, treatment is effected by use of MT103 or by the bispecific antibody encoded by SEQ ID NO:5. In yet other embodiments, formulations of the invention comprise a BiTE® molecule having at least a first and a second binding site specific for CD3 and the EphA2 antigens, respectively. In yet other embodiments, formulations of the invention comprise a BiTE® molecule having at least a first and a second binding site specific for CD3 and the carcinoembryonic antigen (CEA) antigens, respectively. In further embodiments, BiTE® molecules formulated according to the methods of the invention are highly bioavailable upon subcutaneous administration to a subject.

The invention also provides methods for preparing formulations of bispecific antibodies or fragments thereof, which formulations exhibit stability, low to undetectable levels of antibody fragmentation, low to undetectable levels of aggregation, very little to no loss of the biological activities of the bispecific antibodies and very little to no loss of antibody through absorption to contact surfaces during manufacture, preparation, storage and use. In certain embodiments, a formulation described herein is an injectable formulation suitable for intravenous, subcutaneous, or intramuscular administration.

The present invention is further directed to methods for the treatment of B cell disorders or diseases in human subjects, including B cell malignancies, using the lyophilized formulations of bispecific antibodies or fragments thereof that comprise at least a first and a second binding site specific for the CD3 and CD19 antigens, respectively. In one embodiment, treatment is effected by use of a BiTE® molecule specific for CD19. In yet another embodiment, treatment is effected by use of MT103 or by the bispecific antibody encoded by SEQ ID NO:5. The present invention is directed to methods for the treatment and prevention of autoimmune disease as well as the treatment and prevention of graft-versus-host disease (GVHD), humoral rejection, and post-transplantation lymphoproliferative disorder in human transplant recipients using lyophilized formulations of bispecific antibodies or fragments thereof that comprise at least a first and a second binding site specific for the CD3 and CD19 antigens, respectively. In one embodiment, treatment is effected by use of a BiTE® molecule specific for CD19. In yet another embodiment, treatment is effected by use of MT103 or by the bispecific antibody encoded by SEQ ID NO:5.

2. BACKGROUND

Bispecific antibodies are antibodies that have binding specificities for at least two different epitopes. Bispecific antibodies may bind to two different epitopes of a single cell surface marker. Other such antibodies may bind a first cell surface marker and further bind a second cell surface marker on the same cell. A binding arm specific for a surface antigen of a target cell may also be combined with an arm which binds to a triggering molecule on a leukocyte such as a T cell receptor molecule (e.g., CD2 or CD3), or Fc receptors for IgG (FcγR), so as to focus cellular defense mechanisms to the target cell. Bispecific antibodies may also be used to localize cytotoxic agents to a target cell. These antibodies possess a target cell marker-binding arm and an arm which binds the cytotoxic agent (e.g., saporin, anti-interferon-α, vinca alkaloid, ricin A chain, methola-exate or radioactive isotope hapten). Bispecific antibodies can be prepared as full-length antibodies or antibody fragments (e.g., F(ab')).

Methods for making bispecific antibodies are known in the art. (See, for example, Millstein et al., *Nature,* 305:537-539 (1983); Traunecker et al., *EMBO J.,* 10:3655-3659 (1991); Suresh et al., *Methods in Enzymology,* 121:210 (1986); Kostelny et al., *J. Immunol.,* 148(5):1547-1553 (1992); Hollinger et al., *Proc. Natl. Acad. Sci. USA,* 90:6444-6448 (1993); Gruber et al., *J. Immunol.,* 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089.).

MT103 is a recombinant, bispecific single-chain antibody or BiTE® molecule, which binds to CD19 on target cells and the CD3 complex on T effector cells. See Hoffmann P et. al., *Int J Cancer.* 2005 May 20; 115(1):98-104. It is a single polypeptide chain of 55 kDa with the variable binding domains of two murine monoclonal antibodies. By simultaneously binding to target and effector cells, MT103 triggers the T effector cell to form an immunological synapse, and to release perforin and granzymes which induce cell death of target cells. Target cells comprise human B cells of all development stages (with the exception of plasma cells) and malignant cells of most B cell-derived lymphoma and leukemia. Therefore, MT103 is currently in development for treatment of B-cell cancers.

Initial toxicology studies and clinical trials utilized a frozen liquid formulation which consisted of 1 µg/ml MT103 monomer in isotonic phosphate-buffered saline (pH 7.0-7.5) stabilized with 0.1% human serum albumin (HSA), sodium chloride, disodium monohydrogen phosphate, potassium dihydrogen phosphate and potassium chloride. A second lyophilized formulation was later developed to eliminate the use of HSA and enhanced the stability and recovery of MT103. This formulation consists of MT103 at 50 µg/mL in 25 mM citrate at pH 7.0, 500 mM lysine acetate, 15% trehalose dihydrate, 2.5% polyethylene glycol (PEG) 3350, 0.05% polysorbate 80. However, clinical use of the second lyophilized formulation never took place because the formulation presented significant interference in several essential analytical assays due to presence of the excipients lysine acetate and PEG 3350.

Therefore, further development was initiated to generate a formulation that 1) excludes the interfering excipients, 2) minimizes aggregate formation in the liquid bulks during storage, 3) maximizes the recovery of MT103 protein from the lyophilized product, 4) is suitable for intravenous, subcutaneous, or intramuscular administration, and 5) results in high bioavailability of the BiTE® molecules upon subcutaneous administration to a subject. Additional effort was put into optimization of the lyophilization cycle and robustness (boundary condition) studies.

3. SUMMARY OF THE INVENTION

The present invention relates to methods of minimizing the aggregation of BiTE® molecules in solution. In one embodiment, a method of the invention is used to minimize the aggregation of BiTE® molecules in solution. In another embodiment, a method of the invention is used to minimize the aggregation of BiTE® molecules comprising a first and a second binding site specific for the CD3 and CD19 antigens, respectively, wherein said molecule is in solution. In a specific embodiment, the present invention provides methods to minimize the aggregation of the MT103™ BiTE® molecule in solution.

The present invention relates to sterile, stable, liquid formulations of BiTE® molecules. In one embodiment, a liquid formulation of the invention comprises a BiTE® molecule and lysine. In a specific embodiment, a liquid formulation of the invention comprises a BiTE® molecule and lysine HCl. In one embodiment, a liquid formulation of the invention is suitable for lyophilization. In a specific embodiment, a liquid formulation of the invention comprises the MT103™. In a specific embodiment, a liquid formulation of the invention comprises between about 25 micrograms/ml and about 250 micrograms/ml MT103. In a specific embodiment, a liquid MT103 formulation of the invention comprises 25 mM citrate, 15% (w/v) trehalose dihydrate, 200 mM lysine HCl, 0.1% (w/v) polysorbate 80 and has a pH of 7.0. In a specific embodiment, a liquid formulation of the invention comprises MT103, about 30 mM citrate, about 75 mM lysine HCl, about 6.5% trehalose and about 0.02% Polysorbate 80 and has a pH of about 7.0. In a further specific embodiment, a liquid formulation of the invention comprises MT103, about 30 mM citrate, about 75 mM lysine HCl, about 6% trehalose and about 0.02% Polysorbate 80 and has a pH of about 7.0. In a specific embodiment, a liquid formulation of the invention consist of between about 25 micrograms/ml and about 250 micrograms/ml MT103, 25 mM citrate, 15% (w/v) trehalose dihydrate, 200 mM lysine HCl, 0.1% (w/v) polysorbate 80 and has a pH of 7.0. In a further embodiment, a liquid formulation of the invention comprises about 25 mM citrate, about 6% (w/v) trehalose dihydrate, about 50 mM lysine HCl, and about 0.1% (w/v) polysorbate 80 and has a pH of 7.0.

The present invention further provides sterile, stable lyophilized formulations of a BiTE® molecule. In one embodiment, a lyophilized formulation of the invention comprises a BiTE® molecule and lysine. In a specific embodiment, a lyophilized formulation of the invention comprises a BiTE® molecule and lysine HCl. In a specific embodiment, a reconstituted formulation of the invention comprises the MT103™ BiTE® molecule. In a specific embodiment, a lyophilized formulation of the invention comprises the MT103™ BiTE® molecule, citrate, trehalose, lysine HCl, and polysorbate 80.

The present invention further provides sterile, stable reconstituted formulations of a BiTE® molecule. In one embodiment, a reconstituted formulation of the invention comprises a BiTE® molecule and lysine. In a specific embodiment, a reconstituted formulation of the invention comprises a BiTE® molecule and lysine HCl. In a specific embodiment, a lyophilized formulation of the invention comprises the MT103™ BiTE® molecule. In a specific embodiment, a lyophilized formulation of the invention comprises the MT103™ BiTE® molecule, citrate, trehalose, lysine HCl, and polysorbate 80.

The present invention further relates to processes of making sterile, stable liquid formulations; sterile, stable lyophilized formulations; and sterile, stable reconstituted formulations comprising a BiTE® molecule. In a specific embodiment, the processes of the invention may be utilized to make a formulation comprising MT103. In further embodiments, formulations described herein are injectable formulations suitable for intravenous, subcutaneous, or intramuscular administration. In certain embodiments, subcutaneous administration of a BiTE® formulation of the invention results in high bioavailability of the BiTE® molecule.

The present invention also encompasses methods of preventing, managing, treating or ameliorating B cell disorders or diseases such as, but not limited to, B cell malignancies, autoimmune diseases, graft-versus-host disease (GVHD), humoral rejection, and post-transplantation lymphoproliferative disorder in a human subject, said methods comprising administering to a subject in need thereof a prophylactically or therapeutically effective amount of a formulation comprising BiTE® molecules that comprises a first and a second binding site specific for the CD3 and CD19 antigens, respectively. Alternatively, the present invention uses MT103 for the preventing, managing, treating or ameliorating of said diseases.

3.1. Definitions

As used herein, the terms "antibody" and "antibodies" (immunoglobulins) encompass monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, F(ab')$_2$ fragments, antibody fragments that exhibit the desired biological activity, disulfide-linked Fvs (sdFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

In some embodiments, an antibody is a bispecific single chain antibody comprising a first binding domain that comprises a variable heavy (VH) domain and a variable light (VL) domain of an antibody that immunospecifically binds to the T-cell antigen CD3 and a second binding domain that comprises a VH domain and a VL domain of an antibody that immunospecifically binds to an antigen of interest (e.g., CD19 or EphA2 or CEA). The first and second binding domains of a bispecific single chain antibody may be derived from synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFvs) (e.g., including monospecific and bi-specific, etc.), Fab fragments, F(ab') fragments, disulfide-linked Fvs (sdFv), anti-idiotypic (anti-Id) antibodies, and epitope-binding fragments of any of the above. In a specific embodiment, an antibody of a formulation of the invention is a bispecific single chain antibody comprising a first binding domain that comprises a variable heavy (VH) domain and a variable light (VL) domain of an antibody that immunospecifically binds to the T-cell antigen CD3 and a second binding domain that comprises a VH domain and a VL domain of an antibody that immunospecifically binds to CD19, such as, but not limited to, MT103. The antibody that immunospecifically binds to the T-cell antigen CD3 and the antibody that immunospecifically binds CD19 may be derived from synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFvs) (e.g., including monospecific and bi-specific, etc.), Fab fragments, F(ab') fragments, disulfide-linked Fvs (sdFv), anti-idiotypic (anti-Id) antibodies, and epitope-binding fragments of any of the above. In particular, antibodies of the formulations of the present invention include immunoglobulin molecules and immunologically active portions of immunoglobulin molecules, i.e., molecules that contain an antigen-binding domain that immunospecifically binds to an antigen of interest (e.g., CD19 and/or CD3) (e.g., one or more complementarity determining regions (CDRs) of an anti-CD19 or anti-CD3 antibody).

As used herein, the term "binding domain" refers to a domain comprising a three-dimensional structure capable of immunospecifically binding to an epitope. Thus, said domain can comprise the VH and/or VL domain of an antibody chain. In some embodiments, said domain comprises at least the VH domain. On the other hand, said binding domains contained in the antibodies of a formulation of the invention may comprise at least one complementarity determining region (CDR) of an antibody chain recognizing the CD19 and CD3 antigens, respectively. In this respect, it is noted that the domains of the binding domains present in the CD19-BiTE® (e.g., MT103) of the invention may not only be derived from antibodies but also from other CD19 or CD3 binding proteins, such as naturally occurring surface receptors or ligands. In accordance with the invention, said binding domain is comprised in a domain.

As used herein, the term "single-chain Fv" or "scFv" refers to antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. Methods for producing scFvs are well known in the art. For a review of methods for producing scFvs see Pluckthun in The Pharmacology of Monoclonal Antibodies, vol. 113, Rosenburg and Moore eds. Springer-Verlag, New York, pp. 269-315 (1994). In a specific embodiment, the EphA2-BiTE®s of the invention are comprised of scFvs.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, monoclonal antibodies are advantageous in that they can be synthesized by hybridoma cells that are uncontaminated by other immunoglobulin producing cells. Alternative production methods are known to those trained in the art, for example, a monoclonal antibody may be produced by cells stably or transiently transfected with the heavy and light chain genes encoding the monoclonal antibody.

The modifier "monoclonal" indicates the character of the antibody as being obtained from a substantially homogeneous population of antibodies, and is not to be construed as requiring engineering of the antibody by any particular method. The term "monoclonal" is used herein to refer to an antibody that is derived from a clonal population of cells, including any eukaryotic, prokaryotic, or phage clone, and not the method by which the antibody was engineered. For example, the monoclonal antibodies to be used in accordance with the present invention may be made by the hybridoma method first described by Kohler et al., Nature, 256:495 (1975), or may be made by any recombinant DNA method (see, e.g., U.S. Pat. No. 4,816,567), including isolation from phage antibody libraries using the techniques described in Clackson et al., Nature, 352:624-628 (1991) and Marks et al., J. Mol. Biol., 222:581-597 (1991), for example. These methods can be used to produce monoclonal mammalian, chimeric, humanized, human, domain antibodies, diabodies, vaccibodies, linear antibodies, and bispecific antibodies, including BiTE® molecules.

All formulations of antibodies and/or antibody fragments that specifically bind to an antigen of interest (e.g., CD19, or EphA2, or CEA) are herein collectively referred to as "formulations of the invention", "liquid formulations of the invention", "lyophilized formulations of the invention", "reconstituted formulations of the invention", "antibody liquid formulations of the invention", "antibody lyophilized formulations of the invention", "antibody reconstituted formulations of the invention" or "antibody formulations of the invention".

The phrase "pharmaceutically acceptable" as used herein means approved by a regulatory agency of the Federal or a state government, or listed in the U.S. Pharmacopeia, European Pharmacopia or other generally recognized pharmacopeia for use in animals, and more particularly in humans.

The terms "stability" and "stable" as used herein in the context of a formulation comprising BiTE® molecules (e.g., MT103) refer to the resistance of the antibody (including antibody fragment thereof) in the formulation to aggregation, degradation or fragmentation under given manufacture, preparation, transportation and storage conditions. The "stable" formulations of the invention retain biological activity under given manufacture, preparation, transportation and storage conditions. The stability of said antibody (including antibody fragment thereof) can be assessed by degrees of aggregation, degradation or fragmentation, as measured by HPSEC, static light scattering (SLS), Fourier Transform Infrared Spectroscopy (FTIR), circular dichroism (CD), urea unfolding techniques, intrinsic tryptophan fluorescence, differential scanning calorimetry, and/or ANS binding techniques, compared to a reference formulation. For example, a reference formulation may be a reference standard frozen at −70° C. consisting of 10 mg/ml of BiTE® molecules (for example, but not limited to, MT103) in PBS. The overall stability of a formulation comprising BiTE® molecules can be assessed by various immunological assays including, for example, ELISA and radioimmunoassay using isolated antigen molecules.

The phrase "low to undetectable levels of aggregation" as used herein refers to samples containing no more than about 5%, no more than about 4%, no more than about 3%, no more than about 2%, no more than about 1% and no more than about 0.5% aggregation by weight of protein as measured by high performance size exclusion chromatography (HPSEC) or static light scattering (SLS) techniques.

The term "low to undetectable levels of fragmentation" as used herein refers to samples containing equal to or more than about 80%, about 85%, about 90%, about 95%, about 98% or about 99% of the total protein, for example, in a single peak as determined by HPSEC, or reduced Capillary Gel Electrophoresis (rCGE), representing the non-degraded BiTE® molecule or a non-degraded fragment thereof, and containing no other single peaks having more than about 5%, more than about 4%, more than about 3%, more than about 2%, more than about 1%, or more than about 0.5% of the total protein in each. The term "reduced Capillary Gel Electrophoresis" as used herein refers to capillary gel electrophoresis under reducing conditions sufficient to reduce disulfide bonds in an antibody.

"Isolated" when used to describe the various polypeptides and antibodies disclosed herein, means a polypeptide or antibody that has been identified, separated and/or recovered from a component of its production environment. In some embodiments, the isolated polypeptide is free of association with all other components from its production environment. Contaminant components of its production environment, such as that resulting from recombinant transfected cells, are materials that would typically interfere with diagnostic or therapeutic uses for the antibody, and may include enzymes, hormones, and other proteinaceous or non-proteinaceous solutes. In specific embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or silver stain. In some embodiments, an isolated antibody will be prepared by at least one purification step.

The term "excipient" as used herein refers to an inert substance which is commonly used as a diluent, vehicle, preservative, binder or stabilizing agent for drugs which imparts a beneficial physical property to a formulation, such as increased protein stability, increased protein solubility, and decreased viscosity. Examples of excipients include, but are not limited to, proteins (for example, but not limited to, serum albumin), amino acids (for example, but not limited to, aspartic acid, glutamic acid, lysine, arginine, glycine), surfactants (for example, but not limited to, SDS, Tween 20, Tween 80, polysorbate, polysorbate 80 and nonionic surfactants), saccharides (for example, but not limited to, glucose, sucrose, maltose and trehalose), polyols (for example, but not limited to, mannitol and sorbitol), fatty acids and phospholipids (for example, but not limited to, alkyl sulfonates and caprylate). For additional information regarding excipients, see Remington's Pharmaceutical Sciences (by Joseph P. Remington, 18$^{th}$ ed., Mack Publishing Co., Easton, Pa.), which is incorporated herein in its entirety.

The term "lyophilized" or "freeze-dried" includes a state of a substance that has been subjected to a drying procedure such as lyophilization, where at least 50% of moisture has been removed.

The phrase "bulking agent" includes a compound that is pharmaceutically acceptable and that adds bulk to a lyo cake. Bulking agents known to the art include, for example, carbohydrates, including simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin), glycogen, and synthetic monomers and polymers.

A "lyoprotectant" is a molecule which, when combined with a protein of interest, significantly prevents or reduces chemical and/or physical instability of the protein upon lyophilization and subsequent storage. Lyoprotectants include, but are not limited to, sugars and their corresponding sugar alcohols; an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; Pluronics®; and combinations thereof. Additional examples of lyoprotectants include, but are not limited to, glycerin and gelatin, and the sugars mellibiose, melezitose, raffinose, mannotriose and stachyose. Examples of reducing sugars include, but are not limited to, glucose, maltose, lactose, maltulose, iso-maltulose and lactulose. Examples of non-reducing sugars include, but are not limited to, non-reducing glycosides of polyhydroxy compounds selected from sugar alcohols and other straight chain polyalcohols. Examples of sugar alcohols include, but are not limited to, monoglycosides, compounds obtained by reduction of disaccharides such as lactose, maltose, lactulose and maltulose. The glycosidic side group can be either glucosidic or galactosidic. Additional examples of sugar alcohols include, but are not limited to, glucitol, maltitol, lactitol and iso-maltulose. In specific embodiments, trehalose or sucrose is used as a lyoprotectant.

The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

A "reconstituted" formulation is one which has been prepared by dissolving a lyophilized antibody formulation in a diluent such that the antibody is dispersed in the reconstituted formulation. The reconstituted formulation is suitable for administration (e.g. parenteral administration) to a patient to be treated with the protein of interest and, in certain embodiments of the invention, may be one which is suitable for intravenous administration.

The "diluent" of interest herein is one which is pharmaceutically acceptable (safe and non-toxic for administration to a human) and is useful for the preparation of a liquid formulation, such as a formulation reconstituted after lyophilization.

In some embodiments, diluents include, but are not limited to, sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer.

As used herein, the term "subject" includes any human or nonhuman animal. The term "nonhuman animal" includes all vertebrates, for example, but not limited to, mammals and non-mammals, such as nonhuman primates, sheep, dogs, cats, horses, cows, chickens, amphibians, reptiles, etc.

By the terms "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is an inhibition or delay in the progression of the condition and/or prevention or delay of the onset of a disease or illness. Thus, the terms "treat," "treating" or "treatment of" (or grammatically equivalent terms) refer to both prophylactic and therapeutic treatment regimes.

As used herein, a "sufficient amount" or "an amount sufficient to" achieve a particular result refers to an amount of an antibody or composition of the invention that is effective to produce a desired effect, which is optionally a therapeutic effect (i.e., by administration of a therapeutically effective amount). For example, a "sufficient amount" or "an amount sufficient to" can be an amount that is effective to deplete B cells.

A "therapeutically effective" amount as used herein is an amount that provides some improvement or benefit to the subject. Stated in another way, a "therapeutically effective" amount is an amount that provides some alleviation, mitigation, and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject.

Concentrations, amounts, cell counts, percentages and other numerical values may be presented herein in a range format. It is also to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

4. BRIEF DESCRIPTION OF THE DRAWINGS

FIG. 1. Composition of formulations evaluated in the excipient screen study.

FIG. 2. Post-reconstitution recovery from lyophilized formulations.

Figure 3:
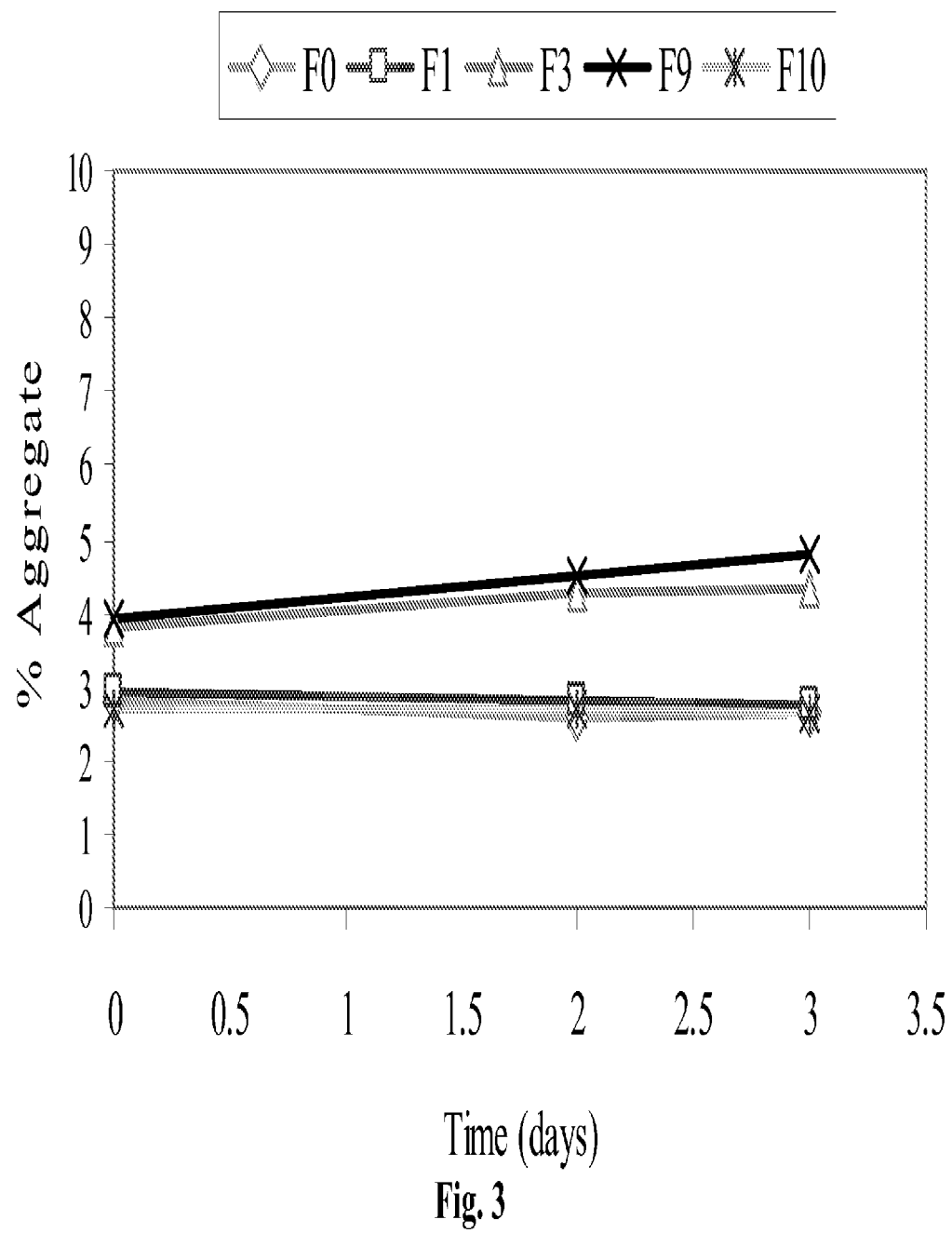

FIG. 3. Bulk liquid stability: Change in % aggregate over time at ~50 ug/mL protein concentration.

Figure 4:
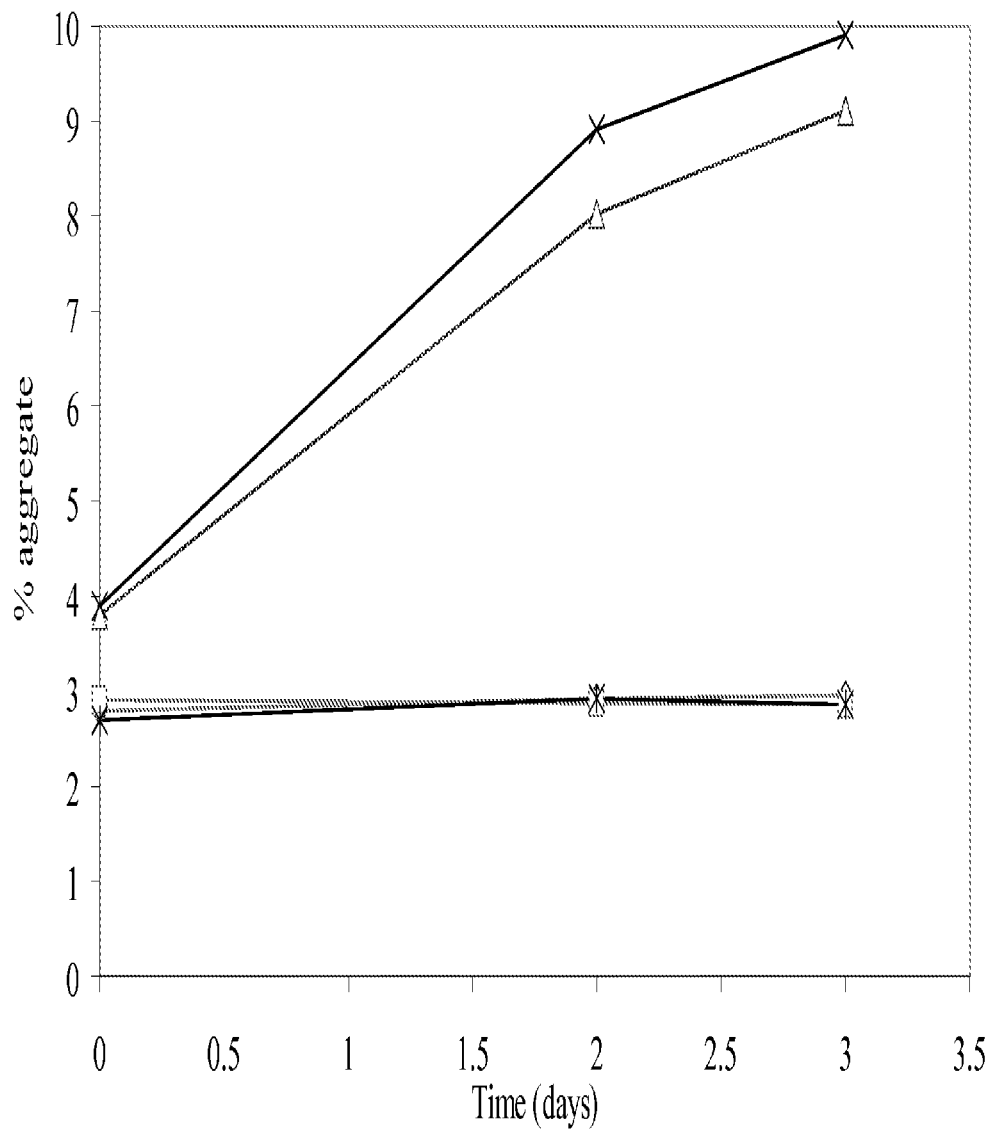

FIG. 4. Bulk liquid stability: Change in % aggregate over time at ~300 ug/mL protein concentration.

Figure 5:
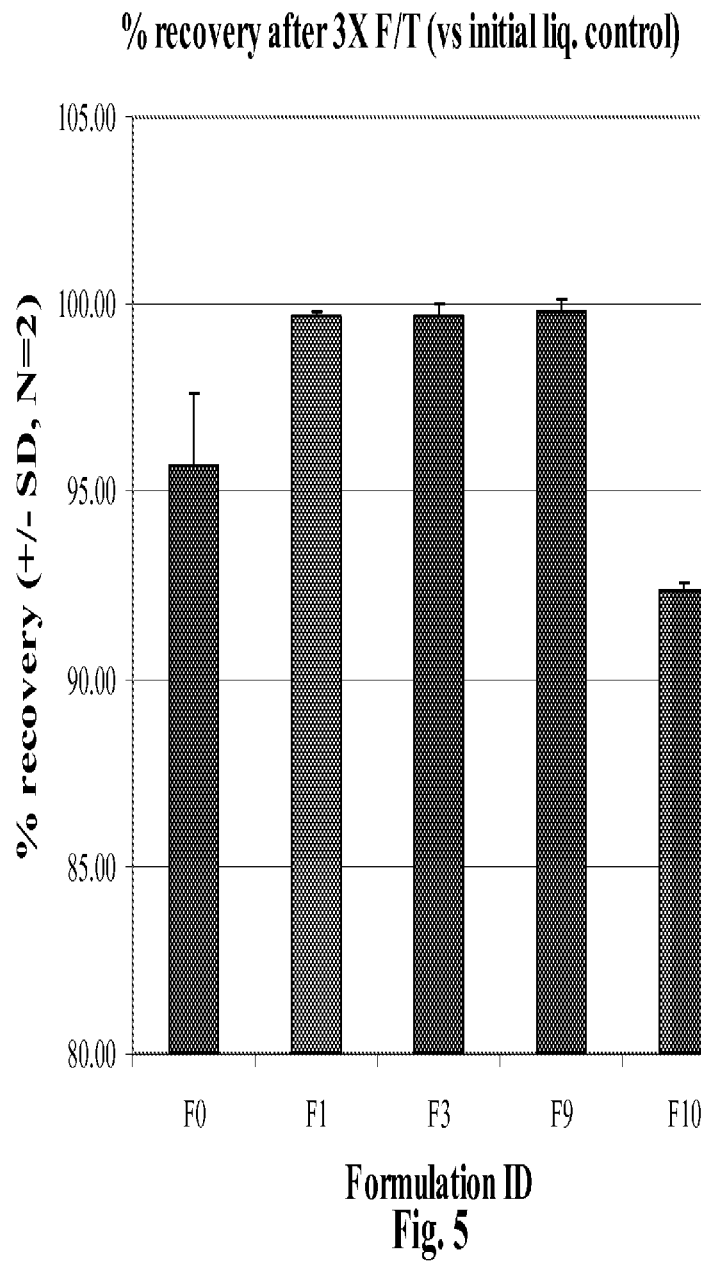

FIG. 5. Percent protein recovery after 3 freeze/thaw cycles. Data normalized to initial liquid control.

Figure 6:
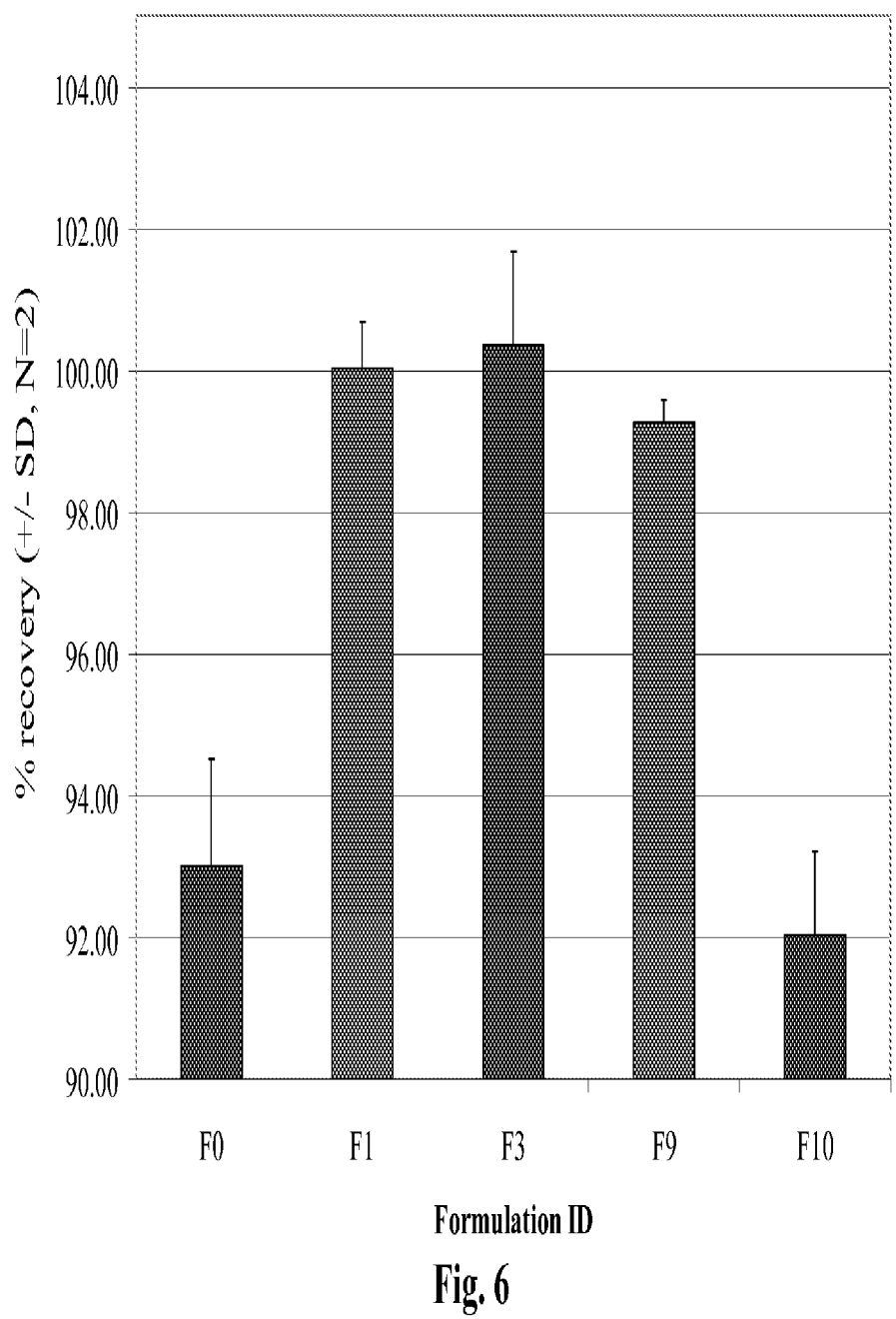

FIG. 6. Percent protein recovery after physical stress (shaking) Data normalized to initial liquid control.

Figure 7:
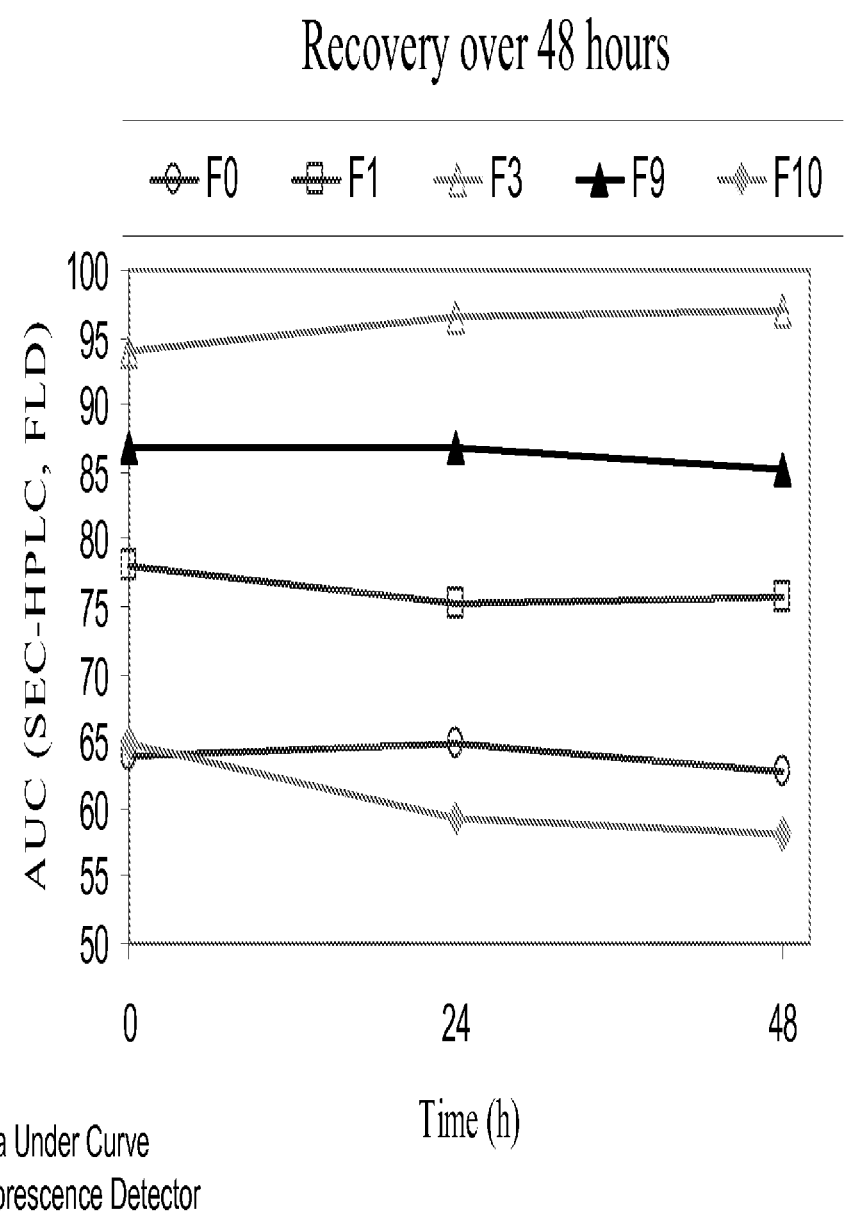

FIG. 7. Post-reconstitution stability at room temperature. Results for each formulation are normalized to their respective pre-lyophilization concentrations.

Figure 8:
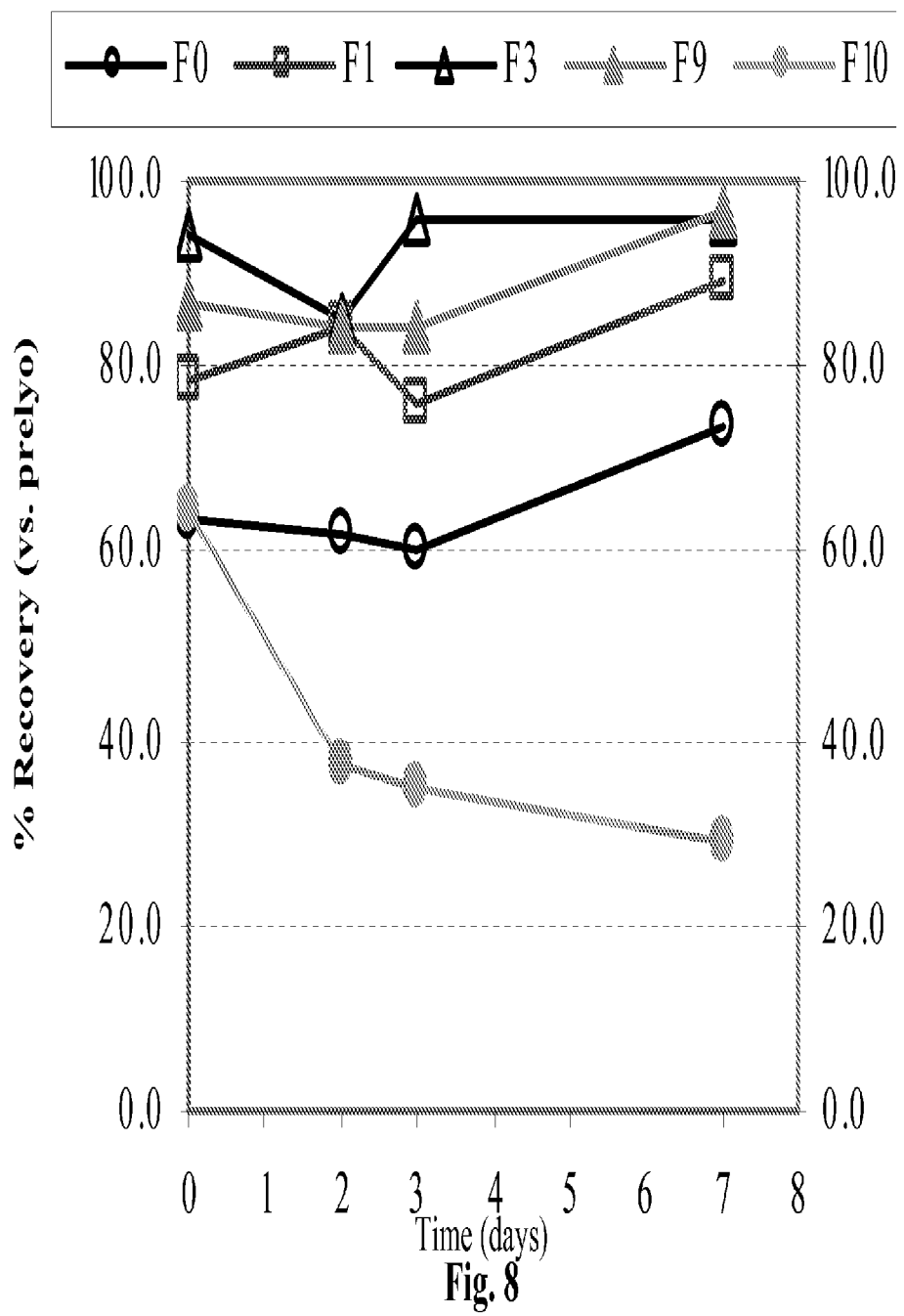

FIG. 8. Stability of lyophilized cakes at 40° C. as measured by percent recovery of MT103 from reconstituted cakes. Results for each formulation are normalized to pre-lyophilization concentrations.

FIG. 9. Composition of formulations evaluated in the pH screen study.

Figure 10:
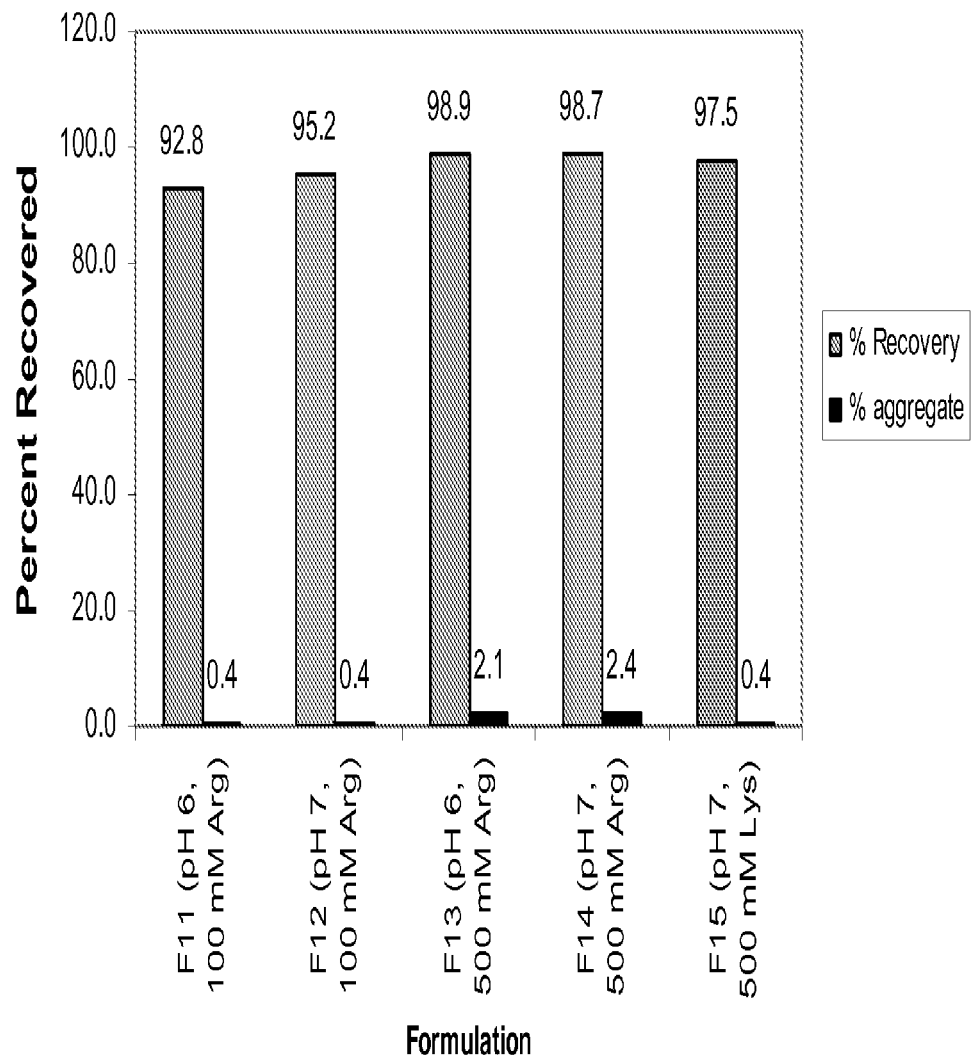

FIG. 10. Effect of pH 6 vs 7 on recovery of MT103 (N=1).

FIG. 11. Composition of formulations evaluated in the lysine HCl screen study.

Figure 12:
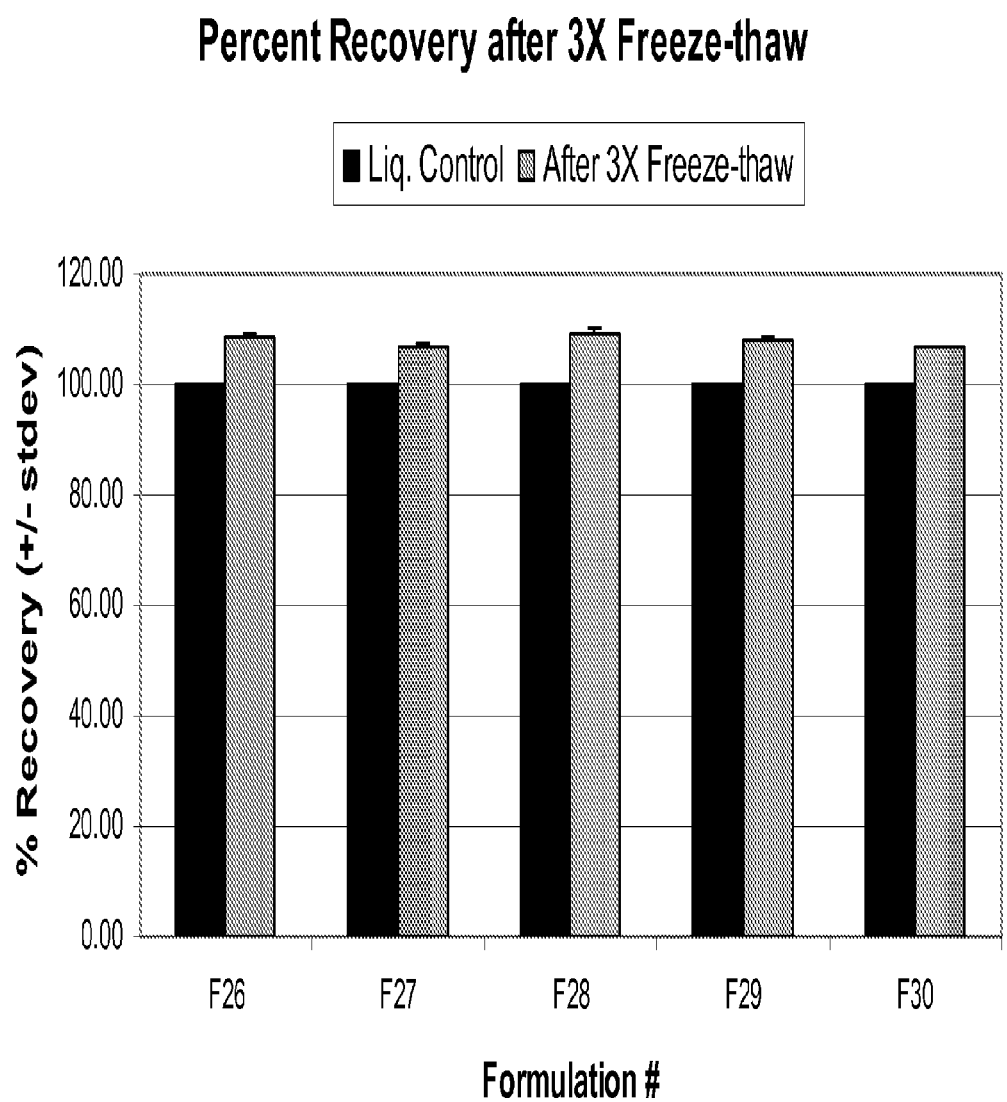

FIG. 12. Percent recovery of MT103 after three freeze-thaw cycles.

Figure 13:
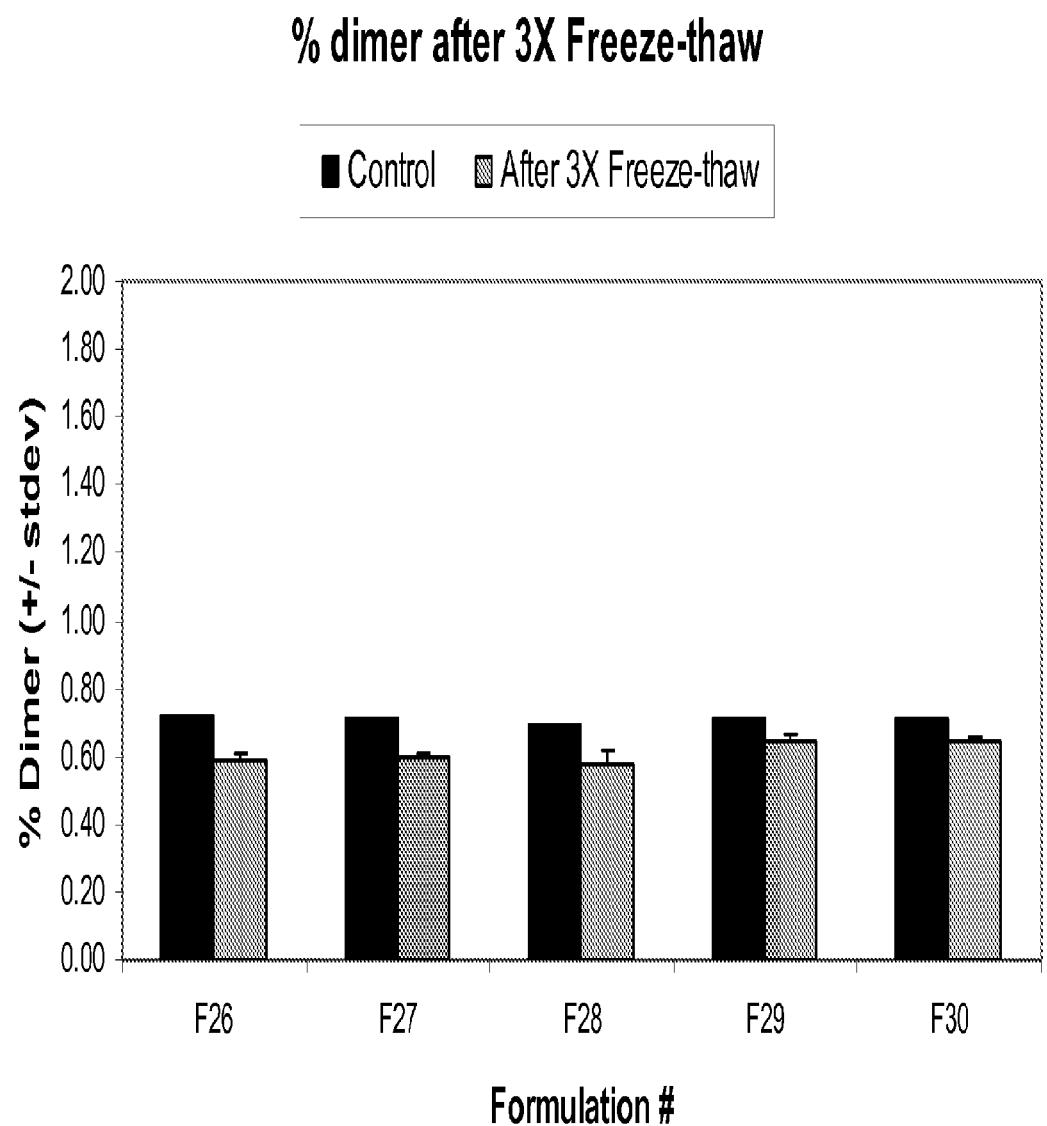

FIG. 13. Percent dimer content after three freeze-thaw cycles.

Figure 14:
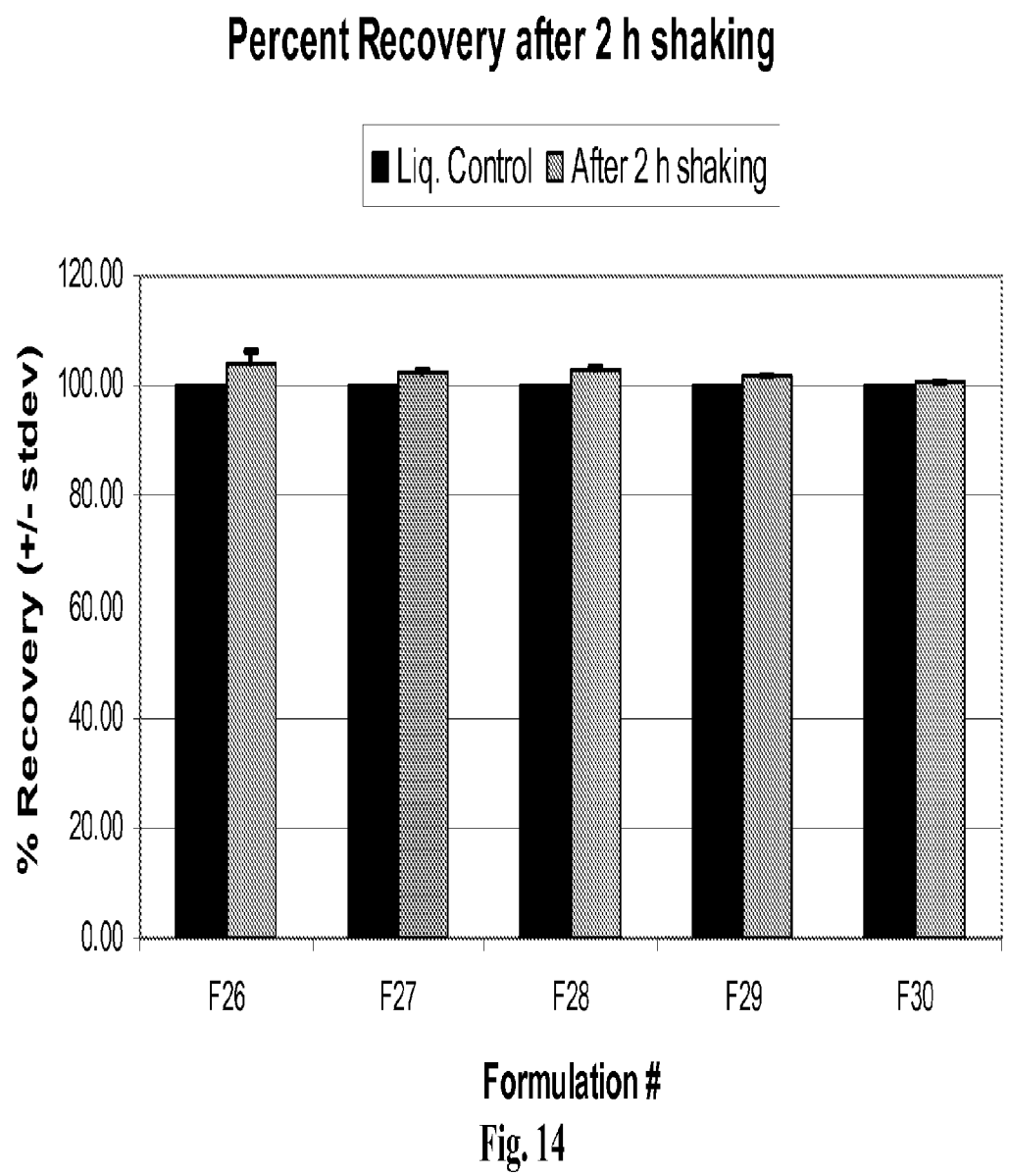

FIG. 14. Percent MT103 recovery after two hours of shaking.

Figure 15:
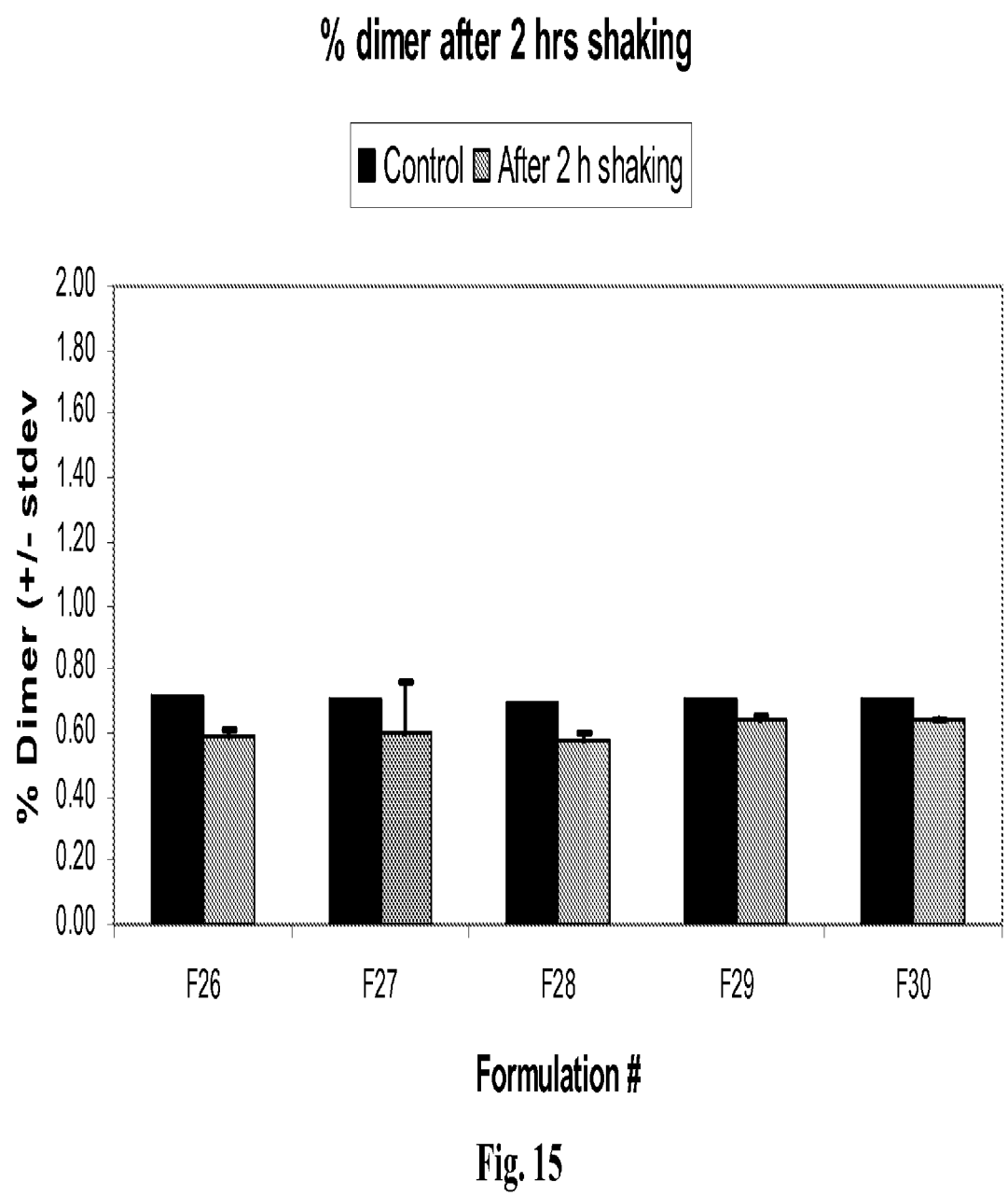

FIG. 15. Percent dimer after two hours of shaking.

Figure 16:
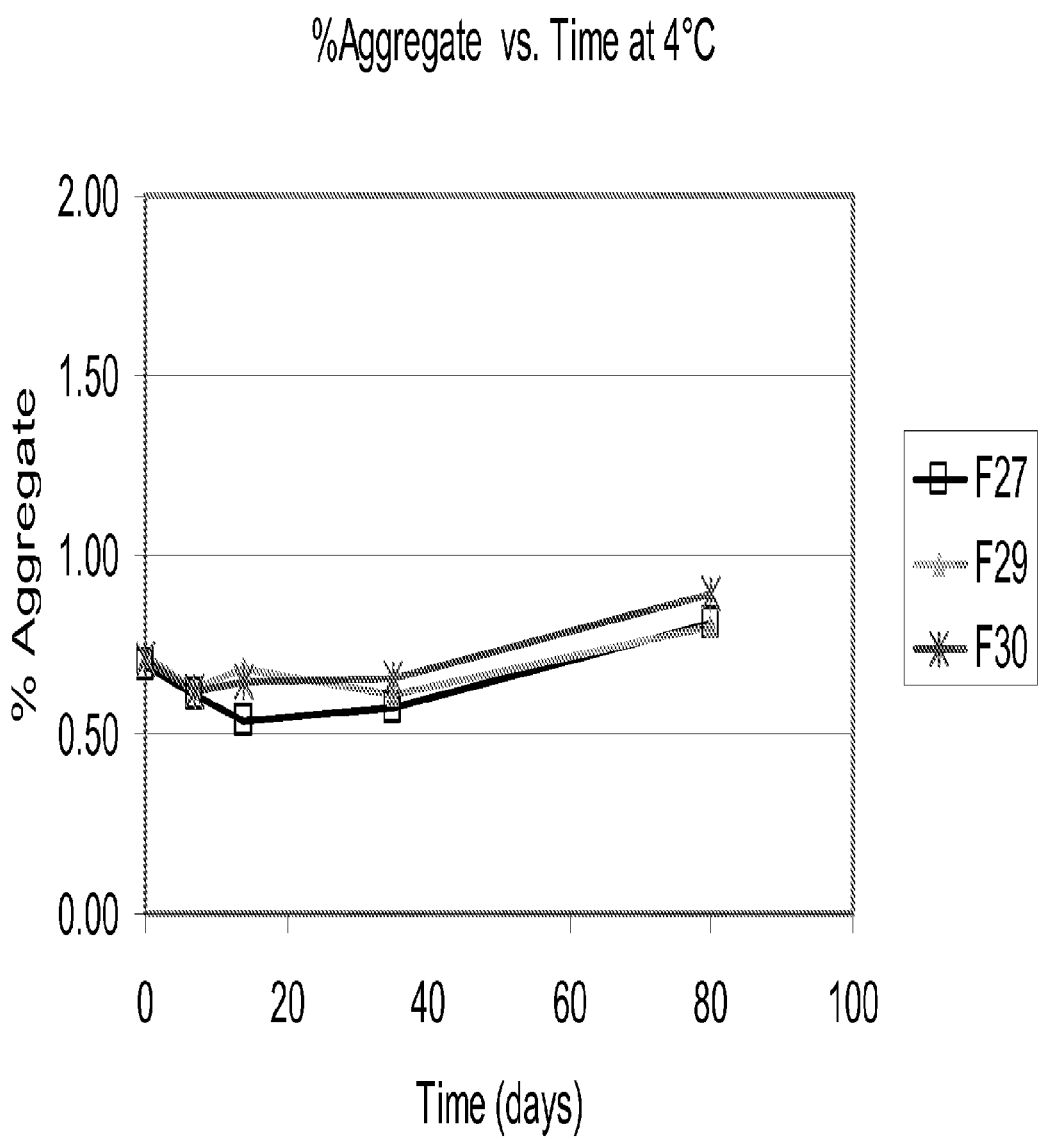

FIG. 16. Stability of MT103 in bulk liquid formulation at 4° C.

Figure 17:
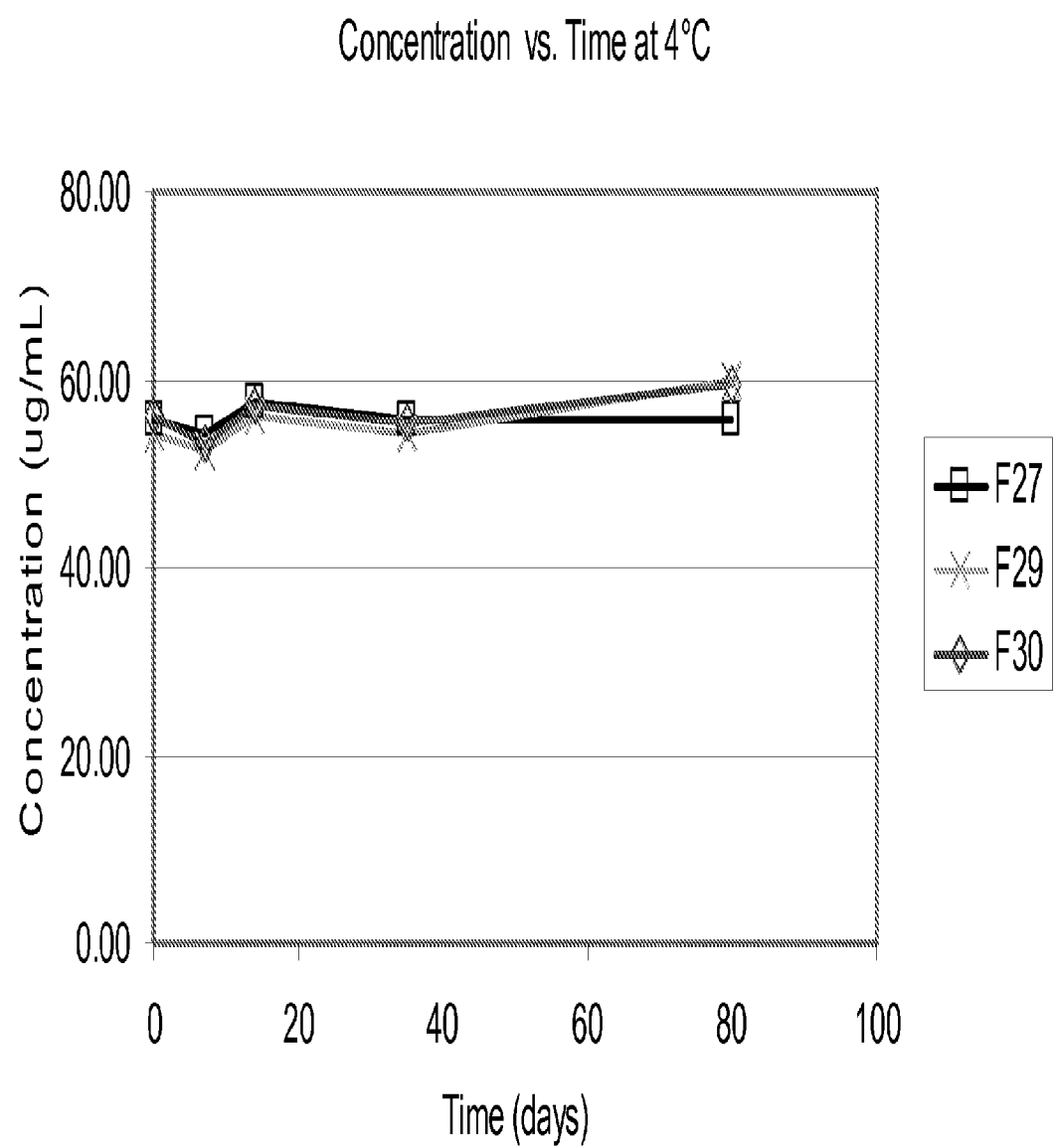

FIG. 17. Stability of MT103 in bulk liquid formulation at 4° C.

Figure 18:
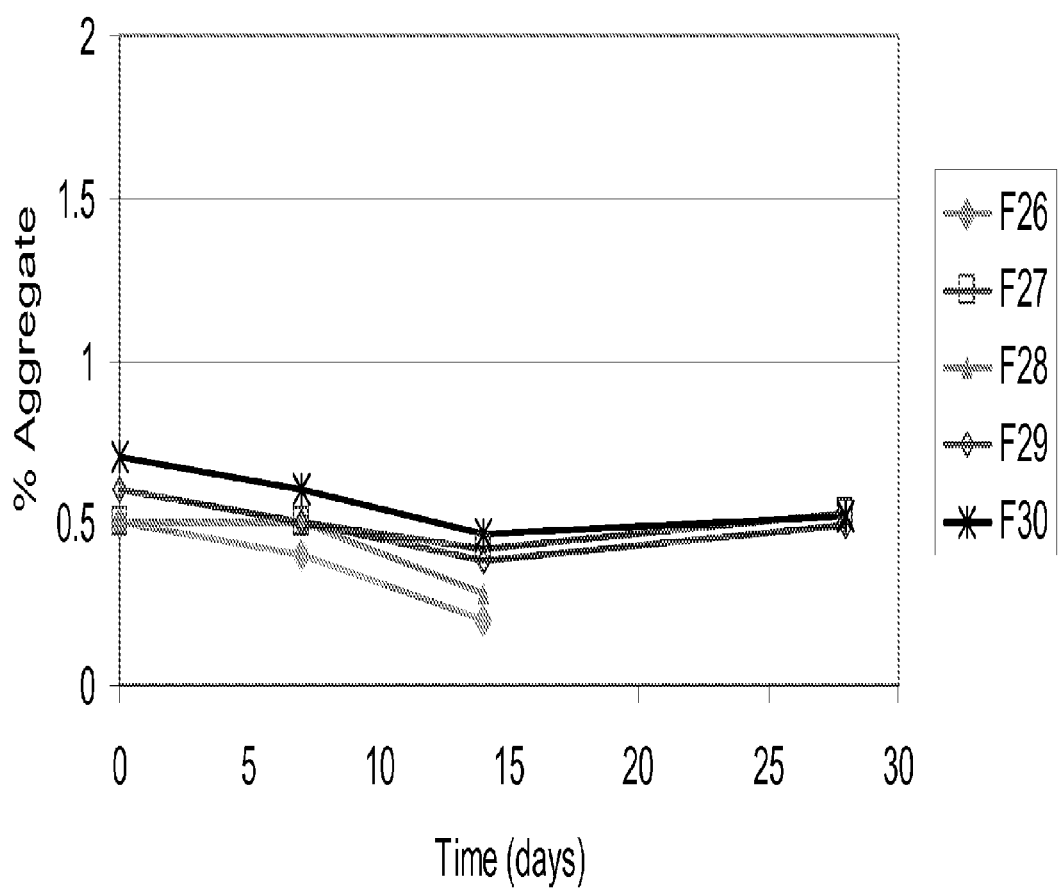

FIG. 18. Stability of lyophilized MT103 stored at 4° C.

Figure 19:
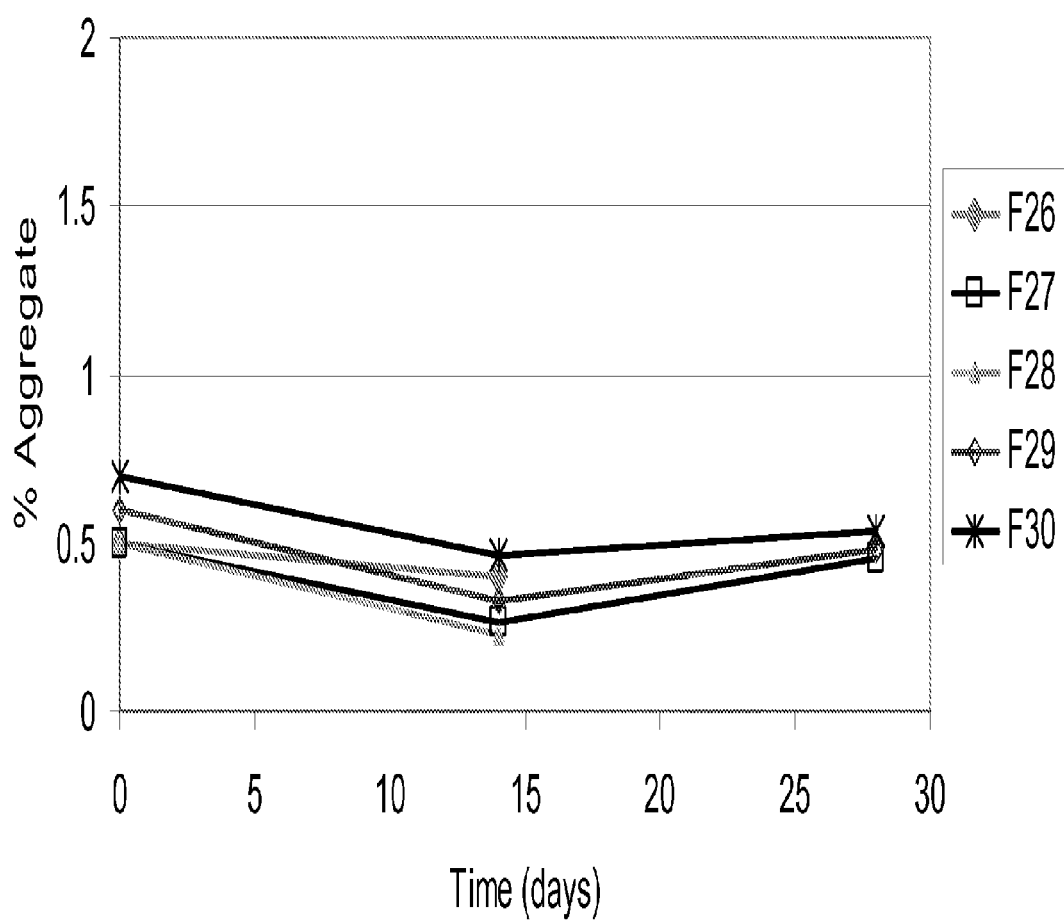

FIG. 19. Stability of lyophilized MT103 stored at 40° C.

Figure 20:
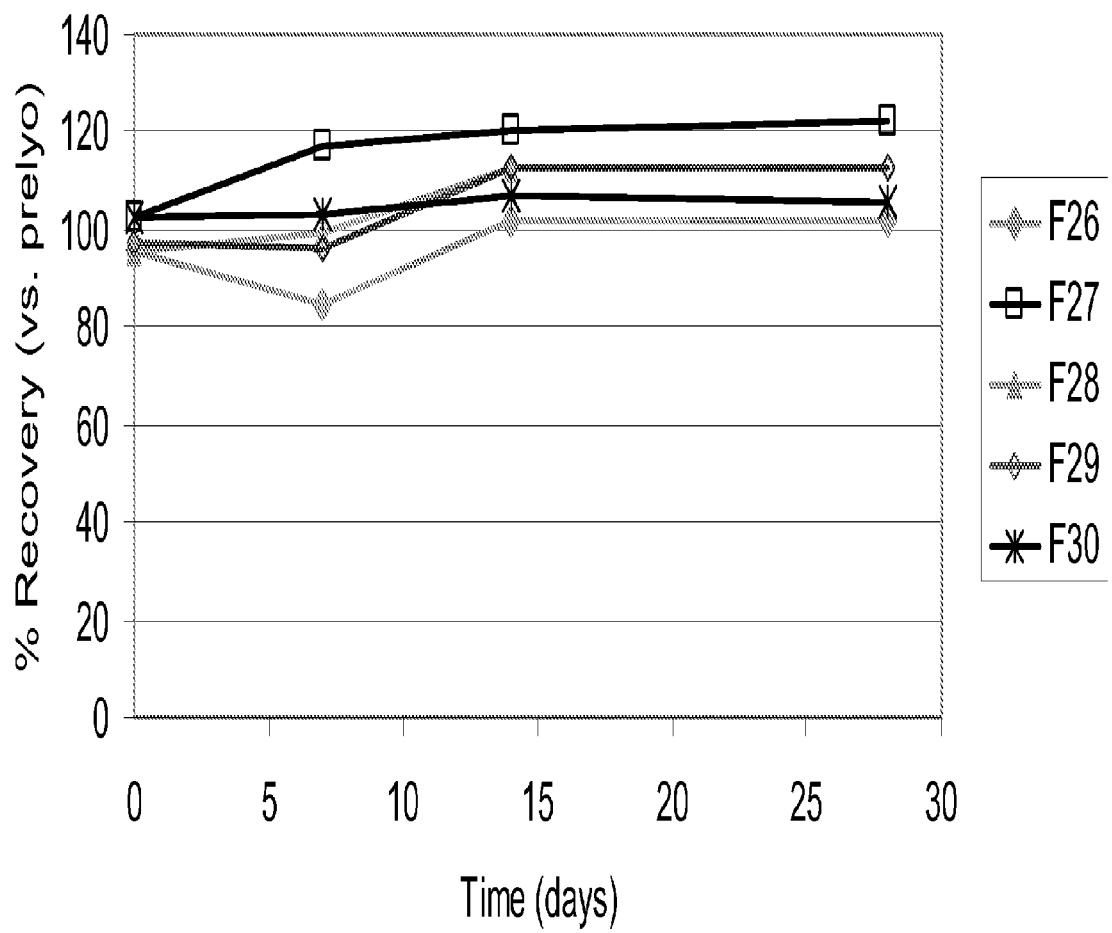

FIG. 20. Stability of lyophilized MT103 stored at 4° C.

Figure 21:
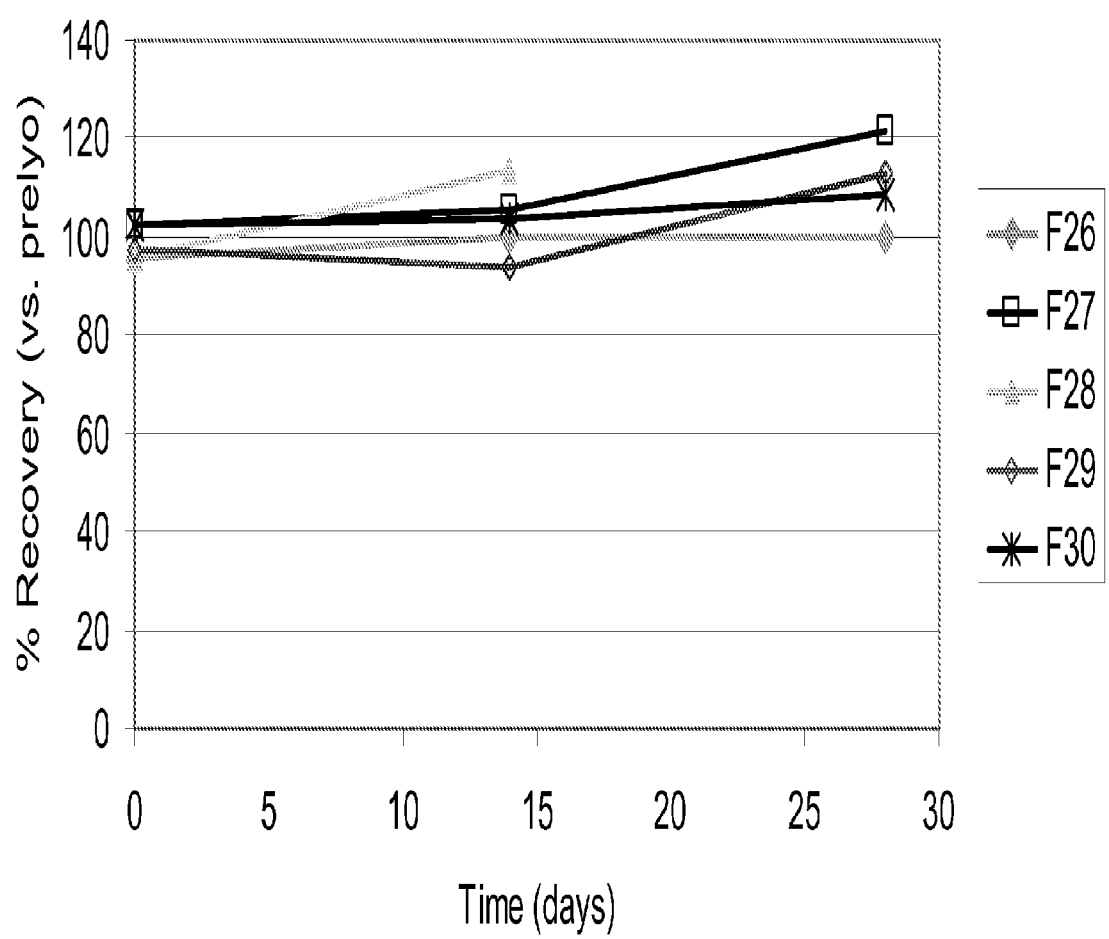

FIG. 21. Stability of lyophilized MT103 stored at 40° C.

Figure 22:
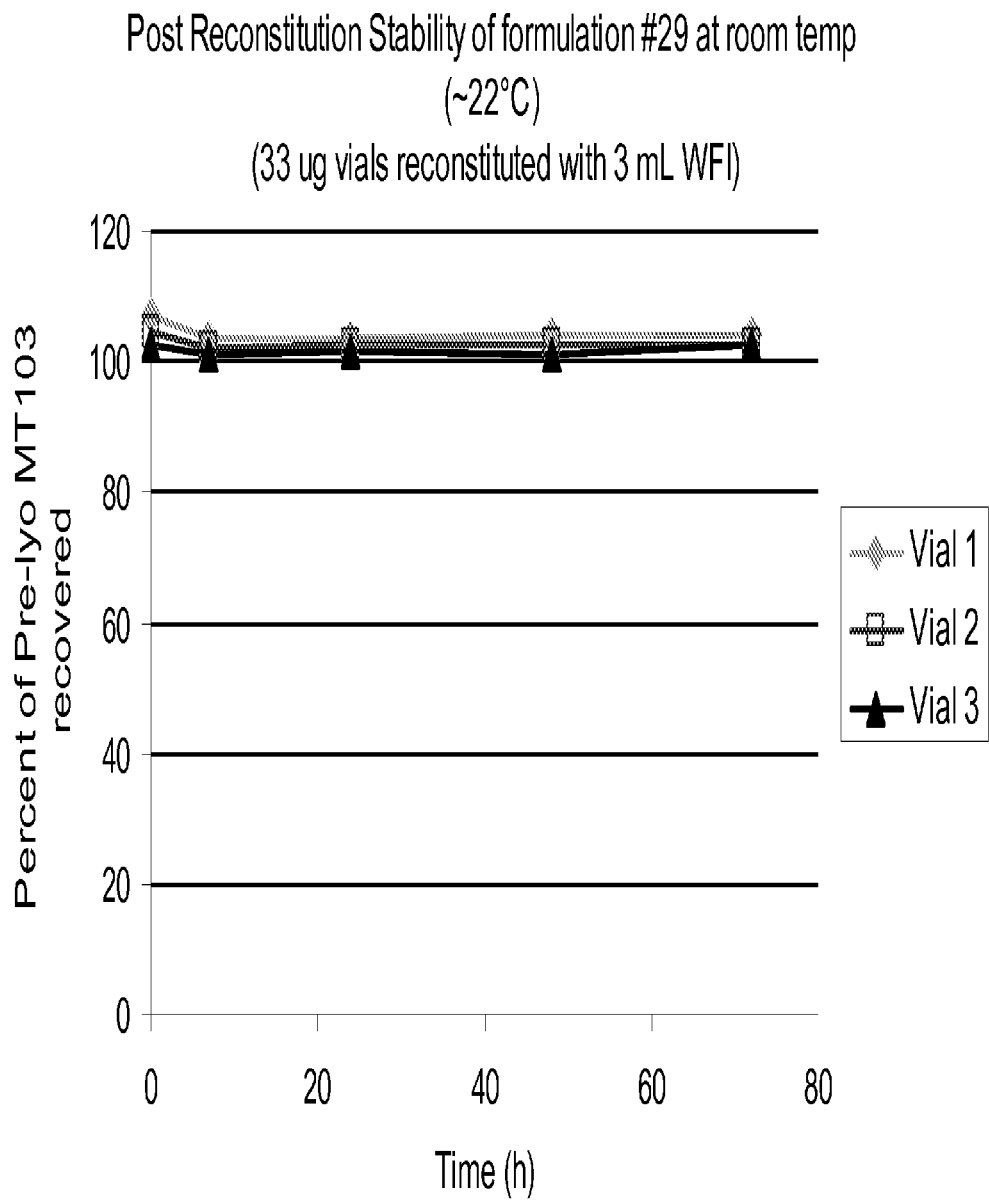

FIG. 22. Post-reconstitution stability of lyophilized MT103 at room temperature (~22° C.) following reconstitution. 55 mg/mL MT103 in formulation #29 was lyophilized and subsequently reconstituted.

Figure 23:
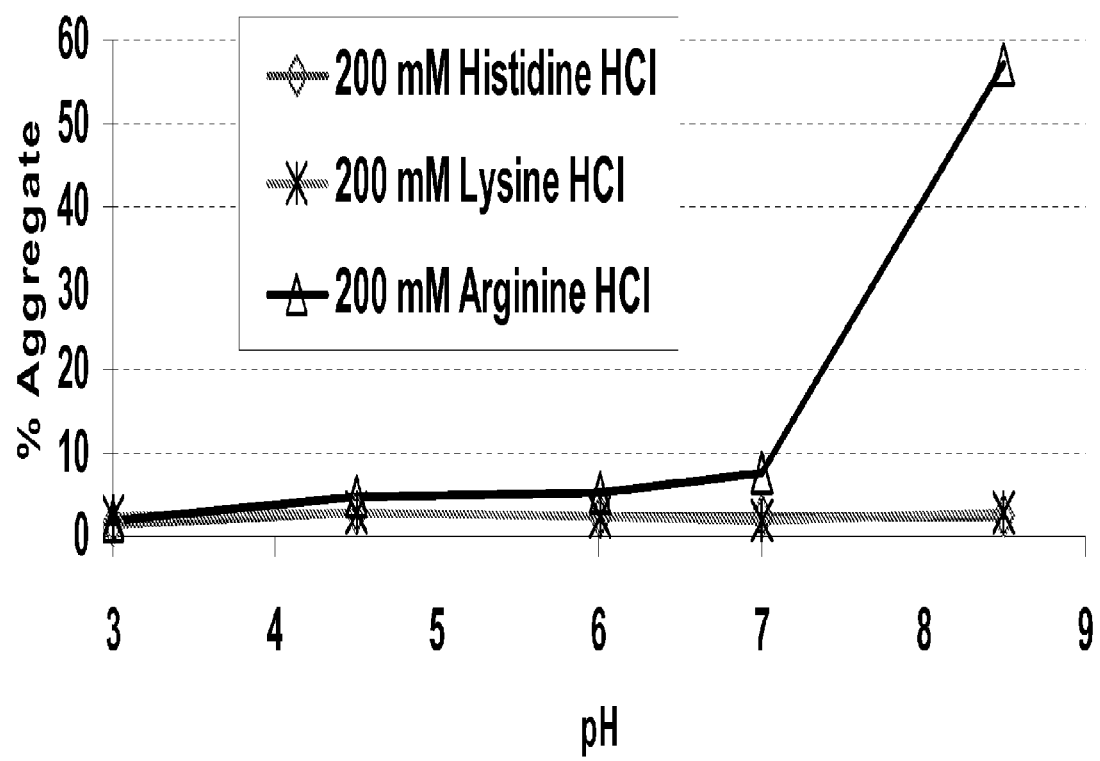

FIG. 23. MT103 aggregation at 5° C. as a function of pH in the presence of basic amino acids.

Figure 24:
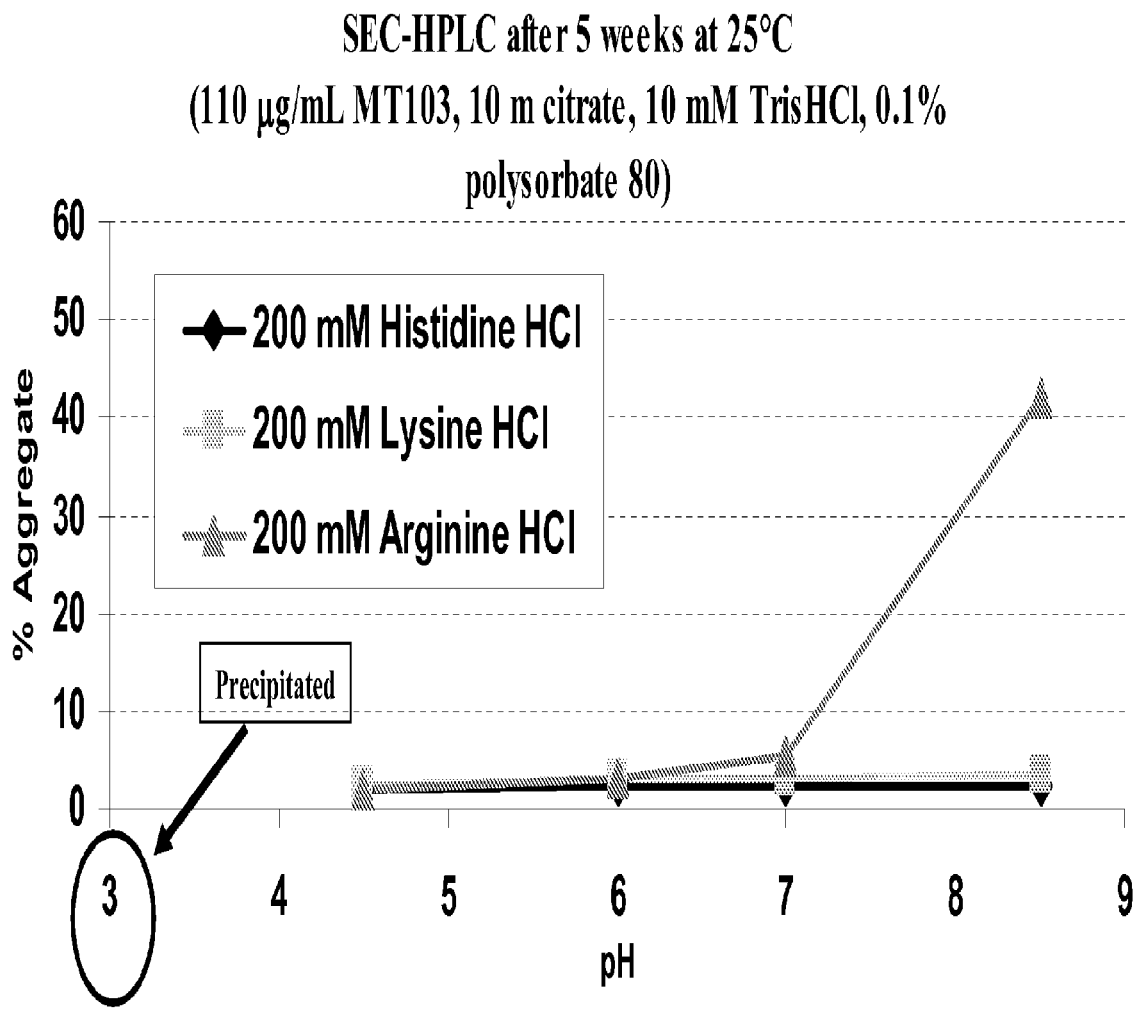

FIG. 24. MT103 aggregation at 25° C. as a function of pH in the presence of basic amino acids.

Figure 25:
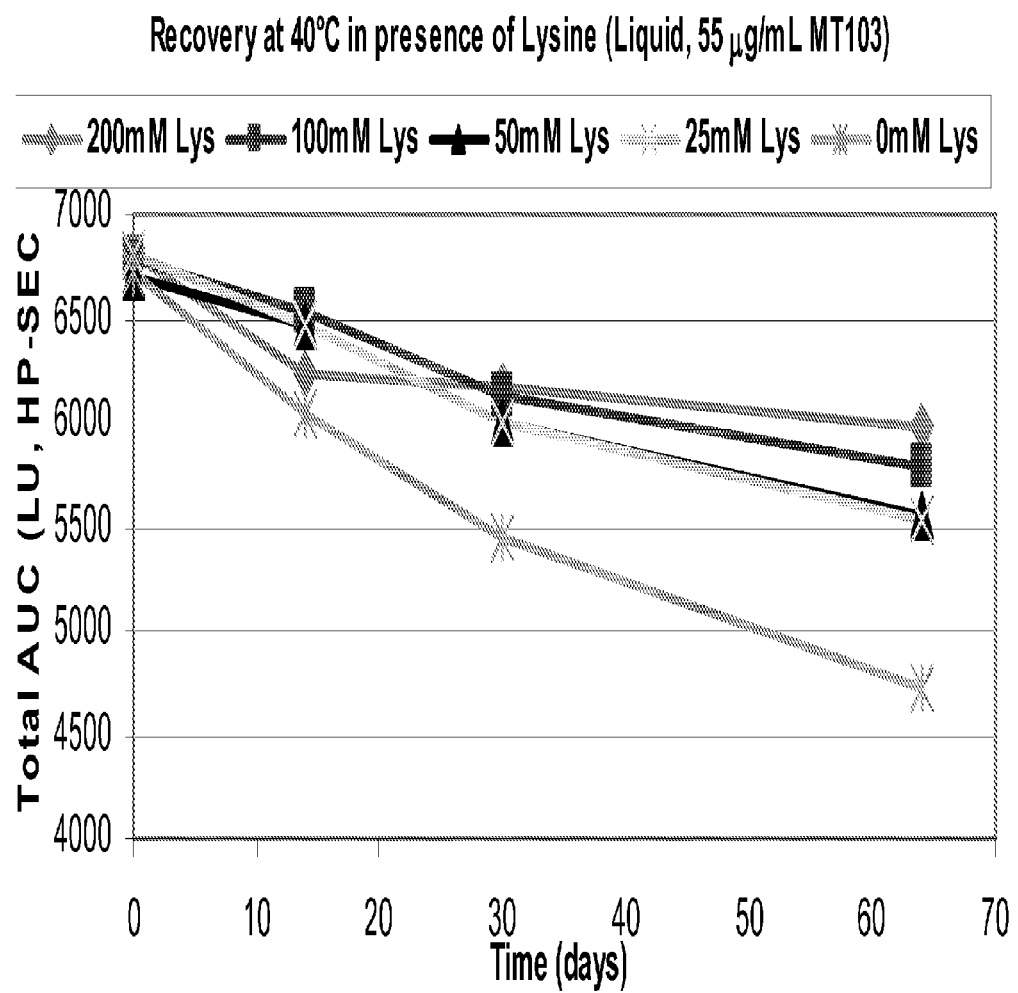

FIG. 25. Determination of threshold levels of excipients. Recovery that 40° C. in the presence of lysine.

Figure 26A:
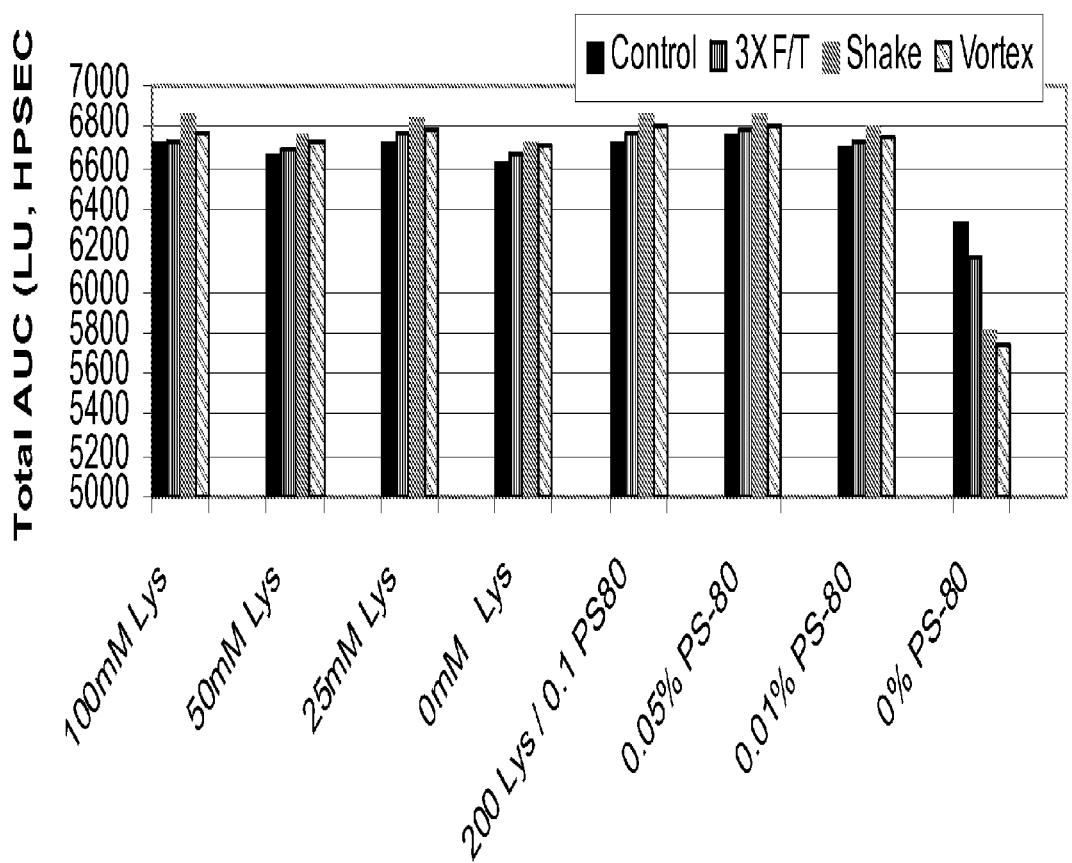
Figure 26B:
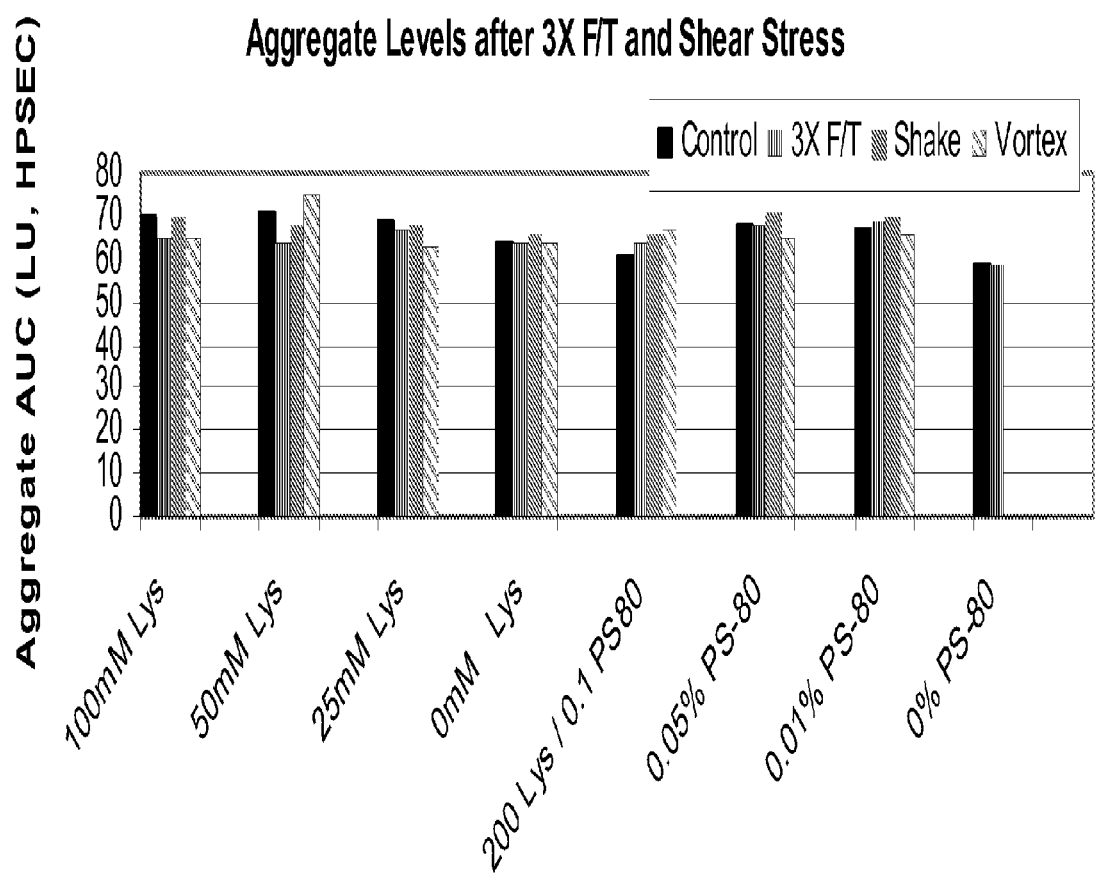

FIG. 26. Determination of threshold levels of excipients. (A) Recovery after three freeze/thaw cycles or following shear stress. (B) Aggreagte levels after three freeze/thaw cycles or following shear stress.

Figure 27B:
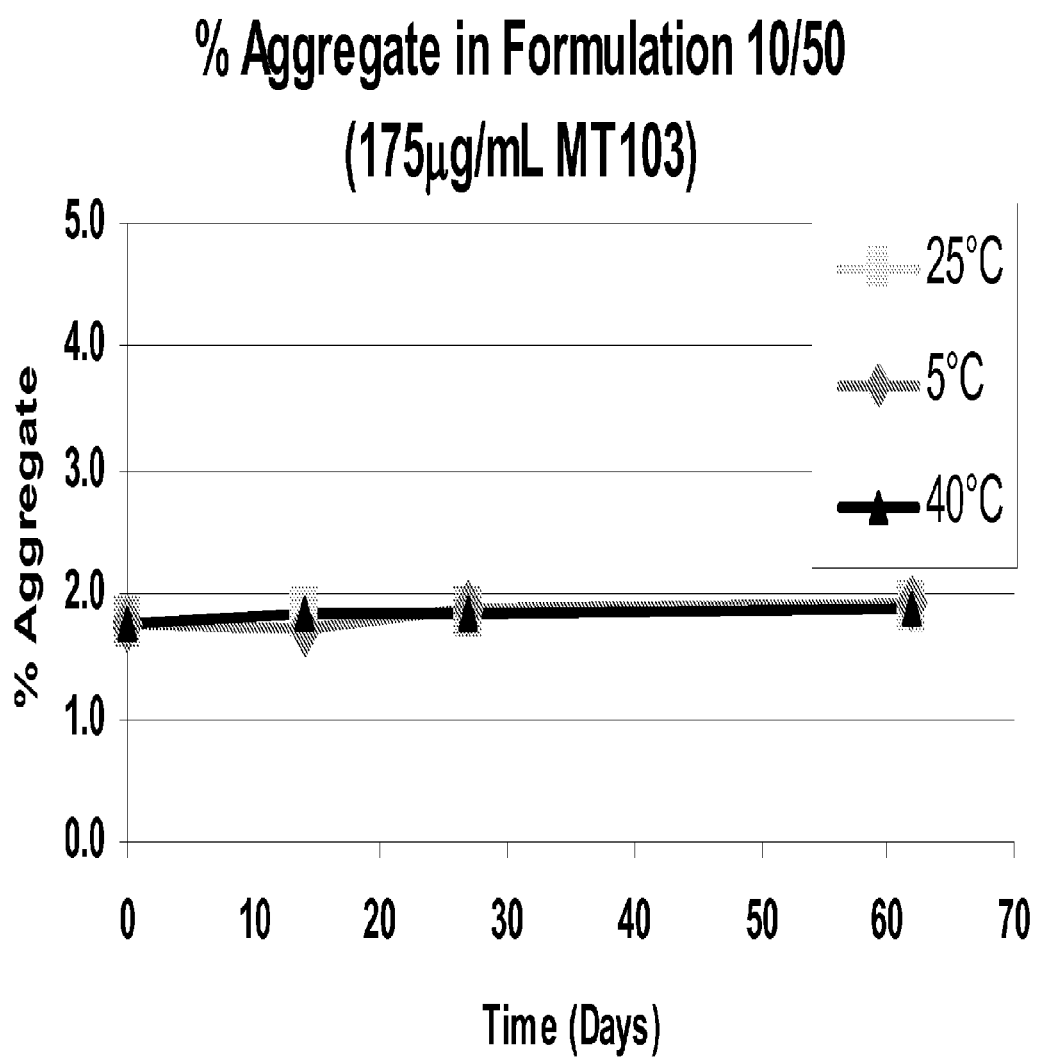
Figure 27C:
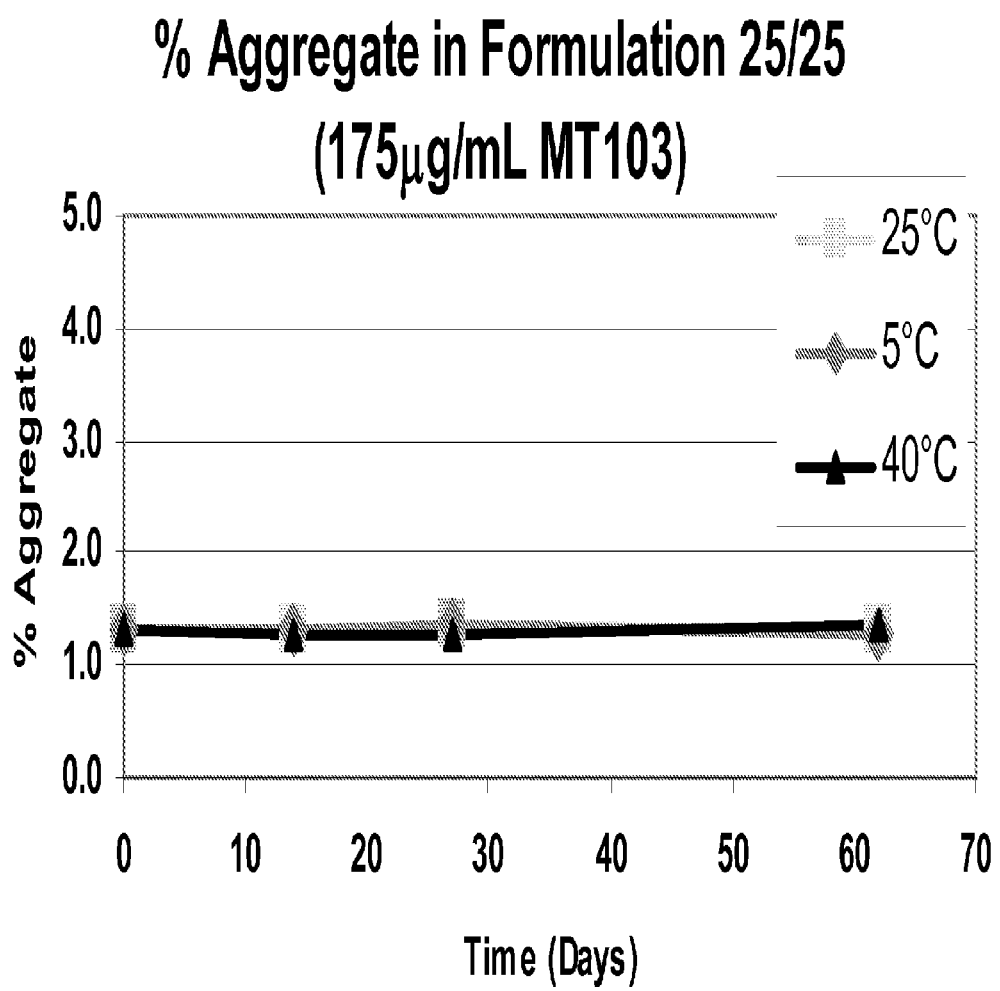

FIG. 27. Short term stability of MT103 formulations 25/25, 10/50, and 25/200. (A) Composition of formulations tested. (B) Aggreagte levels of formulation 10/50 as a function of time at 5° C., 25° C., and 40° C. (C) Aggreagte levels of formulation 25/25 as a function of time at 5° C., 25° C., and 40° C.

Figure 28A:
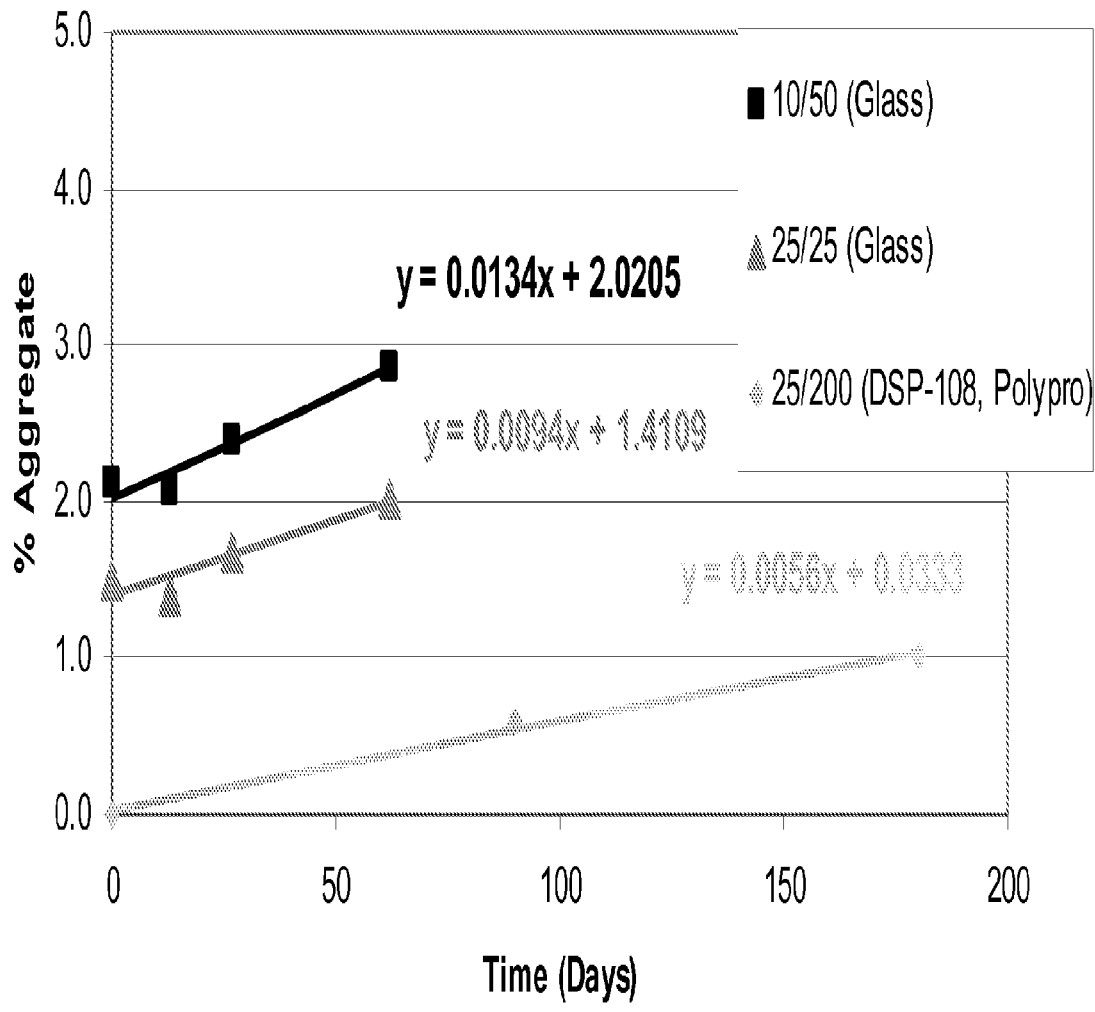
Figure 28B:
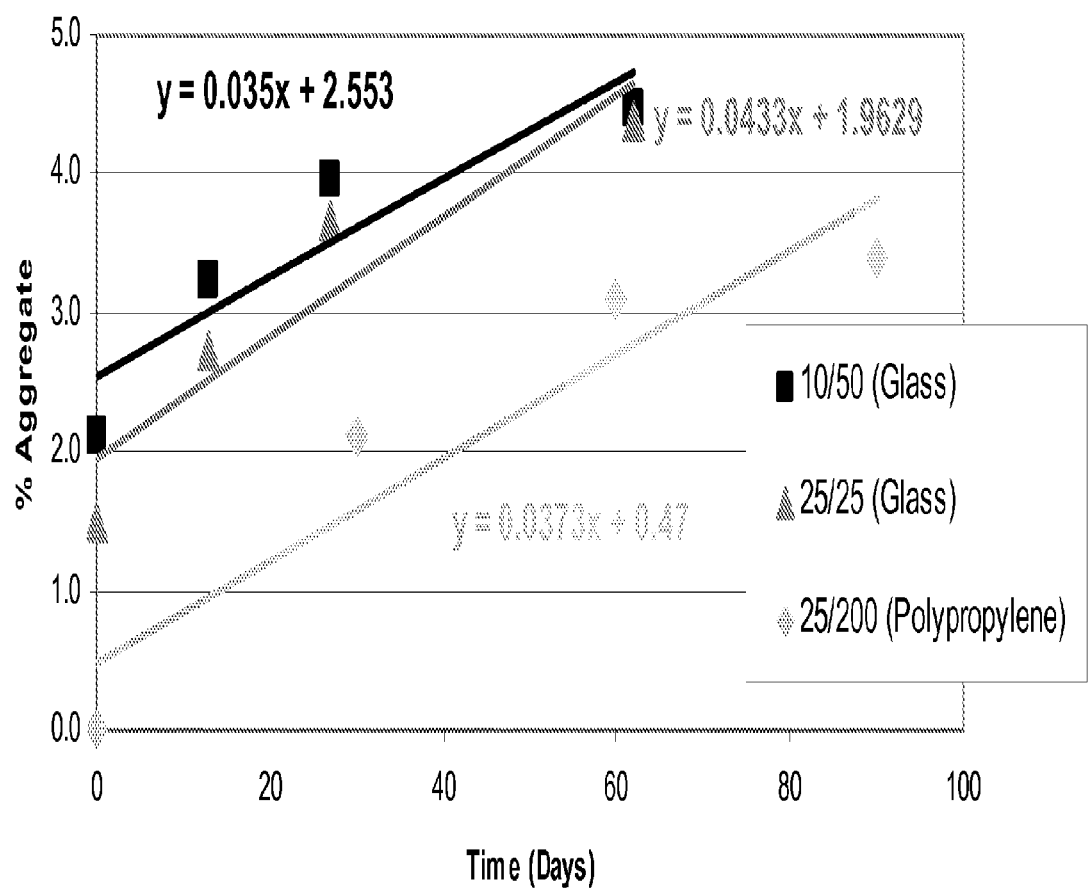

FIG. 28. Stability of bulk liquid formulations 25/25, 10/50, and 25/200 at (A) 5° C. and (B) 25° C.

Figure 29:
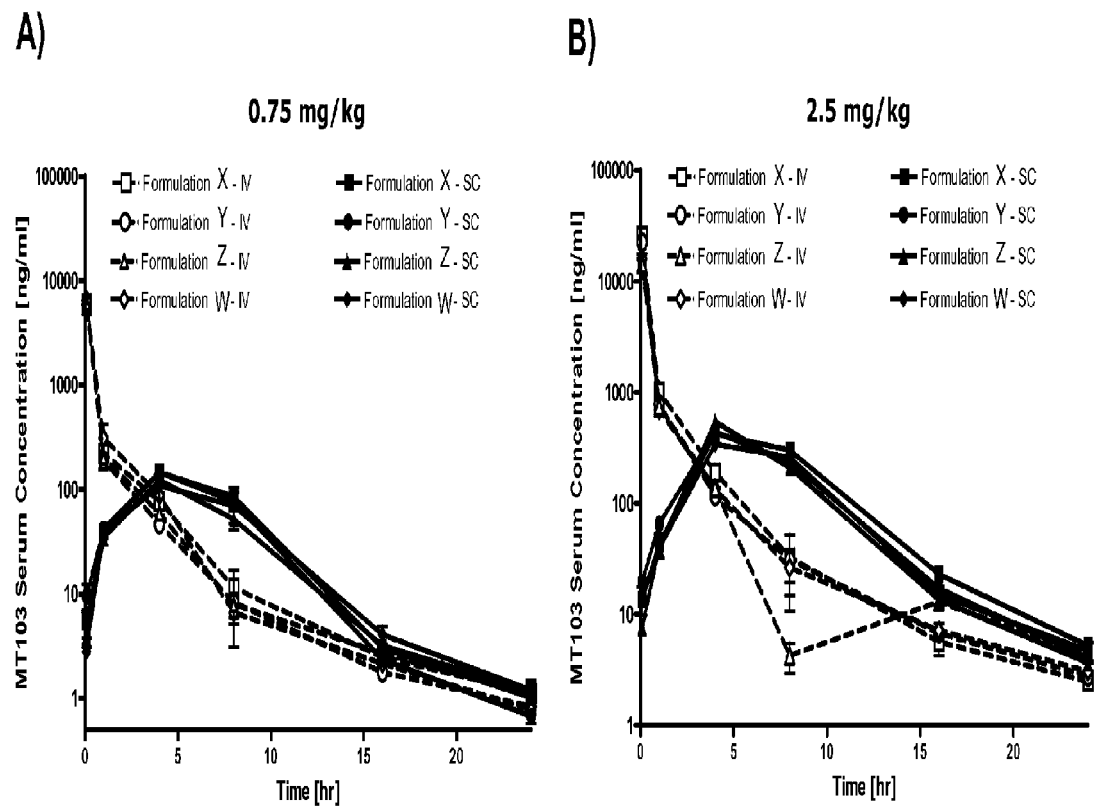

FIG. 29. Mean MT103 serum concentrations in CD-1 mice over a one day period following a single intravenous (IV) or subcutaneous (SC) bolus injection of MT103 in different formulations. The mean MT103 concentration versus time profile of serum samples collected from CD-1 mice after IV or SC bolus infusion of (A) 0.75 mg/kg and (B) 2.5 mg/kg of MT103 in one of four formulations described in Table 12. After bolus injection of MT103 into CD-1 mice (n=4) serum samples were collected at the indicated times. The serum concentrations of MT103 were measured by a specific ELISA method and reported here as the arithmetic mean for each sample at each time interval after infusion.

Figure 30:
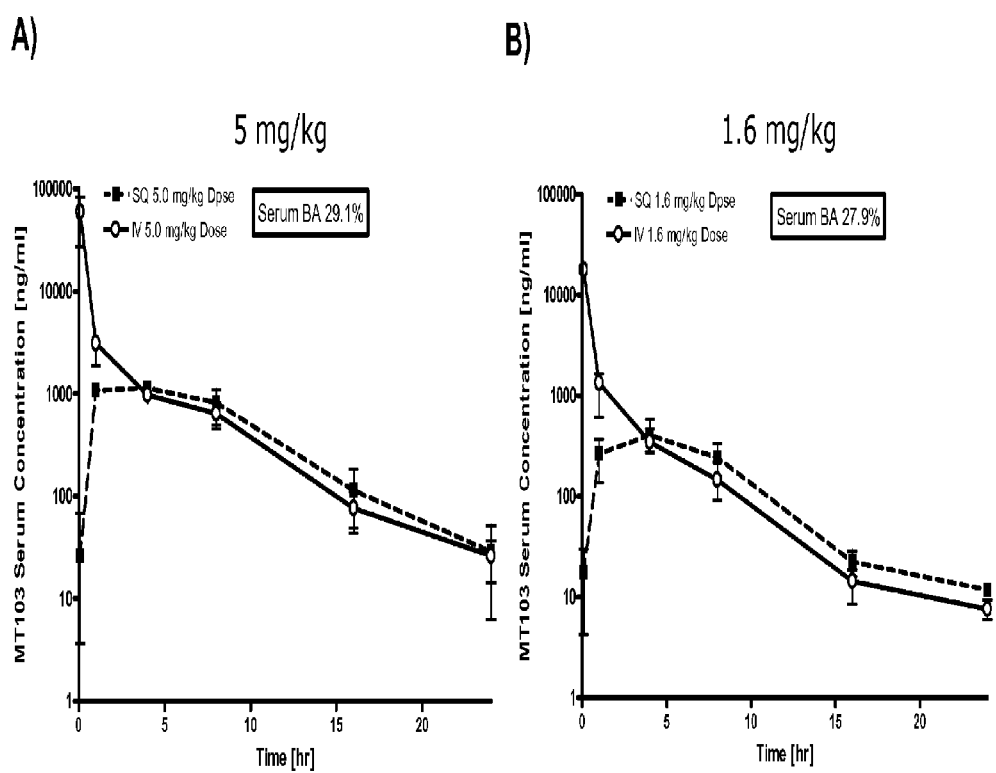

FIG. 30. Mean MT103 serum concentrations in CD-1 mice over a one day period following a single IV or SC bolus infusion of MT103 in Formulation Z. The mean MT103 concentration versus time profile of serum samples collected from CD-1 mice after IV or SC bolus infusion of (A) 5 mg/kg and (B) 1.6 mg/kg of MT103 in Formulation Z. After bolus injection of MT103 into CD-1 mice (n=5) serum samples were collected at the indicated times. The serum concentrations of MT103 were measured by a specific ELISA method and reported here as the arithmetic mean for each sample at each time interval after infusion.

Figure 31A:
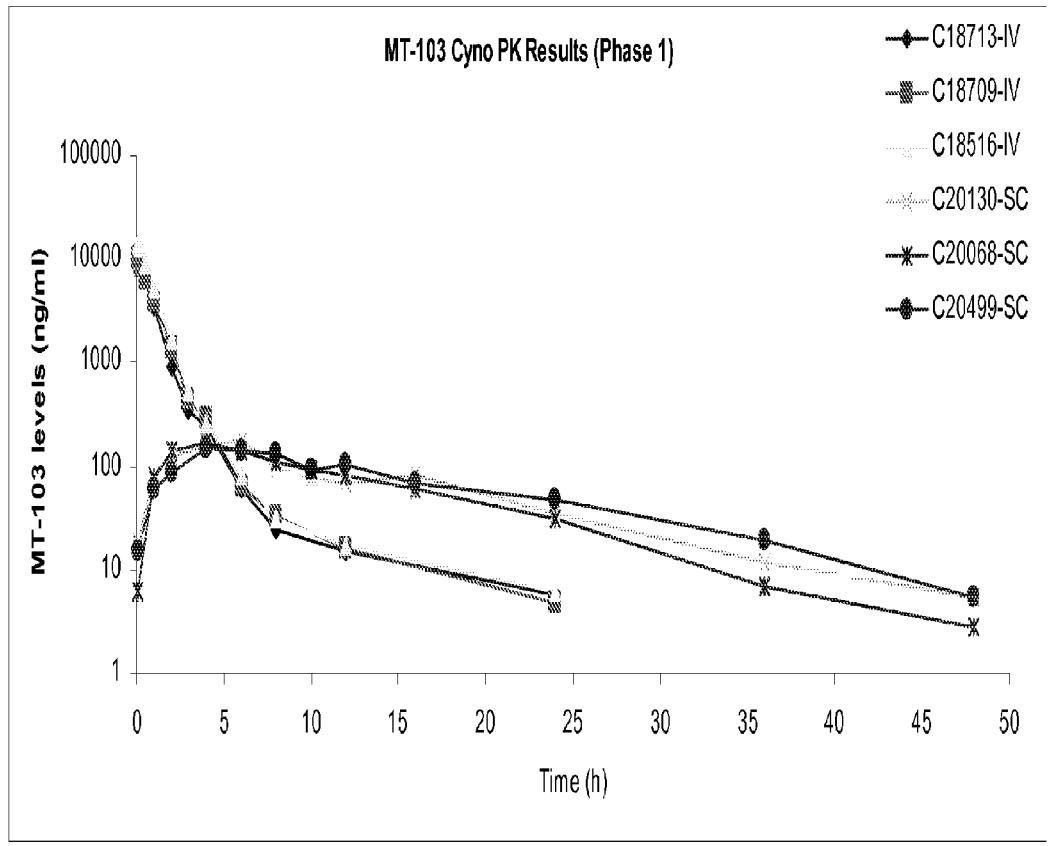
Figure 31B:
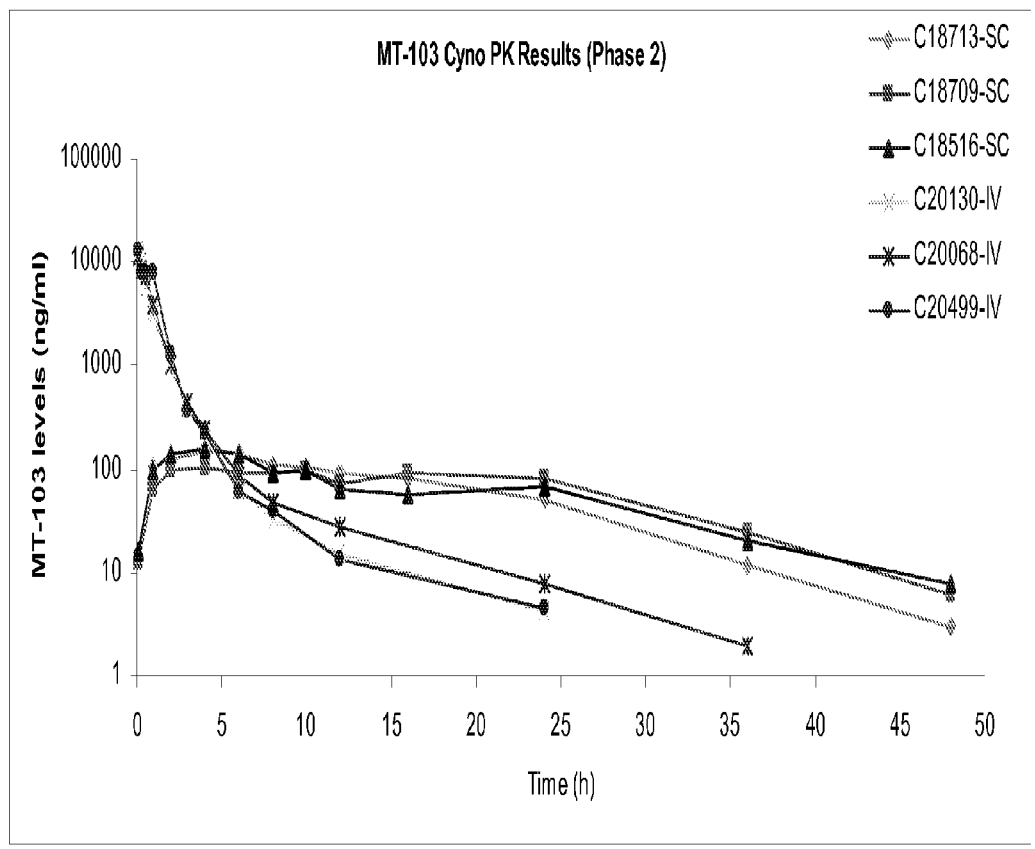

FIG. 31. Mean MT103 serum concentrations in cynomolgus monkeys over a one week period following a single intravenous (IV) or subcutaneous (SC) bolus injection of MT103. The mean MT103 concentration versus time profile of serum samples collected from male cynomolgous monkeys after IV or SC bolus infusion 0.5 mg/kg of MT103 in a cross-over design with a one week washout period between the two phases ((A) Phase I-IV then SC; (B) Phase II-SC then IV). After bolus injection of MT103 into cynomolgus monkeys (n=3) serum samples were collected at the indicated times. The serum concentrations of MT103 were measured by a specific ELISA method and reported here as the arithmetic mean for each sample at each time interval after infusion.

Figure 32:
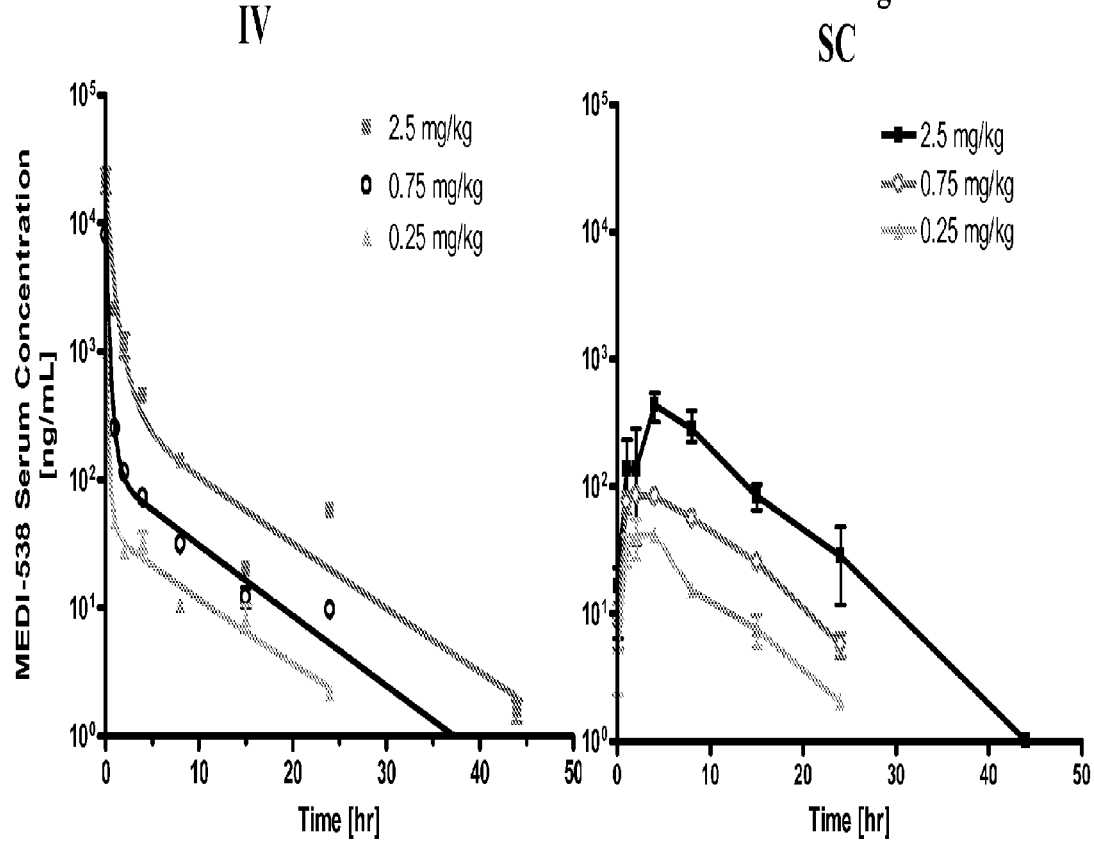

FIG. 32. In CD-1 mice, SC administered MEDI-538 was 20-30% bioavailable and exhibited serum concentrations that were dose-proportional, reached a peak at 4 hrs, and had a similar terminal half-life as IV administered drug. The mean MEDI-538 concentration versus time profile of serum samples collected from CD-1 mice after IV and SC administration of 0.25 (triangles), 0.75 (circles), and 2.5 (squares) mg/kg of MEDI-538 is shown.

Figure 33:
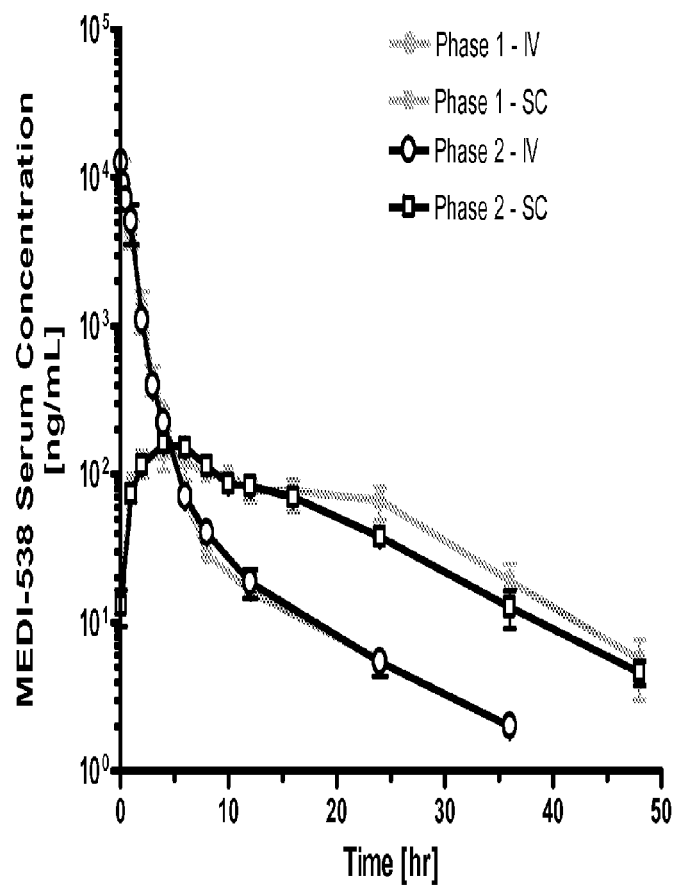

FIG. 33. Following SC administration in cynomolgus monkeys, MEDI-538 was 22% bioavailable and exhibited serum concentrations that reached a peak at 4 hrs, and had a similar terminal half-life as IV administered drug. The mean MEDI-538 concentration versus time profile of serum samples collected from cynomolgus monkeys after IV and SC administration of 0.5 mg/kg of MEDI-538.

Figure 34:
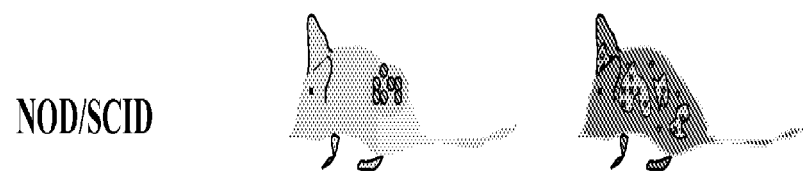

FIG. 34. In vivo mouse models for anti-tumor efficacy.

Figure 35:
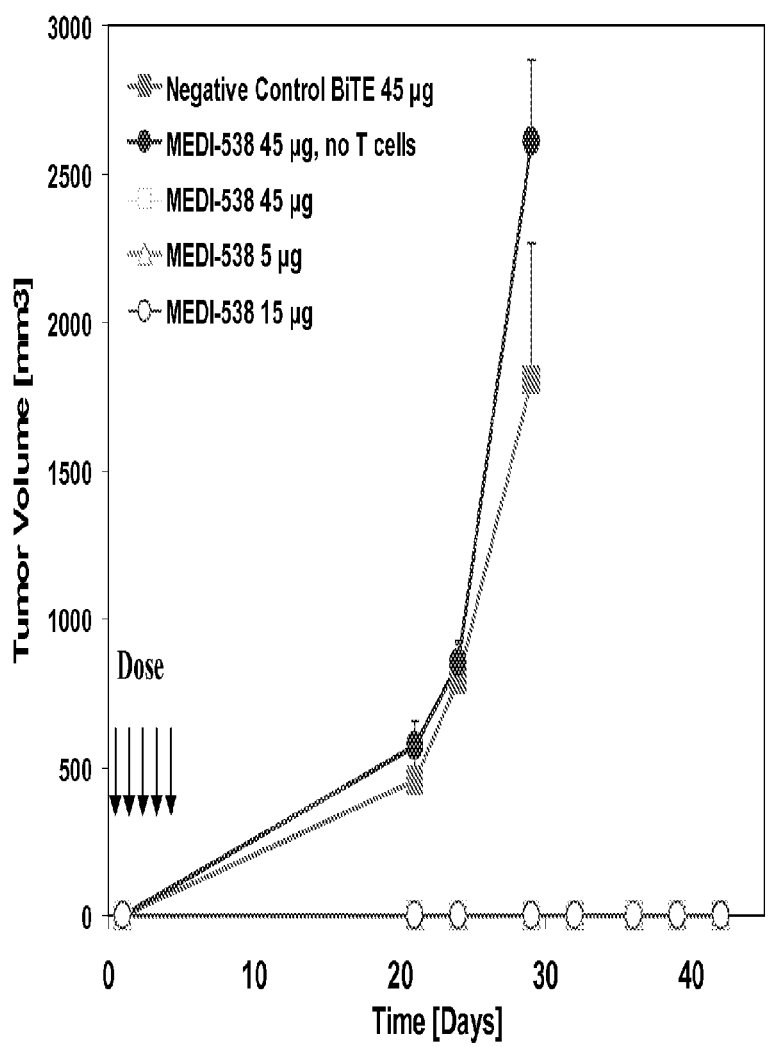

FIG. 35. SC treatment with MEDI-538 completely inhibits the growth of SC engrafted CD19+ Namalwa B-lymphoma cells mixed with human CD3+ T cells in NOD/SCID mice.

Figure 36:
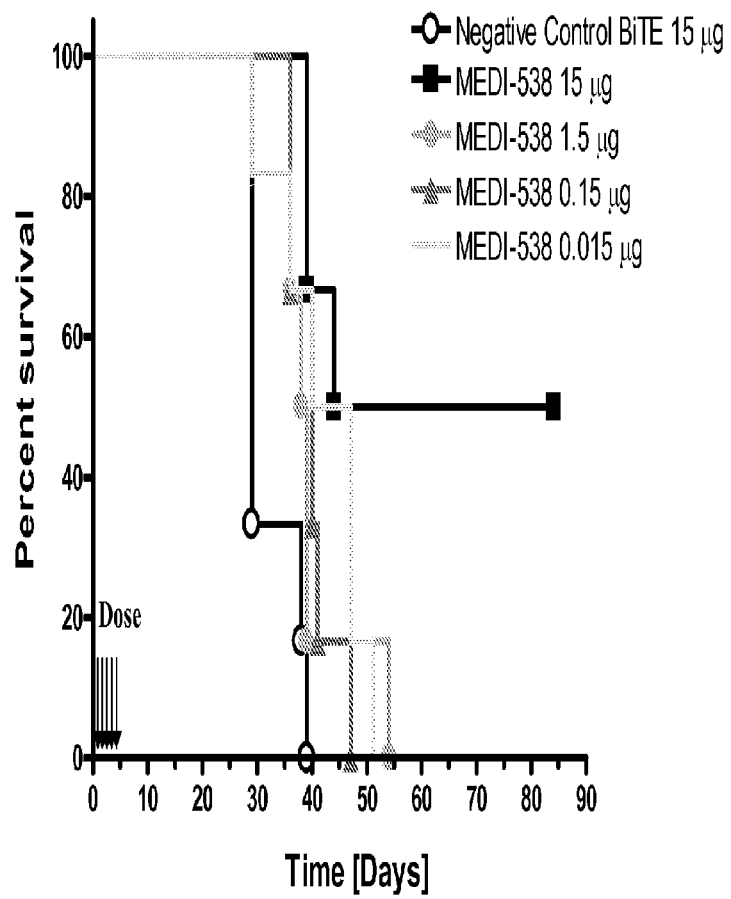

FIG. 36. SC treatment with MEDI-538 prolongs the survival of NOD/SCID mice engrafted IV with CD19+ Ramos B Lymphoma cells and human CD3+ T cells.

Figure 37:
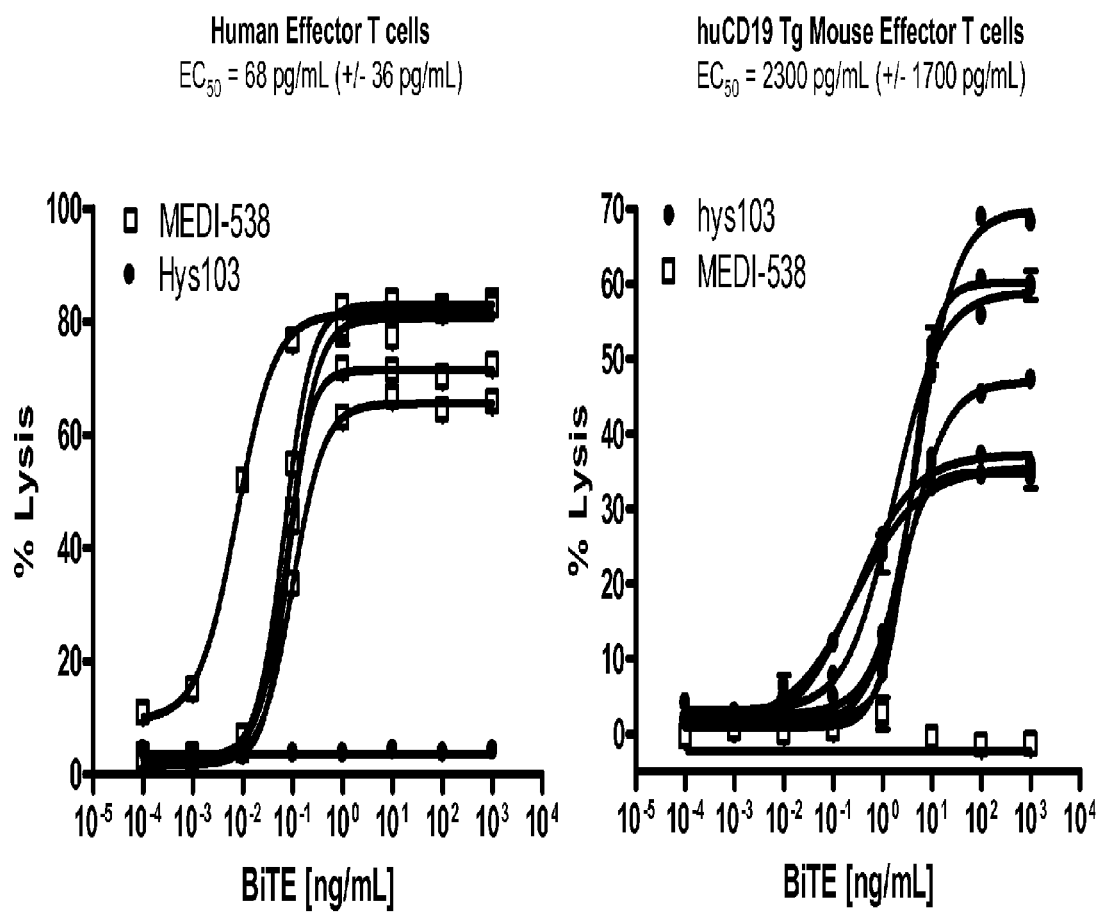

FIG. 37. HyS103 mediates mouse T cell lysis of a B cell lymphoma line (NALM-6).

Figure 38:
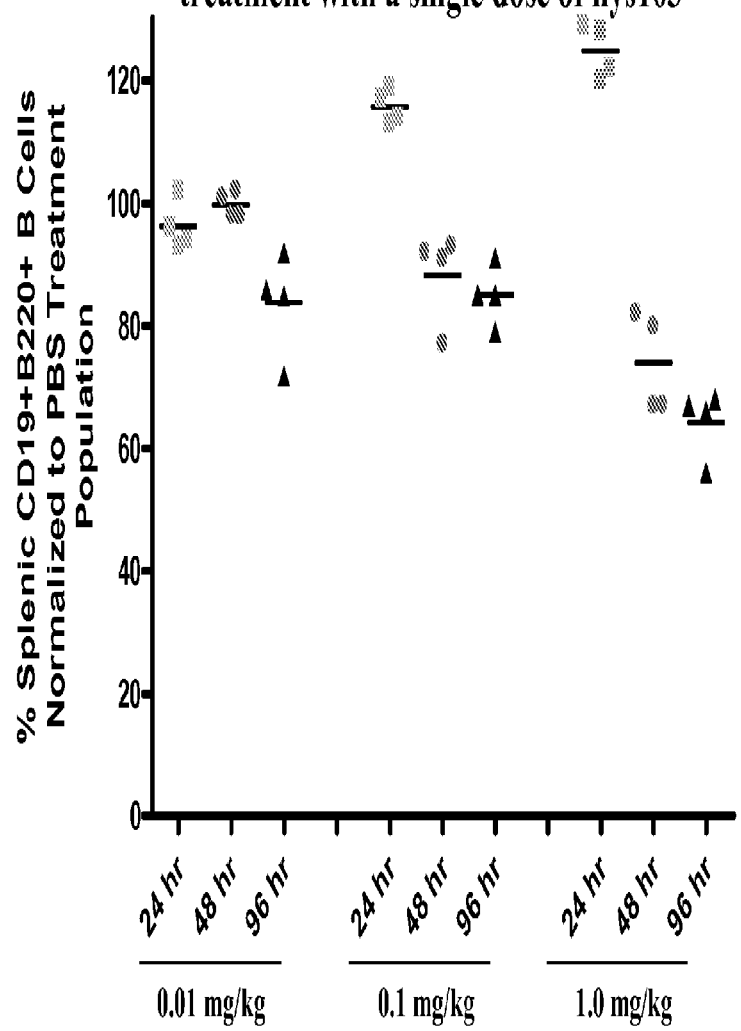

FIG. 38. Dose-dependent reduction of splenic B cells in huCD19 transgenic mice following SC treatment with a single dose of hys103.

Figure 39:
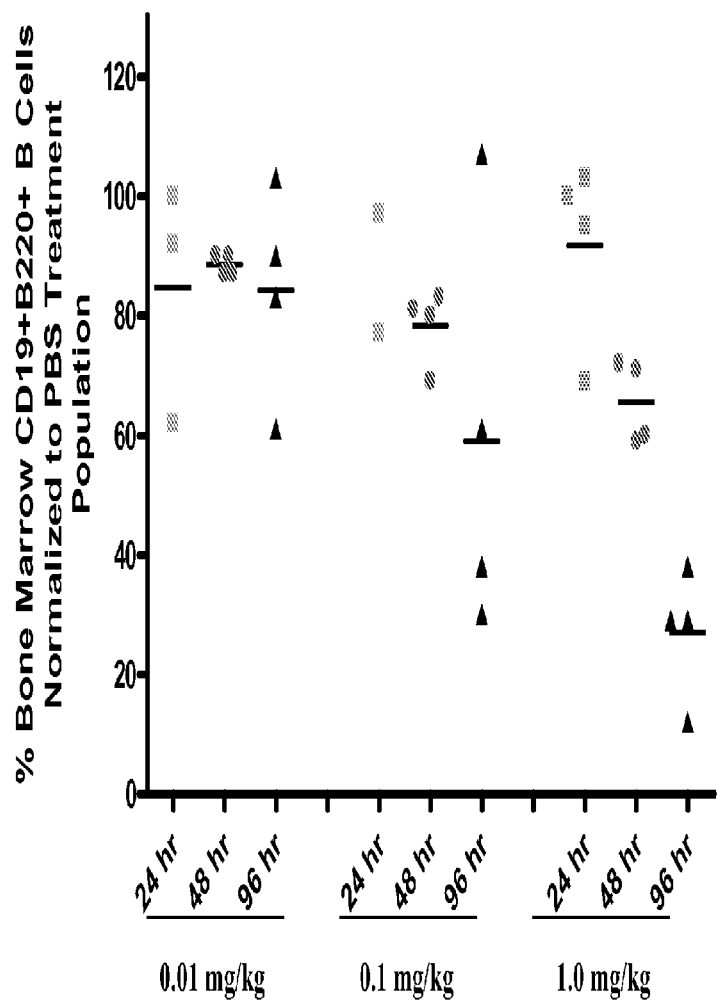

FIG. 39. Dose-dependent reduction of bone marrow B cells in huCD19 transgenic mice following SC treatment with a single dose of hys103.

Figure 40:
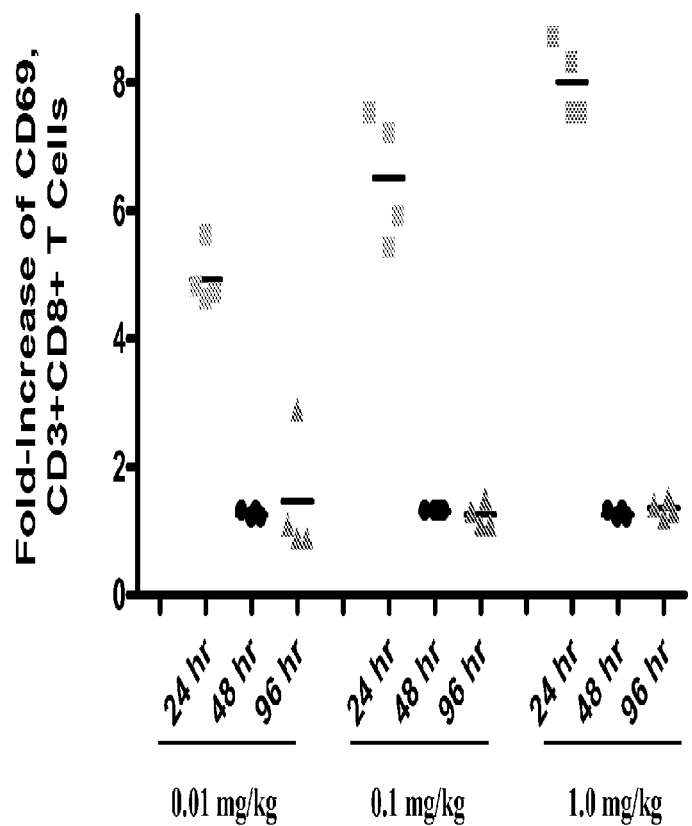

FIG. 40. Dose-dependent activation (CD69) of splenic T cells in huCD19 transgenic mice following a single SC administration of hys103.

Figure 41:
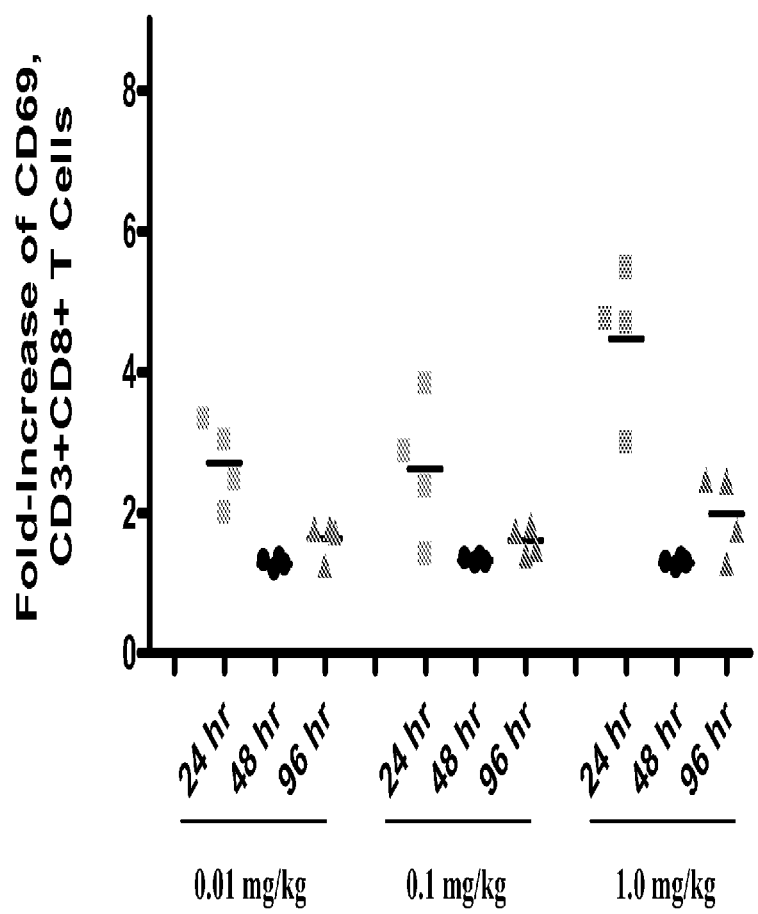

FIG. 41. Dose-dependent activation (CD69) of bone marrow T cells in huCD19 transgenic mice following a single SC administration of hys103.

Figure 42A:
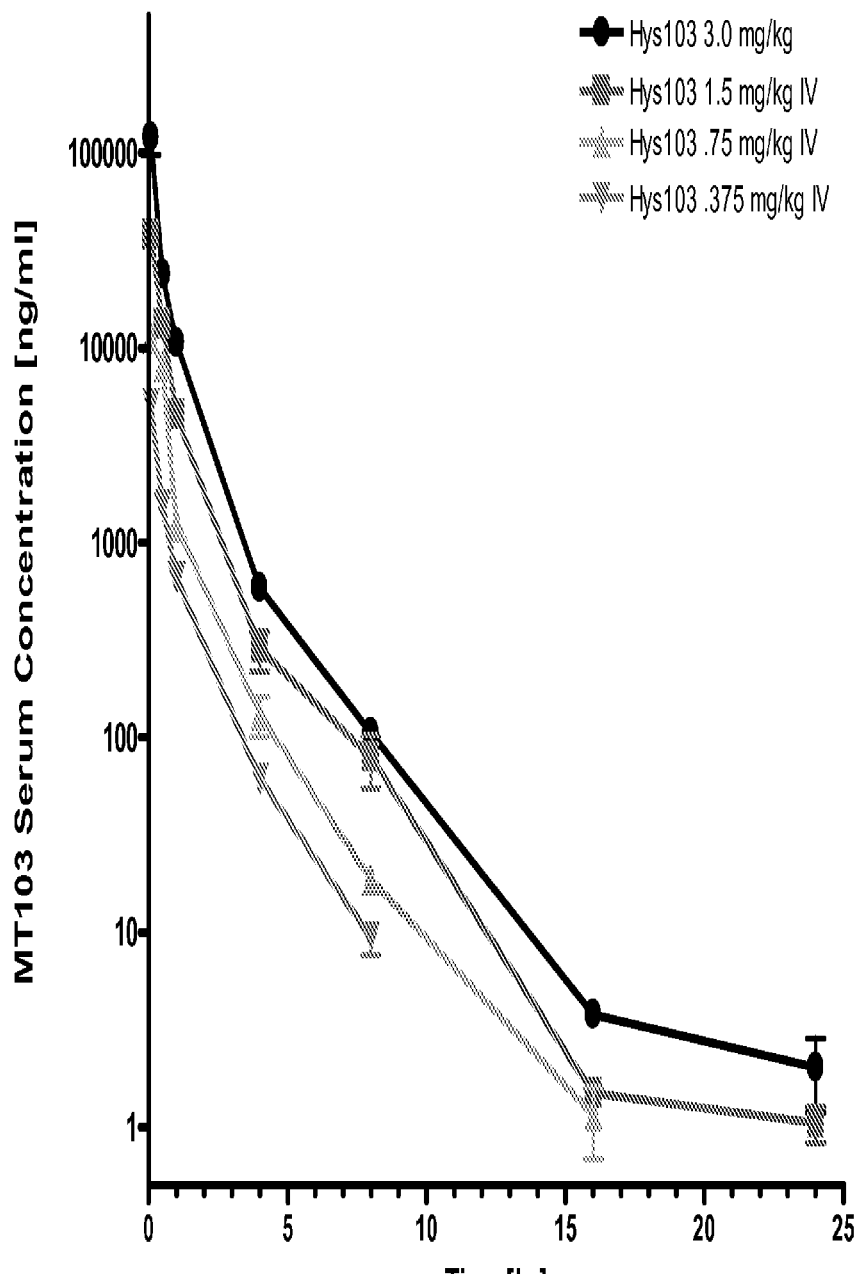
Figure 42B:
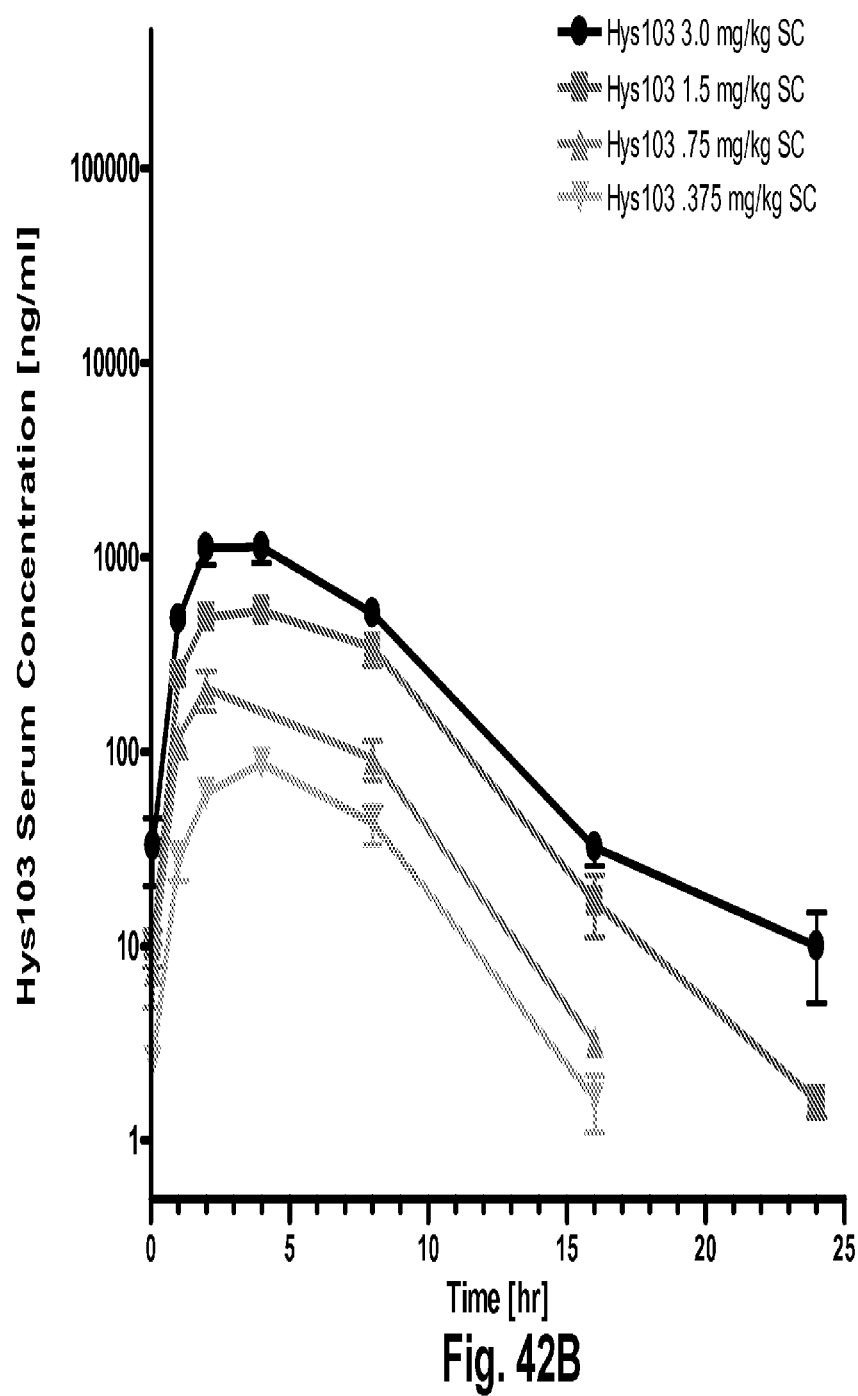

FIG. 42. PK analysis of hys103 in huCD19 transgenic mice. Hys103 serum concentration as a function of time is shown following i.v. (A) or s.c. (B) administration of a single does of hys103.

5. DETAILED DESCRIPTION

The present invention relates to stable formulations of bispecific antibodies. In certain embodiments, the present invention provides formulations of BiTE® molecules comprising a first and a second binding site specific for the CD3 and CD19 antigens, respectively. In a specific embodiment, the present invention provides formulations comprising the MT103™BiTE® molecule. In yet other embodiments, formulations of the invention comprise a BiTE® molecule having at least a first and a second binding site specific for CD3 and the EphA2 antigens, respectively. In yet other embodiments, formulations of the invention comprise a BiTE® molecule having at least a first and a second binding site specific for CD3 and the carcinoembryonic antigen (CEA) antigens, respectively.

In one embodiment, a formulation of the invention is for parenteral administration. In one embodiment, a formulation of the invention is an injectable formulation. In one embodiment, a formulation of the invention is for intravenous, subcutaneous, or intramuscular administration. In certain embodiments, formulations of the invention comprise BiTE® molecules wherein said formulations are for intravenous administration. In a specific embodiment, a formulation of the invention comprise MT103 wherein said formulation is for intravenous administration. In certain embodiments, formulations of the invention comprise BiTE® molecules wherein said formulations are for continuous intravenous administration. In a specific embodiment, a formulation of the invention comprise MT103 wherein said formulation is for continuous intravenous administration. In certain embodiments, formulations of the invention comprise BiTE® molecules wherein said formulations are for subcutaneous administration. In a specific embodiment, a formulation of the invention comprise MT103 wherein said formulation is for subcutaneous administration.

In one embodiment, a formulation of the invention is for continuous intravenous administration wherein said formulation comprises between about 25 μg/ml and about 250 μg/ml of BiTE® molecules or a fragment thereof. In a specific embodiment, a formulation of the invention is for continuous intravenous administration wherein said formulation comprises between about 25 μg/ml and about 250 μg/ml of MT103. In one embodiment, a formulation of the invention is for subcutaneous administration wherein said formulation comprises between about 25 μg/ml and about 250 μg/ml of BiTE® molecules or a fragment thereof. In a specific embodiment, a formulation of the invention is for subcutaneous administration wherein said formulation comprises between about 25 μg/ml and about 250 μg/ml of MT103.

In one embodiment, a formulation of the invention is suitable for subcutaneous delivery. In one embodiment, the bioavailability of a bispecifc antibody formulated according to a composition or method described herein is between about 10% and about 100%.

In one embodiment, a formulation of the invention is for aerosol administration.

The present invention also provides a pharmaceutical unit dosage form suitable for parenteral administration to a human which comprises BiTE® molecules formulation in a suitable container. In one embodiment, a pharmaceutical unit dosage of the invention comprises MT103. In one embodiment, a pharmaceutical unit dosage of the invention comprises an intravenously, subcutaneously, or intramuscularly delivered BiTE® molecule formulation. In another embodiment, a pharmaceutical unit dosage of the invention comprises aerosol delivered BiTE® molecule formulation. In a specific embodiment, a pharmaceutical unit dosage of the invention comprises a subcutaneously delivered MT103 formulation. In another embodiment, a pharmaceutical unit dosage of the invention comprises an intravenously delivered MT103 formulation. In another embodiment, a pharmaceutical unit dosage of the invention comprises an aerosol delivered BiTE® molecule formulation. In a further embodiment, a pharmaceutical unit dosage of the invention comprises an intranasally administered BiTE® molecule formulation.

In one embodiment, a formulation of the invention is provided in a sealed container.

The present invention is further directed to methods for the treatment of B cell disorders or diseases in human subjects, including B cell malignancies, using the formulations of bispecific antibodies or fragments thereof that comprise at least a first and a second binding site specific for the CD3 and CD19 antigens, respectively. The present invention is directed to methods for the treatment and prevention of autoimmune disease as well as the treatment and prevention of graft-versus-host disease (GVHD), humoral rejection, and post-transplantation lymphoproliferative disorder in human transplant recipients using formulations of bispecific antibodies or fragments thereof that comprise at least a first and a second binding site specific for the CD3 and CD19 antigens, respectively. In specific embodiments, the BiTE® molecule of the formulations of the invention is MT103.

5.1. Liquid Formulations

In specific embodiments, the present invention encompasses stable liquid formulations of bispecific antibodies which formulations exhibit stability, low to undetectable levels of antibody fragmentation, low to undetectable levels of aggregation, very little to no loss of the biological activities of the bispecific antibodies, and very little to no loss of antibody through absorption to contact surfaces during manufacture, preparation, transportation, and storage. The present invention also encompasses stable liquid formulations of bispecific antibodies that comprise at least a first and a second binding site specific for the CD3 and CD19 antigens, respectively, said formulations exhibiting low to undetectable levels of antibody fragmentation, low to undetectable levels of aggregation, very little to no loss of the biological activities, and very little to no loss of antibody through absorption to contact surfaces during manufacture, preparation, transportation, and storage. In specific embodiments, the present invention provides stable liquid formulations of MT103 which formulations exhibit stability, low to undetectable levels of antibody fragmentation, low to undetectable levels of aggregation, very little to no loss of the biological activities of MT103, and very little to no loss of antibody through absorption to contact surfaces during manufacture, preparation, transportation, and storage.

In one embodiment, a liquid formulation of the invention is an aqueous formulation. In a specific embodiment, a liquid formulation of the invention is an aqueous formulation wherein the aqueous carrier is distilled water.

In one embodiment, a formulation of the invention is sterile.

In one embodiment, a formulation of the invention is homogeneous.

In one embodiment, a formulation of the invention is isotonic. In one embodiment, a formulation of the invention is hypotonic. In one embodiment, a formulation of the invention is hypertonic.

In certain embodiments, a liquid formulation of the invention is suitable for lyophilization. In one embodiments, a lyophilized formulation of the invention is stable from about one month to about 2, 3, 4 or 5 years. In specific embodiments, a lyophilized formulation of the invention is stable for more than 2 years.

The present invention provides stable liquid formulations of MT103. The MT103 molecule was described in U.S. Pat. No. 7,112,324.

In one embodiment, a liquid formulation of the invention comprises a BiTE® molecule. In one embodiment, a liquid formulation of the invention comprises a BiTE® molecule that comprises at least a first and a second binding domain specific for the CD3 and CD19 antigens, respectively. In one embodiment, a liquid formulation of the invention comprises a BiTE® molecule that comprises at least a first and a second binding domain specific for the CD3 and CD19 antigens, respectively, wherein the first binding domain comprises the amino acid sequence of residues 283-525 of SEQ ID NO:5. In one embodiment, a liquid formulation of the invention comprises a BiTE® molecule that comprises at least a first and a second binding domain specific for the CD3 and CD19 antigens, respectively, wherein the second binding domain comprises the amino acid sequence of residues 28-277 of SEQ ID NO:5. In another embodiment, a liquid formulation of the invention comprises a BiTE® molecule that comprises at least a first and a second binding domain specific for the CD3 and CD19 antigens, respectively, wherein the first binding domain comprises the amino acid sequence of residues 283-525 of SEQ ID NO:5 and the second binding domain comprises the amino acid sequence of residues 28-277 of SEQ ID NO:5. In a further embodiment, a liquid formulation of the invention comprises a BiTE® molecule wherein said BiTE® molecule comprises an anti-CD19 VL domain having the amino acid sequence of SEQ ID NO:1, an anti-CD19 VH domain having the amino acid sequence of SEQ ID NO:2, an anti-CD3 VH domain having the amino acid sequence of SEQ ID NO:3 and an anti-CD3 VL domain having the amino acid sequence of SEQ ID NO:4. In one embodiment, a liquid formulation of the invention comprises a BiTE® molecule, MT103, wherein said a BiTE® molecule comprises the amino acid sequence of residues 28-525 of SEQ ID NO:5. In a specific embodiment, a liquid formulation of the invention comprises a BiTE® molecule, MT103, wherein said a BiTE® molecule comprises the amino acid sequence of SEQ ID NO:5.

The invention encompasses stable liquid formulations comprising a single BiTE® molecule of interest, for example, BiTE® molecules that comprises at least a first and a second binding site specific for the CD3 and CD19 antigens, respectively. The invention also encompasses stable liquid formulations comprising two or more bispecific antibodies of interest, for example, bispecific antibodies that comprise at least a first and a second binding site specific for the CD3 and CD19 antigens, respectively. In a specific embodiment, a stable liquid formulation of the invention comprises MT103. In another embodiment, a stable liquid formulation of the invention comprises two or more bispecific antibodies, wherein one of the bispecific antibodies is MT103.

In one embodiment, a formulation of the invention comprises at least about 1 microgram/ml, at least about 5 micrograms/ml, at least about 10 micrograms/ml, at least about 15 micrograms/ml, at least about 20 micrograms/ml, at least about 25 micrograms/ml, at least about 30 micrograms/ml, at least about 35 micrograms/ml, at least about 40 micrograms/ml, at least about 45 micrograms/ml, at least about 50 micrograms/ml, at least about 55 micrograms/ml, at least about 60 micrograms/ml, at least about 70 micrograms/ml, at least about 80 micrograms/ml, at least about 90 micrograms/ml, at least about 100 micrograms/ml, at least about 110 micrograms/ml, at least about 120 micrograms/ml, at least about 130 micrograms/ml, at least about 140 micrograms/ml, at least about 150 micrograms/ml, at least about 160 micrograms/ml, at least about 170 micrograms/ml, at least about 180 micrograms/ml, at least about 190 micrograms/ml, at least about 200 micrograms/ml, at least about 225 micrograms/ml, at least about 250 micrograms/ml, at least about 275 micrograms/ml, at least about 300 micrograms/ml at least about 325 micrograms/ml, at least about 350 micrograms/ml, at least about 375 micrograms/ml, at least about 400 micrograms/ml, at least about 500 micrograms/ml, at least about 700 micrograms/ml, at least about 900 micrograms/ml, or at least about 1000 micrograms/ml of BiTE® molecules or a fragment thereof. In a further embodiment, a formulation of the invention comprises at least about 1 mg/ml, at least about 2 mg/ml, at least about 3 mg/ml, at least about 4 mg/ml, at least about 5 mg/ml, at least about 7 mg/ml, at least about 9 mg/ml, or at least about 10 mg/ml of BiTE® molecules or a fragment thereof. In a specific embodiment, a formulation of the invention comprises at least about 55 micrograms/ml of BiTE® molecules or a fragment thereof. In a specific embodiment, a formulation of the invention comprises at least about 160 micrograms/ml of BiTE® molecules or a fragment thereof. In a specific embodiment, a formulation of the invention comprises at least about 150 micrograms/ml of BiTE® molecules or a fragment thereof. In a specific embodiment, a BiTE® molecule formulated as described herein is specific for the CD19, EphA2 or CEA antigens.

In another embodiment, a formulation of the invention comprises between about 1 microgram/ml and about 50 micrograms/ml, between about 50 micrograms/ml and about 100 micrograms/ml, between about 100 micrograms/ml and about 150 micrograms/ml, between about 150 micrograms/ml and about 200 micrograms/ml, between about 200 micrograms/ml and about 250 micrograms/ml, between about 250 micrograms/ml and about 300 micrograms/ml, between about 300 micrograms/ml and about 400 micrograms/ml, between about 400 micrograms/ml and about 500 micrograms/ml or between about 500 micrograms/ml and about 1000 micrograms/ml of BiTE® molecules or a fragment thereof. In further embodiment, a formulation of the invention comprises between about 1 mg/ml and about 2 mg/ml, between about 2 mg/ml and about 3 mg/ml, between about 3 mg/ml and about 5 mg/ml, or between about 5 mg/ml and about 10 mg/ml of BiTE® molecules or a fragment thereof. In a specific embodiment, a formulation of the invention comprises between about 25 micrograms/ml and about 75 micrograms/ml of BiTE® molecules or a fragment thereof. In a specific embodiment, a formulation of the invention comprises between about 150 micrograms/ml and about 200 micrograms/ml of BiTE® molecules or a fragment thereof. In a specific embodiment, a formulation of the invention comprises between about 140 micrograms/ml and about 170 micrograms/ml of BiTE® molecules or a fragment thereof. In a specific embodiment, a BiTE® molecule formulated as described herein is specific for the CD19, EphA2 or CEA antigens.

In a further embodiment, a formulation described herein comprises about 5 micrograms/ml, about 10 micrograms/ml, about 20 micrograms/ml, about 30 micrograms/ml, about 40 micrograms/ml, about 50 micrograms/ml, about 60 micrograms/ml, about 70 micrograms/ml, about 80 micrograms/ml, about 90 micrograms/ml, about 100 micrograms/ml, about 110 micrograms/ml, about 120 micrograms/ml, about 130 micrograms/ml, about 140 micrograms/ml, about 150 micrograms/ml, about 160 micrograms/ml, about 170 micrograms/ml, about 180 micrograms/ml, about 190 micrograms/ml, about 200 micrograms/ml, about 210 micrograms/ml, about 220 micrograms/ml, about 230 micrograms/ml, about 240 micrograms/ml, about 250 micrograms/ml, about 260 micrograms/ml, about 270 micrograms/ml, about 280 micrograms/ml, about 290 micrograms/ml, about 300 micrograms/ml, about 310 micrograms/ml, about 320 micrograms/ml, about 330 micrograms/ml, about 340 micrograms/ml, about 350 micrograms/ml, about 500 micrograms/ml, about 700 micrograms/ml, about 900 micrograms/ml, or about 1000 micrograms/ml of BiTE® molecules or a fragment thereof. In a further embodiment, a formulation of the invention comprises about 1 mg/ml, about 2 mg/ml, about 3 mg/ml, about 4 mg/ml, about 5 mg/ml, about 7 mg/ml, about 9 mg/ml, or about 10 mg/ml of BiTE® molecules or a fragment thereof. In a specific embodiment, a formulation of the invention comprises about 55 micrograms/ml of BiTE® molecules or a fragment thereof. In a specific embodiment, a formulation of the invention comprises about 100 micrograms/ml of BiTE® molecules or a fragment thereof. In a specific embodiment, a formulation of the invention comprises about 160 micrograms/ml of BiTE® molecules or a fragment thereof. In a specific embodiment, a formulation of the invention comprises about 150 micrograms/ml of BiTE® molecules or a fragment thereof. In a specific embodiment, a BiTE® molecule formulated as described herein is specific for the CD19, EphA2 or CEA antigens.

In one embodiment, a formulation of the invention comprises at least about 1 microgram/ml, at least about 5 micrograms/ml, at least about 10 micrograms/ml, at least about 15 micrograms/ml, at least about 20 micrograms/ml, at least about 25 micrograms/ml, at least about 30 micrograms/ml, at least about 35 micrograms/ml, at least about 40 micrograms/ml, at least about 45 micrograms/ml, at least about 50 micrograms/ml, at least about 55 micrograms/ml, at least about 60 micrograms/ml, at least about 70 micrograms/ml, at least about 80 micrograms/ml, at least about 90 micrograms/ml, at least about 100 micrograms/ml, at least about 110 micrograms/ml, at least about 120 micrograms/ml, at least about 130 micrograms/ml, at least about 140 micrograms/ml, at least about 150 micrograms/ml, at least about 160 micrograms/ml, at least about 170 micrograms/ml, at least about 180 micrograms/ml, at least about 190 micrograms/ml, at least about 200 micrograms/ml, at least about 225 micrograms/ml, at least about 250 micrograms/ml, at least about 275 micrograms/ml, at least about 300 micrograms/ml at least about 325 micrograms/ml, at least about 350 micrograms/ml, at least about 375 micrograms/ml, at least about 400 micrograms/ml, at least about 500 micrograms/ml, at least about 700 micrograms/ml, at least about 900 micrograms/ml, or at least about 1000 micrograms/ml of MT103 or a fragment thereof. In a further embodiment, a formulation of the invention comprises at least about 1 mg/ml, at least about 2 mg/ml, at least about 3 mg/ml, at least about 4 mg/ml, at least about 5 mg/ml, at least about 7 mg/ml, at least about 9 mg/ml, or at least about 10 mg/ml of MT103 or a fragment thereof. In a specific embodiment, a formulation of the invention comprises at least about 55 micrograms/ml of MT103 or a fragment thereof. In a specific embodiment, a formulation of the invention comprises at least about 160 micrograms/ml of MT103 or a fragment thereof. In a specific embodiment, a formulation of the invention comprises at least about 150 micrograms/ml of MT103 or a fragment thereof.

In another embodiment, a formulation of the invention comprises between about 1 microgram/ml and about 50 micrograms/ml, between about 50 micrograms/ml and about 100 micrograms/ml, between about 100 micrograms/ml and about 150 micrograms/ml, between about 150 micrograms/ml and about 200 micrograms/ml, between about 200 micrograms/ml and about 250 micrograms/ml, between about 250 micrograms/ml and about 300 micrograms/ml, between about 300 micrograms/ml and about 400 micrograms/ml, or between about 400 micrograms/ml and about 500 micrograms/ml of BiTE® molecule or a fragment thereof. In further embodiment, a formulation of the invention comprises between about 1 mg/ml and about 2 mg/ml, between about 2 mg/ml and about 3 mg/ml, between about 3 mg/ml and about 5 mg/ml, or between about 5 mg/ml and about 10 mg/ml of MT103 or a fragment thereof. In a specific embodiment, a formulation of the invention comprises between about 25 micrograms/ml and about 75 micrograms/ml of MT103 or a fragment thereof. In a further embodiment, a formulation of the invention comprises between about 140 micrograms/ml and about 190 micrograms/ml of MT103 or a fragment thereof. In a further embodiment, a formulation of the invention comprises between about 140 micrograms/ml and about 160 micrograms/ml of MT103 or a fragment thereof.

In a further embodiment, a formulation described herein comprises about 5 micrograms/ml, 10 micrograms/ml, 20 micrograms/ml, about 30 micrograms/ml, about 40 micrograms/ml, about 50 micrograms/ml, about 60 micrograms/ml, about 70 micrograms/ml, about 80 micrograms/ml, about 90 micrograms/ml, about 100 micrograms/ml, about 110 micrograms/ml, about 120 micrograms/ml, about 130 micrograms/ml, about 140 micrograms/ml, about 150 micrograms/ml, about 160 micrograms/ml, about 170 micrograms/ml, about 180 micrograms/ml, about 190 micrograms/ml, about 200 micrograms/ml, about 210 micrograms/ml, about 220 micrograms/ml, about 230 micrograms/ml, about 240 micrograms/ml, about 250 micrograms/ml, about 260 micrograms/ml, about 270 micrograms/ml, about 280 micrograms/ml, about 290 micrograms/ml, about 300 micrograms/ml, about 310 micrograms/ml, about 320 micrograms/ml, about 330 micrograms/ml, about 340 micrograms/ml, about 350 micrograms/ml, about 500 micrograms/ml, about 700 micrograms/ml, about 900 micrograms/ml, or about 1000 micrograms/ml of MT103 or a fragment thereof. In a further embodiment, a formulation of the invention comprises about 1 mg/ml, about 2 mg/ml, about 3 mg/ml, about 4 mg/ml, about 5 mg/ml, about 7 mg/ml, about 9 mg/ml, or about 10 mg/ml of MT103 or a fragment thereof. In a specific embodiment, a formulation of the invention comprises about 55 micrograms/ml of MT103 or a fragment thereof. In a specific embodiment, a formulation of the invention comprises about 100 micrograms/ml of MT103 or a fragment thereof. In a specific embodiment, a formulation of the invention comprises about 160 micrograms/ml of MT103 or a fragment thereof. In a specific embodiment, a formulation of the invention comprises about 150 micrograms/ml of MT103 or a fragment thereof.

Optionally, the formulations of the invention may further comprise common excipients and/or additives such as buffering agents, amino acids, saccharides, salts, surfactants, bulking agents, and lyoprotectants. Additionally or alternatively, the formulations of the invention may further comprise common excipients and/or additives, such as, but not limited to, solubilizers, diluents, binders, stabilizers, salts, lipophilic solvents, chelators, preservatives, or the like.

In certain embodiments, the buffering agent is selected from the group consisting of histidine, citrate, phosphate, glycine, and acetate. In other embodiments the saccharide excipient is selected from the group consisting of trehalose, sucrose, mannitol, maltose and raffinose. In still other embodiments the surfactant is selected from the group consisting of polysorbate 20, polysorbate 40, polysorbate 80, and Pluronic F68. In yet other embodiments the salt is selected from the group consisting of NaCl, KCl, $MgCl_2$, and $CaCl_2$. In further embodiments, the bulking agent is selected from the group consisting of dextrose, ribose, fructose, mannitol, inositol, sorbitol, trehalose, sucrose, lactose, starch, dextrans, chitosan, hyaluronate, gelatin, serum albumin, glycogen, synthetic monomers and synthetic polymers. In additional embodiments, the lyoprotectant is selected from the group consisting of monosodium glutamate, histidine; betaine; magnesium sulfate; glycerin, dextran, erythritol, glycerol, arabitol, xylitol, sorbitol, mannitol; propylene glycol; polyethylene glycol; Pluronics®; gelatin, mellibiose, melezitose, raffinose, mannotriose, stachyose, glucose, maltose, lactose, maltulose, iso-maltulose and lactulose, glucitol, maltitol, lactitol, iso-maltulose, trehalose, sucrose and combinations thereof. It is understood that a particular excipient may serve more than one purpose in a formulation, for example, trehalose may serve both as a bulking agent and a lyoprotectant.

Optionally, the formulations of the invention may further comprise other common auxiliary components, such as, but not limited to, suitable excipients, polyols, solubilizers, diluents, binders, stabilizers, lipophilic solvents, chelators, preservatives, or the like.

The liquid formulations of the invention include a buffering or pH adjusting agent to provide improved pH control. In one embodiment, a formulation of the invention has a pH of between about 4.0 and about 9.0, between about 5.0 and about 9.0, between about 6.0 and about 8.0, between about 6.0 and about 7.5, between about 6.5 and about 8.0, or between about 6.5 and about 7.5. In a further embodiment, a formulation of the invention has a pH of about 3.0, about 3.5, about 4.0, about 4.5, about 5.0, about 5.5, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.5, or about 9.0. In a specific embodiment, a formulation of the invention has a pH of about 7.0. In a further embodiment, a formulation of the invention has a pH of about 6.0. The pH of a formulation generally should not be equal to the isoelectric point of the particular BiTE® molecule formulated.

Typically, the buffering agent is a salt prepared from an organic or inorganic acid or base. Representative buffering agents include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In addition, amino acid components can also function in a buffering capacity. Representative amino acid components which may be utilized in the formulations of the invention as buffering agents include, but are not limited to, glycine and histidine. In certain embodiments, the buffering agent is selected from the group consisting of histidine, citrate, phosphate, glycine, and acetate. In a specific embodiment, the buffering agent is histidine. In another specific embodiment, the buffering agent is citrate. The purity of the buffering agent should be at least 98%, or at least 99%, or at least 99.5%. As used herein, the term "purity" in the context of histidine refers to chemical purity of histidine as understood in the art, e.g., as described in The Merck Index, $13^{th}$ ed., O'Neil et al. ed. (Merck & Co., 2001).

Buffering agents are typically used at concentrations between about 1 mM and about 200 mM or any range or value therein, depending on the desired ionic strength and the buffering capacity required. The usual concentrations of conventional buffering agents employed in parenteral formulations can be found in: Pharmaceutical Dosage Form: Parenteral Medications, Volume 1, $2^{nd}$ Edition, Chapter 5, p. 194, De Luca and Boylan, "Formulation of Small Volume Parenterals", Table 5: Commonly used additives in Parenteral Products. In one embodiment, the buffering agent is at a concentration of about 1 mM, or of about 5 mM, or of about 10 mM, or of about 15 mM, or of about 20 mM, or of about 25 mM, or of about 30 mM, or of about 35 mM, or of about 40 mM, or of about 45 mM, or of about 50 mM, or of about 60 mM, or of about 70 mM, or of about 80 mM, or of about 90 mM, or of about 100 mM. In one embodiment, the buffering agent is at a concentration of 1 mM, or of 5 mM, or of 10 mM, or of 15 mM, or of 20 mM, or of 25 mM, or of 30 mM, or of 35 mM, or of 40 mM, or of 45 mM, or of 50 mM, or of 60 mM, or of 70 mM, or of 80 mM, or of 90 mM, or of 100 mM. In a specific embodiment, the buffering agent is at a concentration of between about 10 mM and about 50 mM. In another specific embodiment, the buffering agent is at a concentration of between 10 mM and 50 mM.

In certain embodiments, a formulation of the invention comprises a buffering agent. In one embodiment, said buffering agent is selected from the group consisting of histidine, citrate, phosphate, Tris, glycine, and acetate. In a specific embodiment, a formulation of the invention comprises citrate as a buffering agent. In a further embodiment, a formulation of the invention comprises a citrate buffer.

In one embodiment, a formulation of the invention comprises at least about 1 mM, at least about 5 mM, at least about 10 mM, at least about 20 mM, at least about 30 mM, at least about 40 mM, at least about 50 mM, at least about 75 mM, at least about 100 mM, at least about 150 mM, or at least about 200 mM citrate. In another embodiment, a formulation of the invention comprises between about 1 mM and about 5 mM, between about 5 mM and about 10 mM, between about 10 mM and about 15 mM, between about 15 mM and about 20 mM, between about 20 mM and about 30 mM, between about 30 mM and about 50 mM, between about 50 mM and about 70 mM, between about 70 mM and about 100 mM, between about 100 mM and about 150 mM, between about 150 mM and about 200 mM, or between about 200 mM and about 300 mM citrate. In a further embodiment of the invention comprises about 1 mM, about 5 mM, about 10 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 150 mM, or about 200 mM citrate. In a specific embodiment, a formulation of the invention comprises about 25 mM citrate. In a specific embodiment, a formulation of the invention comprises about 30 mM citrate.

In one embodiment, a formulation of the invention comprises at least about 1 mM, at least about 5 mM, at least about 10 mM, at least about 20 mM, at least about 30 mM, at least about 40 mM, at least about 50 mM, at least about 75 mM, at least about 100 mM, at least about 150 mM, or at least about 200 mM citrate buffer. In another embodiment, a formulation of the invention comprises between about 1 mM and about 5 mM, between about 5 mM and about 10 mM, between about 10 mM and about 15 mM, between about 15 mM and about 20 mM, between about 20 mM and about 30 mM, between about 30 mM and about 50 mM, between about 50 mM and about 70 mM, between about 70 mM and about 100 mM, between about 100 mM and about 150 mM, between about 150 mM and about 200 mM, or between about 200 mM and about 300 mM citrate buffer. In a further embodiment of the invention comprises about 1 mM, about 5 mM, about 10 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 150 mM, or about 200 mM citrate buffer. In a specific embodiment, a formulation of the invention comprises about 25 mM citrate buffer. In a specific embodiment, a formulation of the invention comprises about 30 mM citrate buffer.

In certain embodiments, the formulations of the invention comprise a carbohydrate excipient. Carbohydrate excipients can act, e.g., as viscosity enhancing agents, stabilizers, bulking agents, solubilizing agents, lyoprotectants and/or the like. Carbohydrate excipients are generally present at between about 1% to about 99% by weight/volume. In one embodiment, the carbohydrate excipient is present at between about 0.1% to about 50%. In another embodiment, the carbohydrate excipient is present at between about 0.5% to about 40%. In a specific embodiment, the carbohydrate excipient is present at between about 1% to about 2%, or between about 2% to about 5%, or between about 5% to about 10%, or between about 10% to about 15%, between about 15% and about 20%, between about 20% and about 25%, between about 25% and about 30%, or between about 30% and about 40%. In other specific embodiments, the carbohydrate excipient is present at 1%, or at 2%, or at 3%, or at 5%, or at 6%, or at 6.5%, or at 7%, or at 8%, or at 9%, or at 10%, or at 11%, or at 12%, or at 13%, or at 14%, or at 15%, or at 16%, or at 17%, or at 18%, or at 20%, or at 25%, or at 30%.

Carbohydrate excipients suitable for use in the formulations of the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and the like. In one embodiment, the carbohydrate excipients for use in the present invention are selected from the group consisting of, sucrose, trehalose, lactose, mannitol, and raffinose. In a specific embodiment, the carbohydrate excipient is trehalose. In another specific embodiment, the carbohydrate excipient is mannitol. In yet another specific embodiment, the carbohydrate excipient is sucrose. In still another specific embodiment, the carbohydrate excipient is raffinose. The purity of the carbohydrate excipient should be at least 98%, or at least 99%, or at least 99.5%.

In one embodiment, a formulation of the invention comprises at least about 1%, at least about 2.5%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 30%, or at least about 40% trehalose dihydrate. In another embodiment, a formulation of the invention comprises between about 1% and about 40%, between about 1% and about 5%, between about 5% and about 10%, between about 10% and about 15%, between about 15% and about 20%, between about 20% and about 25%, between about 25% and about 30%, or between about 30% and about 40% trehalose dihydrate. In a further embodiment, a formulation of the invention comprises about 1%, about 2%, about 4%, about 5%, about 6%, about 7%, about 8%, about 9%, about 10%, about 11%, about 12%, about 13%, about 14%, about 15%, about 16%, about 17%, about 18%, about 19%, about 20%, about 30%, or about 40% trehalose dihydrate. In a specific embodiment, a formulation of the invention comprises about 15% trehalose dihydrate. In a specific embodiment, a formulation of the invention comprises about 5% trehalose dihydrate. In a specific embodiment, a formulation of the invention comprises about 6% trehalose dihydrate. In a specific embodiment, a formulation of the invention comprises about 6.5% trehalose dihydrate.

In one embodiment, the molar ratio of a lyoprotectant (e.g., trehalose) and BiTE® molecules of a formulation of the invention is at least about 10,000, at least about 50,000, at least about 100,000, at least about 200,000, at least about 300,000, at least about 400,000, at least about 500,000, at least about 600,000, at least about 700,000, at least about 800,000, at least about 900,000, or at least about 1,000,000. In another embodiment, the molar ratio of a lyoprotectant (e.g., trehalose) and BiTE® molecules of a formulation of the invention is about 10,000, about 50,000, about 100,000, about 200,000, about 300,000, about 400,000, about 500,000, about 600,000, about 700,000, about 800,000, about 900,000, or about 1,000,000. In a further embodiment, the molar ratio of a lyoprotectant (e.g., trehalose) and BiTE® molecules of a formulation of the invention is between about 10,000 and about 1,000,000, between about 100,000 and about 900,000, or between about 500,000 and about 900,000.

In one embodiment, a formulation of the invention comprises an excipient. In a specific embodiment, a formulation of the invention comprises at least one excipient selected from the group consisting of: sugar, salt, surfactant, amino acid, polyol, chelating agent, emulsifier and preservative. In one embodiment, a formulation of the invention comprises a salt. In one embodiment, a formulation of the invention comprises a salt selected from the group consisting of: NaCl, KCl, CaCl$_2$, and MgCl$_2$. In a specific embodiment, a formulation of the invention comprises NaCl.

The formulations of the invention may further comprise a surfactant. The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. Pharmaceutically acceptable surfactants like polysorbates (e.g. polysorbates 20 or 80); polyoxamers (e.g. poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g. Pluronics, PF68 etc), can optionally be added to the formulations of the invention to reduce aggregation. Surfactants are particularly useful if a pump or plastic container is used to administer the formulation. The presence of a pharmaceutically acceptable surfactant mitigates the propensity for the protein to aggregate. In a specific embodiment, the formulations of the invention comprise a polysorbate which is at a concentration ranging from between about 0.001% to about 1%, or about 0.001% to about 0.5%, or about 0.01% to about 0.2%. In other specific embodiments, the formulations of the invention comprise a polysorbate which is at a concentration of 0.01%, or 0.02%, or 0.03%, or 0.04%, or 0.05%, or 0.06%, or 0.07%, or 0.08%, or 0.09%, or 0.1%, or 0.15%, or 0.2%. In another specific embodiment, the polysorbate is polysorbate-80.

In one embodiment, a formulation of the invention comprises a surfactant. In one embodiment, a formulation of the invention comprises Polysorbate 20, Polysorbate 40, Polysorbate 60, or Polysorbate 80. In a specific embodiment, a formulation of the invention comprises Polysorbate 80.

In one embodiment, a formulation of the invention comprises at least about 0.01%, at least about 0.02%, at least about 0.05%, at least about 0.1%, at least about 0.2%, at least about 0.3%, at least about 0.4%, or at least about 0.5% Polysorbate 80. In another embodiment, a formulation of the invention comprises between about 0.01% and about 0.5%, between about 0.01% and about 0.3%, between about 0.001% and about 0.2%, between about 0.02% and about 0.5%, between about 0.02% and about 0.3%, between about 0.02% and about 0.2%, between about 0.05% and about 0.5%, between about 0.05% and about 0.3%, between about 0.05% and about 0.2%, between about 0.075% and about 0.5%, between about 0.075% and about 0.3%, or between about 0.075% and about 0.2% Polysorbate 80. In a further embodiment, a formulation of the invention comprises about 0.01%, about 0.02%, about 0.05%, about 0.1%, about 0.2%, about 0.3%, about 0.4%, or about 0.5% Polysorbate 80. In a specific embodiment, a formulation of the invention comprises about 0.1% Polysorbate 80. In a specific embodiment, a formulation of the invention comprises about 0.01% Polysorbate 80. In a specific embodiment, a formulation of the invention comprises about 0.05% Polysorbate 80. In a specific embodiment, a formulation of the invention comprises about 0.1% Polysorbate 80. In a specific embodiment, a formulation of the invention comprises about 0.02% Polysorbate 80.

In one embodiment, a formulation of the invention comprises an amino acid. In one embodiment, a formulation of the invention comprises an amino acid salt. In one embodiment, a formulation of the invention comprises an amino acid selected from the group consisting of lysine, arginine, and histidine. In one embodiment, a formulation of the invention comprises an amino acid salt selected from the group comprising lysine HCl and arginine HCl. In a specific embodiment, a formulation of the invention comprises lysine HCl.

In one embodiment, a formulation of the invention comprises at least about 25 mM lysine HCl, at least about 50 mM lysine HCl, at least about 100 mM lysine HCl, at least about 150 mM lysine HCl, at least about 200 mM lysine HCl, at least about 250 mM lysine HCl, at least about 300 mM lysine HCl, at least about 350 mM lysine HCl, or at least about 400 mM lysine HCl. In another embodiment, a formulation of the invention comprises between about 25 mM and about 250 mM, between about 25 mM and about 300 mM, between about 25 mM and about 350 mM, between about 25 mM and about 400 mM, between about 50 mM and about 250 mM, between about 50 mM and about 300 mM, between about 50 mM and about 350 mM, between about 50 mM and about 400 mM, between about 100 mM and about 250 mM, between about 100 mM and about 300 mM, between about 100 mM and about 400 mM, between about 150 mM and about 250 mM, between about 150 mM and about 300 mM, or between about 150 mM and about 400 mM lysine HCl. In a further embodiment, a formulation of the invention comprises about 25 mM, about 50 mM, about 100 mM, about 150 mM, about 200 mM, about 250 mM, about 300 mM, about 350 mM, or about 400 mM lysine HCl. In a specific embodiment, a formulation of the invention comprises about 25 mM lysine HCl. In a specific embodiment, a formulation of the invention comprises about 50 mM lysine HCl. In a specific embodiment, a formulation of the invention comprises about 75 mM lysine HCl. In a specific embodiment, a formulation of the invention comprises about 100 mM lysine HCl. In a specific embodiment, a formulation of the invention comprises about 200 mM lysine HCl.

In one embodiment, a formulation of the invention comprises trehalose and lysine HCl. In one embodiment, a formulation of the invention comprises trehalose and lysine HCl at a molar ratio of about 0.1, about 0.5, about 0.75, about 1, about 5, about 10, about 20, about 30, about 40, about 50, about 60, about 70, about 80, about 90, about 100, about 200, or about 300, In one embodiment, a formulation of the invention comprises trehalose and lysine HCl at a molar ratio of about 1.5, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, or about 4. In a specific embodiment, a formulation of the invention comprises trehalose and lysine HCl at a molar ratio of about 2.1. In a specific embodiment, a formulation of the invention comprises trehalose and lysine HCl at a molar ratio of about 2.2. In a specific embodiment, a formulation of the invention comprises trehalose and lysine HCl at a molar ratio of about 2.4. In a specific embodiment, a formulation of the invention comprises trehalose and lysine HCl at a molar ratio of about 2.5. In a specific embodiment, a formulation of the invention comprises trehalose and lysine HCl at a molar ratio of about 2.6. In a specific embodiment, a formulation of the invention comprises trehalose and lysine HCl at a molar ratio of about 2.7.

Optionally, the formulations of the invention may further comprise other common excipients and/or additives including, but not limited to, diluents, binders, stabilizers, lipophilic solvents, preservatives, adjuvants, or the like. Pharmaceutically acceptable excipients and/or additives may be used in the formulations of the invention. Commonly used excipients/additives, such as pharmaceutically acceptable chelators (for example, but not limited to, EDTA, DTPA or EGTA) can optionally be added to the formulations of the invention to reduce aggregation. These additives are particularly useful if a pump or plastic container is used to administer the formulation.

Preservatives, such as phenol, m-cresol, p-cresol, o-cresol, chlorocresol, benzyl alcohol, phenylmercuric nitrite, phenoxyethanol, formaldehyde, chlorobutanol, magnesium chloride (for example, but not limited to, hexahydrate), alkylparaben (methyl, ethyl, propyl, butyl and the like), benzalkonium chloride, benzethonium chloride, sodium dehydroacetate and thimerosal, or mixtures thereof can optionally be added to the formulations of the invention at any suitable concentration such as between about 0.001% to about 5%, or any range or value therein. The concentration of preservative used in the formulations of the invention is a concentration sufficient to yield an microbial effect. Such concentrations are dependent on the preservative selected and are readily determined by the skilled artisan.

Other contemplated excipients/additives, which may be utilized in the formulations of the invention include, for example, flavoring agents, antimicrobial agents, sweeteners, antioxidants, antistatic agents, lipids such as phospholipids or fatty acids, steroids such as cholesterol, protein excipients such as serum albumin (human serum albumin (HSA), recombinant human albumin (rHA)), gelatin, casein, salt-forming counterions such as sodium and the like. These and additional known pharmaceutical excipients and/or additives suitable for use in the formulations of the invention are known in the art, e.g., as listed in "Remington: The Science & Practice of Pharmacy", 21$^{st}$ ed., Lippincott Williams & Wilkins, (2005), and in the "Physician's Desk Reference", 60$^{th}$ ed., Medical Economics, Montvale, N.J. (2005).

It will be understood by one skilled in the art that the formulations of the invention may be isotonic with human blood, that is the formulations of the invention have essentially the same osmotic pressure as human blood. Such isotonic formulations will generally have an osmotic pressure from about 250 mOSm to about 350 mOSm. Isotonicity can be measured by, for example, using a vapor pressure or ice-freezing type osmometer. Tonicity of a formulation is adjusted by the use of tonicity modifiers. "Tonicity modifiers" are those pharmaceutically acceptable inert substances that can be added to the formulation to provide an isotonity of the formulation. Tonicity modifiers suitable for this invention include, but are not limited to, saccharides, salts and amino acids.

In one embodiment, a formulation of the invention comprises citrate, lysine HCl, trehalose, and Polysorbate 80. In one embodiment, a formulation of the invention comprises lysine HCl, trehalose, and Polysorbate 80. In one embodiment, a formulation of the invention comprises citrate, trehalose, and Polysorbate 80. In one embodiment, a formulation of the invention comprises citrate, lysine HCl, and Polysorbate 80. In one embodiment, a formulation of the invention comprises citrate, lysine HCl, and trehalose. In one embodiment, a formulation of the invention comprises citrate and lysine HCl. In one embodiment, a formulation of the invention comprises citrate and trehalose. In one embodiment, a formulation of the invention comprises citrate and Polysorbate 80. In one embodiment, a formulation of the invention comprises lysine HCl and trehalose. In one embodiment, a formulation of the invention comprises lysine HCl and Polysorbate 80. In one embodiment, a formulation of the invention comprises trehalose, and Polysorbate 80. In one embodiment, a formulation of the invention comprises lysine HCl.

In one embodiment, a formulation of the invention comprises citrate, lysine HCl, trehalose and Polysorbate 80. In one embodiment, a formulation of the invention comprises between about 5 mM and about 125 mM citrate, between about 25 mM and about 400 mM lysine HCl, between about 3% and about 50% trehalose, and between about 0.001% and about 1% Polysorbate 80, wherein said formulation has a pH of between about 4.0 and about 8.0. In another embodiment, a formulation of the invention comprises between about 10 mM and about 50 mM citrate, between about 100 mM and about 300 mM lysine HCl, between about 10% and about 20% trehalose, and between about 0.01% and about 0.2% Polysorbate 80, wherein said formulation has a pH of between about 5.0 and about 8.0. In a further embodiment, a formulation of the invention comprises about 25 mM citrate, about 200 mM lysine HCl, about 15% trehalose and about 0.1% Polysorbate 80, wherein said formulation has a pH of about 7.0.

In one embodiment, a formulation of the invention comprises between about 10 micrograms/ml and about 100 micrograms/ml BiTE®, about 25 mM citrate, about 200 mM lysine HCl, about 15% trehalose and about 0.1% Polysorbate 80, wherein said formulation has a pH of about 7.0. In another embodiment, a formulation of the invention comprises between about 50 micrograms/ml and about 60 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises between about 110 micrograms/ml and about 210 micrograms/ml BiTE®, about 25 mM citrate, about 200 mM lysine HCl, about 15% trehalose and about 0.1% Polysorbate 80, wherein said formulation has a pH of about 7.0. In another embodiment, a formulation of the invention comprises between about 150 micrograms/ml and about 170 micrograms/ml BiTE®, about 25 mM citrate, about 200 mM lysine HCl, about 15% trehalose and about 0.1% Polysorbate 80, wherein said formulation has a pH of about 7.0. In a further embodiment, a formulation of the invention comprises about 55 micrograms/ml BiTE®, about 25 mM citrate, about 200 mM lysine HCl, about 15% trehalose and about 0.1% Polysorbate 80, wherein said formulation has a pH of about 7.0. In another embodiment, a formulation of the invention comprises about 160 micrograms/ml BiTE®, about 25 mM citrate, about 200 mM lysine HCl, about 15% trehalose and about 0.1% Polysorbate 80, wherein said formulation has a pH of about 7.0. In another embodiment, a formulation of the invention comprises about 150 micrograms/ml BiTE®, about 30 mM citrate, about 75 mM lysine HCl, about 6.5% trehalose and about 0.02% Polysorbate 80 and has a pH of about 7.0. In another embodiment, a formulation of the invention comprises about 150 micrograms/ml BiTE®, about 30 mM citrate, about 75 mM lysine HCl, about 6% trehalose and about 0.02% Polysorbate 80 and has a pH of about 7.0.

In one embodiment, a formulation of the invention comprises between about 10 micrograms/ml and about 100 micrograms/ml MT103, about 25 mM citrate, about 200 mM lysine HCl, about 15% trehalose and about 0.1% Polysorbate 80, wherein said formulation has a pH of about 7.0. In another embodiment, a formulation of the invention comprises between about 50 micrograms/ml and about 60 micrograms/ml MT103, about 25 mM citrate, about 200 mM lysine HCl, about 15% trehalose and about 0.1% Polysorbate 80, wherein said formulation has a pH of about 7.0. In one embodiment, a formulation of the invention comprises between about 110 micrograms/ml and about 210 micrograms/ml MT103, about 25 mM citrate, about 200 mM lysine HCl, about 15% trehalose and about 0.1% Polysorbate 80, wherein said formulation has a pH of about 7.0. In another embodiment, a formulation of the invention comprises between about 150 micrograms/ml and about 170 micrograms/ml MT103, about 25 mM citrate, about 200 mM lysine HCl, about 15% trehalose and about 0.1% Polysorbate 80, wherein said formulation has a pH of about 7.0. In a further embodiment, a formulation of the invention comprises about 55 micrograms/ml MT103, about 25 mM citrate, about 200 mM lysine HCl, about 15% trehalose and about 0.1% Polysorbate 80, wherein said formulation has a pH of about 7.0. In another embodiment, a formulation of the invention comprises about 160 micrograms/ml MT103, about 25 mM citrate, about 200 mM lysine HCl, about 15% trehalose and about 0.1% Polysorbate 80, wherein said formulation has a pH of about 7.0. In another embodiment, a formulation of the invention comprises about 150 micrograms/ml MT103, about 30 mM citrate, about 75 mM lysine HCl, about 6.5% trehalose and about 0.02% Polysorbate 80 and has a pH of about 7.0. In another embodiment, a formulation of the invention comprises about 150 micrograms/ml MT103, about 30 mM citrate, about 75 mM lysine HCl, about 6% trehalose and about 0.02% Polysorbate 80 and has a pH of about 7.0.

In one embodiment, a formulation of the invention consists of between about 10 micrograms/ml and about 100 micrograms/ml BiTE®, about 25 mM citrate, about 200 mM lysine HCl, about 15% trehalose and about 0.1% Polysorbate 80, wherein said formulation has a pH of about 7.0. In another embodiment, a formulation of the invention consists of between about 50 micrograms/ml and about 60 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention consists of between about 110 micrograms/ml and about 210 micrograms/ml BiTE®, about 25 mM citrate, about 200 mM lysine HCl, about 15% trehalose and about 0.1% Polysorbate 80, wherein said formulation has a pH of about 7.0. In another embodiment, a formulation of the invention consists of between about 150 micrograms/ml and about 170 micrograms/ml BiTE®, about 25 mM citrate, about 200 mM lysine HCl, about 15% trehalose and about 0.1% Polysorbate 80, wherein said formulation has a pH of about 7.0. In a further embodiment, a formulation of the invention consists of about 55 micrograms/ml BiTE®, about 25 mM citrate, about 200 mM lysine HCl, about 15% trehalose and about 0.1% Polysorbate 80, wherein said formulation has a pH of about 7.0. In another embodiment, a formulation of the invention consists of about 160 micrograms/ml BiTE®, about 25 mM citrate, about 200 mM lysine HCl, about 15% trehalose and about 0.1% Polysorbate 80, wherein said formulation has a pH of about 7.0. In another embodiment, a formulation of the invention consists of about 150 micrograms/ml BiTE®, about 30 mM citrate, about 75 mM lysine HCl, about 6.5% trehalose and about 0.02% Polysorbate 80 and has a pH of about 7.0. In another embodiment, a formulation of the invention consists of about 150 micrograms/ml BiTE®, about 30 mM citrate, about 75 mM lysine HCl, about 6% trehalose and about 0.02% Polysorbate 80 and has a pH of about 7.0.

In one embodiment, a formulation of the invention consists of between about 10 micrograms/ml and about 100 micrograms/ml MT103, about 25 mM citrate, about 200 mM lysine HCl, about 15% trehalose and about 0.1% Polysorbate 80, wherein said formulation has a pH of about 7.0. In another embodiment, a formulation of the invention consists of between about 50 micrograms/ml and about 60 micrograms/ml MT103, about 25 mM citrate, about 200 mM lysine HCl, about 15% trehalose and about 0.1% Polysorbate 80, wherein said formulation has a pH of about 7.0. In one embodiment, a formulation of the invention consists of between about 110 micrograms/ml and about 210 micrograms/ml MT103, about 25 mM citrate, about 200 mM lysine HCl, about 15% trehalose and about 0.1% Polysorbate 80, wherein said formulation has a pH of about 7.0. In another embodiment, a formulation of the invention consists of between about 150 micrograms/ml and about 170 micrograms/ml MT103, about 25 mM citrate, about 200 mM lysine HCl, about 15% trehalose and about 0.1% Polysorbate 80, wherein said formulation has a pH of about 7.0. In a further embodiment, a formulation of the invention consists of about 55 micrograms/ml MT103, about 25 mM citrate, about 200 mM lysine HCl, about 15% trehalose and about 0.1% Polysorbate 80, wherein said formulation has a pH of about 7.0. In another embodiment, a formulation of the invention consists of about 160 micrograms/ml MT103, about 25 mM citrate, about 200 mM lysine HCl, about 15% trehalose and about 0.1% Polysorbate 80, wherein said formulation has a pH of about 7.0. In another embodiment, a formulation of the invention consists of about 150 micrograms/ml MT103, about 30 mM citrate, about 75 mM lysine HCl, about 6.5% trehalose and about 0.02% Polysorbate 80 and has a pH of about 7.0. In another embodiment, a formulation of the invention consists of about 150 micrograms/ml MT103, about 30 mM citrate, about 75 mM lysine HCl, about 6% trehalose and about 0.02% Polysorbate 80 and has a pH of about 7.0.

In one embodiment, a formulation of the invention comprises at least about 10 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 20 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 30 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 40 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 50 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 55 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 60 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 70 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 80 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 90 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 100 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 110 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 120 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 130 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 140 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 150 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 160 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 170 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 180 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 190 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises at least about 200 micrograms/ml BiTE®, about 25 mM citrate, about 200 mM lysine HCl, about 15% trehalose and about 0.1% Polysorbate 80, wherein said formulation has a pH of about 7.0.

In one embodiment, a formulation of the invention comprises about 10 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 20 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 30 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 40 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 50 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 55 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 60 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 70 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 80 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 90 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 100 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 110 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 120 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 130 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 140 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 150 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 160 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 170 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 180 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 190 micrograms/ml BiTE®, about 25 mM citrate, about 200 mM lysine HCl, about 15% trehalose and about 0.1% Polysorbate 80, wherein said formulation has a pH of about 7.0. In one embodiment, a formulation of the invention comprises about 200 micrograms/ml BiTE®, about 25 mM citrate, about 200 mM lysine HCl, about 15% trehalose and about 0.1% Polysorbate 80, wherein said formulation has a pH of about 7.0.

In one embodiment, a formulation of the invention comprises at least about 10 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 20 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 30 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 40 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 50 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 55 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 60 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 70 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 80 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 90 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 100 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 110 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 120 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 130 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 140 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 150 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 160 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 170 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 180 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 190 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises at least about 200 micrograms/ml BiTE®, about 25 mM citrate, about 200 mM lysine HCl, about 6.5% trehalose and about 0.02% Polysorbate 80, wherein said formulation has a pH of about 7.0.

In one embodiment, a formulation of the invention comprises about 10 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 20 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 30 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 40 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 50 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 55 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 60 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 70 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 80 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 90 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 100 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 110 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 120 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 130 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 140 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 150 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 160 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 170 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 180 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 190 micrograms/ml BiTE®, about 25 mM citrate, about 200 mM lysine HCl, about 6.5% trehalose and about 0.02% Polysorbate 80, wherein said formulation has a pH of about 7.0. In one embodiment, a formulation of the invention comprises about 200 micrograms/ml BiTE®, about 25 mM citrate, about 200 mM lysine HCl, about 6.5% trehalose and about 0.02% Polysorbate 80, wherein said formulation has a pH of about 7.0.

In one embodiment, a formulation of the invention comprises at least about 10 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 20 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 30 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 40 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 50 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 55 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 60 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 70 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 80 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 90 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 100 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 110 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 120 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 130 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 140 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 150 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 160 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 170 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 180 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 190 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises at least about 200 micrograms/ml BiTE®, about 25 mM citrate, about 200 mM lysine HCl, about 6% trehalose and about 0.02% Polysorbate 80, wherein said formulation has a pH of about 7.0.

In one embodiment, a formulation of the invention comprises about 10 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 20 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 30 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 40 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 50 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 55 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 60 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 70 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 80 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 90 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 100 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 110 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 120 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 130 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 140 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 150 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 160 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 170 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 180 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 190 micrograms/ml BiTE®, about 25 mM citrate, about 200 mM lysine HCl, about 6% trehalose and about 0.02% Polysorbate 80, wherein said formulation has a pH of about 7.0. In one embodiment, a formulation of the invention comprises about 200 micrograms/ml BiTE®, about 25 mM citrate, about 200 mM lysine HCl, about 6% trehalose and about 0.02% Polysorbate 80, wherein said formulation has a pH of about 7.0.

In one embodiment the formulations of the invention are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with antibodies, even trace amounts of harmful and dangerous endotoxin must be removed. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

In one embodiment, the formulations of the invention are sterile. The formulations of the invention may be sterilized by various sterilization methods, including sterile filtration, radiation, etc. In one embodiment, the antibody formulation is filter-sterilized with a presterilized 0.22-micron filter. Sterile compositions for injection can be formulated according to conventional pharmaceutical practice as described in "Remington: The Science & Practice of Pharmacy", 21$^{st}$ ed., Lippincott Williams & Wilkins, (2005). Formulations comprising antibodies, such as those disclosed herein, ordinarily will be stored in lyophilized form or in solution. It is contemplated that sterile compositions comprising antibodies are placed into a container having a sterile access port, for example, an intravenous solution bag or vial having an adapter that allows retrieval of the formulation, such as a stopper pierceable by a hypodermic injection needle.

5.1.1. Stability of Liquid Formulations

In one embodiment, a formulation of the invention comprises BiTE® molecules that is susceptible to aggregation, fragmentation and/or loss due to absorption to contact surfaces.

In one embodiment, a formulation of the invention stabilizes BiTE® molecules. In one embodiment, a formulation of the invention prevents aggregation of BiTE® molecules. In another embodiment, a formulation of the invention prevents fragmentation of BiTE® molecules. In a further embodiment, a formulation of the invention prevents loss of BiTE® molecules due to absorption to contact surfaces.

In one embodiment, a formulation of the invention stabilizes MT103. In one embodiment, a formulation of the invention prevents aggregation of MT103. In another embodiment, a formulation of the invention prevents fragmentation of MT103. In a further embodiment, a formulation of the invention prevents loss of MT103 due to absorption to contact surfaces.

5.1.1.1. Stability Over Time

In one embodiment, a formulation of the invention is stable upon storage at about 40° C. for at least about 1 day, at least about 2 days, at least about 3 days, at least about 4 days, at least about 5 days, at least about 6 days, at least about 7 days, at least about 8 days, at least about 9 days, at least about 10 days, at least about 15 days, at least about 20 days, at least about 25 days, or at least about 30 days. In one embodiment, a formulation of the invention is stable upon storage at about 40° C. for at least about 1 week, at least about 2 weeks, at least about 3 weeks, or at least about 4 weeks. In one embodiment, a formulation of the invention is stable upon storage at about 40° C. for at least about 1 month, at least about 2 months, at least about 3 months, at least about 4 months, at least about 5 months, or at least about 6 months.

In one embodiment, a formulation of the invention is stable upon storage at about 4° C. for at least about 1 day, at least about 2 days, at least about 3 days, at least about 4 days, at least about 5 days, at least about 6 days, at least about 7 days, at least about 8 days, at least about 9 days, at least about 10 days. In one embodiment, a formulation of the invention is stable upon storage at about 4° C. for at least about 1 week, at least about 2 weeks, at least about 3 weeks, or at least about 4 weeks. In one embodiment, a formulation of the invention is stable upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a formulation of the invention is stable upon storage at about 5° C. for at least about 1 year, at least about 2 years, at least about 3 years, at least about 4 years, at least about 5 years, at least about 6 years, at least about 7 years, at least about 8 years, at least about 9 years, at least about 10 years, at least about 11 years, or at least about 12 years.

In one embodiment, a formulation of the invention is stable upon storage at about 40° C. for about 1 day, about 2 days, about 3 days, about 4 days, about 5 days, about 6 days, about 7 days, about 8 days, about 9 days, about 10 days, about 15 days, about 20 days, about 25 days, or about 30 days. In one embodiment, a formulation of the invention is stable upon storage at about 40° C. for about 1 week, about 2 weeks, about 3 weeks, or about 4 weeks. In one embodiment, a formulation of the invention is stable upon storage at about 40° C. for about 1 month, about 2 months, about 3 months, about 4 months, about 5 months, or about 6 months.

In one embodiment, a formulation of the invention is stable upon storage at about 4° C. for about 1 day, about 2 days, about 3 days, about 4 days, about 5 days, about 6 days, about 7 days, about 8 days, about 9 days, about 10 days. In one embodiment, a formulation of the invention is stable upon storage at about 4° C. for about 1 week, about 2 weeks, about 3 weeks, or about 4 weeks. In one embodiment, a formulation of the invention is stable upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a formulation of the invention is stable upon storage at about 5° C. for about 1 year, about 2 years, about 3 years, about 4 years, about 5 years, about 6 years, about 7 years, about 8 years, about 9 years, about 10 years, about 11 years, or about 12 years.

5.1.1.2. Binding Activity

In one embodiment, a formulation of the invention comprises BiTE® molecules, wherein said antibody retains at least 90% of binding ability to its target polypeptides compared to a reference antibody representing the antibody prior to storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein said antibody retains at least 90% of binding ability to its target polypeptides compared to a reference antibody representing the antibody prior to storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein said antibody retains at least 90% of binding ability to its target polypeptides compared to a reference antibody representing the antibody prior to storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein said antibody retains at least 90% of binding ability to its target polypeptides compared to a reference antibody representing the antibody prior to storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein said antibody retains 90% of binding ability to its target polypeptides compared to a reference antibody representing the antibody prior to storage at about 40° C. for about 1 day, about 2 days, about 3 days, about 4 days, about 5 days, about 6 days, or about 7 days. In one embodiment, a formulation of the invention comprises BiTE® molecules, wherein said antibody retains 90% of binding ability to its target polypeptides compared to a reference antibody representing the antibody prior to storage at about 40° C. for about 1 week, about 2 weeks, about 3 weeks, about 4 weeks, about 5 weeks, or about 6 weeks.

In one embodiment, a formulation of the invention comprises BiTE® molecules, wherein said antibody retains 90% of binding ability to its target polypeptides compared to a reference antibody representing the antibody prior to storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein said antibody retains 90% of binding ability to its target polypeptides compared to a reference antibody representing the antibody prior to storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein said antibody retains at least 90% of binding ability to CD19 and CD3 antigens compared to a reference antibody representing the antibody prior to storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein said antibody retains at least 90% of binding ability to CD19 and CD3 antigens compared to a reference antibody representing the antibody prior to storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein said antibody retains at least 90% of binding ability to CD19 and CD3 antigens compared to a reference antibody representing the antibody prior to storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein said antibody retains at least 90% of binding ability to CD19 and CD3 antigens compared to a reference antibody representing the antibody prior to storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein said antibody retains 90% of binding ability to CD19 and CD3 antigens compared to a reference antibody representing the antibody prior to storage at about 40° C. for about 1 day, about 2 days, about 3 days, about 4 days, about 5 days, about 6 days, or about 7 days. In one embodiment, a formulation of the invention comprises MT103, wherein said antibody retains 90% of binding ability to CD19 and CD3 antigens compared to a reference antibody representing the antibody prior to storage at about 40° C. for about 1 week, about 2 weeks, about 3 weeks, about 4 weeks, about 5 weeks, or about 6 weeks.

In one embodiment, a formulation of the invention comprises MT103, wherein said antibody retains 90% of binding ability to CD19 and CD3 antigens compared to a reference antibody representing the antibody prior to storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein said antibody retains 90% of binding ability to CD19 and CD3 antigens compared to a reference antibody representing the antibody prior to storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises BiTE® molecules, wherein said antibody retains at least 95% of binding ability to its target polypeptides compared to a reference antibody representing the antibody prior to storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein said antibody retains at least 95% of binding ability to its target polypeptides compared to a reference antibody representing the antibody prior to storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein said antibody retains at least 95% of binding ability to its target polypeptides compared to a reference antibody representing the antibody prior to storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein said antibody retains at least 95% of binding ability to its target polypeptides compared to a reference antibody representing the antibody prior to storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein said antibody retains 95% of binding ability to its target polypeptides compared to a reference antibody representing the antibody prior to storage at about 40° C. for about 1 day, about 2 days, about 3 days, about 4 days, about 5 days, about 6 days, or about 7 days. In one embodiment, a formulation of the invention comprises BiTE® molecules, wherein said antibody retains 95% of binding ability to its target polypeptides compared to a reference antibody representing the antibody prior to storage at about 40° C. for about 1 week, about 2 weeks, about 3 weeks, about 4 weeks, about 5 weeks, or about 6 weeks.

In one embodiment, a formulation of the invention comprises BiTE® molecules, wherein said antibody retains 95% of binding ability to its target polypeptides compared to a reference antibody representing the antibody prior to storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein said antibody retains 95% of binding ability to its target polypeptides compared to a reference antibody representing the antibody prior to storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein said antibody retains at least 95% of binding ability to CD19 and CD3 antigens compared to a reference antibody representing the antibody prior to storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein said antibody retains at least 95% of binding ability to CD19 and CD3 antigens compared to a reference antibody representing the antibody prior to storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein said antibody retains at least 95% of binding ability to CD19 and CD3 antigens compared to a reference antibody representing the antibody prior to storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein said antibody retains at least 95% of binding ability to CD19 and CD3 antigens compared to a reference antibody representing the antibody prior to storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein said antibody retains 95% of binding ability to CD19 and CD3 antigens compared to a reference antibody representing the antibody prior to storage at about 40° C. for about 1 day, about 2 days, about 3 days, about 4 days, about 5 days, about 6 days, or about 7 days. In one embodiment, a formulation of the invention comprises MT103, wherein said antibody retains 95% of binding ability to CD19 and CD3 antigens compared to a reference antibody representing the antibody prior to storage at about 40° C. for about 1 week, about 2 weeks, about 3 weeks, about 4 weeks, about 5 weeks, or about 6 weeks.

In one embodiment, a formulation of the invention comprises MT103, wherein said antibody retains 95% of binding ability to CD19 and CD3 antigens compared to a reference antibody representing the antibody prior to storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein said antibody retains 95% of binding ability to CD19 and CD3 antigens compared to a reference antibody representing the antibody prior to storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises BiTE® molecules, wherein said antibody retains at least 99% of binding ability to its target polypeptides compared to a reference antibody representing the antibody prior to storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein said antibody retains at least 99% of binding ability to its target polypeptides compared to a reference antibody representing the antibody prior to storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein said antibody retains at least 99% of binding ability to its target polypeptides compared to a reference antibody representing the antibody prior to storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein said antibody retains at least 99% of binding ability to its target polypeptides compared to a reference antibody representing the antibody prior to storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein said antibody retains 99% of binding ability to its target polypeptides compared to a reference antibody representing the antibody prior to storage at about 40° C. for about 1 day, about 2 days, about 3 days, about 4 days, about 5 days, about 6 days, or about 7 days. In one embodiment, a formulation of the invention comprises BiTE® molecules, wherein said antibody retains 99% of binding ability to its target polypeptides compared to a reference antibody representing the antibody prior to storage at about 40° C. for about 1 week, about 2 weeks, about 3 weeks, about 4 weeks, about 5 weeks, or about 6 weeks.

In one embodiment, a formulation of the invention comprises BiTE® molecules, wherein said antibody retains 99% of binding ability to its target polypeptides compared to a reference antibody representing the antibody prior to storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein said antibody retains 99% of binding ability to its target polypeptides compared to a reference antibody representing the antibody prior to storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein said antibody retains at least 99% of binding ability to CD19 and CD3 antigens compared to a reference antibody representing the antibody prior to storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein said antibody retains at least 99% of binding ability to CD19 and CD3 antigens compared to a reference antibody representing the antibody prior to storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein said antibody retains at least 99% of binding ability to CD19 and CD3 antigens compared to a reference antibody representing the antibody prior to storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein said antibody retains at least 99% of binding ability to CD19 and CD3 antigens compared to a reference antibody representing the antibody prior to storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein said antibody retains 99% of binding ability to CD19 and CD3 antigens compared to a reference antibody representing the antibody prior to storage at about 40° C. for about 1 day, about 2 days, about 3 days, about 4 days, about 5 days, about 6 days, or about 7 days. In one embodiment, a formulation of the invention comprises MT103, wherein said antibody retains 99% of binding ability to CD19 and CD3 antigens compared to a reference antibody representing the antibody prior to storage at about 40° C. for about 1 week, about 2 weeks, about 3 weeks, about 4 weeks, about 5 weeks, or about 6 weeks.

5.1.1.3. Aggregate Formation

In one embodiment, a formulation of the invention comprises BiTE® molecules, wherein less than 1% of said antibody forms an aggregate as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein less than 1% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein less than 1% of said antibody forms an aggregate as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein less than 1% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein less than 1% of said antibody forms an aggregate as determined by HPSEC upon storage at about 40° C. for about 1 day, about 2 days, about 3 days, about 4 days, about 5 days, about 6 days, or about 7 days. In one embodiment, a formulation of the invention comprises BiTE® molecules, wherein less than 1% of said antibody forms an aggregate as determined by HPSEC upon storage at about 40° C. for about 1 week, about 2 weeks, about 3 weeks, about 4 weeks, about 5 weeks, or about 6 weeks.

In one embodiment, a formulation of the invention comprises BiTE® molecules, wherein less than 1% of said antibody forms an aggregate as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein less than 1% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein less than 1% of said antibody forms an aggregate as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein less than 1% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein less than 1% of said antibody forms an aggregate as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein less than 1% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein less than 1% of said antibody forms an aggregate as determined by HPSEC upon storage at about 40° C. for about 1 day, about 2 days, about 3 days, about 4 days, about 5 days, about 6 days, or about 7 days. In one embodiment, a formulation of the invention comprises MT103, wherein less than 1% of said antibody forms an aggregate as determined by HPSEC upon storage at about 40° C. for about 1 week, about 2 weeks, about 3 weeks, about 4 weeks, about 5 weeks, or about 6 weeks.

In one embodiment, a formulation of the invention comprises MT103, wherein less than 1% of said antibody forms an aggregate as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein less than 1% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises BiTE® molecules, wherein less than 2% of said antibody forms an aggregate as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein less than 2% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein less than 2% of said antibody forms an aggregate as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein less than 2% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein less than 2% of said antibody forms an aggregate as determined by HPSEC upon storage at about 40° C. for about 1 day, about 2 days, about 3 days, about 4 days, about 5 days, about 6 days, or about 7 days. In one embodiment, a formulation of the invention comprises BiTE® molecules, wherein less than 2% of said antibody forms an aggregate as determined by HPSEC upon storage at about 40° C. for about 1 week, about 2 weeks, about 3 weeks, about 4 weeks, about 5 weeks, or about 6 weeks.

In one embodiment, a formulation of the invention comprises BiTE® molecules, wherein less than 2% of said antibody forms an aggregate as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein less than 2% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein less than 2% of said antibody forms an aggregate as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein less than 2% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein less than 2% of said antibody forms an aggregate as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein less than 2% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein less than 2% of said antibody forms an aggregate as determined by HPSEC upon storage at about 40° C. for about 1 day, about 2 days, about 3 days, about 4 days, about 5 days, about 6 days, or about 7 days. In one embodiment, a formulation of the invention comprises MT103, wherein less than 2% of said antibody forms an aggregate as determined by HPSEC upon storage at about 40° C. for about 1 week, about 2 weeks, about 3 weeks, about 4 weeks, about 5 weeks, or about 6 weeks.

In one embodiment, a formulation of the invention comprises MT103, wherein less than 2% of said antibody forms an aggregate as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein less than 2% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises BiTE® molecules, wherein less than 3% of said antibody forms an aggregate as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein less than 3% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein less than 3% of said antibody forms an aggregate as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein less than 3% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein less than 3% of said antibody forms an aggregate as determined by HPSEC upon storage at about 40° C. for about 1 day, about 2 days, about 3 days, about 4 days, about 5 days, about 6 days, or about 7 days. In one embodiment, a formulation of the invention comprises BiTE® molecules, wherein less than 3% of said antibody forms an aggregate as determined by HPSEC upon storage at about 40° C. for about 1 week, about 2 weeks, about 3 weeks, about 4 weeks, about 5 weeks, or about 6 weeks.

In one embodiment, a formulation of the invention comprises BiTE® molecules, wherein less than 3% of said antibody forms an aggregate as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein less than 3% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein less than 3% of said antibody forms an aggregate as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein less than 3% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein less than 3% of said antibody forms an aggregate as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein less than 3% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein less than 3% of said antibody forms an aggregate as determined by HPSEC upon storage at about 40° C. for about 1 day, about 2 days, about 3 days, about 4 days, about 5 days, about 6 days, or about 7 days. In one embodiment, a formulation of the invention comprises MT103, wherein less than 3% of said antibody forms an aggregate as determined by HPSEC upon storage at about 40° C. for about 1 week, about 2 weeks, about 3 weeks, about 4 weeks, about 5 weeks, or about 6 weeks.

In one embodiment, a formulation of the invention comprises MT103, wherein less than 3% of said antibody forms an aggregate as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein less than 3% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises BiTE® molecules, wherein less than 4% of said antibody forms an aggregate as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein less than 4% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein less than 4% of said antibody forms an aggregate as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein less than 4% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein less than 4% of said antibody forms an aggregate as determined by HPSEC upon storage at about 40° C. for about 1 day, about 2 days, about 3 days, about 4 days, about 5 days, about 6 days, or about 7 days. In one embodiment, a formulation of the invention comprises BiTE® molecules, wherein less than 4% of said antibody forms an aggregate as determined by HPSEC upon storage at about 40° C. for about 1 week, about 2 weeks, about 3 weeks, about 4 weeks, about 5 weeks, or about 6 weeks.

In one embodiment, a formulation of the invention comprises BiTE® molecules, wherein less than 4% of said antibody forms an aggregate as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® moleculesa BiTE® molecule, wherein less than 4% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein less than 4% of said antibody forms an aggregate as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein less than 4% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein less than 4% of said antibody forms an aggregate as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein less than 4% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein less than 4% of said antibody forms an aggregate as determined by HPSEC upon storage at about 40° C. for about 1 day, about 2 days, about 3 days, about 4 days, about 5 days, about 6 days, or about 7 days. In one embodiment, a formulation of the invention comprises MT103, wherein less than 4% of said antibody forms an aggregate as determined by HPSEC upon storage at about 40° C. for about 1 week, about 2 weeks, about 3 weeks, about 4 weeks, about 5 weeks, or about 6 weeks.

In one embodiment, a formulation of the invention comprises MT103, wherein less than 4% of said antibody forms an aggregate as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein less than 4% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises BiTE® moleculesa BiTE® molecule, wherein less than 5% of said antibody forms an aggregate as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® moleculesa BiTE® molecule, wherein less than 5% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® moleculesa BiTE® molecule, wherein less than 5% of said antibody forms an aggregate as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® moleculesa BiTE® molecule, wherein less than 5% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein less than 5% of said antibody forms an aggregate as determined by HPSEC upon storage at about 40° C. for about 1 day, about 2 days, about 3 days, about 4 days, about 5 days, about 6 days, or about 7 days. In one embodiment, a formulation of the invention comprises BiTE® molecules, wherein less than 5% of said antibody forms an aggregate as determined by HPSEC upon storage at about 40° C. for about 1 week, about 2 weeks, about 3 weeks, about 4 weeks, about 5 weeks, or about 6 weeks.

In one embodiment, a formulation of the invention comprises BiTE® molecules, wherein less than 5% of said antibody forms an aggregate as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein less than 5% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103MT103, wherein less than 5% of said antibody forms an aggregate as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein less than 5% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein less than 5% of said antibody forms an aggregate as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein less than 5% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein less than 5% of said antibody forms an aggregate as determined by HPSEC upon storage at about 40° C. for about 1 day, about 2 days, about 3 days, about 4 days, about 5 days, about 6 days, or about 7 days. In one embodiment, a formulation of the invention comprises MT103, wherein less than 5% of said antibody forms an aggregate as determined by HPSEC upon storage at about 40° C. for about 1 week, about 2 weeks, about 3 weeks, about 4 weeks, about 5 weeks, or about 6 weeks.

In one embodiment, a formulation of the invention comprises MT103, wherein less than 5% of said antibody forms an aggregate as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein less than 5% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

5.1.1.4. Dimer Formation

In one embodiment, a formulation of the invention comprises BiTE® molecules, wherein less than 1% of said antibody forms a dimer as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein less than 1% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein less than 1% of said antibody forms a dimer as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein less than 1% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein less than 1% of said antibody forms a dimer as determined by HPSEC upon storage at about 40° C. for about 1 day, about 2 days, about 3 days, about 4 days, about 5 days, about 6 days, or about 7 days. In one embodiment, a formulation of the invention comprises BiTE® molecules, wherein less than 1% of said antibody forms a dimer as determined by HPSEC upon storage at about 40° C. for about 1 week, about 2 weeks, about 3 weeks, about 4 weeks, about 5 weeks, or about 6 weeks.

In one embodiment, a formulation of the invention comprises BiTE® molecules, wherein less than 1% of said antibody forms a dimer as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein less than 1% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein less than 1% of said antibody forms a dimer as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein less than 1% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein less than 1% of said antibody forms a dimer as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein less than 1% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein less than 1% of said antibody forms a dimer as determined by HPSEC upon storage at about 40° C. for about 1 day, about 2 days, about 3 days, about 4 days, about 5 days, about 6 days, or about 7 days. In one embodiment, a formulation of the invention comprises MT103, wherein less than 1% of said antibody forms a dimer as determined by HPSEC upon storage at about 40° C. for about 1 week, about 2 weeks, about 3 weeks, about 4 weeks, about 5 weeks, or about 6 weeks.

In one embodiment, a formulation of the invention comprises MT103, wherein less than 1% of said antibody forms a dimer as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein less than 1% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises BiTE® molecules, wherein less than 2% of said antibody forms a dimer as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein less than 2% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein less than 2% of said antibody forms a dimer as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein less than 2% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein less than 2% of said antibody forms a dimer as determined by HPSEC upon storage at about 40° C. for about 1 day, about 2 days, about 3 days, about 4 days, about 5 days, about 6 days, or about 7 days. In one embodiment, a formulation of the invention comprises BiTE® molecules, wherein less than 2% of said antibody forms a dimer as determined by HPSEC upon storage at about 40° C. for about 1 week, about 2 weeks, about 3 weeks, about 4 weeks, about 5 weeks, or about 6 weeks.

In one embodiment, a formulation of the invention comprises BiTE® molecules, wherein less than 2% of said antibody forms a dimer as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein less than 2% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein less than 2% of said antibody forms a dimer as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein less than 2% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein less than 2% of said antibody forms a dimer as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein less than 2% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein less than 2% of said antibody forms a dimer as determined by HPSEC upon storage at about 40° C. for about 1 day, about 2 days, about 3 days, about 4 days, about 5 days, about 6 days, or about 7 days. In one embodiment, a formulation of the invention comprises MT103, wherein less than 2% of said antibody forms a dimer as determined by HPSEC upon storage at about 40° C. for about 1 week, about 2 weeks, about 3 weeks, about 4 weeks, about 5 weeks, or about 6 weeks.

In one embodiment, a formulation of the invention comprises MT103, wherein less than 2% of said antibody forms a dimer as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecule MT103, wherein less than 2% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises BiTE® molecules, wherein less than 3% of said antibody forms a dimer as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein less than 3% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein less than 3% of said antibody forms a dimer as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein less than 3% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein less than 3% of said antibody forms a dimer as determined by HPSEC upon storage at about 40° C. for about 1 day, about 2 days, about 3 days, about 4 days, about 5 days, about 6 days, or about 7 days. In one embodiment, a formulation of the invention comprises BiTE® molecules, wherein less than 3% of said antibody forms a dimer as determined by HPSEC upon storage at about 40° C. for about 1 week, about 2 weeks, about 3 weeks, about 4 weeks, about 5 weeks, or about 6 weeks.

In one embodiment, a formulation of the invention comprises BiTE® molecules, wherein less than 3% of said antibody forms a dimer as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein less than 3% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein less than 3% of said antibody forms a dimer as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein less than 3% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein less than 3% of said antibody forms a dimer as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein less than 3% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein less than 3% of said antibody forms a dimer as determined by HPSEC upon storage at about 40° C. for about 1 day, about 2 days, about 3 days, about 4 days, about 5 days, about 6 days, or about 7 days. In one embodiment, a formulation of the invention comprises MT103, wherein less than 3% of said antibody forms a dimer as determined by HPSEC upon storage at about 40° C. for about 1 week, about 2 weeks, about 3 weeks, about 4 weeks, about 5 weeks, or about 6 weeks.

In one embodiment, a formulation of the invention comprises MT103, wherein less than 3% of said antibody forms a dimer as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein less than 3% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises BiTE® molecules, wherein less than 4% of said antibody forms a dimer as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein less than 4% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein less than 4% of said antibody forms a dimer as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein less than 4% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein less than 4% of said antibody forms a dimer as determined by HPSEC upon storage at about 40° C. for about 1 day, about 2 days, about 3 days, about 4 days, about 5 days, about 6 days, or about 7 days. In one embodiment, a formulation of the invention comprises BiTE® molecules, wherein less than 4% of said antibody forms a dimer as determined by HPSEC upon storage at about 40° C. for about 1 week, about 2 weeks, about 3 weeks, about 4 weeks, about 5 weeks, or about 6 weeks.

In one embodiment, a formulation of the invention comprises BiTE® molecules, wherein less than 4% of said antibody forms a dimer as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein less than 4% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein less than 4% of said antibody forms a dimer as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein less than 4% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein less than 4% of said antibody forms a dimer as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein less than 4% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein less than 4% of said antibody forms a dimer as determined by HPSEC upon storage at about 40° C. for about 1 day, about 2 days, about 3 days, about 4 days, about 5 days, about 6 days, or about 7 days. In one embodiment, a formulation of the invention comprises MT103, wherein less than 4% of said antibody forms a dimer as determined by HPSEC upon storage at about 40° C. for about 1 week, about 2 weeks, about 3 weeks, about 4 weeks, about 5 weeks, or about 6 weeks.

In one embodiment, a formulation of the invention comprises MT103, wherein less than 4% of said antibody forms a dimer as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein less than 4% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises BiTE® molecules, wherein less than 5% of said antibody forms a dimer as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein less than 5% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein less than 5% of said antibody forms a dimer as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein less than 5% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein less than 5% of said antibody forms a dimer as determined by HPSEC upon storage at about 40° C. for about 1 day, about 2 days, about 3 days, about 4 days, about 5 days, about 6 days, or about 7 days. In one embodiment, a formulation of the invention comprises BiTE® molecules, wherein less than 5% of said antibody forms a dimer as determined by HPSEC upon storage at about 40° C. for about 1 week, about 2 weeks, about 3 weeks, about 4 weeks, about 5 weeks, or about 6 weeks.

In one embodiment, a formulation of the invention comprises BiTE® molecules, wherein less than 5% of said antibody forms a dimer as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein less than 5% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein less than 5% of said antibody forms a dimer as determined by HPSEC upon storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein less than 5% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein less than 5% of said antibody forms a dimer as determined by HPSEC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein less than 5% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein less than 5% of said antibody forms a dimer as determined by HPSEC upon storage at about 40° C. for about 1 day, about 2 days, about 3 days, about 4 days, about 5 days, about 6 days, or about 7 days. In one embodiment, a formulation of the invention comprises MT103, wherein less than 5% of said antibody forms a dimer as determined by HPSEC upon storage at about 40° C. for about 1 week, about 2 weeks, about 3 weeks, about 4 weeks, about 5 weeks, or about 6 weeks.

In one embodiment, a formulation of the invention comprises MT103, wherein less than 5% of said antibody forms a dimer as determined by HPSEC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein less than 5% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months.

5.1.1.5. Protein Recovery Following Shaking or Freeze/Thaw Cycles

In one embodiment, a formulation of the invention comprises BiTE® molecules, wherein less than 1% of said antibody forms an aggregate as determined by HPSEC upon shaking a vial filled to half of its volume with a sample of said formulation for 4 hours at a speed of 400 shakes per minute. In one embodiment, a formulation of the invention comprises BiTE® molecules, wherein less than 1% of said antibody forms an aggregate as determined by HPSEC upon subjecting the formulation to three freeze/thaw cycles.

In one embodiment, a formulation of the invention comprises MT103, wherein less than 1% of said antibody forms an aggregate as determined by HPSEC upon shaking a vial filled to half of its volume with a sample of said formulation for 4 hours at a speed of 400 shakes per minute. In one embodiment, a formulation of the invention comprises MT103, wherein less than 1% of said antibody forms an aggregate as determined by HPSEC upon subjecting the formulation to three freeze/thaw cycles.

In one embodiment, a formulation of the invention comprises BiTE® molecules, wherein less than 2% of said antibody forms an aggregate as determined by HPSEC upon shaking a vial filled to half of its volume with a sample of said formulation for 4 hours at a speed of 400 shakes per minute. In one embodiment, a formulation of the invention comprises BiTE® molecules, wherein less than 2% of said antibody forms an aggregate as determined by HPSEC upon subjecting the formulation to three freeze/thaw cycles.

In one embodiment, a formulation of the invention comprises MT103, wherein less than 2% of said antibody forms an aggregate as determined by HPSEC upon shaking a vial filled to half of its volume with a sample of said formulation for 4 hours at a speed of 400 shakes per minute. In one embodiment, a formulation of the invention comprises MT103, wherein less than 2% of said antibody forms an aggregate as determined by HPSEC upon subjecting the formulation to three freeze/thaw cycles.

In one embodiment, a formulation of the invention comprises BiTE® molecules, wherein less than 3% of said antibody forms an aggregate as determined by HPSEC upon shaking a vial filled to half of its volume with a sample of said formulation for 4 hours at a speed of 400 shakes per minute. In one embodiment, a formulation of the invention comprises BiTE® molecules, wherein less than 3% of said antibody forms an aggregate as determined by HPSEC upon subjecting the formulation to three freeze/thaw cycles.

In one embodiment, a formulation of the invention comprises MT103, wherein less than 3% of said antibody forms an aggregate as determined by HPSEC upon shaking a vial filled to half of its volume with a sample of said formulation for 4 hours at a speed of 400 shakes per minute. In one embodiment, a formulation of the invention comprises MT103, wherein less than 3% of said antibody forms an aggregate as determined by HPSEC upon subjecting the formulation to three freeze/thaw cycles.

In one embodiment, a formulation of the invention comprises BiTE® molecules, wherein less than 4% of said antibody forms an aggregate as determined by HPSEC upon shaking a vial filled to half of its volume with a sample of said formulation for 4 hours at a speed of 400 shakes per minute. In one embodiment, a formulation of the invention comprises BiTE® molecules, wherein less than 4% of said antibody forms an aggregate as determined by HPSEC upon subjecting the formulation to three freeze/thaw cycles.

In one embodiment, a formulation of the invention comprises MT103, wherein less than 4% of said antibody forms an aggregate as determined by HPSEC upon shaking a vial filled to half of its volume with a sample of said formulation for 4 hours at a speed of 400 shakes per minute. In one embodiment, a formulation of the invention comprises MT103, wherein less than 4% of said antibody forms an aggregate as determined by HPSEC upon subjecting the formulation to three freeze/thaw cycles.

In one embodiment, a formulation of the invention comprises BiTE® molecules, wherein less than 5% of said antibody forms an aggregate as determined by HPSEC upon shaking a vial filled to half of its volume with a sample of said formulation for 4 hours at a speed of 400 shakes per minute. In one embodiment, a formulation of the invention comprises BiTE® molecules, wherein less than 5% of said antibody forms an aggregate as determined by HPSEC upon subjecting the formulation to three freeze/thaw cycles.

In one embodiment, a formulation of the invention comprises MT103, wherein less than 5% of said antibody forms an aggregate as determined by HPSEC upon shaking a vial filled to half of its volume with a sample of said formulation for 4 hours at a speed of 400 shakes per minute. In one embodiment, a formulation of the invention comprises MT103, wherein less than 5% of said antibody forms an aggregate as determined by HPSEC upon subjecting the formulation to three freeze/thaw cycles.

5.1.1.6. Dimer Formation Upon Shaking or Freeze/Thaw Cycles

In one embodiment, a formulation of the invention comprises BiTE® molecules, wherein less than 1% of said antibody forms a dimer as determined by HPSEC upon shaking a vial filled to half of its volume with a sample of said formulation for 4 hours at a speed of 400 shakes per minute. In one embodiment, a formulation of the invention comprises BiTE® molecules, wherein less than 1% of said antibody forms a dimer as determined by HPSEC upon subjecting the formulation to three freeze/thaw cycles.

In one embodiment, a formulation of the invention comprises MT103, wherein less than 1% of said antibody forms a dimer as determined by HPSEC upon shaking a vial filled to half of its volume with a sample of said formulation for 4 hours at a speed of 400 shakes per minute. In one embodiment, a formulation of the invention comprises MT103, wherein less than 1% of said antibody forms a dimer as determined by HPSEC upon subjecting the formulation to three freeze/thaw cycles.

In one embodiment, a formulation of the invention comprises BiTE® molecules, wherein less than 2% of said antibody forms a dimer as determined by HPSEC upon shaking a vial filled to half of its volume with a sample of said formulation for 4 hours at a speed of 400 shakes per minute. In one embodiment, a formulation of the invention comprises BiTE® molecules, wherein less than 2% of said antibody forms a dimer as determined by HPSEC upon subjecting the formulation to three freeze/thaw cycles.

In one embodiment, a formulation of the invention comprises MT103, wherein less than 2% of said antibody forms a dimer as determined by HPSEC upon shaking a vial filled to half of its volume with a sample of said formulation for 4 hours at a speed of 400 shakes per minute. In one embodiment, a formulation of the invention comprises MT103, wherein less than 2% of said antibody forms a dimer as determined by HPSEC upon subjecting the formulation to three freeze/thaw cycles.

In one embodiment, a formulation of the invention comprises BiTE® molecules, wherein less than 3% of said antibody forms a dimer as determined by HPSEC upon shaking a vial filled to half of its volume with a sample of said formulation for 4 hours at a speed of 400 shakes per minute. In one embodiment, a formulation of the invention comprises BiTE® molecules, wherein less than 3% of said antibody forms a dimer as determined by HPSEC upon subjecting the formulation to three freeze/thaw cycles.

In one embodiment, a formulation of the invention comprises MT103, wherein less than 3% of said antibody forms a dimer as determined by HPSEC upon shaking a vial filled to half of its volume with a sample of said formulation for 4 hours at a speed of 400 shakes per minute. In one embodiment, a formulation of the invention comprises MT103, wherein less than 3% of said antibody forms a dimer as determined by HPSEC upon subjecting the formulation to three freeze/thaw cycles.

In one embodiment, a formulation of the invention comprises BiTE® molecules, wherein less than 4% of said antibody forms a dimer as determined by HPSEC upon shaking a vial filled to half of its volume with a sample of said formulation for 4 hours at a speed of 400 shakes per minute. In one embodiment, a formulation of the invention comprises BiTE® molecules, wherein less than 4% of said antibody forms a dimer as determined by HPSEC upon subjecting the formulation to three freeze/thaw cycles.

In one embodiment, a formulation of the invention comprises MT103, wherein less than 4% of said antibody forms a dimer as determined by HPSEC upon shaking a vial filled to half of its volume with a sample of said formulation for 4 hours at a speed of 400 shakes per minute. In one embodiment, a formulation of the invention comprises MT103, wherein less than 4% of said antibody forms a dimer as determined by HPSEC upon subjecting the formulation to three freeze/thaw cycles.

In one embodiment, a formulation of the invention comprises BiTE® molecules, wherein less than 5% of said antibody forms a dimer as determined by HPSEC upon shaking a vial filled to half of its volume with a sample of said formulation for 4 hours at a speed of 400 shakes per minute. In one embodiment, a formulation of the invention comprises BiTE® molecules, wherein less than 5% of said antibody forms a dimer as determined by HPSEC upon subjecting the formulation to three freeze/thaw cycles.

In one embodiment, a formulation of the invention comprises MT103, wherein less than 5% of said antibody forms a dimer as determined by HPSEC upon shaking a vial filled to half of its volume with a sample of said formulation for 4 hours at a speed of 400 shakes per minute. In one embodiment, a formulation of the invention comprises MT103, wherein less than 5% of said antibody forms a dimer as determined by HPSEC upon subjecting the formulation to three freeze/thaw cycles.

5.1.1.7. Recovery Following Lyophilization

In one embodiment, a formulation of the invention comprises BiTE® molecules, wherein at least about 90%, at least about 95%, at least about 97%, at least about 98%, or at least about 99% of said antibody may be recovered from a vial upon shaking said vial for 4 hours at a speed of 400 shakes per minute wherein said vial is filled to half of its volume with said formulation. In another embodiment, a formulation of the invention comprises BiTE® molecules, wherein at least about 90%, at least about 95%, at least about 97%, at least about 98%, or at least about 99% of said antibody may be recovered from a vial upon subjecting the formulation to three freeze/thaw cycles wherein said vial is filled to half of its volume with said formulation. In a further embodiment, a formulation of the invention comprises BiTE® molecules, wherein at least about 90%, at least about 95%, at least about 97%, at least about 98%, or at least about 99% of said antibody may be recovered by reconstituting a lyophilized cake generated from said formulation.

In one embodiment, a formulation of the invention comprises MT103, wherein at least about 90%, at least about 95%, at least about 97%, at least about 98%, or at least about 99% of said antibody may be recovered from a vial upon shaking said vial for 4 hours at a speed of 400 shakes per minute wherein said vial is filled to half of its volume with said formulation. In another embodiment, a formulation of the invention comprises MT103, wherein at least about 90%, at least about 95%, at least about 97%, at least about 98%, or at least about 99% of said antibody may be recovered from a vial upon subjecting the formulation to three freeze/thaw cycles wherein said vial is filled to half of its volume with said formulation. In a further embodiment, a formulation of the invention comprises MT103, wherein at least about 90%, at least about 95%, at least about 97%, at least about 98%, or at least about 99% of said antibody may be recovered by reconstituting a lyophilized cake generated from said formulation.

In one embodiment, a formulation of the invention comprises BiTE® molecules, wherein at least about 90% of said antibody may be recovered from a vial upon shaking said vial for 4 hours at a speed of 400 shakes per minute wherein said vial is filled to half of its volume with said formulation. In another embodiment, a formulation of the invention comprises BiTE® molecules, wherein at least about 90% of said antibody may be recovered from a vial upon subjecting the formulation to three freeze/thaw cycles wherein said vial is filled to half of its volume with said formulation. In a further embodiment, a formulation of the invention comprises BiTE® molecules, wherein at least about 90% of said antibody may be recovered by reconstituting a lyophilized cake generated from said formulation.

In one embodiment, a formulation of the invention comprises MT103, wherein at least about 90% of said antibody may be recovered from a vial upon shaking said vial for 4 hours at a speed of 400 shakes per minute wherein said vial is filled to half of its volume with said formulation. In another embodiment, a formulation of the invention comprises MT103, wherein at least about 90% of said antibody may be recovered from a vial upon subjecting the formulation to three freeze/thaw cycles wherein said vial is filled to half of its volume with said formulation. In a further embodiment, a formulation of the invention comprises MT103, wherein at least about 90% of said antibody may be recovered by reconstituting a lyophilized cake generated from said formulation.

In one embodiment, a formulation of the invention comprises BiTE® molecules, wherein at least about 95% of said antibody may be recovered from a vial upon shaking said vial for 4 hours at a speed of 400 shakes per minute wherein said vial is filled to half of its volume with said formulation. In another embodiment, a formulation of the invention comprises BiTE® molecules, wherein at least about 95% of said antibody may be recovered from a vial upon subjecting the formulation to three freeze/thaw cycles wherein said vial is filled to half of its volume with said formulation. In a further embodiment, a formulation of the invention comprises BiTE® molecules, wherein at least about 95% of said antibody may be recovered by reconstituting a lyophilized cake generated from said formulation.

In one embodiment, a formulation of the invention comprises MT103, wherein at least about 95% of said antibody may be recovered from a vial upon shaking said vial for 4 hours at a speed of 400 shakes per minute wherein said vial is filled to half of its volume with said formulation. In another embodiment, a formulation of the invention comprises MT103, wherein at least about 95% of said antibody may be recovered from a vial upon subjecting the formulation to three freeze/thaw cycles wherein said vial is filled to half of its volume with said formulation. In a further embodiment, a formulation of the invention comprises MT103, wherein at least about 95% of said antibody may be recovered by reconstituting a lyophilized cake generated from said formulation.

In one embodiment, a formulation of the invention comprises BiTE® molecules, wherein at least about 97% of said antibody may be recovered from a vial upon shaking said vial for 4 hours at a speed of 400 shakes per minute wherein said vial is filled to half of its volume with said formulation. In another embodiment, a formulation of the invention comprises BiTE® molecules, wherein at least about 97% of said antibody may be recovered from a vial upon subjecting the formulation to three freeze/thaw cycles wherein said vial is filled to half of its volume with said formulation. In a further embodiment, a formulation of the invention comprises BiTE® molecules, wherein at least about 97% of said antibody may be recovered by reconstituting a lyophilized cake generated from said formulation.

In one embodiment, a formulation of the invention comprises MT103, wherein at least about 97% of said antibody may be recovered from a vial upon shaking said vial for 4 hours at a speed of 400 shakes per minute wherein said vial is filled to half of its volume with said formulation. In another embodiment, a formulation of the invention comprises MT103, wherein at least about 97% of said antibody may be recovered from a vial upon subjecting the formulation to three freeze/thaw cycles wherein said vial is filled to half of its volume with said formulation. In a further embodiment, a formulation of the invention comprises MT103, wherein at least about 97% of said antibody may be recovered by reconstituting a lyophilized cake generated from said formulation.

In one embodiment, a formulation of the invention comprises BiTE® molecules, wherein at least about 98% of said antibody may be recovered from a vial upon shaking said vial for 4 hours at a speed of 400 shakes per minute wherein said vial is filled to half of its volume with said formulation. In another embodiment, a formulation of the invention comprises BiTE® molecules, wherein at least about 98% of said antibody may be recovered from a vial upon subjecting the formulation to three freeze/thaw cycles wherein said vial is filled to half of its volume with said formulation. In a further embodiment, a formulation of the invention comprises BiTE® molecules, wherein at least about 98% of said antibody may be recovered by reconstituting a lyophilized cake generated from said formulation.

In one embodiment, a formulation of the invention comprises MT103, wherein at least about 98% of said antibody may be recovered from a vial upon shaking said vial for 4 hours at a speed of 400 shakes per minute wherein said vial is filled to half of its volume with said formulation. In another embodiment, a formulation of the invention comprises MT103, wherein at least about 98% of said antibody may be recovered from a vial upon subjecting the formulation to three freeze/thaw cycles wherein said vial is filled to half of its volume with said formulation. In a further embodiment, a formulation of the invention comprises MT103, wherein at least about 98% of said antibody may be recovered by reconstituting a lyophilized cake generated from said formulation.

In one embodiment, a formulation of the invention comprises BiTE® molecules, wherein at least about 99% of said antibody may be recovered from a vial upon shaking said vial for 4 hours at a speed of 400 shakes per minute wherein said vial is filled to half of its volume with said formulation. In another embodiment, a formulation of the invention comprises BiTE® molecules, wherein at least about 99% of said antibody may be recovered from a vial upon subjecting the formulation to three freeze/thaw cycles wherein said vial is filled to half of its volume with said formulation. In a further embodiment, a formulation of the invention comprises BiTE® molecules, wherein at least about 99% of said antibody may be recovered by reconstituting a lyophilized cake generated from said formulation.

In one embodiment, a formulation of the invention comprises MT103, wherein at least about 99% of said antibody may be recovered from a vial upon shaking said vial for 4 hours at a speed of 400 shakes per minute wherein said vial is filled to half of its volume with said formulation. In another embodiment, a formulation of the invention comprises MT103, wherein at least about 99% of said antibody may be recovered from a vial upon subjecting the formulation to three freeze/thaw cycles wherein said vial is filled to half of its volume with said formulation. In a further embodiment, a formulation of the invention comprises MT103, wherein at least about 99% of said antibody may be recovered by reconstituting a lyophilized cake generated from said formulation.

5.1.1.8. Fragmentation

In one embodiment, a formulation of the invention comprises BiTE® molecules, wherein less than 5% of said antibody is fragmented as determined by RP-HPLC upon storage at about 40° C. for at least about 1 day, at least about 2 days, at least about 3 days, at least about 4 days, at least about 5 days, at least about 6 days, or at least about 7 days. In one embodiment, a formulation of the invention comprises BiTE® molecules, wherein less than 5% of said antibody is fragmented as determined by RP-HPLC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises BiTE® molecules, wherein less than 5% of said antibody is fragmented as determined by RP-HPLC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises BiTE® molecules, wherein less than 5% of said antibody is fragmented as determined by RP-HPLC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises BiTE® molecules, wherein less than 5% of said antibody is fragmented as determined by RP-HPLC upon storage at about 40° C. for about 1 day, about 2 days, about 3 days, about 4 days, about 5 days, about 6 days, or about 7 days. In one embodiment, a formulation of the invention comprises BiTE® molecules, wherein less than 5% of said antibody is fragmented as determined by RP-HPLC upon storage at about 40° C. for about 1 week, about 2 weeks, about 3 weeks, about 4 weeks, about 5 weeks, or about 6 weeks.

In one embodiment, a formulation of the invention comprises BiTE® molecules, wherein less than 5% of said antibody is fragmented as determined by RP-HPLC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises BiTE® molecules, wherein less than 5% of said antibody is fragmented as determined by RP-HPLC upon storage at about 5° C. for about 1 month, about 2 months, about 3 months, about 4 months, about 5 months, about 6 months, about 7 months, about 8 months, about 9 months, about 10 months, about 11 months, or about 12 months.

In one embodiment, a formulation of the invention comprises MT103, wherein less than 5% of said antibody is fragmented as determined by RP-HPLC upon storage at about 40° C. for at least about 1 day, at least about 2 days, at least about 3 days, at least about 4 days, at least about 5 days, at least about 6 days, or at least about 7 days. In one embodiment, a formulation of the invention comprises MT103, wherein less than 5% of said antibody is fragmented as determined by RP-HPLC upon storage at about 40° C. for at least about 1 week, at least about 2 weeks, at least about 3 weeks, at least about 4 weeks, at least about 5 weeks, or at least about 6 weeks.

In one embodiment, a formulation of the invention comprises MT103, wherein less than 5% of said antibody is fragmented as determined by RP-HPLC upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention comprises MT103, wherein less than 5% of said antibody is fragmented as determined by RP-HPLC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention comprises MT103, wherein less than 5% of said antibody is fragmented as determined by RP-HPLC upon storage at about 40° C. for about 1 day, about 2 days, about 3 days, about 4 days, about 5 days, about 6 days, or about 7 days. In one embodiment, a formulation of the invention comprises MT103, wherein less than 5% of said antibody is fragmented as determined by RP-HPLC upon storage at about 40° C. for about 1 week, about 2 weeks, about 3 weeks, about 4 weeks, about 5 weeks, or about 6 weeks.

In one embodiment, a formulation of the invention comprises MT103, wherein less than 5% of said antibody is fragmented as determined by RP-HPLC upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention comprises MT103, wherein less than 5% of said antibody is fragmented as determined by RP-HPLC upon storage at about 5° C. for about 1 month, about 2 months, about 3 months, about 4 months, about 5 months, about 6 months, about 7 months, about 8 months, about 9 months, about 10 months, about 11 months, or about 12 months.

5.1.1.9. Visual Characteristics

In one embodiment, a formulation of the invention is clear and colorless as determined by visual inspection upon storage at about 40° C. f for at least about 1 day, at least about 2 days, at least about 3 days, at least about 4 days, at least about 5 days, at least about 6 days, or at least about 7 days. In one embodiment, a formulation of the invention is clear and colorless as determined by visual inspection upon storage at about 40° C. for at least about 1 week, at least about 2 weeks, at least about 3 weeks, at least about 4 weeks, at least about 5 weeks, or at least about 6 weeks.

In one embodiment, a formulation of the invention is clear and colorless as determined by visual inspection upon storage at about 5° C. for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In one embodiment, a formulation of the invention is clear and colorless as determined by visual inspection upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

In one embodiment, a formulation of the invention is clear and colorless as determined by visual inspection upon storage at about 40° C. f for about 1 day, about 2 days, about 3 days, about 4 days, about 5 days, about 6 days, or about 7 days. In one embodiment, a formulation of the invention is clear and colorless as determined by visual inspection upon storage at about 40° C. for about 1 week, about 2 weeks, about 3 weeks, about 4 weeks, about 5 weeks, or about 6 weeks.

In one embodiment, a formulation of the invention is clear and colorless as determined by visual inspection upon storage at about 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In one embodiment, a formulation of the invention is clear and colorless as determined by visual inspection upon storage at about 5° C. for about 1 month, about 2 months, about 3 months, about 4 months, about 5 months, about 6 months, about 7 months, about 8 months, about 9 months, about 10 months, about 11 months, or about 12 months.

5.2. Lyophilized Formulations

The present invention also encompasses lyophilized formulations comprising bispecific antibodies which formulations exhibit stability, low to undetectable levels of antibody fragmentation, low to undetectable levels of aggregation, and very little to no loss of the biological activities of the bispecific antibodies during manufacture, preparation, transportation, and storage. In certain embodiments, a lyophilized formulation of the invention comprises bispecific antibodies comprising at least a first and a second binding site specific for the CD3 and CD19 antigens, respectively. In specific embodiments, the present invention provides lyophilized formulations comprising MT103 (see, U.S. Pat. No. 7,112,324).

In one embodiment, a lyophilized formulation of the invention comprises BiTE® molecules. In one embodiment, a lyophilized formulation of the invention comprises BiTE® molecules that comprises at least a first and a second binding site specific for the CD3 and CD19 antigens, respectively. In a further embodiment, a lyophilized formulation of the invention comprises BiTE® molecules wherein said antibody comprises an anti-CD19 VL domain having the amino acid sequence of SEQ ID NO:1, an anti-CD19 VH domain having the amino acid sequence of SEQ ID NO:2, an anti-CD3 VH domain having the amino acid sequence of SEQ ID NO:3 and an anti-CD3 VL domain having the amino acid sequence of SEQ ID NO:4. In a specific embodiment, a lyophilized formulation of the invention comprises MT103, wherein said antibody comprises the amino acid sequence of SEQ ID NO:5.

The invention encompasses stable lyophilized formulations comprising a single BiTE® molecule of interest, for example, BiTE® molecules that comprises at least a first and a second binding site specific for the CD3 and CD19 antigens, respectively. The invention also encompasses stable lyophilized formulations comprising two or more bispecific antibodies of interest, for example, bispecific antibodies that comprise at least a first and a second binding site specific for the CD3 and CD19 antigens, respectively. In a specific embodiment, a stable lyophilized formulation of the invention comprises MT103. In another embodiment, a stable lyophilized formulation of the invention comprises two or more bispecific antibodies, wherein one of the bispecific antibodies is MT103.

In one embodiment, a lyophilized formulation of the invention comprises citrate, lysine HCl, trehalose, and Polysorbate 80. In one embodiment, a lyophilized formulation of the invention comprises lysine HCl, trehalose, and Polysorbate 80. In one embodiment, a lyophilized formulation of the invention comprises citrate, trehalose, and Polysorbate 80. In one embodiment, a lyophilized formulation of the invention comprises citrate, lysine HCl, and Polysorbate 80. In one embodiment, a lyophilized formulation of the invention comprises citrate, lysine HCl, and trehalose. In one embodiment, a lyophilized formulation of the invention comprises citrate and lysine HCl. In one embodiment, a lyophilized formulation of the invention comprises citrate and trehalose. In one embodiment, a lyophilized formulation of the invention comprises citrate and Polysorbate 80. In one embodiment, a lyophilized formulation of the invention comprises lysine HCl and trehalose. In one embodiment, a lyophilized formulation of the invention comprises lysine HCl and Polysorbate 80. In one embodiment, a lyophilized formulation of the invention comprises trehalose, and Polysorbate 80. In one embodiment, a lyophilized formulation of the invention comprises lysine HCl.

In one embodiment, a lyophilized formulation of the invention comprises citrate, lysine HCl, trehalose and Polysorbate 80. In one embodiment, a lyophilized formulation of the invention comprises citrate, lysine HCl, and trehalose at a molar ratio of between about 1 and about 5 mole citrate to between about 4 and about 40 mole trehalose to between about 5 and about 20 mole lysine HCl. In a specific embodiment, a lyophilized formulation of the invention comprises citrate, lysine HCl, and trehalose at a molar ratio of about 1 mole citrate to about 16 mole trehalose to about 8 mole lysine HCl.

In a specific embodiment, a lyophilized formulation of the invention comprises MT103, citrate, lysine HCl, trehalose and Polysorbate 80.

In a specific embodiment, a lyophilized formulation of the invention consists of MT103, citrate, lysine HCl, trehalose and Polysorbate 80.

In one embodiment, a lyophilized formulation of the invention has a residual moisture content that is less than about 10%, less than about 5%, less than about 3%, less than about 2%, less than about 1%. In a further embodiment, a lyophilized formulation of the invention has a residual moisture content of about 10%, about 5%, about 4%, about 3%, about 2%, about 1%.

In certain embodiments, a lyophilized formulation of the invention is derived from a liquid formulation of the invention.

5.2.1. Stability of Lyophilized Formulations

In one embodiment, a lyophilized lyophilized formulation of the invention comprises BiTE® molecules that is susceptible to aggregation, fragmentation and/or loss due to absorption to contact surfaces.

In one embodiment, a lyophilized formulation of the invention stabilizes BiTE® molecules. In one embodiment, a lyophilized formulation of the invention prevents aggregation of BiTE® molecules. In another embodiment, a lyophilized formulation of the invention prevents fragmentation of BiTE® molecules. In a further embodiment, a lyophilized formulation of the invention prevents loss of BiTE® molecules due to absorption to contact surfaces.

In one embodiment, a lyophilized formulation of the invention stabilizes MT103. In one embodiment, a lyophilized formulation of the invention prevents aggregation of MT103. In another embodiment, a lyophilized formulation of the invention prevents fragmentation of MT103. In a further embodiment, a lyophilized formulation of the invention prevents loss of MT103 due to absorption to contact surfaces.

In one embodiment, a lyophilized formulation of the invention stabilizes BiTE® molecules. In one embodiment, a lyophilized formulation of the invention reduces aggregation of BiTE® molecules. In another embodiment, a lyophilized formulation of the invention reduces fragmentation of BiTE® molecules. In a further embodiment, a lyophilized formulation of the invention reduces loss of BiTE® molecules due to absorption to contact surfaces.

In one embodiment, a lyophilized formulation of the invention stabilizes MT103. In one embodiment, a lyophilized formulation of the invention reduces aggregation of MT103. In another embodiment, a lyophilized formulation of the invention reduces fragmentation of MT103. In a further embodiment, a lyophilized formulation of the invention reduces loss of MT103 due to absorption to contact surfaces.

5.2.2. Stability Over Time

In one embodiment, a lyophilized formulation of the invention is stable upon storage at about 40° C. for at least about 1 day, at least about 2 days, at least about 3 days, at least about 4 days, at least about 5 days, at least about 6 days, at least about 7 days, at least about 8 days, at least about 9 days, at least about 10 days, at least about 15 days, at least about 20 days, at least about 25 days, or at least about 30 days. In one embodiment, a lyophilized formulation of the invention is stable upon storage at about 40° C. for at least about 1 week, at least about 2 weeks, at least about 3 weeks, or at least about 4 weeks. In one embodiment, a lyophilized formulation of the invention is stable upon storage at about 40° C. for at least about 1 month, at least about 2 months, at least about 3 months, at least about 4 months, at least about 5 months, or at least about 6 months.

In one embodiment, a lyophilized formulation of the invention is stable upon storage at about 4° C. for at least about 1 day, at least about 2 days, at least about 3 days, at least about 4 days, at least about 5 days, at least about 6 days, at least about 7 days, at least about 8 days, at least about 9 days, at least about 10 days. In one embodiment, a lyophilized formulation of the invention is stable upon storage at about 4° C. for at least about 1 week, at least about 2 weeks, at least about 3 weeks, or at least about 4 weeks. In one embodiment, a lyophilized formulation of the invention is stable upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention is stable upon storage at about 5° C. for at least about 1 year, at least about 2 years, at least about 3 years, at least about 4 years, at least about 5 years, at least about 6 years, at least about 7 years, at least about 8 years, at least about 9 years, at least about 10 years, at least about 11 years, or at least about 12 years.

In one embodiment, a lyophilized formulation of the invention is stable upon storage at about 40° C. for about 1 day, about 2 days, about 3 days, about 4 days, about 5 days, about 6 days, about 7 days, about 8 days, about 9 days, about 10 days, about 15 days, about 20 days, about 25 days, or about 30 days. In one embodiment, a lyophilized formulation of the invention is stable upon storage at about 40° C. for about 1 week, about 2 weeks, about 3 weeks, or about 4 weeks. In one embodiment, a lyophilized formulation of the invention is stable upon storage at about 40° C. for about 1 month, about 2 months, about 3 months, about 4 months, about 5 months, or about 6 months.

In one embodiment, a lyophilized formulation of the invention is stable upon storage at about 4° C. for about 1 day, about 2 days, about 3 days, about 4 days, about 5 days, about 6 days, about 7 days, about 8 days, about 9 days, about 10 days. In one embodiment, a lyophilized formulation of the invention is stable upon storage at about 4° C. for about 1 week, about 2 weeks, about 3 weeks, or about 4 weeks. In one embodiment, a lyophilized formulation of the invention is stable upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention is stable upon storage at about 5° C. for about 1 year, about 2 years, about 3 years, about 4 years, about 5 years, about 6 years, about 7 years, about 8 years, about 9 years, about 10 years, about 11 years, or about 12 years.

5.2.2.1. Protein Recovery

In one embodiment, a lyophilized formulation of the invention comprises BiTE® molecules, wherein at least about 90% of said antibody is recovered by reconstituting said lyophilized formulation upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein at least about 90% of said antibody is recovered by reconstituting said lyophilized formulation upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein at least about 90% of said antibody is recovered by reconstituting said lyophilized formulation upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein at least about 90% of said antibody is recovered by reconstituting said lyophilized formulation upon storage at about 5° C. for at least about 1 year, at least about 2 years, at least about 3 years, at least about 4 years, or at least about 5 years.

In one embodiment, a lyophilized formulation of the invention comprises MT103, wherein at least about 90% of said antibody is recovered by reconstituting said lyophilized formulation upon storage at about 40° C. for about 1 week, about 2 weeks, about 3 weeks, about 4 weeks, about 5 weeks, or about 6 weeks. In one embodiment, a lyophilized formulation of the invention comprises MT103, wherein at least about 90% of said antibody is recovered by reconstituting said lyophilized formulation upon storage at about 40° C. for about 1 month, about 2 months, about 3 months, about 4 months, about 5 months, or about 6 months.

In one embodiment, a lyophilized formulation of the invention comprises MT103, wherein at least about 90% of said antibody is recovered by reconstituting said lyophilized formulation upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein at least about 90% of said antibody is recovered by reconstituting said lyophilized formulation upon storage at about 5° C. for about 1 year, about 2 years, about 3 years, about 4 years, or about 5 years.

In one embodiment, a lyophilized formulation of the invention comprises BiTE® molecules, wherein at least about 95% of said antibody is recovered by reconstituting said lyophilized formulation upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein at least about 95% of said antibody is recovered by reconstituting said lyophilized formulation upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein at least about 95% of said antibody is recovered by reconstituting said lyophilized formulation upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein at least about 95% of said antibody is recovered by reconstituting said lyophilized formulation upon storage at about 5° C. for at least about 1 year, at least about 2 years, at least about 3 years, at least about 4 years, or at least about 5 years.

In one embodiment, a lyophilized formulation of the invention comprises MT103, wherein at least about 95% of said antibody is recovered by reconstituting said lyophilized formulation upon storage at about 40° C. for about 1 week, about 2 weeks, about 3 weeks, about 4 weeks, about 5 weeks, or about 6 weeks. In one embodiment, a lyophilized formulation of the invention comprises MT103, wherein at least about 95% of said antibody is recovered by reconstituting said lyophilized formulation upon storage at about 40° C. for about 1 month, about 2 months, about 3 months, about 4 months, about 5 months, or about 6 months.

In one embodiment, a lyophilized formulation of the invention comprises MT103, wherein at least about 95% of said antibody is recovered by reconstituting said lyophilized formulation upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein at least about 95% of said antibody is recovered by reconstituting said lyophilized formulation upon storage at about 5° C. for about 1 year, about 2 years, about 3 years, about 4 years, or about 5 years.

In one embodiment, a lyophilized formulation of the invention comprises BiTE® molecules, wherein at least about 97% of said antibody is recovered by reconstituting said lyophilized formulation upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE®molecules, wherein at least about 97% of said antibody is recovered by reconstituting said lyophilized formulation upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein at least about 97% of said antibody is recovered by reconstituting said lyophilized formulation upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein at least about 97% of said antibody is recovered by reconstituting said lyophilized formulation upon storage at about 5° C. for at least about 1 year, at least about 2 years, at least about 3 years, at least about 4 years, or at least about 5 years.

In one embodiment, a lyophilized formulation of the invention comprises MT103, wherein at least about 97% of said antibody is recovered by reconstituting said lyophilized formulation upon storage at about 40° C. for about 1 week, about 2 weeks, about 3 weeks, about 4 weeks, about 5 weeks, or about 6 weeks. In one embodiment, a lyophilized formulation of the invention comprises MT103, wherein at least about 97% of said antibody is recovered by reconstituting said lyophilized formulation upon storage at about 40° C. for about 1 month, about 2 months, about 3 months, about 4 months, about 5 months, or about 6 months.

In one embodiment, a lyophilized formulation of the invention comprises MT103, wherein at least about 97% of said antibody is recovered by reconstituting said lyophilized formulation upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein at least about 97% of said antibody is recovered by reconstituting said lyophilized formulation upon storage at about 5° C. for about 1 year, about 2 years, about 3 years, about 4 years, or about 5 years.

In one embodiment, a lyophilized formulation of the invention comprises BiTE® molecules, wherein at least about 98% of said antibody is recovered by reconstituting said lyophilized formulation upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein at least about 98% of said antibody is recovered by reconstituting said lyophilized formulation upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein at least about 98% of said antibody is recovered by reconstituting said lyophilized formulation upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein at least about 98% of said antibody is recovered by reconstituting said lyophilized formulation upon storage at about 5° C. for at least about 1 year, at least about 2 years, at least about 3 years, at least about 4 years, or at least about 5 years.

In one embodiment, a lyophilized formulation of the invention comprises MT103, wherein at least about 98% of said antibody is recovered by reconstituting said lyophilized formulation upon storage at about 40° C. for about 1 week, about 2 weeks, about 3 weeks, about 4 weeks, about 5 weeks, or about 6 weeks. In one embodiment, a lyophilized formulation of the invention comprises MT103, wherein at least about 98% of said antibody is recovered by reconstituting said lyophilized formulation upon storage at about 40° C. for about 1 month, about 2 months, about 3 months, about 4 months, about 5 months, or about 6 months.

In one embodiment, a lyophilized formulation of the invention comprises MT103, wherein at least about 98% of said antibody is recovered by reconstituting said lyophilized formulation upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein at least about 98% of said antibody is recovered by reconstituting said lyophilized formulation upon storage at about 5° C. for about 1 year, about 2 years, about 3 years, about 4 years, or about 5 years.

In one embodiment, a lyophilized formulation of the invention comprises BiTE® molecules, wherein at least about 99% of said antibody is recovered by reconstituting said lyophilized formulation upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein at least about 99% of said antibody is recovered by reconstituting said lyophilized formulation upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein at least about 99% of said antibody is recovered by reconstituting said lyophilized formulation upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein at least about 99% of said antibody is recovered by reconstituting said lyophilized formulation upon storage at about 5° C. for at least about 1 year, at least about 2 years, at least about 3 years, at least about 4 years, or at least about 5 years.

In one embodiment, a lyophilized formulation of the invention comprises MT103, wherein at least about 99% of said antibody is recovered by reconstituting said lyophilized formulation upon storage at about 40° C. for about 1 week, about 2 weeks, about 3 weeks, about 4 weeks, about 5 weeks, or about 6 weeks. In one embodiment, a lyophilized formulation of the invention comprises MT103, wherein at least about 99% of said antibody is recovered by reconstituting said lyophilized formulation upon storage at about 40° C. for about 1 month, about 2 months, about 3 months, about 4 months, about 5 months, or about 6 months.

In one embodiment, a lyophilized formulation of the invention comprises MT103, wherein at least about 99% of said antibody is recovered by reconstituting said lyophilized formulation upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein at least about 99% of said antibody is recovered by reconstituting said lyophilized formulation upon storage at about 5° C. for about 1 year, about 2 years, about 3 years, about 4 years, or about 5 years.

5.2.2.2. Binding Activity

In one embodiment, a lyophilized formulation of the invention comprises BiTE® molecules, wherein said antibody retains at least 90% of binding ability to its target polypeptides compared to a reference antibody representing the antibody prior to storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein said antibody retains at least 90% of binding ability to its target polypeptides compared to a reference antibody representing the antibody prior to storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein said antibody retains at least 90% of binding ability to its target polypeptides compared to a reference antibody representing the antibody prior to storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein said antibody retains at least 90% of binding ability to its target polypeptides compared to a reference antibody representing the antibody prior to storage at about 5° C. for at least about 1 year, at least about 2 years, at least about 3 years, at least about 4 years, or at least about 5 years.

In one embodiment, a lyophilized formulation of the invention comprises BiTE® molecules, wherein said antibody retains 90% of binding ability to its target polypeptides compared to a reference antibody representing the antibody prior to storage at about 40° C. for about 1 week, about 2 weeks, about 3 weeks, about 4 weeks, about 5 weeks, or about 6 weeks. In one embodiment, a lyophilized formulation of the invention comprises BiTE® molecules, wherein said antibody retains 90% of binding ability to its target polypeptides compared to a reference antibody representing the antibody prior to storage at about 40° C. for about 1 month, about 2 months, about 3 months, about 4 months, about 5 months, or about 6 months.

In one embodiment, a lyophilized formulation of the invention comprises BiTE® molecules, wherein said antibody retains 90% of binding ability to its target polypeptides compared to a reference antibody representing the antibody prior to storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises BiTE® molecules, wherein said antibody retains 90% of binding ability to its target polypeptides compared to a reference antibody representing the antibody prior to storage at about 5° C. for about 1 year, about 2 years, about 3 years, about 4 years, or about 5 years.

In one embodiment, a lyophilized formulation of the invention comprises MT103, wherein said antibody retains at least 90% of binding ability to CD19 and CD3 antigens compared to a reference antibody representing the antibody prior to storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises MT103, wherein said antibody retains at least 90% of binding ability to CD19 and CD3 antigens compared to a reference antibody representing the antibody prior to storage at about 40° C. for at least about 1 month, at least about 2 months, at least about 3 months, at least about 4 months, at least about 5 months, or at least about 6 months.

In one embodiment, a lyophilized formulation of the invention comprises MT103, wherein said antibody retains at least 90% of binding ability to CD19 and CD3 antigens compared to a reference antibody representing the antibody prior to storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises MT103, wherein said antibody retains at least 90% of binding ability to CD19 and CD3 antigens compared to a reference antibody representing the antibody prior to storage at about 5° C. for at least about 1 year, at least about 2 years, at least about 3 years, at least about 4 years, or at least about 5 years.

In one embodiment, a lyophilized formulation of the invention comprises MT103, wherein said antibody retains 90% of binding ability to CD19 and CD3 antigens compared to a reference antibody representing the antibody prior to storage at about 40° C. for about 1 week, about 2 weeks, about 3 weeks, about 4 weeks, about 5 weeks, or about 6 weeks. In one embodiment, a lyophilized formulation of the invention comprises MT103, wherein said antibody retains 90% of binding ability to CD19 and CD3 antigens compared to a reference antibody representing the antibody prior to storage at about 40° C. for about 1 month, about 2 months, about 3 months, about 4 months, about 5 months, or about 6 months.

In one embodiment, a lyophilized formulation of the invention comprises MT103, wherein said antibody retains 90% of binding ability to CD19 and CD3 antigens compared to a reference antibody representing the antibody prior to storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein said antibody retains 90% of binding ability to CD19 and CD3 antigens compared to a reference antibody representing the antibody prior to storage at about 5° C. for about 1 year, about 2 years, about 3 years, about 4 years, or about 5 years.

5.2.2.3. Aggregate Formation

In one embodiment, a lyophilized formulation of the invention comprises BiTE® molecules, wherein less than 1% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 1% of said antibody forms an aggregate as determined by HPSEC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 1% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 1% of said antibody forms an aggregate as determined by HPSEC upon storage at about 5° C. for at least about 1 year, at least about 2 years, at least about 3 years, at least about 4 years, or at least about 5 years.

In one embodiment, a lyophilized formulation of the invention comprises MT103, wherein less than 1% of said antibody forms an aggregate as determined by HPSEC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 1% of said antibody forms an aggregate as determined by HPSEC upon storage at about 40° C. for about 1 month, about 2 months, about 3 months, about 4 months, about 5 months, or about 6 months.

In one embodiment, a lyophilized formulation of the invention comprises MT103, wherein less than 1% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 1% of said antibody forms an aggregate as determined by HPSEC upon storage at about 5° C. for about 1 year, about 2 years, about 3 years, about 4 years, or about 5 years.

In one embodiment, a lyophilized formulation of the invention comprises BiTE® molecules, wherein less than 2% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 2% of said antibody forms an aggregate as determined by HPSEC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 2% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 2% of said antibody forms an aggregate as determined by HPSEC upon storage at about 5° C. for at least about 1 year, at least about 2 years, at least about 3 years, at least about 4 years, or at least about 5 years.

In one embodiment, a lyophilized formulation of the invention comprises MT103, wherein less than 2% of said antibody forms an aggregate as determined by HPSEC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 2% of said antibody forms an aggregate as determined by HPSEC upon storage at about 40° C. for about 1 month, about 2 months, about 3 months, about 4 months, about 5 months, or about 6 months.

In one embodiment, a lyophilized formulation of the invention comprises MT103, wherein less than 2% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 2% of said antibody forms an aggregate as determined by HPSEC upon storage at about 5° C. for about 1 year, about 2 years, about 3 years, about 4 years, or about 5 years.

In one embodiment, a lyophilized formulation of the invention comprises BiTE® molecules, wherein less than 3% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 3% of said antibody forms an aggregate as determined by HPSEC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 3% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 3% of said antibody forms an aggregate as determined by HPSEC upon storage at about 5° C. for at least about 1 year, at least about 2 years, at least about 3 years, at least about 4 years, or at least about 5 years.

In one embodiment, a lyophilized formulation of the invention comprises MT103, wherein less than 3% of said antibody forms an aggregate as determined by HPSEC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 3% of said antibody forms an aggregate as determined by HPSEC upon storage at about 40° C. for about 1 month, about 2 months, about 3 months, about 4 months, about 5 months, or about 6 months.

In one embodiment, a lyophilized formulation of the invention comprises MT103, wherein less than 3% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 3% of said antibody forms an aggregate as determined by HPSEC upon storage at about 5° C. for about 1 year, about 2 years, about 3 years, about 4 years, or about 5 years.

In one embodiment, a lyophilized formulation of the invention comprises BiTE® molecules, wherein less than 4% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 4% of said antibody forms an aggregate as determined by HPSEC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 4% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 4% of said antibody forms an aggregate as determined by HPSEC upon storage at about 5° C. for at least about 1 year, at least about 2 years, at least about 3 years, at least about 4 years, or at least about 5 years.

In one embodiment, a lyophilized formulation of the invention comprises MT103, wherein less than 4% of said antibody forms an aggregate as determined by HPSEC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 4% of said antibody forms an aggregate as determined by HPSEC upon storage at about 40° C. for about 1 month, about 2 months, about 3 months, about 4 months, about 5 months, or about 6 months.

In one embodiment, a lyophilized formulation of the invention comprises MT103, wherein less than 4% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 4% of said antibody forms an aggregate as determined by HPSEC upon storage at about 5° C. for about 1 year, about 2 years, about 3 years, about 4 years, or about 5 years.

In one embodiment, a lyophilized formulation of the invention comprises BiTE® molecules, wherein less than 5% of said antibody forms an aggregate as determined by HPSEC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 5% of said antibody forms an aggregate as determined by HPSEC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 5% of said antibody forms an aggregate as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 5% of said antibody forms an aggregate as determined by HPSEC upon storage at about 5° C. for at least about 1 year, at least about 2 years, at least about 3 years, at least about 4 years, or at least about 5 years.

In one embodiment, a lyophilized formulation of the invention comprises MT103, wherein less than 5% of said antibody forms an aggregate as determined by HPSEC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 5% of said antibody forms an aggregate as determined by HPSEC upon storage at about 40° C. for about 1 month, about 2 months, about 3 months, about 4 months, about 5 months, or about 6 months.

In one embodiment, a lyophilized formulation of the invention comprises MT103, wherein less than 5% of said antibody forms an aggregate as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 5% of said antibody forms an aggregate as determined by HPSEC upon storage at about 5° C. for about 1 year, about 2 years, about 3 years, about 4 years, or about 5 years.

5.2.2.4. Dimer Formation

In one embodiment, a lyophilized formulation of the invention comprises BiTE® molecules, wherein less than 1% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 1% of said antibody forms a dimer as determined by HPSEC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 1% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 1% of said antibody forms a dimer as determined by HPSEC upon storage at about 5° C. for at least about 1 year, at least about 2 years, at least about 3 years, at least about 4 years, or at least about 5 years.

In one embodiment, a lyophilized formulation of the invention comprises MT103, wherein less than 1% of said antibody forms a dimer as determined by HPSEC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 1% of said antibody forms a dimer as determined by HPSEC upon storage at about 40° C. for about 1 month, about 2 months, about 3 months, about 4 months, about 5 months, or about 6 months.

In one embodiment, a lyophilized formulation of the invention comprises MT103, wherein less than 1% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 1% of said antibody forms a dimer as determined by HPSEC upon storage at about 5° C. for about 1 year, about 2 years, about 3 years, about 4 years, or about 5 years.

In one embodiment, a lyophilized formulation of the invention comprises BiTE® molecules, wherein less than 2% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 2% of said antibody forms a dimer as determined by HPSEC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 2% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 2% of said antibody forms a dimer as determined by HPSEC upon storage at about 5° C. for at least about 1 year, at least about 2 years, at least about 3 years, at least about 4 years, or at least about 5 years.

In one embodiment, a lyophilized formulation of the invention comprises MT103, wherein less than 2% of said antibody forms a dimer as determined by HPSEC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 2% of said antibody forms a dimer as determined by HPSEC upon storage at about 40° C. for about 1 month, about 2 months, about 3 months, about 4 months, about 5 months, or about 6 months.

In one embodiment, a lyophilized formulation of the invention comprises MT103, wherein less than 2% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 2% of said antibody forms a dimer as determined by HPSEC upon storage at about 5° C. for about 1 year, about 2 years, about 3 years, about 4 years, or about 5 years.

In one embodiment, a lyophilized formulation of the invention comprises BiTE® molecules, wherein less than 3% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 3% of said antibody forms a dimer as determined by HPSEC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 3% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 3% of said antibody forms a dimer as determined by HPSEC upon storage at about 5° C. for at least about 1 year, at least about 2 years, at least about 3 years, at least about 4 years, or at least about 5 years.

In one embodiment, a lyophilized formulation of the invention comprises MT103, wherein less than 3% of said antibody forms a dimer as determined by HPSEC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 3% of said antibody forms a dimer as determined by HPSEC upon storage at about 40° C. for about 1 month, about 2 months, about 3 months, about 4 months, about 5 months, or about 6 months.

In one embodiment, a lyophilized formulation of the invention comprises MT103, wherein less than 3% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 3% of said antibody forms a dimer as determined by HPSEC upon storage at about 5° C. for about 1 year, about 2 years, about 3 years, about 4 years, or about 5 years.

In one embodiment, a lyophilized formulation of the invention comprises BiTE® molecules, wherein less than 4% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 4% of said antibody forms a dimer as determined by HPSEC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 4% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 4% of said antibody forms a dimer as determined by HPSEC upon storage at about 5° C. for at least about 1 year, at least about 2 years, at least about 3 years, at least about 4 years, or at least about 5 years.

In one embodiment, a lyophilized formulation of the invention comprises MT103, wherein less than 4% of said antibody forms a dimer as determined by HPSEC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 4% of said antibody forms a dimer as determined by HPSEC upon storage at about 40° C. for about 1 month, about 2 months, about 3 months, about 4 months, about 5 months, or about 6 months.

In one embodiment, a lyophilized formulation of the invention comprises MT103, wherein less than 4% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 4% of said antibody forms a dimer as determined by HPSEC upon storage at about 5° C. for about 1 year, about 2 years, about 3 years, about 4 years, or about 5 years.

In one embodiment, a lyophilized formulation of the invention comprises BiTE® molecules, wherein less than 5% of said antibody forms a dimer as determined by HPSEC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 5% of said antibody forms a dimer as determined by HPSEC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 5% of said antibody forms a dimer as determined by HPSEC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 5% of said antibody forms a dimer as determined by HPSEC upon storage at about 5° C. for at least about 1 year, at least about 2 years, at least about 3 years, at least about 4 years, or at least about 5 years.

In one embodiment, a lyophilized formulation of the invention comprises MT103, wherein less than 5% of said antibody forms a dimer as determined by HPSEC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 5% of said antibody forms a dimer as determined by HPSEC upon storage at about 40° C. for about 1 month, about 2 months, about 3 months, about 4 months, about 5 months, or about 6 months.

In one embodiment, a lyophilized formulation of the invention comprises MT103, wherein less than 5% of said antibody forms a dimer as determined by HPSEC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 5% of said antibody forms a dimer as determined by HPSEC upon storage at about 5° C. for about 1 year, about 2 years, about 3 years, about 4 years, or about 5 years.

5.2.2.5. Fragmentation

In one embodiment, a lyophilized formulation of the invention comprises BiTE® molecules, wherein less than 1% of said antibody is fragmented as determined by RP-HPLC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 1% of said antibody is fragmented as determined by RP-HPLC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 1% of said antibody is fragmented as determined by RP-HPLC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 1% of said antibody is fragmented as determined by RP-HPLC upon storage at about 5° C. for at least about 1 year, at least about 2 years, at least about 3 years, at least about 4 years, or at least about 5 years.

In one embodiment, a lyophilized formulation of the invention comprises MT103, wherein less than 1% of said antibody is fragmented as determined by RP-HPLC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 1% of said antibody is fragmented as determined by RP-HPLC upon storage at about 40° C. for about 1 month, about 2 months, about 3 months, about 4 months, about 5 months, or about 6 months.

In one embodiment, a lyophilized formulation of the invention comprises MT103, wherein less than 1% of said antibody is fragmented as determined by RP-HPLC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 1% of said antibody is fragmented as determined by RP-HPLC upon storage at about 5° C. for about 1 year, about 2 years, about 3 years, about 4 years, or about 5 years.

In one embodiment, a lyophilized formulation of the invention comprises BiTE® molecules, wherein less than 2% of said antibody is fragmented as determined by RP-HPLC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 2% of said antibody is fragmented as determined by RP-HPLC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 2% of said antibody is fragmented as determined by RP-HPLC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 2% of said antibody is fragmented as determined by RP-HPLC upon storage at about 5° C. for at least about 1 year, at least about 2 years, at least about 3 years, at least about 4 years, or at least about 5 years.

In one embodiment, a lyophilized formulation of the invention comprises MT103, wherein less than 2% of said antibody is fragmented as determined by RP-HPLC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 2% of said antibody is fragmented as determined by RP-HPLC upon storage at about 40° C. for about 1 month, about 2 months, about 3 months, about 4 months, about 5 months, or about 6 months.

In one embodiment, a lyophilized formulation of the invention comprises MT103, wherein less than 2% of said antibody is fragmented as determined by RP-HPLC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 2% of said antibody is fragmented as determined by RP-HPLC upon storage at about 5° C. for about 1 year, about 2 years, about 3 years, about 4 years, or about 5 years.

In one embodiment, a lyophilized formulation of the invention comprises BiTE® molecules, wherein less than 3% of said antibody is fragmented as determined by RP-HPLC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 3% of said antibody is fragmented as determined by RP-HPLC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 3% of said antibody is fragmented as determined by RP-HPLC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 3% of said antibody is fragmented as determined by RP-HPLC upon storage at about 5° C. for at least about 1 year, at least about 2 years, at least about 3 years, at least about 4 years, or at least about 5 years.

In one embodiment, a lyophilized formulation of the invention comprises MT103, wherein less than 3% of said antibody is fragmented as determined by RP-HPLC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 3% of said antibody is fragmented as determined by RP-HPLC upon storage at about 40° C. for about 1 month, about 2 months, about 3 months, about 4 months, about 5 months, or about 6 months.

In one embodiment, a lyophilized formulation of the invention comprises MT103, wherein less than 3% of said antibody is fragmented as determined by RP-HPLC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 3% of said antibody is fragmented as determined by RP-HPLC upon storage at about 5° C. for about 1 year, about 2 years, about 3 years, about 4 years, or about 5 years.

In one embodiment, a lyophilized formulation of the invention comprises BiTE® molecules, wherein less than 4% of said antibody is fragmented as determined by RP-HPLC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 4% of said antibody is fragmented as determined by RP-HPLC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 4% of said antibody is fragmented as determined by RP-HPLC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 4% of said antibody is fragmented as determined by RP-HPLC upon storage at about 5° C. for at least about 1 year, at least about 2 years, at least about 3 years, at least about 4 years, or at least about 5 years.

In one embodiment, a lyophilized formulation of the invention comprises MT103, wherein less than 4% of said antibody is fragmented as determined by RP-HPLC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 4% of said antibody is fragmented as determined by RP-HPLC upon storage at about 40° C. for about 1 month, about 2 months, about 3 months, about 4 months, about 5 months, or about 6 months.

In one embodiment, a lyophilized formulation of the invention comprises MT103, wherein less than 4% of said antibody is fragmented as determined by RP-HPLC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 4% of said antibody is fragmented as determined by RP-HPLC upon storage at about 5° C. for about 1 year, about 2 years, about 3 years, about 4 years, or about 5 years.

In one embodiment, a lyophilized formulation of the invention comprises BiTE® molecules, wherein less than 5% of said antibody is fragmented as determined by RP-HPLC upon storage at about 40° C. for at least about 1 week, at least about 2 weeks, at least about 3 weeks, at least about 4 weeks, at least about 5 weeks, or at least about 6 weeks. In one embodiment, a lyophilized formulation of the invention comprises BiTE® molecules, wherein less than 5% of said antibody is fragmented as determined by RP-HPLC upon storage at about 40° C. for at least about 1 month, at least about 2 months, at least about 3 months, at least about 4 months, at least about 5 months, or at least about 6 months.

In one embodiment, a lyophilized formulation of the invention comprises BiTE® molecules, wherein less than 5% of said antibody is fragmented as determined by RP-HPLC upon storage at about 5° C. for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In one embodiment, a lyophilized formulation of the invention comprises BiTE® molecules, wherein less than 5% of said antibody is fragmented as determined by RP-HPLC upon storage at about 5° C. for at least about 1 year, at least about 2 years, at least about 3 years, at least about 4 years, or at least about 5 years.

In one embodiment, a lyophilized formulation of the invention comprises MT103, wherein less than 5% of said antibody is fragmented as determined by RP-HPLC upon storage at about 40° C. for about 1 week, about 2 weeks, about 3 weeks, about 4 weeks, about 5 weeks, or about 6 weeks. In one embodiment, a lyophilized formulation of the invention comprises MT103, wherein less than 5% of said antibody is fragmented as determined by RP-HPLC upon storage at about 40° C. for about 1 month, about 2 months, about 3 months, about 4 months, about 5 months, or about 6 months.

In one embodiment, a lyophilized formulation of the invention comprises MT103, wherein less than 5% of said antibody is fragmented as determined by RP-HPLC upon storage at about 5° C. for about 1 month, about 2 months, about 3 months, about 4 months, about 5 months, about 6 months, about 7 months, about 8 months, about 9 months, about 10 months, about 11 months, or about 12 months. In one embodiment, a lyophilized formulation of the invention comprises MT103, wherein less than 5% of said antibody is fragmented as determined by RP-HPLC upon storage at about 5° C. for about 1 year, about 2 years, about 3 years, about 4 years, or about 5 years.

5.3. Reconstituted Formulations

The present invention further provides reconstituted liquid formulations of bispecific antibodies which formulations exhibit stability, low to undetectable levels of antibody fragmentation, low to undetectable levels of aggregation, very little to no loss of the biological activities of the bispecific antibodies, and very little to no loss of antibody through absorption to contact surfaces during preparation, storage and use. In certain embodiments, a reconstituted liquid formulation of the invention comprises BiTE® molecules comprising at least a first and a second binding site specific for the CD3 and CD19 antigens, respectively. In specific embodiments, a reconstituted liquid formulation of the invention comprises MT103 (see, U.S. Pat. No. 7,112,324).

In certain embodiments, reconstituted liquid formulation of the invention is prepared from a lyophilized formulation described herein.

In one embodiment, a reconstituted liquid formulation of the invention comprises BiTE® molecules at the same concentration as the pre-lyophilized liquid formulation.

In one embodiment, a reconstituted liquid formulation of the invention comprises BiTE® molecules at a higher concentration than the pre-lyophilized liquid formulation. In specific embodiments, a reconstituted liquid formulation of the invention comprises about 2 fold, about 3 fold, about 4 fold, about 5 fold, about 6 fold, about 7 fold, about 8 fold, about 9 fold, about 10 fold, about 15 fold, about 20 fold, about 30 fold, about 40 fold higher concentration of BiTE® molecules than the pre-lyophilized liquid formulation.

In one embodiment, a reconstituted liquid formulation of the invention comprises BiTE® molecules at a lower concentration than the pre-lyophilized liquid formulation. In specific embodiments, a reconstituted liquid formulation of the invention comprises about 2 fold, about 3 fold, about 4 fold, about 5 fold, about 6 fold, about 7 fold, about 8 fold, about 9 fold, about 10 fold, about 15 fold, about 20 fold, about 30 fold, about 40 fold lower concentration of BiTE® molecules than the pre-lyophilized liquid formulation.

In one embodiment, a reconstituted liquid formulation of the invention comprises MT103 at the same concentration as the pre-lyophilized liquid formulation.

In one embodiment, a reconstituted liquid formulation of the invention comprises MT103 at a higher concentration than the pre-lyophilized liquid formulation. In specific embodiments, a reconstituted liquid formulation of the invention comprises about 2 fold, about 3 fold, about 4 fold, about 5 fold, about 6 fold, about 7 fold, about 8 fold, about 9 fold, about 10 fold, about 15 fold, about 20 fold, about 30 fold, about 40 fold higher concentration of MT103 than the pre-lyophilized liquid formulation.

In one embodiment, a reconstituted liquid formulation of the invention comprises MT103 at a lower concentration than the pre-lyophilized liquid formulation. In specific embodiments, a reconstituted liquid formulation of the invention comprises about 2 fold, about 3 fold, about 4 fold, about 5 fold, about 6 fold, about 7 fold, about 8 fold, about 9 fold, about 10 fold, about 15 fold, about 20 fold, about 30 fold, about 40 fold lower concentration of MT103 than the pre-lyophilized liquid formulation.

In one embodiment, a reconstituted liquid formulation of the invention is an aqueous formulation. In a specific embodiment, a reconstituted liquid formulation of the invention is an aqueous formulation wherein the aqueous carrier is distilled water.

In one embodiment, a reconstituted formulation of the invention is sterile.

In one embodiment, a reconstituted formulation of the invention is homogeneous.

In one embodiment, a reconstituted formulation of the invention is isotonic. In one embodiment, a reconstituted formulation of the invention is hypotonic. In one embodiment, a reconstituted formulation of the invention is hypertonic.

In one embodiment, a reconstituted liquid formulation of the invention comprises BiTE® molecules. In one embodiment, a reconstituted liquid formulation of the invention comprises BiTE® molecules that comprises at least a first and a second binding site specific for the CD3 and CD19 antigens, respectively. In a further embodiment, a reconstituted liquid formulation of the invention comprises BiTE® molecules wherein said antibody comprises an anti-CD19 VL domain having the amino acid sequence of SEQ ID NO:1, an anti-CD19 VH domain having the amino acid sequence of SEQ ID NO:2, an anti-CD3 VH domain having the amino acid sequence of SEQ ID NO:3 and an anti-CD3 VL domain having the amino acid sequence of SEQ ID NO:4. In a specific embodiment, a reconstituted liquid formulation of the invention comprises MT103, wherein said antibody comprises the amino acid sequence of SEQ ID NO:5.

The invention encompasses reconstituted liquid formulations comprising a single BiTE® molecule of interest, for example, BiTE® molecules that comprises at least a first and a second binding site specific for the CD3 and CD19 antigens, respectively. The invention also encompasses reconstituted liquid formulations comprising two or more bispecific antibodies of interest, for example, bispecific antibodies that comprise at least a first and a second binding site specific for the CD3 and CD19 antigens, respectively. In a specific embodiment, a reconstituted liquid formulation of the invention comprises MT103. In another embodiment, a reconstituted liquid formulation of the invention comprises two or more bispecific antibodies, wherein one of the bispecific antibodies is MT103.

In one embodiment, a reconstituted liquid formulation of the invention comprises at least one excipient selected from the group consisting of citrate, lysine HCl, trehalose, and Polysorbate 80.

In one embodiment, a lyophilized formulation of the invention comprises citrate, lysine HCl, trehalose and Polysorbate 80. In one embodiment, a lyophilized formulation of the invention comprises citrate, lysine HCl, and trehalose at a molar ratio of between about 1 and about 5 mole citrate to between about 4 and about 40 mole trehalose to between about 5 and about 20 mole lysine HCl. In a specific embodiment, a lyophilized formulation of the invention comprises citrate, lysine HCl, and trehalose at a molar ratio of about 1 mole citrate to about 16 mole trehalose to about 8 mole lysine HCl.

In a specific embodiment, a lyophilized formulation of the invention comprises MT103, citrate, lysine HCl, trehalose and Polysorbate 80.

In a specific embodiment, a lyophilized formulation of the invention consists of MT103, citrate, lysine HCl, trehalose and Polysorbate 80.

In one embodiment, a reconstituted liquid formulation of the invention comprises citrate, lysine HCl, trehalose and Polysorbate 80. In one embodiment, a reconstituted liquid formulation of the invention comprises between about 5 mM and about 125 mM citrate, between about 25 mM and about 400 mM lysine HCl, between about 3% and about 50% trehalose, and between about 0.001% and about 1% Polysorbate 80, wherein said formulation has a pH of between about 4.0 and about 8.0. In another embodiment, a reconstituted liquid formulation of the invention comprises between about 10 mM and about 50 mM citrate, between about 100 mM and about 300 mM lysine HCl, between about 10% and about 20% trehalose, and between about 0.01% and about 0.2% Polysorbate 80, wherein said formulation has a pH of between about 5.0 and about 8.0. In a further embodiment, a reconstituted liquid formulation of the invention comprises about 25 mM citrate, about 200 mM lysine HCl, about 15% trehalose and about 0.1% Polysorbate 80, wherein said formulation has a pH of about 7.0.

In one embodiment, a reconstituted liquid formulation of the invention comprises between about 10 micrograms/ml and about 100 micrograms/ml BiTE®, about 25 mM citrate, about 200 mM lysine HCl, about 15% trehalose and about 0.1% Polysorbate 80, wherein said formulation has a pH of about 7.0. In another embodiment, a reconstituted liquid formulation of the invention comprises between about 50 micrograms/ml and about 60 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises between about 110 micrograms/ml and about 210 micrograms/ml BiTE®, about 25 mM citrate, about 200 mM lysine HCl, about 15% trehalose and about 0.1% Polysorbate 80, wherein said formulation has a pH of about 7.0. In another embodiment, a reconstituted liquid formulation of the invention comprises between about 150 micrograms/ml and about 170 micrograms/ml BiTE®, about 25 mM citrate, about 200 mM lysine HCl, about 15% trehalose and about 0.1% Polysorbate 80, wherein said formulation has a pH of about 7.0. In a further embodiment, a reconstituted liquid formulation of the invention comprises about 55 micrograms/ml BiTE®, about 25 mM citrate, about 200 mM lysine HCl, about 15% trehalose and about 0.1% Polysorbate 80, wherein said formulation has a pH of about 7.0. In another embodiment, a reconstituted liquid formulation of the invention comprises about 160 micrograms/ml BiTE®, about 25 mM citrate, about 200 mM lysine HCl, about 15% trehalose and about 0.1% Polysorbate 80, wherein said formulation has a pH of about 7.0. In another embodiment, a reconstituted liquid formulation of the invention comprises about 150 micrograms/ml BiTE®, about 30 mM citrate, about 75 mM lysine HCl, about 6.5% trehalose and about 0.02% Polysorbate 80 and has a pH of about 7.0. In another embodiment, a reconstituted liquid formulation of the invention comprises about 150 micrograms/ml BiTE®, about 30 mM citrate, about 75 mM lysine HCl, about 6% trehalose and about 0.02% Polysorbate 80 and has a pH of about 7.0.

In one embodiment, a reconstituted liquid formulation of the invention comprises between about 10 micrograms/ml and about 100 micrograms/ml MT103, about 25 mM citrate, about 200 mM lysine HCl, about 15% trehalose and about 0.1% Polysorbate 80, wherein said formulation has a pH of about 7.0. In another embodiment, a reconstituted liquid formulation of the invention comprises between about 50 micrograms/ml and about 60 micrograms/ml MT103, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises between about 110 micrograms/ml and about 210 micrograms/ml MT103, about 25 mM citrate, about 200 mM lysine HCl, about 15% trehalose and about 0.1% Polysorbate 80, wherein said formulation has a pH of about 7.0. In another embodiment, a reconstituted liquid formulation of the invention comprises between about 150 micrograms/ml and about 170 micrograms/ml MT103, about 25 mM citrate, about 200 mM lysine HCl, about 15% trehalose and about 0.1% Polysorbate 80, wherein said formulation has a pH of about 7.0. In a further embodiment, a reconstituted liquid formulation of the invention comprises about 55 micrograms/ml MT103, about 25 mM citrate, about 200 mM lysine HCl, about 15% trehalose and about 0.1% Polysorbate 80, wherein said formulation has a pH of about 7.0. In another embodiment, a reconstituted liquid formulation of the invention comprises about 160 micrograms/ml MT103, about 25 mM citrate, about 200 mM lysine HCl, about 15% trehalose and about 0.1% Polysorbate 80, wherein said formulation has a pH of about 7.0. In another embodiment, a reconstituted liquid formulation of the invention comprises about 150 micrograms/ml MT103, about 30 mM citrate, about 75 mM lysine HCl, about 6.5% trehalose and about 0.02% Polysorbate 80 and has a pH of about 7.0. In another embodiment, a reconstituted liquid formulation of the invention comprises about 150 micrograms/ml MT103, about 30 mM citrate, about 75 mM lysine HCl, about 6% trehalose and about 0.02% Polysorbate 80 and has a pH of about 7.0.

In one embodiment, a reconstituted liquid formulation of the invention consists of between about 10 micrograms/ml and about 100 micrograms/ml BiTE®, about 25 mM citrate, about 200 mM lysine HCl, about 15% trehalose and about 0.1% Polysorbate 80, wherein said formulation has a pH of about 7.0. In another embodiment, a reconstituted liquid formulation of the invention consists of between about 50 micrograms/ml and about 60 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention consists of between about 110 micrograms/ml and about 210 micrograms/ml BiTE®, about 25 mM citrate, about 200 mM lysine HCl, about 15% trehalose and about 0.1% Polysorbate 80, wherein said formulation has a pH of about 7.0. In another embodiment, a reconstituted liquid formulation of the invention consists of between about 150 micrograms/ml and about 170 micrograms/ml BiTE®, about 25 mM citrate, about 200 mM lysine HCl, about 15% trehalose and about 0.1% Polysorbate 80, wherein said formulation has a pH of about 7.0. In a further embodiment, a reconstituted liquid formulation of the invention consists of about 55 micrograms/ml BiTE®, about 25 mM citrate, about 200 mM lysine HCl, about 15% trehalose and about 0.1% Polysorbate 80, wherein said formulation has a pH of about 7.0. In another embodiment, a reconstituted liquid formulation of the invention consists of about 160 micrograms/ml BiTE®, about 25 mM citrate, about 200 mM lysine HCl, about 15% trehalose and about 0.1% Polysorbate 80, wherein said formulation has a pH of about 7.0. In another embodiment, a reconstituted liquid formulation of the invention consists of about 150 micrograms/ml BiTE®, about 30 mM citrate, about 75 mM lysine HCl, about 6.5% trehalose and about 0.02% Polysorbate 80 and has a pH of about 7.0. In another embodiment, a reconstituted liquid formulation of the invention consists of about 150 micrograms/ml BiTE®, about 30 mM citrate, about 75 mM lysine HCl, about 6% trehalose and about 0.02% Polysorbate 80 and has a pH of about 7.0.

In one embodiment, a reconstituted liquid formulation of the invention consists of between about 10 micrograms/ml and about 100 micrograms/ml MT103, about 25 mM citrate, about 200 mM lysine HCl, about 15% trehalose and about 0.1% Polysorbate 80, wherein said formulation has a pH of about 7.0. In another embodiment, a reconstituted liquid formulation of the invention consists of between about 50 micrograms/ml and about 60 micrograms/ml MT103, about 25 mM citrate, about 200 mM lysine HCl, about 15% trehalose and about 0.1% Polysorbate 80, wherein said formulation has a pH of about 7.0. In one embodiment, a reconstituted liquid formulation of the invention consists of between about 110 micrograms/ml and about 210 micrograms/ml MT103, about 25 mM citrate, about 200 mM lysine HCl, about 15% trehalose and about 0.1% Polysorbate 80, wherein said formulation has a pH of about 7.0. In another embodiment, a reconstituted liquid formulation of the invention consists of between about 150 micrograms/ml and about 170 micrograms/ml MT103, about 25 mM citrate, about 200 mM lysine HCl, about 15% trehalose and about 0.1% Polysorbate 80, wherein said formulation has a pH of about 7.0. In a further embodiment, a reconstituted liquid formulation of the invention consists of about 55 micrograms/ml MT103, about 25 mM citrate, about 200 mM lysine HCl, about 15% trehalose and about 0.1% Polysorbate 80, wherein said formulation has a pH of about 7.0. In another embodiment, a reconstituted liquid formulation of the invention consists of about 160 micrograms/ml MT103, about 25 mM citrate, about 200 mM lysine HCl, about 15% trehalose and about 0.1% Polysorbate 80, wherein said formulation has a pH of about 7.0. In another embodiment, a reconstituted liquid formulation of the invention consists of about 150 micrograms/ml MT103, about 30 mM citrate, about 75 mM lysine HCl, about 6.5% trehalose and about 0.02% Polysorbate 80 and has a pH of about 7.0. In another embodiment, a reconstituted liquid formulation of the invention consists of about 150 micrograms/ml MT103, about 30 mM citrate, about 75 mM lysine HCl, about 6% trehalose and about 0.02% Polysorbate 80 and has a pH of about 7.0.

In one embodiment, a reconstituted liquid formulation of the invention comprises at least about 10 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 20 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 30 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 40 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 50 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 55 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 60 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 70 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 80 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 90 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 100 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 110 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 120 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 130 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 140 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 150 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 160 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 170 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 180 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 190 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises at least about 200 micrograms/ml BiTE®, about 25 mM citrate, about 200 mM lysine HCl, about 15% trehalose and about 0.1% Polysorbate 80, wherein said formulation has a pH of about 7.0.

In one embodiment, a reconstituted liquid formulation of the invention comprises about 10 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 20 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 30 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 40 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 50 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 55 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 60 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 70 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 80 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 90 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 100 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 110 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 120 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 130 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 140 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 150 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 160 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 170 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 180 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 190 micrograms/ml BiTE®, about 25 mM citrate, about 200 mM lysine HCl, about 15% trehalose and about 0.1% Polysorbate 80, wherein said formulation has a pH of about 7.0. In one embodiment, a reconstituted liquid formulation of the invention comprises about 200 micrograms/ml BiTE®, about 25 mM citrate, about 200 mM lysine HCl, about 15% trehalose and about 0.1% Polysorbate 80, wherein said formulation has a pH of about 7.0.

In one embodiment, a reconstituted liquid formulation of the invention comprises at least about 10 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 20 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 30 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 40 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 50 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 55 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 60 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 70 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 80 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 90 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 100 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 110 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 120 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 130 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 140 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 150 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 160 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 170 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 180 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 190 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises at least about 200 micrograms/ml BiTE®, about 25 mM citrate, about 200 mM lysine HCl, about 6.5% trehalose and about 0.02% Polysorbate 80, wherein said formulation has a pH of about 7.0.

In one embodiment, a reconstituted liquid formulation of the invention comprises about 10 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 20 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 30 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 40 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 50 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 55 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 60 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 70 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 80 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 90 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 100 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 110 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 120 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 130 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 140 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 150 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 160 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 170 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 180 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 190 micrograms/ml BiTE®, about 25 mM citrate, about 200 mM lysine HCl, about 6.5% trehalose and about 0.02% Polysorbate 80, wherein said formulation has a pH of about 7.0. In one embodiment, a reconstituted liquid formulation of the invention comprises about 200 micrograms/ml BiTE®, about 25 mM citrate, about 200 mM lysine HCl, about 6.5% trehalose and about 0.02% Polysorbate 80, wherein said formulation has a pH of about 7.0.

In one embodiment, a reconstituted liquid formulation of the invention comprises at least about 10 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 20 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 30 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 40 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 50 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 55 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 60 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 70 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 80 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 90 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 100 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 110 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 120 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 130 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 140 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 150 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 160 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 170 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 180 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 190 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises at least about 200 micrograms/ml BiTE®, about 25 mM citrate, about 200 mM lysine HCl, about 6% trehalose and about 0.02% Polysorbate 80, wherein said formulation has a pH of about 7.0.

In one embodiment, a reconstituted liquid formulation of the invention comprises about 10 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 20 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 30 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 40 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 50 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 55 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 60 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 70 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 80 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 90 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 100 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 110 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 120 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 130 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 140 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 150 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 160 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 170 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 180 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 190 micrograms/ml BiTE®, about 25 mM citrate, about 200 mM lysine HCl, about 6% trehalose and about 0.02% Polysorbate 80, wherein said formulation has a pH of about 7.0. In one embodiment, a reconstituted liquid formulation of the invention comprises about 200 micrograms/ml BiTE®, about 25 mM citrate, about 200 mM lysine HCl, about 6% trehalose and about 0.02% Polysorbate 80, wherein said formulation has a pH of about 7.0.

5.3.1. Stability of Reconstituted Formulations

In one embodiment, a reconstituted formulation of the invention comprises BiTE® molecules that is susceptible to aggregation, fragmentation and/or loss due to absorption to contact surfaces.

In one embodiment, a reconstituted formulation of the invention stabilizes BiTE® molecules in that the formulation of the invention prevents aggregation of BiTE® molecules as measured by HPSEC. In another embodiment, a reconstituted formulation of the invention prevents fragmentation of BiTE® molecules as measured by RP-HPLC. In a further embodiment, a reconstituted formulation of the invention prevents loss of BiTE® molecules due to absorption to contact surfaces.

In one embodiment, a reconstituted formulation of the invention stabilizes MT103 in that the formulation of the invention prevents aggregation of MT103 as measured by HPSEC. In another embodiment, a reconstituted formulation of the invention prevents fragmentation of MT103 as measured by RP=HPLC. In a further embodiment, a reconstituted formulation of the invention prevents loss of MT103 due to absorption to contact surfaces.

In one embodiment, a reconstituted formulation of the invention is stable upon storage at room temperature for at least about 1 hour, at least about 2 hours, at least about 3 hours, at least about 4 hours, at least about 5 hours, at least about 6 hours, at least about 7 hours, at least about 8 hours, at least about 9 hours, at least about 12 hours, at least about 18 hours, or at least about 24 hours as measured by HPSEC.

In one embodiment, a reconstituted formulation of the invention is stable upon storage at about 4° C. for at least about 1 hour, at least about 2 hours, at least about 3 hours, at least about 4 hours, at least about 5 hours, at least about 6 hours, at least about 7 hours, at least about 8 hours, at least about 9 hours, at least about 12 hours, at least about 15 hours, at least about 18 hours, or at least about 24 hours as measured by HPSEC.

In one embodiment, a reconstituted formulation of the invention is stable upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours as measured by HPSEC.

In one embodiment, a reconstituted formulation of the invention is stable upon storage at about 4° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours as measured by HPSEC.

5.3.1.1. Binding Activity

In one embodiment, a reconstituted formulation of the invention comprises BiTE® molecules, wherein said antibody retains at least 90% of binding ability to its target polypeptides compared to a reference antibody representing the antibody prior to lyophilization. Binding activity can be measured in a number of ways known to one of skill in the art, for example, by using a BIAcore or ELISA assay.

In one embodiment, a reconstituted formulation of the invention comprises BiTE® molecules, wherein said antibody retains at least 90% of binding ability to its target polypeptides compared to a reference antibody representing the antibody prior to storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein said antibody retains at least 90% of binding ability to its target polypeptides compared to a reference antibody representing the antibody prior to storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein said antibody retains at least 90% of binding ability to CD19 and CD3 antigens compared to a reference antibody representing the antibody prior to lyophilization.

In one embodiment, a reconstituted formulation of the invention comprises MT103, wherein said antibody retains at least 90% of binding ability to CD19 and CD3 antigens compared to a reference antibody representing the antibody prior to storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein said antibody retains at least 90% of binding ability to CD19 and CD3 antigens compared to a reference antibody representing the antibody prior to storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

5.3.1.2. Aggregate Formation

In one embodiment, a reconstituted formulation of the invention comprises BiTE® molecules, wherein less than 1%, less than 2%, less than 3%, less than 4%, or less than 5% of said antibody forms an aggregate as determined by HPSEC.

In one embodiment, a reconstituted formulation of the invention comprises MT103, wherein less than 1%, less than 2%, less than 3%, less than 4%, or less than 5% of said antibody forms an aggregate as determined by HPSEC.

In one embodiment, a reconstituted formulation of the invention comprises BiTE® molecules, wherein less than 1% of said antibody forms an aggregate as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 1% of said antibody forms an aggregate as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 1% of said antibody forms an aggregate as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 1% of said antibody forms an aggregate as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 2% of said antibody forms an aggregate as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 2% of said antibody forms an aggregate as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 2% of said antibody forms an aggregate as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 2% of said antibody forms an aggregate as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 3% of said antibody forms an aggregate as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 3% of said antibody forms an aggregate as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 3% of said antibody forms an aggregate as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 3% of said antibody forms an aggregate as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 4% of said antibody forms an aggregate as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 4% of said antibody forms an aggregate as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 4% of said antibody forms an aggregate as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 4% of said antibody forms an aggregate as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 5% of said antibody forms an aggregate as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 5% of said antibody forms an aggregate as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 5% of said antibody forms an aggregate as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 5% of said antibody forms an aggregate as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

5.3.1.3. Dimer Formation

In one embodiment, a reconstituted formulation of the invention comprises BiTE® molecules, wherein less than 1%, less than 2%, less than 3%, less than 4%, or less than 5% of said antibody forms a dimer as determined by HPSEC.

In one embodiment, a reconstituted formulation of the invention comprises MT103, wherein less than 1%, less than 2%, less than 3%, less than 4%, or less than 5% of said antibody forms a dimer as determined by HPSEC.

In one embodiment, a reconstituted formulation of the invention comprises BiTE® molecules, wherein less than 1% of said antibody forms a dimer as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 1% of said antibody forms a dimer as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 1% of said antibody forms a dimer as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 1% of said antibody forms a dimer as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 2% of said antibody forms a dimer as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 2% of said antibody forms a dimer as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 2% of said antibody forms a dimer as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 2% of said antibody forms a dimer as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 3% of said antibody forms a dimer as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 3% of said antibody forms a dimer as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 3% of said antibody forms a dimer as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 3% of said antibody forms a dimer as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 4% of said antibody forms a dimer as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 4% of said antibody forms a dimer as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 4% of said antibody forms a dimer as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 4% of said antibody forms a dimer as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 5% of said antibody forms a dimer as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 5% of said antibody forms a dimer as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 5% of said antibody forms a dimer as determined by HPSEC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 5% of said antibody forms a dimer as determined by HPSEC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

5.3.1.4. Fragmentation

In one embodiment, a reconstituted formulation of the invention comprises BiTE® molecules, wherein less than 1%, less than 2%, less than 3%, less than 4%, or less than 5% of said antibody is fragmented as determined by RP-HPLC.

In one embodiment, a reconstituted formulation of the invention comprises MT103, wherein less than 1%, less than 2%, less than 3%, less than 4%, or less than 5% of said antibody is fragmented as determined by RP-HPLC.

In one embodiment, a reconstituted formulation of the invention comprises BiTE® molecules, wherein less than 1% of said antibody is fragmented as determined by RP-HPLC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 1% of said antibody is fragmented as determined by RP-HPLC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 1% of said antibody is fragmented as determined by RP-HPLC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 1% of said antibody is fragmented as determined by RP-HPLC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 2% of said antibody is fragmented as determined by RP-HPLC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 2% of said antibody is fragmented as determined by RP-HPLC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 2% of said antibody is fragmented as determined by RP-HPLC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 2% of said antibody is fragmented as determined by RP-HPLC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 3% of said antibody is fragmented as determined by RP-HPLC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 3% of said antibody is fragmented as determined by RP-HPLC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 3% of said antibody is fragmented as determined by RP-HPLC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 3% of said antibody is fragmented as determined by RP-HPLC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 4% of said antibody is fragmented as determined by RP-HPLC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 4% of said antibody is fragmented as determined by RP-HPLC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 4% of said antibody is fragmented as determined by RP-HPLC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 4% of said antibody is fragmented as determined by RP-HPLC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises BiTE® molecules, wherein less than 5% of said antibody is fragmented as determined by RP-HPLC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises BiTE® molecules, wherein less than 5% of said antibody is fragmented as determined by RP-HPLC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention comprises MT103, wherein less than 5% of said antibody is fragmented as determined by RP-HPLC upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention comprises MT103, wherein less than 5% of said antibody is fragmented as determined by RP-HPLC upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

5.3.1.5. Visual Characteristics

In one embodiment, a reconstituted formulation of the invention is clear and colorless as determined by visual inspection.

In one embodiment, a reconstituted formulation of the invention is clear and colorless as determined by visual inspection upon storage at room temperature for about 1 hour, about 2 hours, about 3 hours, about 4 hours, about 5 hours, about 6 hours, about 7 hours, about 8 hours, about 9 hours, about 12 hours, about 18 hours, or about 24 hours.

In one embodiment, a reconstituted formulation of the invention is clear and colorless as determined by visual inspection upon storage at about 5° C. for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours.

In one embodiment, a reconstituted formulation of the invention is clear and colorless as determined by visual inspection upon storage at room temperature for at least about 1 hour, at least about 2 hours, at least about 3 hours, at least about 4 hours, at least about 5 hours, at least about 6 hours, at least about 7 hours, at least about 8 hours, at least about 9 hours, at least about 12 hours, at least about 18 hours, or at least about 24 hours.

In one embodiment, a reconstituted formulation of the invention is clear and colorless as determined by visual inspection upon storage at about 5° C. for at least about 1 hour, at least about 2 hours, at least about 3 hours, at least about 4 hours, at least about 5 hours, at least about 6 hours, at least about 7 hours, at least about 8 hours, at least about 9 hours, at least about 12 hours, at least about 15 hours, at least about 18 hours, or at least about 24 hours.

5.3.1.6. Particle Profile

In certain embodiments, reconstituted formulations of the invention comprise (or consists of as the aggregate fraction) a particle profile of less than about 3.4 E+5 particles/ml of diameter 2-4 μm, less than about 4.0 E+4 particles/ml of diameter 4-10 μm, less than about 4.2 E+3 particles/ml of diameter 10-20 μm, less than about 5.0 E+2 particles/ml of diameter 20-30 μm, less than about 7.5 E+1 particles/ml of diameter 30-40 μm, and less than about 9.4 particles/ml of diameter 40-60 μm as determined by a particle multisizer. In certain embodiments, reconstituted formulations of the invention contain no detectable particles greater than 40 μm, or greater than 30 μm.

In certain embodiments, after storage for about 1 hour, about 2 hours, about 3 hours, about 4 hours, about 5 hours, about 6 hours, about 7 hours, about 8 hours, about 9 hours, about 12 hours, about 15 hours, about 18 hours, or about 24 hours liquid formulations of the invention comprise (or consists of as the aggregate fraction) a particle profile of less than about 3.4 E+5 particles/ml of diameter 2-4 μm, less than about 4.0 E+4 particles/ml of diameter 4-10 μm, less than about 4.2 E+3 particles/ml of diameter 10-20 μm, less than about 5.0 E+2 particles/ml of diameter 20-30 μm, less than about 7.5 E+1 particles/ml of diameter 30-40 μm, and less than about 9.4 particles/ml of diameter 40-60 μm as determined by a particle multisizer. In certain embodiments, liquid formulations of the invention contain no detectable particles greater than 40 μm, or greater than 30 μm.

Numerous methods useful for determining the degree of aggregation, and/or types and/or sizes of aggregates present in a protein formulation (e.g., antibody formulation of the invention) are known in the art, including but not limited to, size exclusion chromatography (SEC), high performance size exclusion chromatography (HPSEC), static light scattering (SLS), Fourier Transform Infrared Spectroscopy (FTIR), circular dichroism (CD), urea-induced protein unfolding techniques, intrinsic tryptophan fluorescence, differential scanning calorimetry, and 1-anilino-8-naphthalenesulfonic acid (ANS) protein binding techniques. For example, size exclusion chromatography (SEC) may be performed to separate molecules on the basis of their size, by passing the molecules over a column packed with the appropriate resin, the larger molecules (e.g. aggregates) will elute before smaller molecules (e.g. monomers). The molecules are generally detected by UV absorbance at 280 nm and may be collected for further characterization. High pressure liquid chromatographic columns are often utilized for SEC analysis (HP-SEC). Specific SEC methods are detailed in the section entitled "Examples" infra. Alternatively, analytical ultracentrifugation (AUC) may be utilized. AUC is an orthogonal technique which determines the sedimentation coefficients (reported in Svedberg, S) of macromolecules in a liquid sample. Like SEC, AUC is capable of separating and detecting antibody fragments/aggregates from monomers and is further able to provide information on molecular mass. Protein aggregation in the formulations may also be characterized by particle counter analysis using a coulter counter or by turbidity measurements using a turbidimeter. Turbidity is a measure of the amount by which the particles in a solution scatter light and, thus, may be used as a general indicator of protein aggregation. In addition, non-reducing polyacrylamide gel electrophoresis (PAGE) or capillary gel electrophoresis (CGE) may be used to characterize the aggregation and/or fragmentation state of antibodies or a fragment thereof in a formulation of the invention.

5.4. Antibodies Useful in the Formulations of the Invention

The present invention relates to formulations of BiTE® molecules, which formulations exhibit stability, low to undetectable levels of antibody fragmentation, low to undetectable levels of aggregation, very little to no loss of the biological activities of the BiTE® molecules and very little to no loss of antibody through absorption to contact surfaces during manufacture, preparation, storage and use. In certain embodiments, a formulation of the invention is a lyophilized formulation, which lyophilized formulation maximizes BiTE® molecule BiTE® molecule recovery from the lyophilized product upon reconstitution.

The invention further provides methods for preparing formulations of BiTE® molecules, which formulations exhibit stability, low to undetectable levels of antibody fragmentation, low to undetectable levels of aggregation, very little to no loss of the biological activities of the BiTE® molecules and very little to no loss of antibody through absorption to contact surfaces during manufacture, preparation, storage and use.

The present invention provides formulations comprising BiTE® molecules.

Bispecific T cell engagers, or BiTE®s™, are a form of bispecific antibodies that are based on tandemly arranged single-chain antibodies (U.S. Pat. No. 7,112,324; reviewed in Wolf et al., *Drug Discov Today.* 10(18):1237-44 (2005)). They form a single polypeptide chain of approximately 55 kDa and are secreted by Chinese hamster ovary (CHO) cells as a mixture of monomers and dimers. With one arm, BiTE®s™ bind to the epsilon (ε) subunit of human CD3, a protein component of the signal-transducing complex of the T cell receptor on T cells. With the other arm, BiTE®s™ recognize an antigen on target cells (for example, but not limited to CD19, CD20, epithelial cell adhesion molecule (Ep-CAM), carcinoembryonic antigen (CEA), EphA2, EphA4, ICOS, IL-5 receptor, INF receptor). T cell activation is only seen when BiTE®s™ are presented to T cells on the surface of target cells.

BiTE®s™ transiently tether T cells and target cells. T cell activation by BiTE®s™ involves upregulation of CD69, CD25 and various cell adhesion molecules, de novo expression and release of cytokines (e.g., IFN-γ, TNF-α, IL-6, IL-2, IL-4 and IL-10), upregulation of granzyme and perforin expression, and cell proliferation. Redirected target cell lysis by BiTE®s™ is independent of T cell receptor specificity, presence of MHC class I and β2 microglobulin, and of any co-stimulatory stimuli. This independence from regular T cell signals and recognition molecules may be explained by the induction through BiTE®s™ of regular cytolytic synapses and maximum membrane proximity. Displacement of negative regulatory proteins such as CD45 from BiTE®™-induced synapses may alleviate the need for co-stimulation.

BiTE®s™ show redirected lysis in vitro with previously unstimulated peripheral polyclonal CD8- and CD4-positive T cells. No activity is seen with naïve CD8- or CD4-positive T cells. CD4 T cells can upregulate granzyme B and perforin expression when stimulated with BiTE®s™ and thereby contribute to CD8-mediated target cell lysis. In vitro, redirected lysis is seen at low picomolar concentrations, suggesting that very low numbers of BiTE® molecules need to be bound to target cells for triggering T cells. In SCID mouse models, sub-μg doses of BiTE®s™ have been shown to completely prevent tumor outgrowth (Dreier et al., 2003, J. Immunol. 170:4397-4402) and to eradicate solid tumors up to 200 mm$^3$ (Schlereth et al., 2005, Cancer Res. 2005 65(7):2882-89).

The invention provides formulations comprising BiTE® molecules. BiTE® molecules comprise a first and second binding domain wherein said first binding domain is specific for CD3 and said second binding domain is specific for a cell surface antigen of a target cell. In particular embodiments, the cell surface antigen of a target cell recognized by a BiTE® of a formulation of the invention is selected from the group consisting of a cytotoxic T-lymphocyte associated antigen (CTLA), such as CTLA-4; receptors for hormones or growth factors such as, for example, EGFR, TGF, VEGFR; interferons such as alpha interferon (α-IFN), beta interferon (β-IFN) and gamma interferon (γ-IFN); interferon receptor components such as interferon receptor 1; CD proteins such as CD2, CD3, CD4, CD 8, CD11a, CD14, CD18, CD19, CD20, CD22, CD23, CD25, CD33, CD34, CD40, CD40L, CD52, CD63, CD64, CD80 and CD147; T-cell receptors; surface membrane proteins; homing receptors; addressins; cell adhesion molecules such as LFA-1, Mac 1, p150.95, VLA-4, ICAM-1, ICAM-3 and VCAM, a4/p7 integrin, and (Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD18, CD61, CD104, beta5, beta6, beta7 and beta8; Integrin subunit combinations including but not limited to, αVβ3, αVβ5 and α4β7; flk2/flt3 receptor; obesity (OB) receptor; mpl receptor; CTLA-4; an Eph receptor such as EphA2, EphA4, EphB2, etc.; a Human Leukocyte Antigen (HLA) such as HLA-DR; a glycoprotein receptor such as GpIbα, GPIIb/IIIa and CD200; cancer antigens including, but not limited to, ALK receptor (pleiotrophin receptor), pleiotrophin, KS 1/4 pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as: CEA, TAG-72, CO17-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 5T4 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16; NY-BR-16 and HER2 antigen (p185$^{HER2}$); polymorphic epithelial mucin (PEM); malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; Myl; VIM-D5; D$_1$56-22 found in colorectal cancer; TRA-1-85 (blood group H); SCP-1 found in testis and ovarian cancer; C14 found in colonic adenocarcinoma; F3 found in lung adenocarcinoma; AH6 found in gastric cancer; Y hapten; Le$^y$ found in embryonal carcinoma cells; TL5 (blood group A); EGF receptor found in A431 cells; E$_1$ series (blood group B) found in pancreatic cancer; FC10.2 found in embryonal carcinoma cells; gastric adenocarcinoma antigen; CO-514 (blood group Le$^a$) found in Adenocarcinoma; NS-10 found in adenocarcinomas; CO-43 (blood group Le$^b$); G49 found in EGF receptor of A431 cells; MH2 (blood group ALe$^b$/Le$^y$) found in colonic adenocarcinoma; 19.9 found in colon cancer; gastric cancer mucins; $T_5A_7$ found in myeloid cells; $R_{24}$ found in melanoma; 4.2, $G_{D3}$, D1.1, OFA-1, $G_{M2}$, OFA-2, $G_{D2}$, and M1:22:25:8 found in embryonal carcinoma cells and SSEA-3 and SSEA-4 found in 4 to 8-cell stage embryos; Cutaneous Tcell Lymphoma antigen; MART-1 antigen; Sialy Tn (STn) antigen; Colon cancer antigen NY-CO-45; Lung cancer antigen NY-LU-12 variant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; TUMOR-ASSOCIATED ANTIGEN CO-029; Tumor-associated antigens MAGE-C1 (cancer/testis antigen CT7), MAGE-B1 (MAGE-XP antigen), MAGE-B2 (DAM6), MAGE-2, MAGE-4a, MAGE-4b and MAGE-X2; Cancer-Testis Antigen (NY-EOS-1); YKL-40 and fragments of any of the above-listed polypeptides.

In specific embodiments, a BiTE® molecule BiTE® molecule of a formulation of the invention is selected from the group consisting of: CD19×CD3 BiTE® (U.S. Pat. No. 7,112,324, US Patent Application US20070123479A1), CD20×CD3 BiTE®, EphA2×CD3 BiTE® (U.S. patent application Ser. No. 11/645,290, filed on Dec. 21, 2006), EphA4× CD3 BiTE®, ICOS×CD3 BiTE®, IFNR (interferon alpha receptor)×CD3 BiTE®, Ep-CAM (epithelial cell adhesion molecule)×CD3 BiTE®, CEA (carcinoembryonic antigen)× CD3 BiTE® (U.S. patent application Ser. No. 12/158,611, PCT Publication No. WO 2007/071426) and IL-5R×CD3 BiTE®.

5.4.1. BiTE® Molecules Having Increased Half-Lives

The present invention provides for formulations of BiTE® molecules (e.g., MT103) which have an extended half-life in vivo. In particular, the present invention provides formulations of BiTE® molecules which have a half-life in a mammal (for example, but not limited to, a human), of greater than 1 hour, greater than 2 hours, greater than 4 hours, greater than 6 hours, greater than 8 hours, greater than 10 hours, greater than 12 hours, greater than 18 hours, greater than 1 day, greater than 2 days, greater than 3 days, greater than 7 days, greater than 10 days, greater than 15 days, greater than 25 days, greater than 30 days, greater than 35 days, greater than 40 days, greater than 45 days, greater than 2 months, greater than 3 months, greater than 4 months, or greater than 5 months.

To prolong the serum circulation of BiTE® molecules in vivo, for example, inert polymer molecules such as high molecular weight polyethyleneglycol (PEG) can be attached to the BiTE® molecules with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the BiTE® molecules. Unreacted PEG can be separated from BiTE® molecule-PEG conjugates by size-exclusion or by ion-exchange chromatography. PEG-derivatized BiTE® molecules can be tested for binding activity as well as for in vivo efficacy using methods known to those of skill in the art, for example, by immunoassays described herein.

Further, BiTE® molecules can be conjugated to albumin in order to make the BiTE® molecules more stable in vivo or have a longer half life in vivo. The techniques are well known in the art, see e.g., International Publication Nos. WO 93/15199, WO 93/15200, and WO 01/77137; and European Patent No. EP 413, 622, all of which are incorporated herein by reference.

5.5. Methods of Preparing the BiTE® Molecule Formulations

The invention further provides a method for preparing a stable reconstituted formulation comprising reconstituting a lyophilized mixture of BiTE® molecules and a lyoprotectant in a diluent such that the BiTE® molecule BiTE® molecule concentration in the reconstituted formulation is between about 30 micrograms/ml and about 70 micrograms/ml.

In yet a further embodiment, the invention provides a method for preparing a formulation comprising the steps of: (a) lyophilizing a mixture of BiTE® molecules and a lyoprotectant; and (b) reconstituting the lyophilized mixture of step (a) in a diluent such that the reconstituted formulation is stable and has a protein concentration of between about 30 micrograms/ml and about 70 micrograms/ml.

The BiTE® molecule to be formulated is prepared using techniques which are well established in the art including synthetic techniques such as recombinant techniques and peptide synthesis or a combination of these techniques. In certain embodiments of the invention, the BiTE® molecule BiTE® molecule of choice is MT103.

After preparation of the BiTE® molecule BiTE® molecule of interest, a "bulk liquid formulation" is produced. The amount of BiTE® molecule present in the bulk liquid formulation is determined taking into account the desired dose volumes, mode(s) of administration etc. In certain embodiments, a concentration of between about 20 micrograms/ml and about 300 micrograms/ml BiTE® molecule may be used as a starting protein concentration. The BiTE® molecule is generally present in solution. For example, the BiTE® molecule may be present in a pH-buffered solution at a pH from about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation).

The lyoprotectant is added to the pre-lyophilized formulation. In certain embodiments, the lyoprotectant is a non-reducing sugar such as sucrose or trehalose. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. Where the lyoprotectant is a sugar (such as sucrose or trehalose) and the protein is a BiTE® molecule, exemplary lyoprotectant concentrations in the pre-lyophilized formulation are from about 10 mM to about 400 mM. The ratio of protein to lyoprotectant is selected for each protein and lyoprotectant combination.

In certain embodiments, a surfactant is added to the pre-lyophilized formulation. Alternatively, or in addition, the surfactant may be added to the lyophilized formulation and/or the reconstituted formulation. Suitable surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

In certain embodiments of the invention, a mixture of the lyoprotectant (such as sucrose or trehalose) and a bulking agent (e.g. mannitol or glycine) is used in the preparation of the pre-lyophilization formulation. The bulking agent may allow for the production of a uniform lyophilized cake without excessive pockets therein etc.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The formulation herein may also contain more than one BiTE® moleculeas necessary for the particular indication being treated, preferably those with complementary activities that do not adversely affect the other protein.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for the BiTE® molecule, at about 120° C. for about 30 minutes, for example.

After the protein, lyoprotectant and other optional components are mixed together, the formulation is lyophilized. Many different freeze-dryers are available for this purpose such as Hull150™ (Hull, USA) or GT20™ (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). A secondary drying stage may be carried out at about 0-40° C., depending primarily on the type and size of container and the type of protein employed. However, it was found herein that a secondary drying step may not be necessary. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial.

As a general proposition, lyophilization will result in a lyophilized formulation in which the moisture content thereof is less than about 5%, and preferably less than about 3%.

At the desired stage, typically when it is time to administer the BiTE® molecule to the patient, the lyophilized formulation may be reconstituted with a diluent such that the BiTE® molecule concentration in the reconstituted formulation is between about 20 micrograms/ml and about 300 micrograms/ml. High BiTE® molecule concentrations in the reconstituted formulation are considered to be particularly useful where subcutaneous delivery of the reconstituted formulation is intended. However, for other routes of administration, such as intravenous administration, lower concentrations of the BiTE® molecule in the reconstituted formulation may be desired. In certain embodiments, the protein concentration in the reconstituted formulation is significantly higher than that in the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. In certain embodiments diluents include sterile water, bacteriostatic water for injection (BWFI), a pH buffered solution (e.g. phosphate-buffered saline), sterile saline solution, Ringer's solution or dextrose solution. The diluent optionally contains a preservative. Examples of preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Preferably, the reconstituted formulation has less than 6000 particles per vial which are >10 micron size.

5.6. Methods of Preparing BiTE® Molecules

Generating BiTE® molecules that specifically bind to an antigen have been described elsewhere—see Brishwein K et. al., *Mol. Immunol.* 2006 43:1129; Drier T et. al., *Int. J. Cancer* 2002 100:690; U.S. Pat. No. 7,112,324, each of which is incorporated by reference in their entireties.

Antibodies, including antibody fragments thereof, can be produced by any method known in the art for the synthesis of antibodies, in particular, by chemical synthesis or by recombinant expression techniques (see, US Patent Publication 2007/0014724A1).

Polyclonal antibodies specific for an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981), and Harlow et al., Using Antibodies: A laboratory Manual, Cold Spring Harbor Laboratory Press (1999) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a non-murine antigen and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization multiple sites) technique can be used to immunize an animal (Kilpatrack et al., 1997, Hybridoma 16:381-9, incorporated herein by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

The present invention provides methods of generating monoclonal antibodies as well as antibodies produced by the method comprising culturing a hybridoma cell secreting an antibody of the invention wherein the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments which recognize specific particular epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; International application No. PCT/GB91/O1 134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, 5,969,108, 6,33,187, 5,824,520, and 5,702,892; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

For some uses, including in vivo use of antibodies in humans and in vitro detection assays, it may be appropriate to use humanized antibodies. Completely human antibodies and humanized antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immuoglobulin. A humanized antibody comprises substantially all of at least one, and typically two, variable domains (Fab, Fab', F(ab')$_2$, Fabc, Fv) in which all or substantially all of the CDR regions correspond to those of a non-human immunoglobulin (i.e., donor antibody) and all or substantially all of the framework regions are those of a human immunoglobulin consensus sequence. In one embodiment, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG$_1$, IgG$_2$, IgG$_3$ and IgG$_4$. Usually the constant domain is a complement fixing constant domain where it is desired that the humanized antibody exhibit cytotoxic activity, and the class is typically IgG$_1$. Where such cytotoxic activity is not desirable, the constant domain may be of the IgG$_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and greater than 95%. Humanized antibody can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519, 596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169:1119-25 (2002), Caldas et al., Protein Eng. 13(5):353-60 (2000), Morea et al., Methods 20(3):267-79 (2000), Baca et al., J. Biol. Chem. 272(16): 10678-84 (1997), Roguska et al., Protein Eng. 9(10):895-904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). Often, framework residues in the framework regions will be substituted with the corresponding residue from the CDR donor antibody to alter, preferably improve, antigen binding. These framework substitutions are identified by methods well known in the art, for example, but not limited to, by modeling of the interactions of the CDR and framework residues to identify framework residues important for antigen binding and sequence comparison to identify unusual framework residues at particular positions (see, e.g., Queen et al., U.S. Pat. No. 5,585,089; and Riechmann et al., 1988, Nature 332:323, which are incorporated herein by reference in their entireties).

Single domain antibodies, for example, antibodies lacking the light chains, can be produced by methods well-known in the art. See Riechmann et al., 1999, J. Immuno. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

5.7. Recombinant Expression of Bispecific Antibodies

Bispecific antibodies (e.g., BiTE®™) may be produced by any methods known to one of skill in the art including, but not limited to, chemical synthesis or recombinant expression techniques described in U.S. Pat. No. 7,112,324 which is incorporated by reference herein in its entirety.

Polynucleotides encoding BiTE® molecules can be used alone or as part of a vector to express the BiTE® molecule in cells. The polynucleotides or vectors containing the DNA sequence(s) encoding BiTE® molecules is introduced into host cells which in turn produce the polypeptide of interest (e.g., MT103). Accordingly, recombinant expression of BiTE® molecules requires construction of an expression vector containing a polynucleotide that encodes the antibody. Polynucleotides encoding a particular BiTE® molecule may be obtained and sequenced by any method known in the art. For example, a polynucleotide encoding BiTE® molecules used in the methods of the invention may be assembled from chemically synthesized oligonucleotides (e.g., as described in Kutmeier et al., 1994, *BioTechniques* 17:242), which, briefly, involves the synthesis of overlapping oligonucleotides containing fragments of the sequence encoding the polypeptide, annealing and ligating of those oligonucleotides, and then amplification of the ligated oligonucleotides by PCR.

Once a polynucleotide encoding BiTE® molecules has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce BiTE® molecules (e.g., MT103). A variety of host-expression vector systems may be utilized to express BiTE® molecules (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli* may be used for the expression of a recombinant antibody molecule. Eukaryotic cells may also be used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45:101; and Cockett et al., 1990, *BioTechnology* 8:2). In a specific example, the expression of nucleotide sequences encoding BiTE® molecules is regulated by a constitutive promoter, inducible promoter or tissue specific promoter. Alternatively, the polynucleotides of the invention may be expressed in a transgenic plant expression system, such as, for instance, the LEX System™ disclosed in U.S. Pat. No. 6,040,498, international application published on Feb. 18, 1999 (WO 99/07210), and international application published on Feb. 7, 2002 (WO 02/10414). Another transgenic plant expression system that may be utilized is the Plantibodies™ technology described in U.S. Pat. Nos. 5,202,422; 5,639,947; 5,959,177; and 6,417,429.

In bacterial systems, a number of expression vectors may be advantageously selected depending upon the use intended for the molecule being expressed. For example, when a large quantity of such a protein is to be produced, for the generation of pharmaceutical compositions of an BiTE® molecule, vectors which direct the expression of high levels of fusion protein products that are readily purified may be desirable. Such vectors include, but are not limited to, the *E. coli* expression vector pUR278 (Ruther et al., 1983, EMBO 12:1791), in which the BiTE® molecule coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety. Another microbial system that may be used to express the polynucleotides of the invention is the Pf$\bar{e}$nex Expression Technology is based on novel strains of *Pseudomonas fluorescens*, as described in Squires et al., Bio-Process Int'l p. 54 December 2004; and Squires et al., Specialty Chemicals July/August 2004.

In an insect system, *Autographa californica* nuclear polyhedrosis virus (AcNPV) is used as a vector to express foreign genes. The virus grows in *Spodoptera frugiperda* cells. The BiTE® molecule coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the BiTE® molecule coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the BiTE® molecule in infected hosts (e.g., see Logan & Shenk, 1984, *PNAS* 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, *Methods in Enzymol.* 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, BT483, Hs578T, HTB2, BT20, NS1, and T47D, NS0

(a murine myeloma cell line that does not endogenously produce any immunoglobulin chains), CRL7O3O and HsS78BsT-cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the BiTE® molecule. Such engineered cell lines may be particularly useful in screening and evaluation of compositions that interact directly or indirectly with the BiTE® molecule.

A number of selection systems may be used, including but not limited to, the herpes simplex virus thymidine kinase (Wigler et al., 1977, *Cell* 11:223), glutamine synthase, hypoxanthine guanine phosphoribosyltransferase (Szybalska & Szybalski, 1992, Proc. Natl. Acad. Sci. USA 48:202), and adenine phosphoribosyltransferase (Lowy et al., 1980, *Cell* 22:8-17) genes can be employed in tk-, gs-, hgprt- or aprt- cells, respectively. Also, antimetabolite resistance can be used as the basis of selection for the following genes: dhfr, which confers resistance to methotrexate (Wigler et al., 1980, *PNAS* 77:357; O'Hare et al., 1981, *PNAS* 78:1527); gpt, which confers resistance to mycophenolic acid (Mulligan & Berg, 1981, *PNAS* 78:2072); neo, which confers resistance to the aminoglycoside G-418 (Wu and Wu, 1991, *Biotherapy* 3:87; Tolstoshev, 1993, *Ann. Rev. Pharmacol. Toxicol.* 32:573; Mulligan, 1993, *Science* 260:926; and Morgan and Anderson, 1993, *Ann. Rev. Biochem.* 62: 191; May, 1993, *TIB TECH* 11:155-); and hygro, which confers resistance to hygromycin (Santerre et al., 1984, *Gene* 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., 1981, *J. Mol. Biol.* 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the BiTE® molecule will also increase (Crouse et al., 1983, *Mol. Cell. Biol.* 3:257).

Once BiTE® molecules (e.g., BiTE®) has been produced by recombinant expression, it may be purified by any method known in the art for purification of an immunoglobulin molecule, for example, by chromatography (e.g., ion exchange chromatography, affinity chromatography, and size exclusion chromatography), centrifugation, differential solubility, or by any other standard technique for the purification of proteins. Further, BiTE® molecules may be fused to heterologous polypeptide sequences known in the art to facilitate protein purification.

5.8. BiTE® Molecule Purification and Isolation

Recombinantly produced BiTE® molecule s (e.g., BiTE®™) may be purified by any methods known to one of skill in the art including, but not limited to, chromatography techniques described in U.S. Pat. No. 7,112,324 which is incorporated by reference herein in its entirety.

When using recombinant techniques, the BiTE® molecule can be produced intracellularly, in the periplasmic space, or directly secreted into the medium. If the BiTE® molecule is produced intracellularly, as a first step, the particulate debris, either host cells or lysed fragments, is removed, for example, by centrifugation or ultrafiltration. Carter et al., Bio/Technology, 10:163-167 (1992) describe a procedure for isolating BiTE® molecule which are secreted into the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the BiTE® molecule mutant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The BiTE® molecule composition prepared from the cells can be purified using, for example, hydroxylapatite chromatography, hydrophobic interaction chromatography, ion exchange chromatography, gel electrophoresis, dialysis, and/ or affinity chromatography either alone or in combination with other purification steps. The suitability of protein A as an affinity ligand depends on the species and isotype of any immunoglobulin Fc domain that is present in the antibody mutant. Protein A can be used to purify antibodies that are based on human γ1, γ2, or γ4 heavy chains (Lindmark et al., J. Immunol. Methods, 62:1-13 (1983)). Protein G is recommended for all mouse isotypes and for human γ3 (Guss et al., EMBO J., 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the BiTE® molecules of interest and contaminants may be subjected to low pH hydrophobic interaction chromatography using an elution buffer at a pH between about 2.5-4.5, and performed at low salt concentrations (e.g., from about 0-0.25 M salt).

5.9. Administration and Dosing

Administration of formulations of the invention to a human patient can be by any route, including but not limited to intravenous, intradermal, transdermal, subcutaneous, intramuscular, inhalation (e.g., via an aerosol), buccal (e.g., sublingual), topical (i.e., both skin and mucosal surfaces, including airway surfaces), intrathecal, intraarticular, intraplural, intracerebral, intra-arterial, intraperitoneal, oral, intralymphatic, intranasal, rectal or vaginal administration, by perfusion through a regional catheter, or by direct intralesional injection. In one embodiment, formulations of the invention are administered by intravenous push or intravenous infusion given over a defined period (e.g., 0.5 to 4 hours). In another embodiment, formulations of the invention are administered by continuous intravenous infusion given over a defined period (e.g., 4 to 40 days). Compositions of the invention can be delivered by peristaltic means or in the form of a depot, although the most suitable route in any given case will depend, as is well known in the art, on such factors as the species, age, gender and overall condition of the subject, the nature and severity of the condition being treated and/or on the nature of the particular formulation (i.e., dosage) that is being administered. In particular embodiments, the route of administration is via bolus or continuous infusion over a period of time, once or twice a week. In other particular embodiments, the route of administration is by subcutaneous injection, optionally once or twice weekly. In one embodiment, compositions, and/or methods of the invention are administered on an outpatient basis.

In certain embodiments, a formulation of the present invention is a lyophilized formulation. A lyophilized formulation is reconstituted into a liquid formulation by dissolving the lyophilized cake in a diluent. In certain embodiments, diluent that may be used for the reconstitution of a lyophilized formulation of the invention include, but are not limited to, sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

In certain embodiments, a reconstituted formulation of the invention may be further diluted prior to administration to a patient. A reconstituted formulation may be diluted by at least about 2 fold, at least about 3 fold, at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, at least about 100 fold, at least about 150 fold, at least about 200 fold, at least about 250 fold, at least about 300 fold, at least about 500 fold, or at least about 1000 fold.

In certain embodiments, a reconstituted formulation of the invention may be diluted prior to administration to a patient. A reconstituted formulation of the invention may be diluted in, for example, but not limited to, a pH buffered solution (e.g. phosphate-buffered saline), sterile saline solution, Ringer's solution or dextrose solution. The solution used for dilution of a reconstituted formulation of the invention may further comprise additional excipients, such as, but not limited to, proteins (for example, but not limited to, serum albumin), amino acids (for example, but not limited to, aspartic acid, glutamic acid, lysine, arginine, glycine), surfactants (for example, but not limited to, SDS, Tween 20, Tween 80, polysorbate, polysorbate 80 and nonionic surfactants), saccharides (for example, but not limited to, glucose, sucrose, maltose and trehalose), polyols (for example, but not limited to, mannitol and sorbitol), fatty acids and phospholipids (for example, but not limited to, alkyl sulfonates and caprylate). In further embodiments, a reconstituted formulation of the invention may be diluted with a buffered saline solution comprising lysine HCl and polysorbate 80. In a specific embodiment, a reconstituted formulation of the invention may be diluted into a saline solution comprising about 25 mM lysine HCl and 0.02% polysorbate 80.

In certain embodiments, a formulation of the invention is administered subcutaneously. The bioavailability of subcutaneously delivered BiTE® molecules is generally lower than that of intravenously delivered BiTE® molecules. The present invention provides BiTE® formulations that result in high bioavailability of BiTE® molecules upon subcutaneous delivery of the formulation. In certain embodiments, the bioavailability of BiTE® molecules following subcutaneous delivery of a formulation of the invention is between about 10% and about 90%, between about 10% and about 75%, between about 10% and about 60%, between about 20% and about 60%, or between about 10% and about 50%, of the bioavailability of the BiTE® molecules following intravenous delivery of the same dose of the formulation. In certain embodiments, the bioavailability of BiTE® molecules following subcutaneous delivery of a formulation of the invention is at least about 10%, at least about 20%, at least about 30%, at least about 40%, at least about 50%, at least about 60%, at least about 70%, at least about 80%, or at least about 90% of the bioavailability of the BiTE® molecules following intravenous delivery of the same dose of the formulation. In certain embodiments, the bioavailability of BiTE® molecules following subcutaneous delivery of a formulation of the invention is about 10%, about 20%, about 30%, about 40%, about 50%, about 60%, about 70%, about 80%, or about 90% of the bioavailability of the BiTE® molecules following intravenous delivery of the same dose of the formulation. In a specific embodiment, the bioavailability of BiTE® molecules following subcutaneous delivery of a formulation of the invention is about 10% of the bioavailability of the BiTE® molecules following intravenous delivery of the same dose of the formulation. In a specific embodiment, the bioavailability of BiTE® molecules following subcutaneous delivery of a formulation of the invention is about 10% of the bioavailability of the BiTE® molecules following intravenous delivery of the same dose of the formulation. In a specific embodiment, the bioavailability of BiTE® molecules following subcutaneous delivery of a formulation of the invention is about 20% of the bioavailability of the BiTE® molecules following intravenous delivery of the same dose of the formulation. In a specific embodiment, the bioavailability of BiTE® molecules following subcutaneous delivery of a formulation of the invention is about 30% of the bioavailability of the BiTE® molecules following intravenous delivery of the same dose of the formulation. In a specific embodiment, the bioavailability of BiTE® molecules following subcutaneous delivery of a formulation of the invention is about 40% of the bioavailability of the BiTE® molecules following intravenous delivery of the same dose of the formulation. In a specific embodiment, the bioavailability of BiTE® molecules following subcutaneous delivery of a formulation of the invention is about 50% of the bioavailability of the BiTE® molecules following intravenous delivery of the same dose of the formulation. In a specific embodiment, the bioavailability of BiTE® molecules following subcutaneous delivery of a formulation of the invention is about 60% of the bioavailability of the BiTE® molecules following intravenous delivery of the same dose of the formulation.

In certain embodiments, the dose of a formulation comprising BiTE® molecules (e.g., MT103) is measured in units of mg/kg of patient body weight. In other embodiments, the dose of a formulation comprising BiTE® molecules (e.g., MT103) is measured in units of mg/kg of patient lean body weight (i.e., body weight minus body fat content). In yet other embodiments, the dose of a formulation comprising BiTE® molecules (e.g., MT103) is in units of mg/m$^2$ of patient body surface area. In yet other embodiments, the dose of a composition comprising a formulation comprising BiTE® molecules (e.g., MT103) is measured in units of mg per dose administered to a patient. Any measurement of dose can be used in conjunction with compositions and methods of the invention and dosage units can be converted by means standard in the art.

Those skilled in the art will appreciate that dosages can be selected based on a number of factors including the age, sex, species and condition of the subject (e.g., stage of B cell malignancy), the desired degree of cellular depletion, the disease to be treated and/or the particular BiTE® molecule being used and can be determined by one of skill in the art. For example, effective amounts of compositions of the invention may be extrapolated from dose-response curves derived in vitro test systems or from animal model (e.g., the cotton rat or monkey) test systems. Models and methods for evaluation of the effects of BiTE® molecules are known in the art (Wooldridge et al., *Blood,* 89(8): 2994-2998 (1997)), incorporated by reference herein in its entirety). In specific embodiments, for particular B cell malignancies, therapeutic regimens standard in the art for antibody therapy can be used with formulations and methods of the invention.

Examples of dosing regimens that can be used in methods of the invention include, but are not limited to, daily, three times weekly (intermittent), weekly, or every 14 days. In certain embodiments, dosing regimens include, but are not limited to, monthly dosing or dosing every 6-8 weeks.

Those skilled in the art will appreciate that dosages may be higher and/or frequency of administration greater for initial treatment as compared with maintenance regimens.

In certain embodiments, dosages of BiTE® molecules (e.g., MT103) (optionally in a pharmaceutically acceptable carrier as part of a pharmaceutical composition) are at least about 0.0005, 0.001, 0.01, 0.02, 0.03, 0.04, 0.05, 0.06, 0.07, 0.08, 0.09, 0.1, 0.25, 0.375, 0.5, 1, 2.5, 5, 10, 20, 37.5, or 50 mg/m$^2$ and/or less than about 500, 475, 450, 425, 400, 375, 350, 325, 300, 275, 250, 225, 200, 175, 150, 125, 100, 75, 60, 50, 37.5, 20, 15, 10, 5, 2.5, 1, 0.5, 0.375, 0.2, 0.1, 0.09, 0.08, 0.075, 0.05, 0.04, 0.03, 0.02, or 0.01 mg/m$^2$. In certain embodiments, the dosage is between about 0.0005 to about 200 mg/m$^2$, between about 0.001 and 150 mg/m$^2$, between about 0.01 and 100 mg/m$^2$, between about 0.05 and 50 mg/m$^2$, between about 0.05 and 25 mg/m$^2$, between about 0.05 and 10 mg/m$^2$, and between about 0.05 and 5 mg/m$^2$. In related embodiments, the dosage of BiTE® molecules (e.g., MT103) used is at least about 0.0001, 0.0005, 0.001, 0.0025, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 3, 5 mg/kg of body weight of a patient. In certain embodiments, the dose of BiTE® molecules used is at least about 0.1 to 1, 0.5 to 1.5, 1 to 2, or 1.5 to 2.5 micrograms/kg of body weight of a patient. In certain embodiments, the dose of a bispecific used is at least about 0.1 to 2, 0.3 to 5, or 0.5 to 10 micrograms/kg of body weight of a patient. In other embodiments, the dose of BiTE® molecules used is at least about 0.1, 0.5, 0.6, 0.7, 0.8, 0.9, 1, 2, 5, or 10 micrograms/kg of body weight of a patient. In certain embodiments, a single dosage unit of the BiTE® molecule (optionally in a pharmaceutically acceptable carrier as part of a pharmaceutical formulation) can be at least about 0.5, 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 204, 206, 208, 210, 212, 214, 216, 218, 220, 222, 224, 226, 228, 230, 232, 234, 236, 238, 240, 242, 244, 246, 248, or 250 micrograms/m$^2$. In other embodiments, dose is up to 1 g per single dosage unit.

In specific embodiments of the invention, CD19×CD3 bispecific antibodies (e.g., MT103) bind to B cells and may result in efficient (i.e., at low dosage) depletion of B cells. Higher degrees of binding may be achieved where the density of human CD19 on the surface of a patient's B cells is high. In specific embodiments, dosages of MT103 (e.g., MT103) (optionally in a pharmaceutically acceptable carrier as part of a pharmaceutical composition) are at least about 0.0005, 0.001, 0.01, 0.02, 0.03, 0.04, 0.05, 0.06, 0.07, 0.08, 0.09, 0.1, 0.25, 0.375, 0.5, 1, 2.5, 5, 10, 20, 37.5, or 50 mg/m$^2$ and/or less than about 500, 475, 450, 425, 400, 375, 350, 325, 300, 275, 250, 225, 200, 175, 150, 125, 100, 75, 60, 50, 37.5, 20, 15, 10, 5, 2.5, 1, 0.5, 0.375, 0.2, 0.1, 0.09, 0.08, 0.075, 0.05, 0.04, 0.03, 0.02, or 0.01 mg/m$^2$. In specific embodiments, the dosage is between about 0.0005 to about 200 mg/m$^2$, between about 0.001 and 150 mg/m$^2$, between about 0.01 and 100 mg/m$^2$, between about 0.05 and 50 mg/m$^2$, between about 0.05 and 25 mg/m$^2$, between about 0.05 and 10 mg/m$^2$, and between about 0.05 and 5 mg/m$^2$. In related specific embodiments, the dosage of MT103 used is at least about 0.0001, 0.0005, 0.001, 0.0025, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 3, 5 mg/kg of body weight of a patient. In certain specific embodiments, the dose of MT103 used is at least about 0.1 to 1, 0.5 to 1.5, 1 to 2, or 1.5 to 2.5 micrograms/kg of body weight of a patient. In certain specific embodiments, the dose of MT103 used is at least about 0.1 to 2, 0.3 to 5, or 0.5 to 10 micrograms/kg of body weight of a patient. In other specific embodiments, the dose of MT103 used is at least about 0.1, 0.5, 0.6, 0.7, 0.8, 0.9, 1, 2, 5, or 10 micrograms/kg of body weight of a patient. In certain specific embodiments, a single dosage unit of MT1103 (optionally in a pharmaceutically acceptable carrier as part of a pharmaceutical formulation) can be at least about 0.5, 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 204, 206, 208, 210, 212, 214, 216, 218, 220, 222, 224, 226, 228, 230, 232, 234, 236, 238, 240, 242, 244, 246, 248, or 250 micrograms/m$^2$. In other specific embodiments, dose is up to 1 g per single dosage unit.

In some embodiments of methods of this invention, formulations of this invention can be administered at BiTE® molecules dose lower than about 375 mg/m$^2$; at a dose lower than about 37.5 mg/m²; at a dose lower than about 0.375 mg/m²; at a dose lower than about 0.0375 mg/m²; and/or at a dose between about 0.015 mg/m² and about 125 mg/m². In certain embodiments of methods of the invention, dosage regimens comprise low doses, administered at repeated intervals. For example, in one embodiment, formulations of the invention can be administered at a dose lower than about 0.375 mg/m² at intervals of approximately every 1, 2, 3, 4, 5, 6, 7, 8, 9, 10, 15, 20, 25, 30, 35, 40, 45, 50, 60, 70, 80, 90, 100, 125, 150, 175, or 200 days. In further embodiments of methods of the invention, dosage regimens comprise low doses, administered via continuous intravenous infusion. For example, in one embodiment, compositions of the invention can be administered at a dose lower than about 0.375 mg/m² for 1, 2, 3, 4, 5, 6, 7, 8, 9, 10, 15, 20, 25, 30, 35, 40, 45, 50, 60, 70, 80, 90, 100, 125, 150, 175, or 200 days.

In specific embodiments of methods of this invention, MT103 formulations of this invention can be administered at BiTE® molecules dose lower than about 375 mg/m²; at a dose lower than about 37.5 mg/m²; at a dose lower than about 0.375 mg/m²; at a dose lower than about 0.0375 mg/m²; and/or at a dose between about 0.015 m g/m² and about 125 mg/m². In certain specific embodiments of methods of the invention, dosage regimens comprise low doses, administered at repeated intervals. For example, in one embodiment, MT103 formulations of the invention can be administered at a dose lower than about 0.375 mg/m² at intervals of approximately every 1, 2, 3, 4, 5, 6, 7, 8, 9, 10, 15, 20, 25, 30, 35, 40, 45, 50, 60, 70, 80, 90, 100, 125, 150, 175, or 200 days. In further specific embodiments of methods of the invention, dosage regimens comprise low doses, administered via continuous intravenous infusion. For example, in one embodiment, compositions of the invention can be administered at a dose lower than about 0.375 mg/m² for 1, 2, 3, 4, 5, 6, 7, 8, 9, 10, 15, 20, 25, 30, 35, 40, 45, 50, 60, 70, 80, 90, 100, 125, 150, 175, or 200 days.

In specific embodiments, the specified dosage can result in B cell depletion in the human treated using MT103 formulations and methods of the invention for a period of at least about 1, 2, 3, 5, 7, 10, 14, 20, 30, 45, 60, 75, 90, 120, 150 or 180 days or longer. In certain embodiments, pre-B cells (not expressing surface immunoglobulin) are depleted. In certain embodiments, mature B cells (expressing surface immunogloblin) are depleted. In other embodiments, all non-malignant types of B cells can exhibit depletion. Any of these types of B cells can be used to measure B cell depletion. B cell depletion can be measured in bodily fluids such as blood serum, or in tissues such as bone marrow. In certain embodiments of methods of the invention, B cells are depleted by at least 30%, 40%, 50%, 60%, 70%, 80%, 90%, or 100% in comparison to B cell levels in the patient being treated before use of compositions and methods of the invention. In other embodiments of methods of the invention, B cells are depleted by at least 30%, 40%, 50%, 60%, 70%, 80%, 90%, or 100% in comparison to typical standard B cell levels for humans. In related embodiments, the typical standard B cell levels for humans are determined using patients comparable to the patient being treated with respect to age, sex, weight, and other factors.

In various embodiments, the therapies (e.g., prophylactic or therapeutic agents) are administered as a continuous infusion, less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patient visit.

In certain embodiments, BiTE® molecule of a formulation of the invention and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of BiTE® molecules of a formulation of the invention may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of a therapy (e.g., a prophylactic or therapeutic agent) other than BiTE® molecules of a formulation of the invention may be repeated and the administration may be separated by at least at least 1 day, 2 days, 3 days, 5 days, 10 days, 15 days, 30 days, 45 days, 2 months, 75 days, 3 months, or at least 6 months.

In certain embodiments of the invention, the dose can be escalated or reduced to maintain a constant dose in the blood or in a tissue, such as, but not limited to, bone marrow. In related embodiments, the dose is escalated or reduced by about 2%, 5%, 8%, 10%, 15%, 20%, 30%, 40%, 50%, 60%, 70%, 80%, 90%, and 95% in order to maintain a desired level of BiTE® molecules of formulations and methods of the invention.

In certain embodiments, the dosage can be adjusted and/or the infusion rate can be reduced based on patient's immunogenic response to BiTE® molecules formulated according to the methods of the invention.

Bioavailability of a formulation measures the fraction of an administered dose of unchanged drug that reaches the systemic circulation. Bioavailability of intravenously delivered drug is deemed 100%. The bioavailability of drug substance administered via other routes (e.g., subcutaneous injection) is below 100% due to incomplete absorption and first-pass metabolism. Absolute bioavailability compares the bioavailability (estimated as area under the curve, or AUC) of the active drug in systemic circulation following non-intravenous administration (e.g., subcutaneous administration), with the bioavailability of the same drug following intravenous administration. In order to determine absolute bioavailability of a drug, a pharmacokinetic study must be done to obtain a plasma drug concentration as a function of time plot for the drug after both intravenous (IV) and non-intravenous (e.g., subcutaneous) administration. The absolute bioavailability is the dose-corrected area under curve (AUC) non-intravenous divided by AUC intravenous.

The bioavailability of a bispecifc antibody formulated according to a composition or method described herein may be determined using any methods known to one of skill in the art. For example, the serum levels of a bispecific antibody may be monitored by an ELISA assay. Bioavailability may be determined in a human subject or in any one of the suitable non-human experimental systems including, but not limited to non-human primates (e.g., cyno) and rodents (e.g., mouse).

In one embodiment, a formulation of the invention is suitable for subcutaneous delivery. In one embodiment, the bioavailability of a bispecifc antibody formulated according to a composition or method described herein is between about 10% and about 100%, between about 10% and about 90%, between about 10% and about 80%, between about 10% and about 70%, between about 10% and about 60%, between about 10% and about 50%, between about 10% and about 40%, between about 10% and about 30%, between about 10% and about 20%, between about 20% and about 80%, between about 20% and about 60%, between about 20% and about 40%, between about 30% and about 100%, or between about 30% and about 60%. In another embodiment, the bioavailability of a bispecifc antibody formulated according to a composition or method described herein is between 10% and 100%, between 10% and 90%, between 10% and 80%, between 10% and 70%, between 10% and 60%, between 10% and 50%, between 10% and 40%, between 10% and 30%, between 10% and 20%, between 20% and 80%, between 20% and 60%, between 20% and 40%, between 30% and 100%, or between 30% and 60%. In a further embodiment, the bioavailability of a bispecifc antibody formulated according to a composition or method described herein is at least about 10%, at least about 20%, at least about 30%, at least about 40%, at least about 60%, at least about 70%, at least about 80%, or at least about 90%. In a further embodiment, the bioavailability of a bispecifc antibody formulated according to a composition or method described herein is at least 10%, at least 20%, at least 30%, at least 40%, at least 60%, at least 70%, at least 80%, or at least 90%. In a further embodiment, the bioavailability of a bispecifc antibody formulated according to a composition or method described herein is about 10%, about 20%, about 30%, about 40%, about 60%, about 70%, about 80%, or about 90%. In a further embodiment, the bioavailability of a bispecifc antibody formulated according to a composition or method described herein is 10%, 20%, 30%, 40%, 60%, 70%, 80%, or 90%.

5.9.1. Toxicity Testing

The tolerance, toxicity and/or efficacy of the formulations and/or treatment regimens of the present invention can be determined by standard pharmaceutical procedures in cell cultures or experimental animals, e.g., for determining the LD50 (the dose lethal to 50% of the population), the ED50 (the dose therapeutically effective in 50% of the population), and IC50 (the dose effective to achieve a 50% inhibition). In a specific embodiment, the dose is a dose effective to achieve at least a 60%, 70%, 80%, 90%, 95%, or 99% depletion of circulating B cells or circulating immunoglobulin, or both. The dose ratio between toxic and therapeutic effects is the therapeutic index and it can be expressed as the ratio LD50/ED50. Therapies that exhibit large therapeutic indices may be preferred.

Data obtained from the cell culture assays and animal studies can be used in formulating a range of dosages of the formulations and/or treatment regimens for use in humans. The dosage of such agents may lie within a range of circulating concentrations that include the ED50 with little or no toxicity. The dosage may vary within this range depending upon the dosage form employed and the route of administration utilized. For any therapy used in methods of the invention, a therapeutically effective dose can be estimated by appropriate animal models. Depending on the species of the animal model, the dose can be scaled for human use according to art-accepted formulas, for example, as provided by Freireich et al., Quantitative comparison of toxicity of anticancer agents in mouse, rat, monkey, dog, and human, *Cancer Chemotherapy Reports*, NCI 1966 40:219-244. Data obtained from cell culture assays can be useful for predicting potential toxicity. Animal studies can be used to formulate a specific dose to achieve a circulating plasma concentration range that includes the IC50 (i.e., the concentration of the test compound that achieves a half-maximal inhibition of symptoms) as determined in cell culture. Such information can be used to more accurately determine useful doses in humans. Plasma drug levels may be measured, for example, by high performance liquid chromatography, ELISA, or by cell based assays.

5.10. Patient Diagnosis, Staging and Therapeutic Regimens in Oncology

According to certain aspects of the invention, the treatment regimen and dose used with CD19×CD3 BiTE® molecule (e.g., MT103) formulations and methods of the invention is chosen based on a number of factors including, but not limited to, the stage of the B cell disease or disorder being treated. Appropriate treatment regimens can be determined by one of skill in the art for particular stages of a B cell disease or disorder in a patient or patient population. Dose response curves can be generated using standard protocols in the art in order to determine the effective amount of anti-CD19 BiTE® formulations of the invention for treating patients having different stages of a B cell disease or disorder. In general, patients having more advanced stages of a B cell disease or disorder will require higher doses and/or more frequent doses which may be administered over longer periods of time in comparison to patients having an early stage B cell disease or disorder.

CD19×CD3 BiTE® molecule (e.g., MT103) formulations and methods of the invention may be practiced to treat B cell diseases, including B cell malignancies. The term "B cell malignancy" includes any malignancy that is derived from a cell of the B cell lineage. Exemplary B cell malignancies include, but are not limited to: B cell subtype non-Hodgkin's lymphoma (NHL) including low grade/follicular NHL, small lymphocytic (SL) NHL, intermediate grade/follicular NHL, intermediate grade diffuse NHL, high grade immunoblastic NHL, high grade lymphoblastic NHL, high grade small non-cleaved cell NHL; mantle-cell lymphoma, and bulky disease NHL; Burkitt's lymphoma; multiple myeloma; pre-B acute lymphoblastic leukemia and other malignancies that derive from early B cell precursors; common acute lymphocytic leukemia (ALL); chronic lymphocytic leukemia (CLL) including immunoglobulin-mutated CLL and immunoglobulin-unmutated CLL; hairy cell leukemia; Null-acute lymphoblastic leukemia; Waldenstrom's Macroglobulinemia; diffuse large B cell lymphoma (DLBCL) including germinal center B cell-like (GCB) DLBCL, activated B cell-like (ABC) DLBCL, and type 3 DLBCL; pro-lymphocytic leukemia; light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); Hodgkin's lymphoma including classical and nodular lymphocyte pre-dominant type; lymphoplasmacytic lymphoma (LPL); and marginal-zone lymphoma including gastric mucosal-associated lymphoid tissue (MALT) lymphoma.

In a further embodiment the invention can be employed to treat mature B cell malignancies (i.e., express Ig on the cell surface) including but not limited to follicular lymphoma, mantle-cell lymphoma, Burkitt's lymphoma, multiple myeloma, diffuse large B-cell lymphoma (DLBCL) including germinal center B cell-like (GCB) DLBCL, activated B cell-like (ABC) DLBCL, and type 3 DLBCL, Hodgkin's lymphoma including classical and nodular lymphocyte predominant type, lymphoplasmacytic lymphoma (LPL), marginal-zone lymphoma including gastric mucosal-associated lymphoid tissue (MALT) lymphoma, and chronic lymphocytic leukemia (CLL) including immunoglobulin-mutated CLL and immunoglobulin-unmutated CLL.

Further, CD19 is expressed earlier in B cell development than, for example, CD20, and is therefore particularly suited for treating pre-B cell and immature B cell malignancies (i.e., do not express Ig on the cell surface), for example, in the bone marrow. Illustrative pre-B cell and immature B cell malignancies include, but are not limited to, acute lymphoblastic leukemia.

In other particular embodiments, the invention can be practiced to treat extranodal tumors.

5.10.1. Diagnosis and Staging of B Cell Malignancies

The progression of cancer, such as a B cell disease or disorder capable of tumor formation (e.g., non-Hodgkin lymphoma, diffuse large B cell lymphoma, follicular lymphoma, and Burkitt lymphoma) is typically characterized by the degree to which the cancer has spread through the body and is often broken into the following four stages which are prognostic of outcome. Stage I: The cancer is localized to a particular tissue and has not spread to the lymph nodes. Stage II: The cancer has spread to the nearby lymph nodes, i.e., metastasis. Stage III: The cancer is found in the lymph nodes in regions of the body away from the tissue of origin and may comprise a mass or multiple tumors as opposed to one. Stage IV: The cancer has spread to a distant part of the body. The stage of a cancer can be determined by clinical observations and testing methods that are well known to those of skill in the art. The stages of cancer described above are traditionally used in conjunction with clinical diagnosis of cancers characterized by tumor formation, and can be used in conjunction with the formulations and methods of the present invention to treat B cell diseases and disorders. Typically early stage disease means that the disease remains localized to a portion of a patient's body or has not metastasized.

With respect to non-tumor forming B cell diseases and disorders such as, but not limited to, multiple myeloma, the criteria for determining the stage of disease differs. The Durie-Salmon Staging System has been widely used. In this staging system, clinical stage of disease (stage I, II, or III) is based on several measurements, including levels of M protein, the number of lytic bone lesions, hemoglobin values, and serum calcium levels. Stages are further divided according to renal (kidney) function (classified as A or B). According to the Durie-Salmon Staging System Stage I (low cell mass) is characterized by all of the following: Hemoglobin value >10 g/dL; Serum calcium value normal or ≤12 mg/dL; Bone x-ray, normal bone structure (scale 0) or solitary bone plasmacytoma only; and Low M-component production rate: IgG value <5 g/dL, IgA value <3 g/d, Bence Jones protein <4 g/24 h. Stage I patients typically have no related organ or tissue impairment or symptoms. Stage II (intermediate cell mass) is characterized by fitting neither stage I nor stage III. Stage III (high cell mass) is characterized by one or more of the following: Hemoglobin value <8.5 g/dL; Serum calcium value >12 mg/dL; Advanced lytic bone lesions (scale 3); High M-component production rate: IgG value >7 g/dL, IgA value >5 g/dL, Bence Jones protein >12 g/24 h Subclassification (either A or B), where A is Relatively normal renal function (serum creatinine value <2.0 mg/dL) and B is Abnormal renal function (serum creatinine value ≥2.0 mg/dL).

Another staging system for myeloma is the International Staging System (ISS) for myeloma. This system can more effectively discriminate between staging groups and is based on easily measured serum levels of beta 2-microglobulin ($\beta$2-M) and albumin. According to the ISS for myeloma, Stage I is characterized by $\beta$2-M<3.5 and Albumin ≥3.5, Stage II is characterized by $\beta$2-M<3.5 and albumin <3.5 or $\beta$2-M 3.5-5.5, and Stage III is characterized by $\beta$2-M>5.5 (Multiple Myeloma Research Foundation, New Canaan, Conn.).

The stage of a B cell malignancy in a patient is a clinical determination. As indicated above, with respect to solid tumors, the spread, location, and number of tumors are the primary factors in the clinical determination of stage. Determination of stage in patients with non-tumor forming B cell malignancies can be more complex requiring serum level measurements as described above.

The descriptions of stages of B cell diseases and disorders above are not limiting. Other characteristics known in the art for the diagnosis of B cell diseases and disorders can be used as criteria for patients to determine stages of B cell diseases or disorders.

5.10.2. Clinical Criteria for Diagnosing B Cell Malignancies

Diagnostic criteria for different B cell malignancies are known in the art. Historically, diagnosis is typically based on a combination of microscopic appearance and immunophenotype. More recently, molecular techniques such as gene-expression profiling have been applied to develop molecular definitions of B cell malignancies (see, e.g., Shaffer et al., *Nature* 2:920-932 (2002)). Exemplary methods for clinical diagnosis of particular B cell malignancies are provided below. Other suitable methods will be apparent to those skilled in the art.

5.11. Patient Diagnosis and Therapeutic Regimens in Transplantation

According to certain aspects of the invention, the treatment regimen and dose used with formulations and methods of the invention is chosen based on a number of factors including, for example, clinical manifestation that place a patient at risk for developing a humoral rejection, or clinical evidence that such a rejection is developing. The terms "humoral" and "antibody-mediated" are used interchangeably herein.

The criteria for assessing the risk that a patient will develop a humoral rejection are established according to the knowledge and skill in the art. In one embodiment, a positive complement dependent cytotoxicity or antiglobulin enhanced complement dependent cytotoxicity crossmatch indicates that a patient is at high risk for humoral rejection. In one embodiment, a positive crossmatch or a prior positive complement dependent cytotoxicity or anti-globulin enhanced complement dependent cytotoxicity crossmatch indicates that a patient is at an intermediate risk for humoral rejection. In one embodiment, a negative crossmatch indicates that a patient is at a low risk for humoral rejection.

In another embodiment, a transplant recipient in need of prophylaxis against graft rejection may be identified as a patient or patient population having detectable circulating anti-HLA allo antibodies prior to transplantation. In another example, the patient or patient population is identified as having panel reactive antibodies prior to transplantation. The presence of detectable circulating anti-HLA allo antibodies in a transplant recipient post-transplantation can also be used to identify the patient or patient population in need of treatment for humoral rejection according to the invention. The patient or patient population in need of treatment for humoral rejection can also be identified according to other clinical criteria that indicate that a transplant recipient is at risk for developing a humoral rejection or has already developed a humoral rejection. For example, a transplant recipient in need of treatment of humoral rejection may be identified as a patient or population in an early stage of humoral rejection, such as a latent humoral response characterized by circulating anti-donor allo antibodies. An early stage of humoral rejection may also be a silent reaction characterized by circulating anti-donor allo antibodies and C4d deposition, or a subclinical rejection characterized by circulating anti-donor allo antibodies, C4d deposition, and tissue pathology. In later stages, the recipient is identified as a patient or patient population presenting with clinical indications of humoral rejection characterized according to the knowledge and skill in the art, for example, by circulating anti-donor allo antibodies, C4d deposition, tissue pathology, and graft dysfunction.

The present invention provides therapeutic formulations, methods and regimens effective to reduce the incidence, severity, or duration of GVHD, a rejection episode, or post-transplant lymphoproliferative disorder. In certain embodiments, CD19×CD3 BiTE® molecule (e.g., MT103) formulations and methods of the invention are effective to attenuate the host response to ischemic reperfusion injury of a solid tissue or organ graft. In one embodiment, CD19×CD3 BiTE® molecule (e.g., MT103) formulations and methods of the invention are effective to prolong survival of a graft in a transplant recipient.

The present invention encompasses grafts that are autologous, allogeneic, or xenogeneic to the recipient. The types of grafts encompassed by the invention include tissue and organ grafts, including but not limited to, bone marrow grafts, peripheral stem cell grafts, skin grafts, arterial and venous grafts, pancreatic islet cell grafts, and transplants of the kidney, liver, pancreas, thyroid, and heart. The terms "graft" and "transplant" are used interchangeably herein. In one embodiment, the autologous graft is a bone marrow graft, an arterial graft, a venous graft or a skin graft. In one embodiment, the allograft is a bone marrow graft, a corneal graft, a kidney transplant, a pancreatic islet cell transplant, or a combined transplant of a kidney and pancreas. In one embodiment, the graft is a xenograft, wherein the possible animal donors include, but are not limited to pigs. The formulations and methods of the present invention may also be used to suppress a deleterious immune response to a non-biological graft or implant, including but not limited to an artificial joint, a stent, or a pacemaker device.

CD19×CD3 BiTE® molecule (e.g., MT103) formulations and methods of the invention may be used to treat or prevent GVHD, humoral rejection, or post-transplant lymphoproliferative disorder without regard to the particular indications initially giving rise to the need for the transplant or the particular type of tissue transplanted.

Therapeutic formulations and regimens of the present invention are described for treating human subjects diagnosed with autoimmune diseases or disorders, including but not limited to, rheumatoid arthritis, SLE, ITP, pemphigus-related disorders, diabetes, and scleroderma.

Appropriate treatment regimens can be determined by one of skill in the art for the particular patient or patient population. In particular embodiments, the treatment regimen is a pre-transplant conditioning regimen, a post-transplant maintenance regimen, or post-transplant treatment regimen for an acute or a chronic rejection. In certain embodiments, the particular regimen is varied for a patient who is assessed as being at a high or intermediate risk of developing a humoral response, compared with the regimen for a patient who is assessed as being at a low risk of developing a humoral response.

In certain embodiments, the particular regimen is varied according to the stage of humoral rejection, with more aggressive therapy being indicated for patients at later stages of rejection. The stages of humoral rejection may be classified according to the knowledge and skill in the art. For example, the stages of humoral rejection may be classified as one of stages I to IV according to the following criteria: Stage I Latent Response, characterized by circulating anti-donor allo antibodies, especially anti-HLA antibodies; Stage II Silent Reaction, characterized by circulating anti-donor allo antibodies, especially anti-HLA antibodies, and C4d deposition, but without histologic changes or graft dysfunction; Stage III Subclinical Rejection: characterized by circulating anti-donor allo antibodies, especially anti-HLA antibodies, C4d deposition, and tissue pathology, but without graft dysfunction; Stage IV Humoral Rejection: characterized by circulating anti-donor allo antibodies, especially anti-HLA antibodies, C4d deposition, tissue pathology, and graft dysfunction.

Dose response curves can be generated using standard protocols in the art in order to determine the effective amount of CD19×CD3 BiTE® molecule (e.g., MT103) formulations of the invention for use in a particular regimen, for example, in conditioning regimens prior to transplantation, and in post-transplantation regimens for prophylaxis and treatment of GVHD, humoral rejection, or post-transplantation lymphoproliferative disorders. In general, patients at high risk for developing a humoral rejection and those already exhibiting one or more clinical indicators of rejection will require higher doses and/or more frequent doses which may be administered over longer periods of time in comparison to patients who are not at high risk or who do not exhibit any indications of active rejection.

CD19×CD3 BiTE® molecule (e.g., MT103) formulations and methods of the invention may be practiced to treat or prevent GVHD, humoral rejection, or post-transplantation lymphoproliferative disorders, either alone or in combination with other therapeutic agents or treatment regimens. Other therapeutic regimens for the treatment or prevention of GVHD, humoral rejection, or post-transplantation lymphoproliferative disorders may comprise, for example, one or more of anti-lymphocyte therapy, steroid therapy, antibody depletion therapy, immunosuppression therapy, and plasmapheresis.

Anti-lymphocyte therapy may comprise the administration to the transplant recipient of anti-thymocyte globulins, also referred to as thymoglobulin. Anti-lymphocyte therapy may also comprise the administration of one or more monoclonal antibodies directed against T cell surface antigens. Examples of such antibodies include, without limitation, CAMPATH™-1H (alemtuzumab), CAMPATH™-1G, CAMPATH™-1M, SIMULECT™ (basiliximab), and ZENAPAX™ (daclizumab). In a specific embodiment, the anti-lymphocyte therapy comprises one or more additional antibodies directed against B cells, including, without limitation, RITUXAN™ (rituximab).

Steroid therapy may comprise administration to the transplant recipient of one or more steroids selected from the group consisting of cortisol, prednisone, methyl prednisolone, dexamethazone, and indomethacin. One or more of the steroids may be corticosteroids, including without limitation, cortisol, prednisone, and methylprednisolone.

Antibody depletion therapy may include, for example, administration to the transplant recipient of intravenous immunoglobulin. Antibody depletion therapy may also comprise immunoadsorption therapy applied to the graft ex vivo, prior to transplantation. Immunoadsorption may be accomplished using any suitable technique, for example, protein A affinity, or antibody based affinity techniques using antibodies directed against T cell or B cell surface markers such as anti-CD3 antibodies, anti-CD20 antibodies, and anti-CD19 antibodies.

Immunosuppression therapy may comprise the administration of one or more immunosuppressive agents such as inhibitors of cytokine transcription (e.g., cyclosporin A, tacrolimus), nucleotide synthesis (e.g., azathiopurine, mycophenolate mofetil), growth factor signal transduction (e.g., sirolimus, rapamycin), and the T cell interleukin 2 receptor (e.g., daclizumab, basiliximab). In a particular embodiment, an immunosuppressant agent used in combination with formulations and methods of the invention includes one or more of the following: adriamycin, azathiopurine, busulfan, cyclophosphamide, cyclosporin A ("CyA"), cytoxin, fludarabine, 5-fluorouracil, methotrexate, mycophenolate mofetil (MOFETIL), nonsteroidal anti-inflammatories (NSAIDs), rapamycin, and tacrolimus (FK506). Immunosuppressive agents may also comprise inhibitors of complement, for example, soluble complement receptor-1, anti-C5 antibody, or a small molecule inhibitor of C1s, for example as described in Buerke et al. (*J. Immunol.*, 167:5375-80 (2001).

In one embodiment, formulations and methods of the invention are used in combination with one or more therapeutic regimens for suppressing humoral rejection, including, without limitation, tacrolimus and mycophenolate mofetil therapy, immunoadsorption, intravenous immunoglobulin therapy, and plasmapheresis.

5.11.1. Diagnosis and Clinical Criteria

The present invention provides CD19×CD3 BiTE® molecule (e.g., MT103) formulations and methods for treating and preventing GVHD, humoral rejection, and post-transplant lymphoproliferative disorder in human transplant recipients. Formulations and methods of the invention can be used regardless of the particular indications which gave rise to the need for a transplant. Similarly, the use of formulations and methods of the invention for the treatment and prevention of GVHD, humoral rejection, and post-transplant lymphoproliferative disorders is not limited by the particular type of tissue which is intended for transplantation or which has been transplanted.

In one embodiment, the invention provides CD19×CD3 BiTE® molecule (e.g., MT103) formulations and methods for the prevention of humoral rejection in a human transplant recipient wherein the transplant recipient is identified as a patient or patient population at increased risk for developing a humoral rejection. Such patients may also be referred to as "sensitized." The criteria for the identification of sensitized patients is known to the skilled practitioner. Such criteria may include, for example, patients having detectable levels of circulating antibodies against HLA antigens, e.g., anti-HLA allo antibodies. Such criteria may also include patients who have undergone previous transplantations, a pregnancy, or multiple blood transfusions. Patients who are at an increased risk for humoral rejection also include those having imperfect donor-recipient HLA matching, and those transplantations which are ABO-incompatible. Sensitized individuals are candidates for pretreatment or conditioning prior to transplantation. Sensitized individuals are also candidates for post-transplantation maintenance regimens for the prevention of humoral rejection.

In one embodiment, CD19×CD3 BiTE® molecule (e.g., MT103) formulations and methods of the invention comprise or are used in combination with a therapeutic regimen for the treatment of an acute or chronic rejection. In particular embodiments, the rejection is characterized as a Stage I, a Stage II, a Stage III, or a Stage IV humoral rejection.

In one embodiment, CD19×CD3 BiTE® molecule (e.g., MT103) formulations and methods of the invention comprise or are used in combination with a therapeutic regimen for the treatment of an early stage humoral rejection. In particular embodiments, the early stage humoral rejection is a Stage I, II, or III rejection. Clinical indications of an early stage humoral rejection are determined according to the knowledge and skill in the art and may include, for example, the development in the patient of circulating donor-specific anti-HLA antibodies, the presence of complement markers of antibody activity such as C4d and C3d deposits in graft biopsies, and the presence of anti-HLA antibodies in graft biopsies. Other indicators of an early stage humoral rejection are known to the skilled practioner and may include, for example, the development of antiendothelial antibodies, especially antivimentin antibodies, and the development of nonclassical MHC class I-related chain A (MICA) allo antibodies.

In one embodiment, CD19×CD3 BiTE® molecule (e.g., MT103) formulations and methods of the invention comprise or are used in combination with a therapeutic regimen for the treatment of humoral rejection characterized in part by graft dysfunction. In particular embodiments, the patient or patient population in need of treatment for humoral rejection is identified according to criteria known in the art for graft dysfunction. Examples of such criteria for particular types of grafts are provided in the sections that follow. In other embodiments, the patient or patient population in need of treatment for humoral rejection is identified according to other criteria that are particular to the type of tissue graft, such as histological criteria. Examples of such criteria are also provided in the sections that follow.

5.11.2. Bone Marrow Transplants

CD19×CD3 BiTE® molecule (e.g., MT103) formulations and methods of the invention are useful for treating or preventing GVHD, humoral rejection, and post-transplant lymphoproliferative disorder in a bone marrow transplant recipient. In one embodiment, formulations and methods of the invention comprise or are used in combination with a pretransplant conditioning regimen.

In one embodiment, the indication is a B cell associated autoimmune condition and formulations and methods of the invention may be used to eliminate the deleterious B cells from the patient without the need for chemotherapy or radiation therapy conditioning regimens. In one embodiment, formulations of the invention are administered in combination with a chemotherapy or radiation therapy regimen, which regimen comprises a lower dose of one or more chemotherapeutic agents, or a lower dose of radiation, than the dose that is administered in the absence of formulations of the invention.

A patient or patient population in need of, or likely to benefit from, a bone marrow transplant is identified according to the knowledge and skill in the art. Examples of patients that may be candidates for bone marrow transplantation include patients who have undergone chemotherapy or radiation therapy for the treatment of a cancer or an autoimmune disease or disorder, and patients who are unable to clear a viral infection residing in cells of the immune system.

5.11.3. Post-Transplant Lymphoproliferative Disorder

The immunosuppression necessary for successful transplantation can give rise to a post-transplant lymphoproliferative disorder of B cell origin. Generally, a post-transplant lymphoproliferative disorder is associated with Epstein-Barr virus infected cells. Post-transplant lymphoproliferative disorder (PTLD) can range in severity from a benign self-limiting mononucleosis-like syndrome to an aggressive non-Hodgkins lymphoma. Formulations and methods of the present invention may be used to treat PTLD arising from any transplant. The transplant may be a solid organ transplant, for example a heart transplant, a liver transplant, a kidney transplant, or a combined kidney-pancreas transplant. In one embodiment, formulations and methods of the invention are used to treat PTLD as part of a therapeutic regimen that includes a temporary cessation or reduction of other immunosuppressive therapy.

In one embodiment, CD19×CD3 BiTE® molecule (e.g., MT103) formulations are administered as part of a therapeutic regimen including one or more of the following: high dose intravenous gamma globulin, a cytokine, an anti-viral agent, and an anti-CD20 monoclonal antibody. The therapeutic regimen may include a temporary cessation or reduction of immunosuppression therapy. In one embodiment, intravenous gamma globulin is administered at a daily dose of 0.4 g/kg for 1 to 5 days, preferably for 3 days, and the cytokine is interferon alpha administered for at least 7 days. In one embodiment, one or more cytokines is used in the regimen. In one embodiment, one or more anti-viral agents is used in the regimen. The anti-viral agent may be selected from any suitable anti-viral agent known to those of skill in the art. In one embodiment, the anti-viral agent is aciclovir or ganciclovir. The anti-viral agent may be administered for at least one or two weeks. The anti-viral agent may also be administered for longer periods, for example, 1 month, 2 months, 3 months, 4 months, or 5 months.

5.12. Patient Diagnosis and Therapeutic Regimens in Autoimmune Disease

According to certain aspects of the invention, the treatment regimen and dose used with CD19×CD3 BiTE® molecule (e.g., MT103) formulations and methods of the invention is chosen based on a number of factors including, but not limited to, the stage of the autoimmune disease or disorder being treated. Appropriate treatment regimens can be determined by one of skill in the art for particular stages of an autoimmune disease or disorder in a patient or patient population. Dose response curves can be generated using standard protocols in the art in order to determine the effective amount of CD19×CD3 BiTE® molecule (e.g., MT103) formulations of the invention for treating patients having different stages of a autoimmune disease or disorder. In general, patients having more activity of a autoimmune disease or disorder will require higher doses and/or more frequent doses which may be administered over longer periods of time in comparison to patients having less activity of an autoimmune disease or disorder.

CD19×CD3 BiTE® molecule (e.g., MT103) formulations and methods may be practiced to treat an autoimmune disease or disorder. The term "autoimmune disease or disorder" refers to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, including, but not limited to chronic inflammation. Autoimmune disorders may or may not be associated with inflammation. Moreover, inflammation may or may not be caused by an autoimmune disorder. Thus, certain disorders may be characterized as both autoimmune and inflammatory disorders. Exemplary autoimmune diseases or disorders include, but are not limited to: alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes, eosinophilic fascites, fibromyalgia-fibromyositis, glomerulonephritis, Graves' disease, Guillain-Barre, Hashimoto's thyroiditis, Henoch-Schönlein purpura, idiopathic pulmonary fibrosis, idiopathic/autoimmune thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus-related disorders (e.g., pemphigus vulgaris), pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, Vogt-Koyanagi-Hareda syndrome and chronic inflammation resulting from chronic viral or bacteria infections.

CD19 is expressed on immature B cells, therefore an anti-CD19 BiTE® molecule (e.g., CD19×CD3 BiTE® molecule (e.g., MT103)) may be particularly suited for depleting pre-B cells and immature B cells, e.g, in the bone marrow.

5.12.1. Diagnosis of Autoimmune Diseases or Disorders

The diagnosis of an autoimmune disease or disorder is complicated in that each type of autoimmune disease or disorder manifests differently among patients. This heterogeneity of symptoms means that multiple factors are typically used to arrive at a clinical diagnosis. Generally, clinicians use factors, such as, but not limited to, the presence of auto antibodies, elevated cytokine levels, specific organ dysfunction, skin rashes, joint swelling, pain, bone remodeling, and/or loss of movement as primarily indicators of an autoimmune disease or disorder. For certain autoimmune diseases or disorders, such as RA and SLE, standards for diagnosis are known in the art. For certain autoimmune diseases or disorders, stages of disease have been characterized and are well known in the art. These art recognized methods for diagnosing autoimmune diseases and disorders as well as stages of disease and scales of activity and/or severity of disease that are well known in the art can be used to identify patients and patient populations in need of treatment for an autoimmune disease or disorder using formulations and methods of the invention.

5.12.2. Clinical Criteria for Diagnosing Autoimmune Diseases or Disorders

Diagnostic criteria for different autoimmune diseases or disorders are known in the art. Historically, diagnosis is typically based on a combination of physical symptoms. More recently, molecular techniques such as gene-expression profiling have been applied to develop molecular definitions of autoimmune diseases or disorders. Exemplary methods for clinical diagnosis of particular autoimmune diseases or disorders are provided below. Other suitable methods will be apparent to those skilled in the art.

In certain embodiments, patients with low levels of autoimmune disease activity or patients with an early stage of an autoimmune disease (for diseases where stages are recognized) can be identified for treatment using CD19×CD3 BiTE® molecule (e.g., MT103) formulations and methods. The early diagnosis of autoimmune disease is difficult due to the general symptoms and overlap of symptoms among diseases. In such embodiments, a patient treated at an early stage or with low levels of an autoimmune disease activity has symptoms comprising at least one symptom of an autoimmune disease or disorder. In related embodiments, a patient treated at an early stage or with low levels of an autoimmune disease has symptoms comprising at least 1, 2, 3, 4, 5, 6, 7, 8, 9, 10, 11, 12, 13, 14, or 15 symptoms of an autoimmune disease or disorder. The symptoms may be of any autoimmune diseases and disorders or a combination thereof. Examples of autoimmune disease and disorder symptoms are described below.

5.13. Determining CD19 Density in a Sample or Subject

While not required, assays for CD19 density can be employed to further characterize the patient's diagnosis. Methods of determining the density of anti-CD19 antibody binding to cells are known to those skilled in the art (See, e.g., Sato et al., *J. Immunology* 165:6635-6643 (2000); which discloses a method of assessing cell surface density of specific CD antigens). Other standard methods include Scatchard analysis. For example, an anti-CD19 antibody or fragment can be isolated, radiolabeled, and the specific activity of the radiolabeled antibody determined. The antibody is then contacted with a target cell expressing CD19. The radioactivity associated with the cell can be measured and, based on the specific activity, the amount of antibody or antibody fragment bound to the cell determined.

Fluorescence activated flow cytometry can also be employed. Generally, the antibody or antibody fragment is bound to a target cell expressing CD19. A second reagent that binds to the antibody is then added, for example, a fluorochrome labeled anti-immunoglobulin antibody. Fluorochrome staining can then be measured and used to determine the density of antibody or antibody fragment binding to the cell.

As another suitable method, the antibody or antibody fragment can be directly labeled with a detectable label, such as a fluorophore, and bound to a target cell. The ratio of label to protein is determined and compared with standard beads with known amounts of label bound thereto. Comparison of the amount of label bound to the cell with the known standards can be used to calculate the amount of antibody bound to the cell.

In yet another aspect, the present invention provides a method for detecting in vitro or in vivo the presence and/or density of CD19 in a sample or individual. This can also be useful for monitoring disease and effect of treatment and for determining and adjusting the dose of the CD19×CD3 BiTE® molecule (e.g., MT103) formulation to be administered. The in vivo method can be performed using imaging techniques such as PET (positron emission tomography) or SPECT (single photon emission computed tomography). One could also label an anti-CD19 antibody with Indium using a covalently attached chelator. The resulting antibody can be imaged using standard gamma cameras the same way as ZEVALIN™ (Indium labeled anti-CD20 mAb) (Biogen Idec, Cambridge Mass.) is used to image CD20 antigen.

In one embodiment, the in vivo method can be performed by contacting a sample to be tested, optionally along with a control sample, with a human anti-CD19 antibody under conditions that allow for formation of a complex between the antibody and the human CD19 antigen. Complex formation is then detected (e.g., using fluorescent activated flow cytometry or Western blotting). When using a control sample along with the test sample, a complex is detected in both samples and any statistically significant difference in the formation of complexes between the samples is indicative of the presence of human CD19 in the test sample.

In other embodiments, mean florescence intensity can be used as a measure of CD19 density. In such embodiments, B cells are removed from a patient and stained with a CD19 antibodies that have been labeled with a florescent label and the fluorescence intensity is measured using flow cytometry. Fluorescence intensities can be measured and expressed as an average of intensity per B cell. Using such methods, mean florescence intensities that are representative of CD19 density can be compared for a patient before and after treatment using methods and formulations of the invention, or between patients and normal levels of hCD19 on B cells.

In patients where the density of CD19 expression on B cells has been determined, the density of CD19 may influence the determination and/or adjustment of the dosage and/or treatment regimen used with CD19×CD3 BiTE® molecule (e.g., MT103) formulations and methods of the invention. For example, where density of CD19 is high, it may be possible to use a lower dosage of an CD19×CD3 BiTE® molecule (e.g., MT103) formulation of the invention. In certain embodiments, where the patient treated using formulations and methods of the invention has a low CD19 density, a higher dosage of an CD19×CD3 BiTE® molecule (e.g., MT103) formulation of the invention may be used. In other embodiments, where the patient treated using formulations and methods of the invention has a low CD19 density, a low dosage of an CD19×CD3 BiTE® molecule (e.g., MT103) formulation of the invention may be used. In certain embodiments, where the patient treated using formulations and methods of the invention has a high CD19 density, a higher dosage of an CD19×CD3 BiTE® molecule (e.g., MT103) formulation of the invention may be used. In certain embodiments, CD19 density can be compared to CD20 density in a patient, CD19 density can be compared to an average CD19 density for humans or for a particular patient population, or CD19 density can be compared to CD19 levels in the patient prior to therapy or prior to onset of a B cell disease or disorder. In certain embodiments, the patient treated using formulations and methods of the invention has a B cell malignancy where CD19 is present on the surface of B cells.

5.14. Immunotherapeutic Protocols

CD19×CD3 BiTE® molecule (e.g., MT103) formulations used in therapeutic regimen/protocols, referred to herein as "anti-CD19 immunotherapy", can be used as a single agent therapy or in combination with other therapeutic agents or regimens. CD19×CD3 BiTE® molecule (e.g., MT103) formulations can be administered prior to, concurrently with, or following the administration of one or more therapeutic agents. Therapeutic agents that can be used in combination therapeutic regimens with formulations of the invention include any substance that inhibits or prevents the function of cells and/or causes destruction of cells. Examples include, but are not limited to, radioactive isotopes, chemotherapeutic agents, and toxins such as enzymatically active toxins of bacterial, fungal, plant or animal origin, or fragments thereof.

The therapeutic regimens described herein, or any desired treatment regimen can be tested for efficacy using a transgenic animal model which expresses human CD19 antigen in place of native CD19 antigen. Thus, an CD19×CD3 BiTE® molecule (e.g., MT103) formulation treatment regimen can be tested in an animal model to determine efficacy before administration to a human.

CD19×CD3 BiTE® molecule (e.g., MT103) formulations and methods may be practiced to treat B cell diseases, including B cell malignancies. The term "B cell malignancy" includes any malignancy that is derived from a cell of the B cell lineage. Exemplary B cell malignancies include, but are not limited to: B cell subtype non-Hodgkin's lymphoma (NHL) including low grade/follicular, NHL, small lymphocytic (SL) NHL, intermediate grade/follicular NHL, intermediate grade diffuse NHL, high grade immunoblastic NHL, high grade lymphoblastic NHL, high grade small noncleaved cell NHL; mantle-cell lymphoma, and bulky disease NHL; Burkitt's lymphoma; multiple myeloma; pre-B acute lymphoblastic leukemia and other malignancies that derive from early B cell precursors; common acute lymphocytic leukemia (ALL); chronic lymphocytic leukemia (CLL) including immunoglobulin-mutated CLL and immunoglobulin-unmutated CLL; hairy cell leukemia; Null-acute lymphoblastic leukemia; Waldenström's Macroglobulinemia; diffuse large B cell lymphoma (DLBCL) including germinal center B cell-like (GCB) DLBCL, activated B cell-like (ABC) DLBCL, and type 3 DLBCL; pro-lymphocytic leukemia; light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); Hodgkin's lymphoma including classical and nodular lymphocyte pre-dominant type; lymphoplasmacytic lymphoma (LPL); and marginal-zone lymphoma including gastric mucosal-associated lymphoid tissue (MALT) lymphoma.

In a further embodiment the invention can be employed to treat mature B cell malignancies (i.e., express Ig on the cell surface) including but not limited to follicular lymphoma, mantle-cell lymphoma, Burkitt's lymphoma, multiple myeloma, diffuse large B-cell lymphoma (DLBCL) including germinal center B cell-like (GCB) DLBCL, activated B cell-like (ABC) DLBCL, and type 3 DLBCL, Hodgkin's lymphoma including classical and nodular lymphocyte pre-dominant type, lymphoplasmacytic lymphoma (LPL), marginal-zone lymphoma including gastric mucosal-associated lymphoid tissue (MALT) lymphoma, and chronic lymphocytic leukemia (CLL) including immunoglobulin-mutated CLL and immunoglobulin-unmutated CLL.

Further, CD19 is expressed earlier in B cell development than, for example, CD20, and is therefore particularly suited for treating pre-B cell and immature B cell malignancies (i.e., do not express Ig on the cell surface), for example, in the bone marrow. Illustrative pre-B cell and immature B cell malignancies include but are not limited to acute lymphoblastic leukemia In other particular embodiments, the invention can be practiced to treat extranodal tumors.

5.15. Anti-CD19 Immunotherapy

In accordance with the present invention "anti-CD19 immunotherapy" encompasses the administration of any of the CD19×CD3 BiTE® molecule (e.g., MT103) formulations of the invention in accordance with any therapeutic regimen described herein.

Anti-CD19 immunotherapy encompasses the administration of an CD19×CD3 BiTE® molecule (e.g., MT103) formulation as a single agent therapeutic for the treatment of a B cell malignancy. Anti-CD19 immunotherapy encompasses methods of treating an early stage disease resulting from a B cell malignancy. Anti-CD19 immunotherapy encompasses methods of treating a B cell malignancy wherein an CD19×CD3 BiTE® molecule (e.g., MT103) formulation mediates depletion of B cells. Anti-CD19 immunotherapy encompasses methods of treating a B cell malignancy wherein an CD19×CD3 BiTE® molecule (e.g., MT103) formulation is administered before the patient has received any treatment for the malignancy, whether that therapy is chemotherapy, radio chemical based therapy or surgical therapy.

In one embodiment, a human subject having a B cell malignancy can be treated by administering a CD19×CD3 BiTE® molecule (e.g., MT103) formulation that may be able to mediate B cell depletion.

In one embodiment, the dose of CD19×CD3 BiTE® molecule (e.g., MT103) formulation used should be sufficient to deplete circulating B cells. Progress of the therapy can be monitored in the patient by analyzing blood samples. Other signs of clinical improvement can be used to monitor therapy.

Methods for measuring depletion of B cells that can be used in connection with formulations and methods of the invention are well known in the art and include, but are not limited to the following embodiments. In one embodiment, circulating B cells depletion can be measured with flow cytometry using a reagent other than an anti-CD19 BiTE® molecule that binds to B cells to define the amount of B cells. In other embodiments, B cell levels in the blood can be monitored using standard serum analysis. In such embodiments, B cell depletion is indirectly measured by defining the amount of an antibody known to be produced by B cells. The level of that antibody is then monitored to determine the depletion and/or functional depletion of B cells. In another embodiment, B cell depletion can be measured by immunochemical staining to identify B cells. In such embodiments, B cells or tissues or serum comprising B cells extracted from a patient can be placed on microscope slides, labeled and examined for presence or absence. In related embodiments, a comparison is made between B cells extracted prior to therapy and after therapy to determine differences in the presence of B cells.

Tumor burden can be measured and used in connection with formulations and methods of the invention. Methods for measuring tumor burden are well known in the art and include, but are not limited to the following embodiments. In certain embodiments, PET scans can be used to measure metabolic activity and identify areas of higher activity which are indicative of tumors. CT scans and MRI can also be used to examine soft tissue for the presence and size of tumors. In other embodiments, bone scan can be used to measure tumor volume and location. In yet other embodiments, tumor burden can be measured by examining the blood flow into and out of a tumor using doppler technology (e.g., ultrasound). In such embodiments, changes in blood flow over time or deviations from normal blood flow in the appropriate tissue of a patient can be used to calculate an estimate to tumor burden. Such methods for measuring tumor burden can be used prior to and following methods of treatment of the invention.

In embodiments of the invention where an CD19×CD3 BiTE® molecule (e.g., MT103) formulation is administered as a single agent therapy, the invention contemplates use of different treatment regimens.

According to certain aspects of the invention, the dose of CD19×CD3 BiTE® molecule (e.g., MT103) used is at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5 µg/kg of body weight of a patient. In certain embodiments, the dose of CD19×CD3 BiTE® molecule (e.g., MT103) used is at least about 0.01 to 0.1, 0.05 to 0.2, 0.1 to 0.5, or 0.2 to 1 µg/kg of body weight of a patient. In certain embodiments, the dose of CD19×CD3 BiTE® molecule (e.g., MT103) used is at least about 0.5 to 2, 1 to 5, or 3 to 10 µg/kg of body weight of a patient.

In certain embodiments, the dose comprises at least about 1, 2, 3, 4, 5, 6, 7, 8, 9, 10, 12, 15, 20, 25, 30, 35, 40, 45, 50, 55, 60, 70, 80, 90, 100, 125, 150, 175, 200, 250, 300, 350, 400, 450, 500 µg/m$^2$ of CD19×CD3 BiTE® molecule (e.g., MT103) administered daily for 10 to 50 consecutive days. In certain embodiments, the dose is at least about 10, 12, 15, 20, 25, 30, 35, 40, 45, 50, 55, 60, 70, 80, 90, 100, 125, 150, 175, 200 µg/m$^2$ of CD19×CD3 BiTE® molecule (e.g., MT103) administered daily for 10 to 50 consecutive days.

In one embodiment, the above doses are single dose injections. In other embodiments, the doses are administered over a period of time. In specific embodiments, the doses are administered by continuous IV. In other embodiments, the doses are administered multiple times over a period of time. The period of time may be measured in hours, days, weeks, or months. Multiple doses of CD19×CD3 BiTE® molecule (e.g., MT103) can be administered at intervals suitable to achieve a therapeutic benefit while balancing toxic side effects.

In certain embodiments, CD19×CD3 BiTE® molecule (e.g., MT103) formulations of the invention are administered to a human patient as long as the patient is responsive to therapy. In other embodiments, formulations of the invention are administered to a human patient as long as the patient's disease does not progress. In related embodiments, formulations of the invention are administered to a human patient until a patient's disease does not progress or has not progressed for a period of time, then the patient is not administered formulations of the invention unless the disease reoccurs or begins to progress again. For example, a patient can be treated with any of the above doses for about 10 to 50 days, during which time the patient is monitored for disease progression. If disease progression stops or reverses, then the patient will not be administered formulations of the invention until that patient relapses, i.e., the disease being treated reoccurs or progresses. Upon this reoccurrence or progression, the patient can be treated again with the same dosing regimen initially used or using other doses described above.

In certain embodiments, CD19×CD3 BiTE® molecule (e.g., MT103) formulations of the invention can be administered as a loading dose followed by multiple lower doses (maintenance doses) over a period of time. In such embodiments, the doses may be timed and the amount adjusted to maintain effective B cell depletion. The maintenance doses can be continued indefinitely, until toxicity is present, until platelet count decreases, until there is no disease progression, until the patient exhibits immunogenicity, or until disease progresses to a terminal state. In yet other embodiments, formulations of the invention are administered to a human patient until the disease progresses to a terminal stage.

5.16. Combination with Chemotherapeutic Agents

Anti-CD19 immunotherapy using CD19×CD3 BiTE® molecule (e.g., MT103) can be used in conjunction with other therapies including but not limited to, chemotherapy, radio-immunotherapy (RIT), chemotherapy and external beam radiation (combined modality therapy, CMT), or combined modality radioimmunotherapy (CMRIT) alone or in combination, etc. In certain embodiments, a CD19×CD3 BiTE® molecule (e.g., MT103) therapy of the present invention can be administered in conjunction with CHOP (Cyclophosphamide-Hydroxydoxorubicin-Oncovin (vincristine)-Prednisolone), the most common chemotherapy regimen for treating non-Hodgkin's lymphoma. As used herein, the term "administered in conjunction with" means that an anti-CD19 immunotherapy can be administered before, during, or subsequent to the other therapy employed.

In certain embodiments, a CD19×CD3 BiTE® molecule (e.g., MT103) immunotherapy is in conjunction with a cytotoxic radionuclide or radiotherapeutic isotope. For example, an alpha-emitting isotope such as $^{225}$Ac, $^{224}$Ac, $^{211}$At, $^{212}$Bi, $^{213}$Bi, $^{212}$Pb, $^{224}$Ra, or $^{223}$Ra. The cytotoxic radionuclide may also be a beta-emitting isotope such as $^{186}$Re, $^{188}$Re, $^{90}$Y, $^{131}$I, $^{67}$Cu, $^{177}$Lu, $^{153}$Sm, $^{166}$Ho, or $^{64}$Cu. Further, the cytotoxic radionuclide may emit Auger and low energy electrons and include the isotopes $^{125}$I, $^{123}$I or $^{77}$Br. In other embodiments the isotope may be $^{198}$Au, $^{32}$P, and the like. In certain embodiments, the amount of the radionuclide administered to the subject is between about 0.001 mCi/kg and about 10 mCi/kg.

In some embodiments, the amount of the radionuclide administered to the subject is between about 0.1 mCi/kg and about 1.0 mCi/kg. In other embodiments, the amount of the radionuclide administered to the subject is between about 0.005 mCi/kg and 0.1 mCi/kg.

In certain embodiments, a CD19×CD3 BiTE® molecule (e.g., MT103) immunotherapy is in conjunction with a chemical toxin or chemotherapeutic agent. The chemical toxin or chemotherapeutic agent may be selected from the group consisting of an enediyne such as calicheamicin and esperamicin; duocarmycin, methotrexate, doxorubicin, melphalan, chlorambucil, ARA-C, vindesine, mitomycin C, cis-platinum, etoposide, bleomycin and 5-fluorouracil.

Suitable chemical toxins or chemotherapeutic agents that can be used in combination therapies with a CD19×CD3 BiTE® molecule (e.g., MT103) immunotherapy include members of the enediyne family of molecules, such as calicheamicin and esperamicin. Chemical toxins can also be taken from the group consisting of duocarmycin (see, e.g., U.S. Pat. No. 5,703,080 and U.S. Pat. No. 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincristine, Vinorelbine, Carboplatin, Teniposide, Daunomycin, Caminomycin, Aminopterin, Dactinomycin, Mitomycins, Esperamicins (see, U.S. Pat. No. 4,675,187), Melphalan and other related nitrogen mustards.

In other embodiments, for example, "CVB" (1.5 g/m$^2$ cyclophosphamide, 200-400 mg/m$^2$ etoposide, and 150-200 mg/m$^2$ carmustine) can be used in combination therapies of the invention. CVB is a regimen used to treat non-Hodgkin's lymphoma. Patti et al., *Eur. J. Haematol.* 51:18 (1993). Other suitable combination chemotherapeutic regimens are well-known to those of skill in the art. See, for example, Freedman et al., "*Non-Hodgkin's Lymphomas*," in CANCER MEDICINE, VOLUME 2, 3rd Edition, Holland et al. (eds.), pp. 2028-2068 (Lea & Febiger 1993). As an illustration, first generation chemotherapeutic regimens for treatment of intermediate-grade non-Hodgkin's lymphoma include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and brostatin-1. In a multimodal therapy, both chemotherapeutic drugs and cytokines are co-administered with a CD19xCD3 BiTE® molecule (e.g., MT103) formulation according to the present invention. The cytokines, chemotherapeutic drugs and CD19xCD3 BiTE® molecule (e.g., MT103) formulation can be administered in any order, or together.

Other toxins that may be used in formulations and methods of the invention include poisonous lectins, plant toxins such as ricin, abrin, modeccin, botulina and diphtheria toxins.

Suitable toxins and chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985). Other suitable toxins and/or chemotherapeutic agents are known to those of skill in the art.

In certain embodiments, administration of formulations and methods of the invention may enable the postponement of toxic therapy and may help avoid unnecessary side effects and the risks of complications associated with chemotherapy and delay development of resistance to chemotherapy. In certain embodiments, toxic therapies and/or resistance to toxic therapies is delayed in patients administered formulations and methods of the invention delay for up to about 6 months, 1, 2, 3, 4, 5, 6, 7, 8, 9, or 10 years.

5.17. Combination with Therapeutic Antibodies

A CD19xCD3 BiTE® molecule (e.g., MT103) immunotherapy described herein may be administered in combination with other antibodies, including, but not limited to, anti-CD20 mAb, anti-CD52 mAb, anti-CD22 antibody, and anti-CD20 antibodies, such as RITUXAN™ (C2B8; RITUXIMAB™; IDEC Pharmaceuticals). Other examples of therapeutic antibodies that can be used in combination with methods of the invention or used in formulations of the invention include, but are not limited to, HERCEPTIN™ (Trastuzumab; Genentech), MYLOTARG™ (Gemtuzumab ozogamicin; Wyeth Pharmaceuticals), CAMPATH™ (Alemtuzumab; Berlex), ZEVALIN™ (Ipritumomab tiuxetan; Biogen Idec), BEXXAR™ (Tositumomab; Glaxo SmithKline Corixa), ERBITUX™ (Cetuximab; Imclone), and AVASTIN™ (Bevacizumab; Genentech).

In certain embodiments, a CD19xCD3 BiTE® molecule (e.g., MT103) and an anti-CD20 and/or an anti-CD22 mAb and/or an anti-CD52 mAb can be administered, optionally in the same pharmaceutical formulation, in any suitable ratio.

5.18. Combination with Immunoregulatory Agents

A CD19xCD3 BiTE® molecule (e.g., MT103) immunotherapy may also be in conjunction with an immunoregulatory agent. The term "immunoregulatory agent" as used herein for combination therapy refers to substances that act to suppress, mask, or enhance the immune system of the host. This would include substances that suppress cytokine production, downregulate or suppress self-antigen expression, or mask the MHC antigens. Examples of such agents include 2-amino-6-aryl-5-substituted pyrimidines (see, U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or -α antibodies; anti-tumor necrosis factor-α antibodies; anti-tumor necrosis factor-β antibodies; anti-interleukin-2 antibodies and anti-IL-2 receptor antibodies; anti-L3T4 antibodies; heterologous anti-lymphocyte globulin; pan-T antibodies, for example anti-CD3 or anti-CD4/CD4a antibodies; soluble peptide containing a LFA-3 binding domain (WO 90/08187 published Jul. 26, 1990); streptokinase; TGF-β; streptodornase; RNA or DNA from the host; FK506; RS-61443; deoxyspergualin; rapamycin; T-cell receptor (U.S. Pat. No. 5,114,721); T-cell receptor fragments (Offner et al., *Science* 251:430-432 (1991); WO 90/11294; and WO 91/01133); and T-cell receptor antibodies (EP 340,109) such as T10B9. Examples of cytokines include, but are not limited to, lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-α; insulin-like growth factor-I and -II; erythropoietin (EPO); osteoinductive factors; interferons; colony stimulating factors (CSFs) such as macrophage-CSF (M-CSF); granulocyte-macrophage-CgP (GM-CSP); and granulocyte-CSF (G-CSF); interleukins (ILs) such as IL-1, IL-1a, IL-2, IL-3, IL-4, IL-5, IL-6, IL-7, IL-8, IL-9, IL-1 I, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines. In certain embodiments, the methods further include administering to the subject one or more immunomodulatory agents, for example a cytokine Suitable cytokines may be selected from the group consisting of interleukin-1 (IL-1), IL-2, IL-3, IL-12, IL-15, IL-18, G-CSF, GM-CSF, thrombopoietin, and γ interferon.

These immunoregulatory agents are administered at the same time or at separate times from a CD19xCD3 BiTE® molecule (e.g., MT103). The choice of immunoregulatory agent will depend on many factors, including the type of disorder being treated, as well as the patient's history, but the agent frequently may be selected from cyclosporin A, a glucocorticosteroid (for example prednisone or methylprednisolone), azathioprine, bromocryptine, heterologous anti-lymphocyte globulin, or a mixture thereof.

5.19. Combination with Other Therapeutic Agents

Agents that act on the tumor neovasculature can also be used in conjunction with a CD19×CD3 BiTE® molecule (e.g., MT103) and include tubulin-binding agents such as combrestatin A4 (Griggs et al., *Lancet Oncol.* 2:82, (2001)) and angiostatin and endostatin (reviewed in Rosen, *Oncologist* 5:20 (2000), incorporated by reference herein). Immunomodulators suitable for use in combination with CD19×CD3 bispecific antibodies (e.g., MT103) include, but are not limited to, of α-interferon, γ-interferon, and tumor necrosis factor alpha (TNFα). In certain embodiments, the therapeutic agents used in combination therapies using formulations and methods of the invention are peptides.

In certain embodiments, a CD19×CD3 BiTE® molecule (e.g., MT103) immunotherapy is in conjunction with one or more calicheamicin molecules. The calicheamicin family of antibiotics are capable of producing double-stranded DNA breaks at sub-picomolar concentrations. Structural analogues of calicheamicin which may be used include, but are not limited to, $\gamma 1^I$, $\gamma 2^I$, $\gamma 3^I$, N-acetyl-$\gamma 1^I$, PSAG and 011 Hinman et al., *Cancer Research* 53:3336-3342 (1993) and Lode et al., *Cancer Research* 58: 2925-2928 (1998)).

In certain embodiments, a treatment regimen includes compounds that mitigate the cytotoxic effects of a CD19×CD3 BiTE® molecule (e.g., MT103) formulation. Such compounds include analgesics (e.g., acetaminophen), bisphosphonates, antihistamines (e.g., chlorpheniramine maleate), and steroids (e.g., dexamethasone, retinoids, deltoids, betamethasone, cortisol, cortisone, prednisone, dehydrotestosterone, glucocorticoids, mineralocorticoids, estrogen, testosterone, progestins).

In certain embodiments, the therapeutic agent used in combination with a CD19×CD3 BiTE® molecule (e.g., MT103) immunotherapy is a small molecule (i.e., inorganic or organic compounds having a molecular weight of less than about 2500 daltons). For example, libraries of small molecules may be commercially obtained from Specs and BioSpecs B.V. (Rijswijk, The Netherlands), Chembridge Corporation (San Diego, Calif.), Comgenex USA Inc. (Princeton, N.J.), and Maybridge Chemicals Ltd. (Cornwall PL34 OHW, United Kingdom).

In certain embodiments a CD19×CD3 BiTE® molecule (e.g., MT103) immunotherapy can be administered in combination with an anti-bacterial agent. Non-limiting examples of anti-bacterial agents include proteins, polypeptides, peptides, fusion proteins, antibodies, nucleic acid molecules, organic molecules, inorganic molecules, and small molecules that inhibit and/or reduce a bacterial infection, inhibit and/or reduce the replication of bacteria, or inhibit and/or reduce the spread of bacteria to other cells or subjects. Specific examples of anti-bacterial agents include, but are not limited to, antibiotics such as penicillin, cephalosporin, imipenem, axtreonam, vancomycin, cycloserine, bacitracin, chloramphenicol, erythromycin, clindamycin, tetracycline, streptomycin, tobramycin, gentamicin, amikacin, kanamycin, neomycin, spectinomycin, trimethoprim, norfloxacin, rifampin, polymyxin, amphotericin B, nystatin, ketoconazole, isoniazid, metronidazole, and pentamidine.

In certain embodiments a CD19×CD3 BiTE® molecule (e.g., MT103) immunotherapy can be administered in combination with an anti-fungal agent. Specific examples of anti-fungal agents include, but are not limited to, azole drugs (e.g., miconazole, ketoconazole (NIZORAL®), caspofungin acetate (CANCIDAS®), imidazole, triazoles (e.g., fluconazole))(DIFLUCAN®)), and itraconazole))(SPORANOX®)), polyene (e.g., nystatin, amphotericin B (FUNGIZONE), amphotericin B lipid complex ("ABLC") (ABELCET®), amphotericin B colloidal dispersion ("ABCD") (AMPHOTEC®), liposomal amphotericin B (AMBISONE®)), potassium iodide (KI), pyrimidine (e.g., flucytosine (ANCOBON®), and voriconazole (VFEND®)). Administration of anti bacterial and anti-fungal agents can mitigate the effects or escalation of infectious disease that may occur in methods of the invention where a patient's B cells are significantly depleted.

In certain embodiments of the invention, a CD19×CD3 BiTE® molecule (e.g., MT103) immunotherapy can be administered in combination with one or more of the agents described above to mitigate the toxic side effects that may accompany administration of formulations of the invention. In other embodiments, a CD19×CD3 BiTE® molecule (e.g., MT103) immunotherapy can be administered in combination with one or more agents that are well known in the art for use in mitigating the side effects of antibody administration, chemotherapy, toxins, or drugs.

In certain embodiments of the invention where a CD19×CD3 BiTE® molecule (e.g., MT103) immunotherapy is administered to treat multiple myeloma, formulations of the invention may be administered in combination with or in treatment regimens with high-dose chemotherapy (melphalan, melphalan/prednisone (MP), vincristine/doxorubicin/dexamethasone (VAD), liposomal doxorubicin/vincristine, dexamethasone (DVd), cyclophosphamide, etoposide/dexamethasone/cytarabine, cisplatin (EDAP)), stem cell transplants (e.g., autologous stem cell transplantation or allogeneic stem cell transplantation, and/or mini-allogeneic (non-myeloablative) stem cell transplantation), radiation therapy, steroids (e.g., corticosteroids, dexamethasone, thalidomide/dexamethasone, prednisone, melphalan/prednisone), supportive therapy (e.g., bisphosphonates, growth factors, antibiotics, intravenous immunoglobulin, low-dose radiotherapy, and/or orthopedic interventions), THALOMID™ (thalidomide, Celgene), and/or VELCADE™ (bortezomib, Millennium).

In embodiments of the invention where a CD19×CD3 BiTE® molecule (e.g., MT103) immunotherapy is administered in combination with another antibody or antibodies and/or agent, the additional antibody or antibodies and/or agents can be administered in any sequence relative to the administration of the CD19×CD3 BiTE® molecule (e.g., MT103). For example, the additional antibody or antibodies can be administered before, concurrently with, and/or subsequent to administration of a CD19×CD3 BiTE® molecule (e.g., MT103) to the human subject. The additional antibody or antibodies can be present in the same pharmaceutical formulation as a CD19×CD3 BiTE® molecule (e.g., MT103), and/or present in a different pharmaceutical formulation. The dose and mode of administration of a CD19×CD3 BiTE® molecule (e.g., MT103) and the dose of the additional antibody or antibodies can be the same or different, in accordance with any of the teachings of dosage amounts and modes of administration as provided in this application and as are well known in the art.

5.20. Kits

The present invention provides kits that can be used in the above-described methods. The invention provides a pharmaceutical pack or kit comprising a lyophilized formulation of the invention in one or more containers. In one embodiment, a kit comprises a formulation of the invention, in one or more containers. In another embodiment, a kit comprises a formulation of the invention, in one or more containers, and further comprises a suitable diluent (e.g. BWFI), in one or more containers. In a further embodiment, a kit comprises a formulation of the invention, in one or more containers, and one or more other prophylactic or therapeutic agents. The kit may further comprise instructions for method of administration of a reconstituted formulation of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The invention provides a pharmaceutical pack or kit comprising one or more containers filled with a lyophilized formulation of a CD19×CD3 BiTE® molecule (e.g., MT103) for the prevention, treatment, management or amelioration of B cell diseases and disorders, such as, but not limited to, B cell malignancies, autoimmune diseases, graft-versus-host disease (GVHD), humoral rejection, and post-transplantation lymphoproliferative disorder, or one or more symptoms thereof, in a human subject. In one embodiment, a kit comprises a CD19×CD3 BiTE® molecule (e.g., MT103) lyophilized formulation of the invention, in one or more containers. In another embodiment, a kit comprises a CD19×CD3 BiTE® molecule (e.g., MT103) formulation of the invention, in one or more containers, and further comprises a suitable diluent (e.g. BWFI), in one or more containers. In a further embodiment, a kit comprises a CD19×CD3 BiTE® molecule (e.g., MT103) formulation of the invention, in one or more containers, and one or more other prophylactic or therapeutic agents useful for the prevention, treatment, management or amelioration of B cell diseases and disorders, such as, but not limited to, B cell malignancies, autoimmune diseases, graft-versus-host disease (GVHD), humoral rejection, and post-transplantation lymphoproliferative disorder, or one or more symptoms thereof, in a human subject. In a specific embodiment, the lyophilized formulations of the invention are formulated in single dose vials as a sterile lyophilized cake consisting of MT103, citrate, trehalose dehydrate, lysine HCl, and polysorbate 80. The formulations of the invention may be supplied in 3 cc USP Type I borosilicate amber vials (e.g., West Pharmaceutical Serices—Part No. 6800-0675). The kit may further comprise instructions for method of administration of a reconstituted formulation of a CD19×CD3 BiTE® molecule (e.g., MT103) described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

5.21. Articles of Manufacture

The present invention also encompasses a finished packaged and labeled pharmaceutical product. This article of manufacture includes the appropriate unit dosage form in an appropriate vessel or container such as a glass vial or other container that is hermetically sealed. The unit dosage form is provided as a sterile lyophilized powder comprising BiTE® molecules wherein said lyophilized powder is suitable for reconstitution and subsequent parenteral administration. In one embodiment, a unit dosage form is provided as a sterile lyophilized powder comprising a CD19×CD3 BiTE® molecule wherein said lyophilized powder is suitable for reconstitution and subsequent parenteral administration. In a specific embodiment, a unit dosage form is provided as a sterile lyophilized powder comprising MT103 wherein said lyophilized powder is suitable for reconstitution and subsequent parenteral administration. In one embodiment, the reconstituted unit dosage form is suitable for intravenous, intramuscular, intranasal, oral, topical or subcutaneous delivery. Thus, the invention encompasses sterile solutions suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises a lyophilized formulation containing BiTE® molecules (e.g., MT103). The packaging material includes instruction means which indicate that said BiTE® molecule can be used to prevent, treat, manage or ameliorate one or more symptoms associated with a B cell disease and disorder, such as, but not limited to, B cell malignancy, autoimmune disease, graft-versus-host disease (GVHD), humoral rejection, and post-transplantation lymphoproliferative disorder in a human subject by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a lyophilized formulation containing a CD19×CD3 BiTE® molecule (e.g., MT103) and the other pharmaceutical agent comprises a prophylactic or therapeutic agent other than an antibody, and wherein said packaging material includes instruction means which indicate that said agents can be used to prevent, treat and/or manage one or more symptoms associated with a B cell disease and disorder, such as, but not limited to, B cell malignancy, autoimmune disease, graft-versus-host disease (GVHD), humoral rejection, and post-transplantation lymphoproliferative disorder in a human subject by administering specific doses and using specific dosing regimens as described herein.

The present invention provides that the adverse effects that may be reduced or avoided by the methods of the invention are indicated in informational material enclosed in an article of manufacture for use in preventing, treating and/or managing one or more symptoms associated with a B cell disease and disorder, such as, but not limited to, B cell malignancy, autoimmune disease, graft-versus-host disease (GVHD), humoral rejection, and post-transplantation lymphoproliferative disorder in a human subject. Adverse effects that may be reduced or avoided by the methods of the invention include, but are not limited to, vital sign abnormalities (fever, tachycardia, bardycardia, hypertension, hypotension), hematological events (anemia, lymphopenia, leukopenia, thrombocytopenia), headache, chills, dizziness, nausea, asthenia, back pain, chest pain (chest pressure), diarrhea, myalgia, pain, pruritus, psoriasis, rhinitis, sweating, injection site reaction, and vasodilatation.

5.22. Specific Embodiments

Those skilled in the art will recognize, or be able to ascertain using no more than routine experimentation, many equivalents to the specific embodiments of the invention described herein. Such equivalents are intended to be encompassed by the following claims.

1. A sterile liquid pharmaceutical formulation comprising a bispecific antibody and lysine, wherein the bispecific antibody comprises a first and second binding domains, wherein the first binding domain specifically binds the CD3 T cell surface antigen.

2. The formulation of claim 1, wherein the formulation is a reconstituted liquid formulation.

3. The formulation of any one of claim 1 or 2, wherein the first binding domain comprises the amino acid sequence of residues 283-525 of SEQ ID NO:5.

4. The formulation of any one of claims 1-3, wherein the second binding domain specifically binds an antigen selected from the group consisting of: CD19, CD20, CD22, EphA2, EphA4, INFR, ICOS, Ep-CAM, CEA, and IL-5 receptor.

5. The formulation of claim 4, wherein the second binding domain specifically binds CD19.

6. The formulation of claim 5, wherein the second binding domain comprises the amino acid sequence of residues 28-277 of SEQ ID NO:5.

7. The formulation of claim 5, wherein the bispecific antibody comprises the amino acid sequence of residues 28-525 of SEQ ID NO:5.

8. The formulation of any one of claims 1-7, wherein the formulation is an aqueous formulation.

9. The formulation of any one of claims 1-8, wherein the formulation is isotonic, hypertonic, or hypotonic.

10. The formulation of any one of claim 1 or 2-9, wherein the formulation is suitable for lyophilization.

11. The formulation of any one of claims 1-10, wherein the formulation comprises between about 1 microgram/ml and about 300 micrograms/ml of the bispecific antibody.

12. The formulation of any one of claims 1-11, wherein the formulation further comprises a buffering agent selected from the group consisting of: histidine, citrate, phosphate, glycine, and acetate.

13. The formulation of any one of claims 1-12, wherein the formulation further comprises a carbohydrate excipient selected from the group consisting of: sucrose, trehalose, lactose, mannitol, and raffinose.

14. The formulation of any one of claims 1-13, wherein the formulation further comprises a surfactant selected from the group consisting of: Polysorbate 20, Polysorbate 40, Polysorbate 60, or Polysorbate 80.

15. The formulation of any one of claims 1-11, wherein the formulation further comprises citrate, trehalose, and Polysorbate 80.

16. The formulation of claim 15, wherein the formulation comprises between about 5 mM and about 125 mM citrate, between about 25 mM and about 400 mM lysine, between about 3% and about 50% trehalose, and between about 0.01% and about 1% Polysorbate 80, and has a pH of between about 4.0 and about 8.0.

17. The formulation of any one of claims 1-16, wherein the formulation comprises about 55 micrograms/ml bispecific antibody, about 25 mM citrate, about 200 mM lysine, about 15% trehalose and about 0.1% Polysorbate 80, and has a pH of about 7.0.

18. The formulation of any one of claims 1-16, wherein the formulation comprises about 150 micrograms/ml bispecific antibody, about 30 mM citrate, about 75 mM lysine, about 6.5% trehalose and about 0.02% Polysorbate 80 and has a pH of about 7.0.

19. The formulation of any one of claims 1-16, wherein the formulation comprises about 150 micrograms/ml bispecific antibody, about 30 mM citrate, about 75 mM lysine, about 6% trehalose and about 0.02% Polysorbate 80 and has a pH of about 7.0.

20. The formulation of any one of claims 1-16, wherein the formulation comprises about 160 micrograms/ml bispecific antibody, about 25 mM citrate, about 200 mM lysine, about 15% trehalose and about 0.1% Polysorbate 80, and has a pH of about 7.0.

21. The formulation of any one of claims 1-16, wherein the bispecific antibody retains at least 90% of binding ability to CD19 and CD3 antigens during storage at about 5° C. for at least about 1 month as compared to a reference antibody representing the antibody prior to said storage.

22. The formulation of any one of claims 1-16, wherein less than 5% of the bispecific antibody forms an aggregate as determined by HPSEC upon storage at about 5° C. for about 1 month.

23. The formulation of any one of claims 1-16, wherein less than 5% of the bispecific antibody forms a dimer as determined by HPSEC upon storage at about 5° C. for about 1 month.

24. The formulation of any one of claims 1-16, wherein less than 5% of the bispecific antibody forms an aggregate as determined by HPSEC upon shaking a vial filled to half of its volume with a sample of said formulation for 4 hours at a speed of 400 shakes per minute.

25. The formulation of any one of claims 1-16, wherein less than 5% of the antibody forms an aggregate as determined by HPSEC upon subjecting the formulation to three freeze/thaw cycles.

26. The formulation of any one of claims 1-16, wherein less than 5% of the antibody forms a dimer as determined by HPSEC upon shaking a vial filled to half of its volume with a sample of said formulation for 4 hours at a speed of 400 shakes per minute.

27. The formulation of any one of claims 1-16, wherein less than 5% of the antibody forms a dimer as determined by HPSEC upon subjecting the formulation to three freeze/thaw cycles.

28. The formulation of any one of claims 1-16, wherein at least about 95% of the antibody is recovered by reconstituting a lyophilized cake generated from the formulation.

29. The formulation of any one of claims 1-16, wherein the formulation is clear and colorless as determined by visual inspection upon storage at about 5° C. for at least about 1 month.

30. A sterile lyophilized pharmaceutical formulation comprising a bispecific antibody and lysine, wherein the bispecific antibody comprises a first and second binding domains, wherein the first binding domain specifically binds the CD3 T cell surface antigen.

31. The formulation of claim 30, wherein the first binding domain comprises the amino acid sequence of residues 283-525 of SEQ ID NO:5.

32. The formulation of any one of claim 30 or 31, wherein the second binding domain specifically binds an antigen selected from the group consisting of: CD19, CD20, CD22, EphA2, EphA4, INFR, ICOS, Ep-CAM, CEA, and IL-5 receptor.

33. The formulation of claim 32, wherein the second binding domain specifically binds CD19.

34. The formulation of claim 33, wherein the second binding domain comprises the amino acid sequence of residues 28-277 of SEQ ID NO:5.

35. The formulation of claim 33, wherein the bispecific antibody comprises the amino acid sequence of residues 28-525 of SEQ ID NO:5.

36. The formulation of any one of claims 30-35, wherein the formulation further comprises a buffering agent selected from the group consisting of: histidine, citrate, phosphate, glycine, and acetate.

37. The formulation of any one of claims 30-36, wherein the formulation further comprises a carbohydrate excipient selected from the group consisting of: sucrose, trehalose, lactose, mannitol, and raffinose.

38. The formulation of any one of claims 30-37, wherein the formulation further comprises a surfactant selected from the group consisting of: Polysorbate 20, Polysorbate 40, Polysorbate 60, or Polysorbate 80.

39. The formulation of any one of claims 30-35, wherein the formulation further comprises citrate, trehalose, and Polysorbate 80.

40. The formulation of any one of claims 30-39, wherein at least about 90% of the bispecific antibody is recovered by reconstituting the lyophilized formulation upon storage at about 5° C. for at least about 1 year.

41. The formulation of any one of claims 30-39, wherein less than 5% of the bispecific antibody forms an aggregate as determined by HPSEC upon reconstitution following storage of the lyophilized formulation at about 5° C. for at least about 1 year.

42. The formulation of any one of claims 30-39, wherein less than 5% of the bispecific antibody forms a dimer as determined by HPSEC upon reconstitution following storage of the lyophilized formulation at about 5° C. for at least about 1 year.

43. The formulation of any one of claims 30-39, wherein following storage of the lyophilized formulation at about 5° C. for at least about 1 month, upon reconstitution the bispecific antibody retains at least 90% of binding ability to CD19 and CD3 antigens as compared to a reference antibody representing the antibody prior to said storage.

44. A sterile liquid reconstituted pharmaceutical formulation comprising a bispecific antibody and lysine, wherein the bispecific antibody comprises a first and second binding domains, wherein the first binding domain specifically binds the CD3 T cell surface antigen.

45. The formulation of claim 44, wherein the first binding domain comprises the amino acid sequence of residues 283-525 of SEQ ID NO:5.

46. The formulation of any one of claim 44 or 45, wherein the second binding domain specifically binds an antigen selected from the group consisting of: CD19, CD20, CD22, EphA2, EphA4, INFR, ICOS, Ep-CAM, CEA, and IL-5 receptor.

47. The formulation of claim 46, wherein the second binding domain specifically binds CD19.

48. The formulation of claim 47, wherein the second binding domain comprises the amino acid sequence of residues 28-277 of SEQ ID NO:5.

49. The formulation of claim 47, wherein the bispecific antibody comprises the amino acid sequence of residues 28-525 of SEQ ID NO:5.

50. The formulation of any one of claims 44-49, wherein the formulation is an aqueous formulation.

51. The formulation of any one of claims 44-50, wherein the formulation is isotonic, hypertonic, or hypotonic.

52. The formulation of any one of claims 44-51, wherein the formulation comprises between about 1 microgram/ml and about 300 micrograms/ml of the bispecific antibody.

53. The formulation of any one of claims 44-52, wherein the formulation further comprises a buffering agent selected from the group consisting of: histidine, citrate, phosphate, glycine, and acetate.

54. The formulation of any one of claims 44-53, wherein the formulation further comprises a carbohydrate excipient selected from the group consisting of: sucrose, trehalose, lactose, mannitol, and raffinose.

55. The formulation of any one of claims 44-54, wherein the formulation further comprises a surfactant selected from the group consisting of: Polysorbate 20, Polysorbate 40, Polysorbate 60, or Polysorbate 80.

56. The formulation of any one of claims 44-52, wherein the formulation further comprises citrate, trehalose, and Polysorbate 80.

57. The formulation of any one of claims 44-56, wherein the formulation comprises between about 5 mM and about 125 mM citrate, between about 25 mM and about 400 mM lysine, between about 3% and about 50% trehalose, and between about 0.01% and about 1% Polysorbate 80, and has a pH between about 4.0 and 8.0.

58. The formulation of any one of claims 44-56, wherein the formulation comprises about 55 micrograms/ml bispecific antibody, about 25 mM citrate, about 200 mM lysine, about 15% trehalose and about 0.1% Polysorbate 80, and has a pH of about 7.0.

59. The formulation of any one of claims 44-56, wherein the formulation comprises about 150 micrograms/ml bispecific antibody, about 30 mM citrate, about 75 mM lysine, about 6.5% trehalose and about 0.02% Polysorbate 80 and has a pH of about 7.0.

60. The formulation of any one of claims 44-56, wherein the formulation comprises about 150 micrograms/ml bispecific antibody, about 30 mM citrate, about 75 mM lysine, about 6% trehalose and about 0.02% Polysorbate 80 and has a pH of about 7.0.

61. The formulation of any one of claims 44-56, wherein the formulation comprises about 160 micrograms/ml bispecific antibody, about 25 mM citrate, about 200 mM lysine, about 15% trehalose and about 0.1% Polysorbate 80, and has a pH of about 7.0.

62. The formulation of any one of claims 44-61, wherein the bispecific antibody retains at least 90% of binding ability to the CD19 and CD3 antigens during storage at about 5° C. for at least about 12 hours as compared to a reference antibody representing the antibody prior to said storage.

63. The formulation of any one of claims 44-61, wherein less than 5% of the bispecific antibody forms an aggregate as determined by HPSEC upon storage at about 5° C. for about 12 hours.

64. The formulation of any one of claims 44-61, wherein less than 5% of the bispecific antibody forms a dimer as determined by HPSEC upon storage at about 5° C. for about 12 hours.

65. The formulation of any one of claims 44-61, wherein the formulation is clear and colorless as determined by visual inspection upon storage at about 5° C. for at least about 12 hours.

66. The formulation of any one of claim 1-29 or 44-65, wherein the formulation is an injectable formulation.

67. The formulation of claim 66, wherein the formulation is for intravenous, subcutaneous, or intramuscular administration.

68. The formulation of claim 67, wherein the formulation is suitable for subcutaneous administration.

69. The formulation of claim 68, wherein the bioavailability of the bispecific antibody following subcutaneous delivery of the formulation is between about 10% and about 50% as compared to the bioavailability of the bispecific antibody following intravenous delivery of the same dose of the formulation.

70. The pharmaceutical unit dosage form of a formulation of any one of claims 1-69, wherein the antibody formulation is administered intravenously, subcutaneously, or intramuscularly.

71. A sealed container containing the formulation of any one of claims 1-69.

72. A kit comprising the formulation of any one of claims 1-69.

73. A method of preventing, managing, treating or ameliorating B cell disorders or diseases such as, B cell malignancies, autoimmune diseases, graft-versus-host disease (GVHD), humoral rejection, and post-transplantation lymphoproliferative disorder in a human subject, said methods comprising administering to a subject in need thereof a prophylactically or therapeutically effective amount of the formulation of any one of claims 1-69.

74. The method of claim 73, wherein the disease or disorder is a B cell malignancy.

75. A method of making the formulation of any one of claims 1-69, comprising: combining the bispecific antibody with lysine.

76. A method of stabilizing a bispecific antibody, comprising: combining said antibody with lysine, wherein the bispecific antibody comprises a first and second binding domains, wherein the first binding domain specifically binds the CD3 T cell surface antigen.

6. EXAMPLES

6.1. Development of MT103 Lyophilized Formulation I

All chemicals used were USP grade or higher. Trehalose dehydrate was obtained from Ferro Pfanstiehl; polysorbate 80, arginine HCl, lysine HCl, citrate, sodium sulphate and potassium phosphate may be obtained from JT Baker or Sigma; NaOH and HCl was obtained from VWR.

6.1.1. Analytical Methods

Visual Inspection: Visual inspection of lyophilized cakes was performed by visually examining the cakes for their general shape and for any visible signs of collapse, melt back, flakiness, cracks, shrinkage, or other apparent defects. Reconstituted vials were inspected for presence of particulates.

Size Exclusion Chromatography (SEC): SEC was used to determine the level of aggregate present in a sample and to determine the concentration of MT103 protein in the sample. SEC analysis was performed by injecting 2 to 100 µL of the sample on an Agilent HPLC system with a TosoHaas G3000 $SW_xL$ column (7.8×300 mm) using fluorescence detection (Excitation at 280 nm, Emission at 345 nm) at a flow rate of 1 mL per minute. The mobile phase consisted of 0.1 M $KH_2PO_4$, 0.2 M $Na_2SO_4$ at pH 6.6 in HPLC grade water. MT103 was quantitated using a three point bracketed standard curve generated by injecting a working reference standard on each run. The SEC assay served as a surrogate tool for A280 measurements because the concentration of the working reference standard was previously correlated with UV absorbance at 280 nm (A280) using the extinction coefficient determined from amino acid analysis ($\epsilon$=2.16).

Moisture Analysis: Residual moisture content of lyophilized cakes was determined by Coulometric Karl Fisher titration. Briefly, lyophilized cakes were weighed and dissolved in 1 ml anhydrous methanol. A fixed weight of the dissolved sample was transferred into a coulometric Karl Fisher titrator with a diaphragm-free cell. The residual moisture content of the lyophilized sample is expressed as % w/w.

Determination of protein recovery: Vials containing lyophilized MT103 were accurately weighed before and after reconstitution. The MT103 protein solution was then transferred to another vial and the original vial was thoroughly rinsed, dried and weighed. Concentration of reconstituted MT103 protein was determined by SEC analysis. The protein recovery was calculated using the experimentally determined net weight of the reconstituted cakes in each vial as described above, and the concentration determined by SEC.

6.1.2. Formulation

Buffer Preparation: Buffers were prepared with USP or multi-compendial grade chemicals. All pH adjustments were done with either 1 N HCl or 1 N NaOH as appropriate. All buffers were filtered through 0.22 µm filters and stored at 2 to 8° C. and were used within two weeks of preparation.

Dialysis: Buffer exchanges were performed using Pierce dialysis cassettes with capacities ranging from 0.5 to 12 mL as appropriate for the volume to be dialyzed. All exchanges were performed prior to addition of polysorbate 80. At a minimum, two serial exchanges were performed, each with at least a 100-fold excess of the target formulation buffer over a minimum period of 4 hours. Complete exchange was confirmed by matching the osmolality and pH of the dialyzed protein solution recovered from the dialysis cassette with that of the target formulation buffer. Protein recovered from the dialysis cassettes was immediately formulated with polysorbate 80 where appropriate, and filtered through 0.22 µm syringe filters and stored at 2 to 8° C. until used.

Evaluation of stability to freeze-thaw stress: Samples (0.5 to 1.0 mL) were transferred into 1 mL polypropylene cryovials and subjected to three freeze-thaw cycles. Vials of the matching formulation that served as a control were maintained at 2 to 8° C. and did not undergo any freeze-thaw. Each freeze-thaw cycle consisted of freezing in a −70° C. environmental chamber for a minimum of 8 hours and thawing at 2 to 8° C. until completely thawed. Following the final thaw, the samples were gently mixed and analyzed by SEC.

Evaluation of stability to shaking stress: Shaking studies were performed at room temperature in a thermally insulated container on a laboratory benchtop shaker (VWR Digital Mini Vortexer) at the maximum setting of 10 (approx. 400 shakes per minute) over a period of 2 to 4 hours. The vials were placed horizontally with the length of the vials along the direction of shaking with the objective of maximizing turbulence, leading to an increase in the surface area of the air-liquid interface. Vials of the matching formulation that served as a control were maintained at 2 to 8° C. and did not undergo any shaking Samples from the shaken vials and the unshaken controls were then analyzed by SEC.

Fill/Finish procedure: All glass vials were triple rinsed with deionized water and sterilized prior to use. The rubber stoppers were purchased pre-washed and were sterilized prior to use. All fills were done manually using Eppendorf repeat pipettor (model) and were carried out inside a laminar flow hood. All solutions were filtered inside the laminar flow hood through 0.22 µm sterilizing filter before the fills. Vials were each filled with 0.6 mL of the respective formulations (setting #3 when using a 10 mL Eppendorf disposable cartridge insert). Vials were then stoppled and transferred onto lyophilization trays for transfer to the shelves on the lyophilizer. Following lyophilization, the vials were capped with 13 mm aluminum overseals either manually or with a semi-automated capper.

Lyophilization: During the course of these studies two lyophilization cycle variations were evaluated. The cycles are defined in Table 1 below. Evaluations were performed using an external condenser lyophilizer (Quantum 20X retrofitted by Hull).

TABLE 1

Lyophilization cycle variations tested.

| | Description | Non annealing cycle (L1) | Annealing cycle (L2) |
|---|---|---|---|
| Thermal Treatment Phase | Total Lyo Cycle Length | 96 hr | 103 hr |
| | Load Temp | 20° C. | 20° C. |
| | Initial Temp | 8° C. | 8° C. |
| | Freeze Temp | | −40° C. |
| | Ramp rate | | 0.3° C./min |
| | Hold Time at freeze temp | | 150 min |
| | Annealing Temp | | −25° C. |
| | Annealing ramp rate | | 0.5° C./min |
| | Hold Time at Annealing temp | | 300 min |
| | Final Freeze Temp | −40° C. | −40° C. |
| | Ramp rate | 0.3° C./min | 0.5° C./min |
| | Hold Time at Final Freeze temp | 150 min | 60 min |

TABLE 1-continued

Lyophilization cycle variations tested.

| | Description | Non annealing cycle (L1) | Annealing cycle (L2) |
|---|---|---|---|
| | Condenser temp set | −50° C. | −50° C. |
| | Vacuum set | 60 mT | 60 mT |
| Primary Drying | Temp Set | −35° C. | −35° C. |
| | Hold Time | 68 hr | 68 hr |
| Secondary Drying | Temp Set | 20° C. | 20° C. |
| | Ramp rate | 0.3° C./min | 0.3° C./min |
| | Hold Time | 19 hr | 19 hr |
| Stoppering | Backfill | Nitrogen | Nitrogen |

6.1.3. Overview of Formulation Studies 17 different formulations were evaluated in sequential campaigns, with each campaign consisting of three to five formulations lyophilized in the same run. A non-annealing lyophilization cycle (L1, Table 1) was used as the default cycle for all formulations except where the annealing L2 cycle is specifically indicated. All formulations discussed in this report were formulated at a target concentration of 50 to 55 µg of MT103 per mL. All formulations were prepared with 25 mM citrate as the buffering agent, and none of the formulations contained lysine acetate or PEG 3350. Formulations in select campaigns were evaluated for stability to freeze-thaw, shaking stresses and accelerated stability in the liquid form. Lyophilized formulations were evaluated for visual appearance, aggregate and concentration (SEC-HPLC), accelerated stability, and protein recovery. Residual moisture content was determined for selected formulations; moisture content was within the ≤2% specification. The various formulations evaluated are listed in FIGS. 1, 9, and 11, and Table 2.

TABLE 2

Summary of formulations analysed.

| ID # | Formulation Composition Each formulation consists of 25 mM citrate PLUS the following: |
|---|---|
| 0 | 15% trehalose dihydrate ph 7 |
| 1 | 15% trehalose dihydrate 0.1% polysorbate 80 pH 7 |
| 2 | 15% trehalose dihydrate 0.1% polysorbate 80, 100 mM arginine HCl pH 7 |
| 3, 14 | 15% trehalose dihydrate 0.1% polysorbate 80, 500 mM arginine HCl pH 7 |
| 4 | 15% trehalose dihydrate, 0.1% polysorbate 80, 100 mM NaCl pH 7 |
| 5 | 15% trehalose dihydrate, 0.1% polysorbate 80, 500 mM NaCl pH 7 |
| 6, 15, 16 | 15% trehalose dihydrate, 0.1% polysorbate 80, 500 mM lysine HCl pH 7 |
| 7 | 15% trehalose dihydrate, 0.1% polysorbate 80, 625 mM lysine base pH 7 |
| 8 | 5% mannitol, 0.1% polysorbate 80 pH 7 |
| 9 | 5% trehalose dihydrate, 0.1% polysorbate 80, 500 mM arginine HCl pH 7 |
| 10 | 5% Mannitol pH 7 |
| 11 | 15% trehalose dihydrate, 0.1% polysorbate 80, 100 mM arginine HCl pH 6 |
| 12 | 15% trehalose dihydrate, 0.1% polysorbate 80, 100 mM arginine HCl pH 7 |
| 13 | 15% trehalose dihydrate, 0.1% polysorbate 80, 500 mM arginine HCl pH 6 |
| 17, 30, 33 | 15% trehalose dihydrate, 0.1% polysorbate 80, 300 mM lysine HCl pH 7 |
| 18, 27, 31 | 15% trehalose dihydrate, 0.1% polysorbate 80, 100 mM lysine HCl pH 7 |
| 19 | 15% trehalose dihydrate, 0.175% polysorbate 80, 100 mM lysine HCl pH 7 |
| 20, 28 | 15% trehalose dihydrate, 0.25% polysorbate 80, 100 mM lysine HCl pH 7 |
| 21 | 10% trehalose dihydrate, 0.1% polysorbate 80, 500 mM lysine HCl pH 7 |
| 22 | 10% trehalose dihydrate, 0.1% polysorbate 80, 300 mM lysine HCl pH 7 |
| 23 | 10% trehalose dihydrate, 0.1% polysorbate 80, 100 mM lysine HCl pH 7 |
| 24 | 10% trehalose dihydrate, 0.175% polysorbate 80, 100 mM lysine HCl pH 7 |
| 25 | 10% trehalose dihydrate, 0.25% polysorbate 80, 100 mM lysine HCl pH 7 |
| 26 | 15% trehalose dihydrate, 0.25% polysorbate 80 pH 7 |
| 29, 32 | 15% trehalose dihydrate, 0.1% polysorbate 80, 200 mM lysine HCl pH 7 |

The first campaign focused on assessing the need for the presence of trehalose dihydrate and polysorbate 80. A formulation containing arginine hydrochloride (500 mM) was evaluated as a replacement for lysine acetate. A formulation containing only 5% mannitol was utilized as a negative control.

The second campaign focused on an evaluation of arginine hydrochloride (100 mM or 500 mM), lysine hydrochloride (500 mM) and the effect of pH (pH 6 or pH 7).

The third campaign focused on determining the optimal level of lysine hydrochloride (100, 300 and 500 mM) and polysorbate 80 (0.1, 0.175, 0.25% w/v) in presence of 25 mM citrate at pH 7 and 15% trehalose dihydrate. These studies were repeated in placebo formulations in presence of 25 mM citrate at pH 7 and 10% trehalose dihydrate in an attempt to reduce the amount of the sugar.

A subsequent campaign focused on further narrowing the level of lysine hydrochloride by evaluating 100, 200 or 300 mM lysine hydrochloride in presence of 25 mM citrate at pH 7 and 15% trehalose dihydrate, and 0.1% polysorbate 80. Both non-annealing (L1) and annealing (L2) cycles were studied for these formulations.

An optimization of the lyophilization cycle was then performed to determine if the durations of primary and secondary cycles could be shortened without any product impact. This was accomplished by pulling vials from the lyophilizer at various time points prior to completion of the primary and secondary cycles using a sample thief.

Finally, the lyophilization of the selected formulation was repeated using the selected cycle to confirm reproducibility.

6.1.4. Excipient Screening

Formulations evaluated in the excipient screening study are listed in FIG. 1.

FIG. 2 shows that the excipients polysorbate 80 and trehalose markedly improve the recovery of MT103 from lyophilized formulations. Addition of 15% trehalose (in formulation F0) improves protein recovery from 40 percent (formulation F10) to 70 percent. A further 20 percent improvement in recovery is obtained upon inclusion of 0.1% polysorbate 80 (formulation F1) with the 15% trehalose. Inclusion of 100 or 500 mM arginine HCl did not further improve recovery, however, it contributed towards the formation of very elegant lyophilized cakes.

Upon evaluating the excipients in a liquid stability, several interesting findings came to light. Arginine HCl induced the formation of protein aggregates in the liquid state. The rate of aggregation increased with an increase in arginine HCl concentration from 100 mM to 500 mM (FIGS. 3 and 4). The rate of aggregation also increased with an increase in protein concentration from 50 to 300 µg/mL (FIGS. 3 and 4).

Quantitation of protein recovery from the formulations in a freeze-thaw study demonstrated that formulations containing trehalose and polysorbate 80 (F3) conferred better protection to the protein during the freezing stresses compared to formulations lacking polysorbate (F1) or both polysorbate and trehalose (F10). Presence of arginine HCl did not contribute any additional benefit. Identical findings were obtained in a shaking study (FIG. 6).

Evaluation of recovery in liquid bulks in a short-term liquid stability study at 40° C. over a period of 7 days further confirmed the above findings.

In a post-reconstitution evaluation of stability of MT103 over 48 hours was performed.

6.1.5. Formulation Optimization

Selection of formulation pH: Formulations evaluated in the pH screening study are listed in FIG. 9. The pH evaluation was limited to within a narrow range of 6 and 7 because it was desirable to be as close to neutral as possible. Higher pHs were avoided due to the enhanced likelihood of deamidation at NG motifs in the MT103 sequence. The present efforts were aimed at determining if recovery could be improved marginally by a small change in the formulation pH. Formulations pairs F11-F12 and F13-F14 compared the effect of pH in presence of either 100 or 500 mM Arginine HCl, respectively, while the other excipients were held constant. Lysine HCl was introduced in this set for evaluation as a potential replacement for arginine HCl due to the earlier observation that arginine HCl promoted rapid aggregation in liquid MT103 formulations.

There did not appear to be any significant effect of the formulation pH on recoveries (FIG. 10). However, as before, a significant increase in the aggregate levels was seen with the formulations containing 500 mM arginine HCl (F13 and F14) irrespective of the pH. It was determined that this increase occurred in the liquid state prior to lyophilization, and there was no further change after lyophilization (data not shown). Interestingly, formulation F15 with lysine HCl at a comparable concentration (500 mM) showed no increase in aggregate levels while providing comparable recoveries to F14. However, F15 exhibited signs of significant collapse, suggesting that it may not yield visually acceptable cakes.

Based on the evidence obtained thus far, it appeared that arginine HCl promoted aggregation in the liquid state and was therefore undesirable as an excipient. Lysine HCl was found to be a suitable replacement that prevented aggregation in liquid formulations, but needed further lyophilization optimization. pH 7, which is closer to physiologic, was selected as the pH of choice for the formulation because there was no difference between pH 6 and 7 on MT103 recovery or aggregate levels.

Selection of Trehalose concentration: Two levels of trehalose (10% and 15%) were evaluated using blank (placebo) formulations to conserve protein. It was assumed that due to the extremely high trehalose/protein ratios which were far in excess of levels minimally recommended for effective cryo- and lyo-protection of protein, the effects would be limited to visual appearance of the cakes, and there would be no impact on protein recovery or aggregation.

TABLE 3

Formulations analysed in trehalose concentration screen.

| ID # | Formulation Composition<br>Each formulation consists of 25 mM citrate PLUS the following: |
|---|---|
| B16 | 15% trehalose dihydrate, 0.1% polysorbate 80, 500 mM lysine HCl pH 7 |
| B17 | 15% trehalose dihydrate, 0.1% polysorbate 80, 300 mM lysine HCl pH 7 |
| B18 | 15% trehalose dihydrate, 0.1% polysorbate 80, 100 mM lysine HCl pH 7 |
| B19 | 15% trehalose dihydrate, 0.175% polysorbate 80, 100 mM lysine HCl pH 7 |
| B20 | 15% trehalose dihydrate, 0.25% polysorbate 80, 100 mM lysine HCl pH 7 |
| B21 | 10% trehalose dihydrate, 0.1% polysorbate 80, 500 mM lysine HCl pH 7 |

TABLE 3-continued

Formulations analysed in trehalose concentration screen.

| ID # | Formulation Composition<br>Each formulation consists of 25 mM citrate PLUS the following: |
|---|---|
| B22 | 10% trehalose dihydrate, 0.1% polysorbate 80, 300 mM lysine HCl pH 7 |
| B23 | 10% trehalose dihydrate, 0.1% polysorbate 80, 100 mM lysine HCl pH 7 |
| B24 | 10% trehalose dihydrate, 0.175% polysorbate 80, 100 mM lysine HCl pH 7 |
| B25 | 10% trehalose dihydrate, 0.25% polysorbate 80, 100 mM lysine HCl pH 7 |

Upon visually examining four placebo formulation pairs which were otherwise perfectly excipient matched except for containing 10% or 15% trehalose (B17-B22; B18-B23; B19-B24; B20-B25), it was observed that the cake height for formulations with the 10% trehalose was low at less than 4 mm. This effect was attributed to the lower total solids content, combined with the lack of a suitable bulking agent, and a low 0.6 mL initial fill volume. The formulations with 15% trehalose had cake heights of approx 5 mm or greater, and looked more aesthetic. The formulation containing 10% trehalose with a lysine HCl concentration of 300 mM (B22) showed total collapse but the matching 15% trehalose formulation (B17) had a well formed cake, presumably due to the extra bulk. At a higher lysine content of 500 mM, both the 10% trehalose (B16) and the 15% trehalose (B21) formulations completely collapsed. This suggested that higher trehalose content could provide enough additional bulk to protect against collapse in presence of lysine HCl concentrations up to 300 mM. Mechanistically, this phenomenon can be explained by the fact that pure lysine HCl has a Tg' well below −50° C. (Lueckel, et al, 1997), and the additional trehalose, with a Tg' of −28° C., helps in raising the collapse temperature of the mixture to above that of the effective primary drying temperature during lyophilization.

Based on these observations, 15% trehalose concentration was selected because it allowed for successful lyophilization with the use of as much as 300 mM lysine HCl.

Selection of Polysorbate 80 concentration: The initial excipient screen demonstrated that the presence of the non-ionic surfactant polysorbate 80 in formulation F1 at a concentration of 0.1% significantly improved recovery by approximately 20% when compared to formulation F0 that lacked the polysorbate 80. FIGS. 12 to 15 show that 0.25% polysorbate 80 (F27) does not provide any additional benefit over 0.1% polysorbate 80 (F28). In order to address the concerns that 0.1% polysorbate could have potential adverse effects on the formation of lyophilized cakes due to its ability to act as a plasticizer, matched placebo formulations differing only in the concentration of polysorbate 80 (0.1, 0.175 and 0.25%) were lyophilized and visually inspected (B18, B19, B20 in Table 4). No visible differences were observed in the lyophilized cakes. There were no differences in the moisture levels of the cakes as determined by thermogravimetric analysis. Moisture levels for the two bracketing formulations B18 and B20 were determined to be comparable at 1.7%±0.6 for B18 (N=5) and 1.7±0.8 for B20 (N=4). Therefore it was concluded that 0.1% polysorbate 80 was an acceptable concentration and had no adverse effects on cake formation. Lower polysorbate 80 concentrations may be evaluated during future optimization of this formulation.

TABLE 4

Formulations analysed in polysorbate concentration optimization screen.

| ID # | Formulation Composition<br>Each formulation consists of<br>25 mM citrate PLUS the following: |
|---|---|
| F0 | 15% trehalose dihydrate ph 7 |
| F1 | 15% trehalose dihydrate 0.1% polysorbate 80 pH 7 |
| B18 | 15% trehalose dihydrate, 0.1% polysorbate 80, 100 mM lysine HCl pH 7 |
| B19 | 15% trehalose dihydrate, 0.175% polysorbate 80, 100 mM lysine HCl pH 7 |
| B20 | 15% trehalose dihydrate, 0.25% polysorbate 80, 100 mM lysine HCl pH 7 |

Lysine hydrochloride: The effect of lysine HCl in inhibiting aggregation in liquid formulations was further evaluated by analyzing the formulations listed in FIG. 11. FIGS. 12-15 demonstrate that lysine does not contribute to stabilization of MT103 against the stresses of freeze-thaw or shaking as evidenced by no changes seen in aggregate levels or recovery either in absence of lysine HCl or in presence of 100, 200 or 300 mM lysine HCl. Consequently, it was selected as an excipient solely to minimize the tendency of MT103 to aggregate in liquid bulks. Based on the results shown in FIGS. 12-15, lysine HCl concentrations between 100 and 300 mM provide identical results. Higher concentrations had shown a tendency to lead to collapsed lyophilized cakes, and absence of lysine HCl was shown to promote aggregation.

Stability of each of the three lysine containing liquid formulations with 0.1% polysorbate 80 (F27, F29, F30) was evaluated over 80 days and found to be stable with no decrease in recovery and no significant increase in aggregate levels at 4° C. in polypropylene 1 mL tubes (FIGS. 16 and 17).

Stability of each of the three lysine containing lyophilized formulations with 0.1% polysorbate 80 (F27, F29, F30) was evaluated over 2 to 4 weeks and found to be stable with no significant changes in the aggregate levels or recoveries (FIGS. 18 to 21). The residual moistures for selected formulations (F27, F30) were 0.7% and 1.2%, respectively, as determined by the Karl Fisher method.

Based on the above evaluations, the formulation F29 comprising 25 mM citrate, 15% trehalose dihydrate, 200 mM lysine HCl, 0.1% polysorbate 80 was selected. F29 formulation afforded adequate protection to MT103 from freeze-thaw stresses and shaking stresses, and also provided acceptable MT103 stability and recovery from liquid and lyophilized formulations.

6.1.6. Lyophilization Cycle Development

Evaluation of annealing vs. non-annealing cycle: The effect of annealing was evaluated on all three formulations (the lead formulation and the two backups) by lyophilizing the same batch of formulations (F31, F32, F33) containing 100, 200, and 300 mM lysine HCl with a non-annealing (L1) and annealing (L2) lyophilization cycle. The lyophilized formulations were visually examined and their stability was evaluated at 4, and 40° C. over a period of approx 8 weeks (Tables 5 to 8). Recoveries of MT103 were assessed immediately after lyophilization and also at various time points for both 4 and 40° C. conditions (Tables 9 and 10). Based on these data, the non-annealed formulation with 200 mM lysine HCl was selected.

TABLE 5

Stability of formulations F31, F32, F32 lyophilized in large lyophilizer, using an annealing cycle. Lyophilized vials were stored at 4° C.

| ID | Composition | Signal Type | Pre-lyo | Day 0 | Day 22 | Day 35 | Day 59 |
|---|---|---|---|---|---|---|---|
| F31 | 25 mM citrate, 15% trehalose, 100 mM Lysine HCl, 0.1% Tween80, pH 7 | % Dimer<br>% Monomer<br>Conc (ug/mL) | 1.31<br>98.69<br>58.2 | 0.58<br>99.42<br>52.4 | 0.73<br>99.27<br>49.8 | 1.18<br>98.82<br>56.7 | 1.15<br>98.85<br>52.0 |
| F32 | 25 mM citrate, 15% trehalose, 200 mM Lysine HCl, 0.1% Tween80, pH 7 | % Dimer<br>% Monomer<br>Conc (ug/mL) | 1.25<br>98.75<br>58.3 | 0.76<br>99.24<br>53.2 | 0.84<br>99.16<br>51.3 | 1.41<br>98.59<br>56.5 | 1.18<br>98.82<br>52.8 |
| F33 | 25 mM citrate, 15% trehalose, 300 mM Lysine HCl, 0.1% Tween80, pH 7 | % Dimer<br>% Monomer<br>Conc (ug/mL) | 1.26<br>98.74<br>58.3 | 0.77<br>99.23<br>53.4 | 0.94<br>99.06<br>51.1 | 1.49<br>98.51<br>55.3 | 1.31<br>98.69<br>52.3 |

TABLE 6

Stability of formulations F31, F32, F32 lyophilized in large lyophilizer, using an annealing cycle. Lyophilized vials were stored at 40° C.

| ID | Composition | Signal Type | Pre-lyo | Day 0 | Day 22 | Day 35 | Day 59 |
|---|---|---|---|---|---|---|---|
| F31 | 25 mM citrate, 15% trehalose, 100 mM Lysine HCl, 0.1% Tween80, pH 7 | % Dimer<br>% Monomer<br>Conc. (ug/mL) | 1.31<br>98.69<br>58.2 | 0.58<br>99.42<br>52.4 | 0.85<br>99.15<br>51.2 | 1.17<br>98.83<br>54.1 | 1.3<br>98.7<br>52.7 |
| F32 | 25 mM citrate, 15% trehalose, 200 mM Lysine HCl, 0.1% Tween80, pH 7 | % Dimer<br>% Monomer<br>Conc (ug/mL) | 1.25<br>98.75<br>58.3 | 0.76<br>99.24<br>53.2 | 0.85<br>99.15<br>50.9 | 1.3<br>98.7<br>54.7 | 1.19<br>98.81<br>51.9 |
| F33 | 25 mM citrate, 15% trehalose, 300 mM Lysine HCl, 0.1% Tween80, pH 7 | % Dimer<br>% Monomer<br>Conc. (ug/mL) | 1.26<br>98.74<br>58.3 | 0.77<br>99.23<br>53.4 | 0.92<br>99.08<br>51.0 | 1.33<br>98.67<br>53.9 | 1.27<br>98.73<br>51.6 |

TABLE 7

Stability of formulations F31, F32, F32 lyophilized in large lyophilizer, using a non-annealing cycle. Lyophilized vials were stored at 4° C.

| ID | Composition | Signal Type | Pre-lyo | Day 0 | Day 15 | Day 28 | Day 52 |
|---|---|---|---|---|---|---|---|
| F31 | 25 mM citrate, 15% trehalose, 100 mM Lysine HCl, 0.1% Tween80, pH 7 | % Dimer<br>% Monomer<br>Conc (ug/mL) | 0.96<br>99.04<br>55.7 | 0.72<br>99.28<br>58.2 | 0.94<br>99.06<br>50.6 | 1.2<br>98.8<br>52.8 | 1.08<br>98.92<br>51.8 |
| F32 | 25 mM citrate, 15% trehalose, 200 mM Lysine HCl, 0.1% Tween80, pH 7 | % Dimer<br>% Monomer<br>Conc (ug/mL) | 0.87<br>99.13<br>56.2 | 0.85<br>99.15<br>53.7 | 0.93<br>99.07<br>50.8 | 1.32<br>98.68<br>54.2 | 1.42<br>98.58<br>53.0 |
| F33 | 25 mM citrate, 15% trehalose, 300 mM Lysine HCl, 0.1% Tween80, pH 7 | % Dimer<br>% Monomer<br>Conc (ug/mL) | 0.75<br>99.25<br>55.5 | 0.85<br>99.15<br>53.0 | 0.99<br>99.01<br>50.8 | 1.43<br>98.57<br>54.3 | 1.32<br>98.68<br>52.4 |

TABLE 8

Stability of formulations F31, F32, F32 lyophilized in large lyophilizer, using a non-annealing cycle. Lyophilized vials were stored at 40° C.

| ID | Composition | Signal Type | Pre-lyo | Day 0 | Day 15 | Day 28 | Day 52 |
|---|---|---|---|---|---|---|---|
| F31 | 25 mM citrate, 15% trehalose, 100 mM Lysine HCl, 0.1% Tween80, pH 7 | % Dimer<br>% Monomer<br>Conc (ug/mL) | 0.96<br>99.04<br>55.7 | 0.72<br>99.28<br>58.2 | 0.87<br>99.13<br>50.5 | 1.77<br>98.23<br>53.6 | 1.07<br>98.93<br>52.2 |
| F32 | 25 mM citrate, 15% trehalose, 200 mM Lysine HCl, 0.1% Tween80, pH 7 | % Dimer<br>% Monomer<br>Conc (ug/mL) | 0.87<br>99.13<br>56.2 | 0.85<br>99.15<br>53.7 | 1.01<br>98.99<br>51.0 | 1.36<br>98.64<br>54.0 | 1.19<br>98.81<br>52.0 |
| F33 | 25 mM citrate, 15% trehalose, 300 mM Lysine HCl, 0.1% Tween80, pH 7 | % Dimer<br>% Monomer<br>Conc (ug/mL) | 0.75<br>99.25<br>55.5 | 0.85<br>99.15<br>53.0 | 0.99<br>99.01<br>50.8 | 1.49<br>98.51<br>53.6 | 1.28<br>98.72<br>51.9 |

TABLE 9

Protein recovery from formulations F31, F32, F32 lyophilized in
large lyophilizer, using a non-annealing cycle.
Recovery of MT103 from cakes lyophilized in a
Non-Annealing Cycle (L1)

| | | Percent Recovery | | |
|---|---|---|---|---|
| Time | Temperature | F31 | F32 | F33 |
| Initial | N/A | 95.8 | 96.4 | 98.2 |
| 7 week | 4° C. (N = 1) | 94.6 | 95.9 | 96.4 |
| | 40° C. (N = 3) | 95.1 | 94.1 | 95.1 |

TABLE 9

Protein recovery from formulations F31, F32, F32 lyophilized in
large lyophilizer, using an annealing cycle.
Recovery of MT103 from cakes lyophilized in a
Annealing Cycle (L2)

| | | Percent Recovery | | |
|---|---|---|---|---|
| Time | Temperature | F31 | F32 | F33 |
| Initial | N/A | 96.4 | 98.5 | 97.4 |
| 8 week | 4° C. (N = 1) | 94.6 | 95.8 | 96.1 |
| | 40° C. (N = 3) | 96.1 | 93.9 | 94.9 |

Post-reconstitution stability of the MT103 formulation F29 was determined using multiple independent vials (N=3). Protein recovery from reconstituted vials stored on bench after reconstitution was assessed over 3 days (FIG. 22).

6.2. Development of MT103 Lyophilized Formulation II

Further studies were performed to characterize the MT103 formulations described in the previous section. In particular, the studies described herein elucidated: 1) the acceptable pH range for MT103 formulations, 2) the threshold concentrations of stabilizing excipients. The short term stability of liquid and lyophilized MT103 formulations comprising threshold concentration of stabilizing excipients was also determined.

6.2.1. Optimal pH Range of MT103 Formulations

Liquid formulations consisting of 110 μg/ml MT103, 10 mM citrate, 10 mM TrisHCl, 0.1% polysorbate 80 and 200 mM of a basic amino acid selected from the group consisting of histidine, lysine and arginine were prepared following the standard protocols. Aliquots of each formulation were adjusted to pH 3.0, 4.5, 6.0, 7.0, or 8.5. Aggregate content of each MT103 formulation tested was determined by SEC-HPLC following storage at 5° C. or 25° C. for 5 weeks. Data obtained is displayed in FIGS. 23 and 24.

All formulations tested but one contained less than 5% aggregate following storage at 5° C. The MT103 formulation comprising 200 mM arginine at pH 8.0 contained over 50% aggregate material following storage at 5° C. Formulations stored at 25° C. displayed a different stability profile. MT103 precipitated out of solution in all pH 3.0 formulations stored at 25° C. All other MT103 formulations except for the formulation comprising 200 mM arginine at pH 8.0 remained in solution with less than 5% aggregate formed. The 200 mM arginine/pH 8.0 formulation contained over 40% of MT103 in aggregate form following storage at 25° C.

6.2.2. Threshold Level of Stabilizing Excipients

Threshold concentration of lysine and polysorbate 80 was determined by comparing the stability of MT-103 formulations that were identical to each other except for the concentration of lysine or polysorbate 80, respectively. The base formulation consisted of 55 μg/ml MT103, 10 mM citrate, 10 mM TrisHCl, 200 mM Lysine HCl, and 0.1% polysorbate 80 at a pH of 6.0. Excipient concentrations tested are 0, 25, 50, 100, and 200 mM lysine HCl and 0, 0.01, 0.05, 0.1% of polysorbate 80. Stability of a formulation was characterized by measuring the total non-aggregated MT103 protein recoverable following extended storage, freeze/thaw cycles, or shear stress.

FIG. 24 displays the stability of MT103 liquid formulations comprising various concentrations of lysine HCl following extended storage at 40° C. The amount of MT103 protein recoverable from formulations comprising 25, 50, 100, or 200 mM lysine HCl is substantially identical over the 65 days time period of the experiment. There was no change in The protein recovery from formulations stored at 5° C. or 25° C. did not change over the 65 day time period of the experiment (data not shown).

FIGS. 25 and 26 display the stability of MT formulations comprising various concentrations of lysine HCl or polysorbate 80 following exposure to i) three freeze/thaw cycles, ii) mechanical stress on a rocking shaker, or iii) shear stress on a vortex mixer. The stability of formulations is assessed either by measuring the total MT103 protein recoverable from a formulation exposed to stress (FIG. 25) or by measuring the total amount of aggregates in a formulation exposed to stress (FIG. 26). Changes in lysine concentration did not significantly alter the amount of MT103 recoverable or the aggregate formation following stress. Formulations comprising 0.01, 0.05, or 0.1% polysorbate 80 also displayed identical stability profiles as characterized by the above described measurements. The formulation comprising 0% polysorbate (0% PS-80) had a reduced stability profile. The amount of MT103 recoverable from the unstressed 0% PS-80 formulation was already significantly reduced; freeze/thaw, mechanical or shear stress further reduced the amount of recoverable MT103 protein. A significant amount of MT103 protein precipitated out of the 0% PS-80 formulation. Because of the precipitation, the level of HPSEC measured aggregate levels were slightly reduced in unstressed or freeze/thaw stressed formulations and were not detectable in the 0% PS-80 formulation following shaking or vortex treatment.

6.2.3. Threshold Level of Trehalose

Trehalose incorporated into the MT103 formulations described herein may function as a bulking agent during lyophilization. The amount of trehalose necessary for the formation of a lyophilized cake was ascertained by lyophilizing buffer only (no MT103 protein) formulations comprising various amounts of trehalose. The buffer only formulations tested are described in Table 10. All buffers tested produced adequate bulk when subjected to lyophilization. The cake characteristics and reconstitution times were comparable for all buffers tested.

TABLE 10

Buffer only formulations lyophilized (P80 = polysorbate 80).

| | |
|---|---|
| B1 | 25 mM Citrate, 25 mM lysine HCl, 6% trehalose, 0.02% P80 at pH 6.0 |
| B2 | 10 mM Citrate, 50 mM lysine HCl, 5.5% Trehalose, 0.02% P80 at pH 6.0 |
| B3 | 10 mM Citrate, 25 mM lysine HCl, 7.5% Trehalose, 0.05% P80 at pH 6.0 |
| B4 | 25 mM Citrate, 8% Trehalose, 0.02% P80 at pH 6.0 |
| B5 | 50 mM Citrate, 6% Trehalose, 0.02% P80 at pH6.0 |

6.2.4. Short Term Stability of MT103 Formulations

Short term stability of formulations 25/25, 10/50, and 25/200 (FIG. 27A) was determined. Stability of the lyophilized formulations was ascertained by reconstituting lyophilized cakes following storage at 5° C., 25° C., and 40° C. and measuring aggregate concentration in the reconstituted liquid. Lyophilized cakes were prepared in individual vials filled with 0.6 ml of 25/25, 10/50, and 25/200 formulation comprising 175 µg/ml MT103 using the L1 lyophilization cycle described herein. Aggregate content of the reconstituted liquid was measured by SEC and is displayed as a function of lyophilized cake storage time in FIGS. 27B and C. The level of aggregates found in reconstituted liquid formulations 10/50 and 25/25 comprising 175 µg/ml MT103 remained substantially the same during the 60 days time span of the experiment at all three temperatures examined (5° C., 25° C., and 40° C.). Aggregate levels in both reconstituted formulation were below 2%.

Stability of pre-lyophilized liquid formulations 25/25, 10/50, and 25/200 comprising 160 µg/ml MT103 (FIG. 27A) was also determined. Small aliquots of each formulations were stored in a glass (25/25, 10/50) or polypropylene (25/200) vial at 5° C. or 25° C. for extended periods of time. Stability of the formulations were assessed by measuring the level of aggregate formation using SEC. The % aggregate levels as a function of time are displayed in FIGS. 28A and B. Aggregate levels in 10/50 were approximately 3% and 4.5% following ~60 days of storage at 5° C. and 25° C., respectively. Aggregate levels in 25/25 were approximately 2% and 4.5% following ~60 days of storage at 5° C. and 25° C., respectively. Aggregate levels in 25/200 were approximately 0.5% and 3% following ~60 days of storage at 5° C. and 25° C., respectively. Aggregate levels in formulation 25/200 rose to 1% by day ~180 of storage at 5° C., and to 3.5% by day ~90 of storage at 25° C.

6.3. Development of a Lyophilized MT-103 Formulation for Subcutaneous Delivery A lyophilized formulation for subcutaneous delivery was developed by optimizing excipient concentrations to achieve isotonicity while maintaining protein stability. MT103 concentration was set at 160 µg/ml for the pre-lyophilized liquid bulk. Lyophilization of candidate formulations was done by using the optimized 96 hrs lyophilization cycle described above.

The stability and lyophilized cake characteristics of the following formulations were evaluated in an initial set of experiments:

a) 25 mM citrate, 25 mM lysine HCl, 6% trehalose, 0.02% polysorbate 80 at pH 6.0;
b) 10 mM citrate, 25 mM lysine HCl, 7.5% trehalose, 0.05% polysorbate 80 at pH 6.0;
c) 10 mM citrate, 50 mM lysine HCl, 5.5% trehalose, 0.02% polysorbate 80 at pH 6.0;
d) 25 mM citrate, 8% trehalose, 0.02% polysorbate 80 at pH 6.0; and
e) 50 mM citrate, 6% trehalose, 0.02% polysorbate 80 at pH 6.0.

Stability of the liquid formulations were assessed by measuring the % protein aggregate level following storage at 5 or 25° C. Liquid formulations used for the stability experiments comprised 160 µg/ml MT103 protein. Experimental results are shown in FIG. 27.

The cake characteristics and reconstitution times were comparable for all formulations tested.

Excipient concentrations and formulation pH were optimized using a 3 level, 4 factor Box-Behnken experimental design. Response variable was the change in % aggregate levels in the formulation following four weeks of storage at 25° C. The factors optimized and the levels tested for each factor are listed in Table 11. The stability of 25 different formulations, including the center point formulation, was determined in three blocks following the standard Box-Behnken experimental design. The stability of the center point formulation was measured in duplicates in each experimental block to improve the statistical significance of the results. Data analyses predicted that an optimal isotonic formulation would comprise 30 mM citrate, 75 mM lysine HCl, and 6.5% trehalose, and has a pH of 7.0.

TABLE 11

Excipient concentrations used in optimization experiment.

|  |  | Levels | | |
|---|---|---|---|---|
|  |  | High | Medium | Low |
| Factors | pH | 5.0 | 6.0 | 7.0 |
|  | Lysine HCl | 30 mM | 50 mM | 70 mM |
|  | Citrate | 10 mM | 30 mM | 50 mM |
|  | Trehalose | 5% | 6.5% | 8% |

6.4. In Vivo Bioavailability of MT103

Candidate formulations of MT103 drug product were evaluated in a mouse model for serum bioavailability following subcutaneous route of administration. A formulation was identified that consistently yielded the highest level of bioavailability in the mouse model, and was evaluated in cynomolgus monkeys. Bioavailability following subcutaneous bolus injection in cynomolgus monkeys was comparable to that observed in mice. These animals represent pharmacologically non-relevant models for evaluating off-target activity of MT103 (MEDI-538) based on its lack of specific binding to T and B cells in these species.

6.4.1. Methods

ELISA for the detection of MT103 in mouse serum: A specific MT103-capture ELISA was employed to determine the concentration of MT103 in serum samples of CD-1 mice. The ELISA assay utilized two unique and non-competing anti-MT103 monoclonal Abs (F3 and 6E12) to capture the analyte, which was subsequently detected with a ruthinylated antibody against the hexahistidine (6×-his) tag of the molecule. For the final assay method, F3 and 6E12 were both spotted in 5 µL on the same well of a Meso Scale Discovery (MSD) Hi Bind plate using phosphate buffered saline (PBS). Plates were dried overnight and non-specific sites were blocked with 1% BSA+PBS for 1 hr at room temperature (RT) with shaking A MT103 standard curve was prepared with serial 1:2 dilutions from 800 ng/mL to 0.39 ng/mL in a pool of normal CD-1 mouse serum. Plates were washed 3 times with PBS+0.5% Tween-20 and standard curve calibrators, quality control (QC) samples and mouse samples were added to the blocked wells neat or with dilution (up to 1:250) at 25 µL per well and incubated for 1 hour at RT, with rotation (approximately 600 rpm). For detection of captured MT103, a rabbit anti-6×-His polyclonal Ab was conjugated to MSD Sulfo-Tag (ST) and 25 µL per well of the conjugated reagent was added subsequently to the plates in assay buffer (PBS+1% casein). Plates were incubated for one additional hour at RT, with rotation. Plates were washed 3 times with PBS+

0.05% Tween-20 and developed using 2×MSD Read Buffer (150 µL per well). Plates were immediately read on the MSD Sector 6000 reader and data analysis was conducted using MSD Workbench software. Concentrations of MT103 present in the mouse serum samples were estimated by non-linear regression analysis from a 4-parameter fit model of the MT103 standard data set. The lower limit of quantitation for this assay was determined to be 0.4 ng of MT103 per mL of mouse serum.

ELISA for the detection of MT103 in cynomolgus monkey serum: Samples were tested using an electrochemiluminescent (ECL) assay to quantitate the levels of MT103 in cynomolgus serum. Meso Scale Discovery (MSD) 96 well plates were coated with two monoclonal antibodies (mAb) specific for MT103 (F3 and 6E12). F3 and 6E12 were diluted to 50 µg/mL and 90 µg/mL, respectively, in Dulbecco's Phosphate Buffered Saline (D-PBS) containing 0.015% Tween-20 and 5 µl of this solution was spotted on the surface of the MSD plate. Plates were dried overnight and non-specific sites were blocked with 1% BSA+D-PBS for 1 hr at room temperature (RT). A MT103 standard curve was prepared with serial 1:2.5 dilutions from 1200 ng/mL to 0.126 ng/mL in normal cynomolgus serum (NCS). Plates were washed 4 times with D-PBS+0.1% Tween-20 and standard curve calibrators, quality control (QC) samples and study samples were added to the blocked wells without dilution at 25 µL per well and incubated for 1 hour at RT, with rotation (approximately 600 rpm). For detection of captured MT103, a rabbit anti-hexa-histidine polyclonal Ab was conjugated to MSD Sulfo-Tag (ST) and 25 µL per well of the conjugated reagent at 1.5 µg/mL was added subsequently to the plates in assay buffer (D-PBS+1% casein). Plates were incubated for one additional hour at RT, with rotation. Plates were washed 4 times with D-PBS+0.1% Tween-20 and developed using 2×MSD Read Buffer (150 µL per well). Plates were immediately read on the SECTOR Imager 6000 instrument (MSD) to measure the ECL signal and data was analyzed using the Discovery Workbench Software, version 2.0 (MSD). The lower limit and upper limits of quantitation for this assay were determined to be 200 ng/mL and 1.5 ng/mL, respectively.

6.4.2. Results 6.4.2.1. Bioavailability of MT103 Following a Single-Dose Intravenous (IV) or Subcutaneous (SC) Bolus Administration of Four Different MT103 Formulations in CD-1 Mice.

In a single-dose IV and SC pharmacokinetic study, serum levels of MT103 were determined in samples collected during a single day. CD-1 mice (n=4/group) were treated with a single bolus IV or SC infusion of 4 different formulations of MT103 at two dose levels (0.75 and 2.5 mg/kg). Formulations utilized in this study are detailed in Table 12. Serum samples were collected at 6 different time points over a time interval of 24 hours after administration. The concentrations of MT103 in serum samples were determined using a specific ELISA method with a LLOQ of 0.4 ng/mL. The plot of the mean serum concentrations versus time profile of MT103 is presented in FIG. 29. Absolute bioavailability was estimated by taking the ratio of the mean area under the curve (AUC) for the SC treatment groups and the mean AUC of the IV treatment groups. The bioavailability was 17%, 33%, 35%, and 24% for groups of mice treated with 0.75 mg/kg of Formulation X, Y, Z and W, respectively, and 21%, 26%, 30%, and 37% for groups of mice treated with 2.5 mg/kg of Formulation X, Y, Z, and W, respectively. Formulation Z was chosen for subsequent studies.

TABLE 12

| | Formulations of MT103 | | | | |
|---|---|---|---|---|---|
| | Citrate, pH 7.0 (mM) | Lysine HCL (mM) | Trehalose (% w/v) | Polysorbate 80 (% v/v) | Estimated Osmolarity (mOs) |
| Formulation X | 25 | 200 | 15 | 0.1 | 1100 |
| Formulation Y | 25 | 200 | | | 400 |
| Formulation Z | 25 | 25 | 6 | 0.02 | 520 |
| Formulation W | 10 | 50 | 5.5 | 0.02 | 400 |

In CD-1 mice, SC administered MEDI-538 (MT103) was 20-30% bioavailable and exhibited serum concentrations that were dose-proportional, reached a peak at 4 hrs, and had a similar terminal half-life as IV administered drug (FIG. 32). After injection of 0.25, 0.75, or 2.5 mg/kg of MEDI-538, serum samples were collected at 5 min, 1, 2, 4, 8, 15, 24, and 44 hrs. Serum concentration of MEDI-538 were measured by ELISA method and reported here as a the arithmetic mean for each sample at each time interval after injection. A two-phase exponential decay, non-linear regression model was used for IV treated mice. Dose optimization studies showed that varying the dose concentration or volume for a given dose level did not effect the concentration of MEDI-538 in the serum after SC administration.

TABLE 13

| Pharmacokinetic parameters of MEDI-538 in CD-1 mice. | | | | | | | |
|---|---|---|---|---|---|---|---|
| Route (dose) | N | $C_{max}$ (ng/ml) | $T_{max}$ (hr) | $t_{1/2}$ (hr) | $AUC_{obs}$ (ng · hr/ml) | $AUC_{inf}$ (ng · hr/ml) | CL (ml/hr/kg) | Bioavailibility |
| IV (2.5 mg/kg) | 7 | 23,100 | 0.0083 | 4.7 | 17,700 | 17,600 | 140 | 1.00 |
| IV (0.75 mg/kg) | 5 | 8,090 | 0.083 | 6.2 | 4,670 | 4,760 | 160 | 1.00 |
| IV (0.25 mg/kg) | 6 | 1,030 | 0.083 | 5.7 | 809 | 827 | 300 | 1.00 |
| SC (2.5 mg/kg) | 4 | 437 | 4 | 4.4 | 4,430 | 4,440 | 560 | 0.25 |

TABLE 13-continued

Pharmacokinetic parameters of MEDI-538 in CD-1 mice.

| Route (dose) | N | $C_{max}$ (ng/ml) | $T_{max}$ (hr) | $t_{1/2}$ (hr) | $AUC_{obs}$ (ng · hr/ml) | $AUC_{inf}$ (ng · hr/ml) | CL (ml/hr/kg) | Bioavailibility |
|---|---|---|---|---|---|---|---|---|
| SC (0.75 mg/kg) | 4 | 151 | 4 | 4.5 | 1,330 | 1,380 | 550 | 0.28 |
| SC (0.25 mg/kg) | 4 | 106 | 4 | 4.6 | 543 | 554 | 450 | 0.67 |

N listed for each dataset.
Cmax, peak serum concentration;
Tmax, time to peak serum concentration;
$t_{1/2}$, half-life of serum concentration;
AUCobs, are under the serum concentration-time curve up to the last measureable sampling time;
AUCinf, are under the serum-concentration-time curve to infinity;
CL, total body plasma clearance estimated as Dose/AUCinf after intravenous administration;
Bioavailability, absolute bioavailability estimated as AUCinf (SC)/AUCinf (IV).

6.4.2.2. Bioavailability of MT103 Following a Single-Dose Intravenous (IV) or Subcutaneous (SC) Bolus Administration of the Lead Formulation of MT103 in CD-1 Mice.

In a single-dose IV and SC pharmacokinetic study, serum levels of MT103 were determined in samples collected during a single day. CD-1 mice (n=5/group) were treated with a single bolus IV or SC infusion of MT103 in the lead formulation (Formulation Z) at two dose levels (1.6 and 5.0 mg/kg). Serum samples were collected at 6 different time points over a time interval of 24 hours after administration. The concentrations of MT103 in serum samples were determined using a specific ELISA method with a LLOQ of 0.4 ng/mL. The plot of the mean serum concentrations versus time profile of MT103 is presented in FIG. 30. Absolute bioavailability was 28% and 29% for groups of mice treated with 1.6 mg/kg and 5.0 mg/kg, respectively, and was comparable to the bioavailability observed following a single-dose IV and SC pharmacokinetic study in cynomolgus monkeys. Thus, the results of the cynomolgus monkeys supported the results observed in the mouse model.

6.4.2.3. Bioavailability of MT103 Following a Single-Dose Intravenous (IV) or Subcutaneous (SC) Bolus Administration of MT103 in Cynomolgus Monkey.

A study was conducted to compare the bioavailability of MT103 when delivered by a single intravenous (IV) bolus or subcutaneous (SC) injection at 0.5 mg/kg to male cynomolgus monkeys over a one-week period (FIG. 31). The study used a cross-over design with one week washout period between two phases. Three animals were randomized in each of two groups. During Phase 1, Group 1 animals were dosed intravenously and Group 2 animals were dosed subcutaneously and vice-versa during Phase 2. MT103, formulated in 25 mM Citrate, 25 mM Lysine HCL, 6% Trehalose, 0.02% Polysorbate 80, pH 6.0, was delivered in a 1 mL per kg dose volume for both routes. All animals appeared healthy throughout the study with no signs of irritation at the sites of injection. Serum concentrations of MT103 were determined using a sensitive and specific ELISA assay based on electrochemiluminescence (ECL) detection with a lower limit of quantitation (LLOQ) equal to 1.5 ng/ml. PK analysis results showed the average half-life of MT103 was approximately 6.3 and 7.5 hours for intravenous (IV) and subcutaneous (SC) groups, respectively. The average Cmax was 12393 and 152 µg/mL, and was attained 0.1 and 4.3 hours post-dose for the IV and SC groups, respectively. The mean observed AUC for the IV and SC groups was 12723.1 and 2655.28 µg·hr/mL, respectively, whereas the average AUC(0-∞) was 12766.0 and 2711.2 µg·hr/mL, respectively, for the two groups. The clearance (CL) of MT103 following IV injection is 39.96 mL/hr/kg and the apparent clearance (CL/F) following SC injection is 185.63 mL/hr/kg. The bioavailability of MT103 delivered via a single SC dose was 22% estimated based on the ratio of AUC(0-∞). Bioavailability data obtained is summarized in FIG. 33.

TABLE 14

Pharmacokinetic parameters of MEDI-538 in cynomolgus monkeys.

| Route | $C_{max}$ (ng/ml) | $T_{max}$ (hr) | $t_{1/2}$ (hr) | $AUC_{obs}$ (ng · hr/ml) | $AUC_{inf}$ (ng · hr/ml) | CL (ml/hr/kg) | Bioavailibility |
|---|---|---|---|---|---|---|---|
| IV | 12,400 (1370) | 0.1 (0.0) | 6.3 (1.1) | 12,700 (2,100) | 12,800 (2,100) | 40 (5.9) | 1.00 |
| SC | 150 (25) | 4.3 (0.8) | 7.5 (1.3) | 2,660 (220) | 2,700 (230) | 186 (17) | 0.22 (0.033) |

N = 6 (3 M, 3F).
Cmax, peak serum concentration;
Tmax, time to peak serum concentration;
$t_{1/2}$, half-life of serum concentration;
AUCobs, are under the serum concentration-time curve up to the last measureable sampling time;
AUCinf, are under the serum-concentration-time curve to infinity;
CL, total body plasma clearance estimated as Dose/AUCinf after intravenous administration;
Bioavailability, absolute bioavailability estimated as AUCinf (SC)/AUCinf (IV).
Values in parentheses, standard deviation of the mean for each parameter.

6.5. Pharmacodynamic Activity, and Anti-Tumor Efficacy of the CD19/CD3 Specific BiTE® Antibody MEDI-538 (MT103/Blinatumomab) Delivered Subcutaneously in Animal Models Animal models were utilized to evaluate the bioavailability, pharmacodynamic effects, and anti-tumor potency of MEDI-538 following subcutaneous (SC) administration.

RESULTS: MEDI-538 provided anti-tumor efficacy following SC administration in NOD/SCID mice that were engrafted with human B cell tumor cells mixed with human PBMC and that were capable of demonstrating human T cell-mediated killing of tumor cells. Pharmacodynamic effects were observed following SC administration of hys103 (anti-human CD19×anti-mouse CD3), a hybrid mouse surrogate form of MEDI-538, to immunocompetent human CD19 transgenic knock-in mice. Hys103 recruits murine T cells for redirected lysis of human CD19 expressing mouse B cells. Treatment caused a reduction in B cells and an increase in activated T cells in the spleen as measured by flow cytometry These results demonstrated that SC delivery of MEDI-538 yielded comparable PK characteristics in multiple animal models, provided sufficient systemic levels for efficacy against tumor challenge in xenograft mouse models, and depleted B cells in an immunocompetent mouse model. Taken together, the data support the SC route of administration as an alternative method for delivery of MEDI-538.

6.5.1. In Vivo Anti-Tumor Efficacy.

Experimental design of in vivo mouse tumor models used are outlined in FIG. 34.

Cohorts of 6 NOD/SCID mice were inoculated SC with $10^6$ Namalwa cells in the absence (without T cells) or presence of $2\times10^6$ human CD3+ T cells isolated from healthy donors. Five daily doses of MEDI-538 as indicated or a negative control BiTE® were administered by subcutaneous injection on the indicated days following tumor cell/T cell engraftment. Mean values of tumor growth curves are shown in FIG. 35.

Cohorts of 6 NOD/SCID mice were inoculated IV with 105 Ramos cells mixed with $5\times10^6$ human PBMCs isolated from healthy donors. Five daily doses of MEDI-538 as indicated or a negative control BiTE® were administered by subcutaneous injection on the indicated days following tumor cell/PBMC engraftment. The number of mice alive versus time after treatment is graphed. Animals were euthanized when overt signs of paralysis were observed. Results are shown in FIG. 36.

6.5.2. Pharmacodynamic Effects.

Pharmacodynamic effects were evaluated using hys103 (anti-human CD19×anti-mouse CD3), a hybrid mouse surrogate form of MEDI-538, and immunocompetent human CD19 (huCD19) transgenic knock-in mice. The huCD19 transgenic mice was established by Tom Tedder's laboratory. The expression of huCD19 is restricted to B cells and can replace the function of murine CD19. The expression level of huCD19 on the murine transgenic B cells is comparable to the expression level observed on normal human blood B cells. Functional characteristics of T cells from the huCD19 transgenic mouse are comparable to that of T cells from the background mouse strain (C57BL/6).

CD3+ human T cells or CD3+ mouse T cells from huCD19 transgenic mice (spleen) were combined with $DiOC_{18}(3)$-labeled human CD19+ NALM-6 targets cells in the presence of the indicated concentrations of MEDI-538 or hys103. After 18 hrs for the human T cells and 42 hrs for the mouse T cells, specific cell lysis was determined by means of a flow cytometry-based assay. E:T ratio was 5:1. EC50 is the concentration at half maximal target cell lysis. Results for replicate experiments are shown in FIG. 37.

Four huCD19 transgenic mice were administered a single SC dose of hys103 at various dose levels. Hys103-induced effects on the splenic and bone marrow CD19+B220+B cell populations were monitored by flow cytometry analysis at various time intervals following treatment, and reported as the percentage of B cells following treatment normalized to the number of B cells present in PBS treated mice in FIGS. 38 and 39.

Four huCD19 transgenic mice were administered a single SC dose of hys103 at various dose levels. Hys103-induced effects on the splenic and bone marrow CD3+CD8+ T cell populations were monitored by flow cytometry analysis at various time intervals following treatment, and reported as the fold increase of the mean fluorescence intensity (MFI) of CD69 following hys103 treatment as compared to the MFI of CD69 on T cells in PBS treated mice evaluated at the same time interval (FIGS. 40 and 41). Similar levels of CD69 activation were observed with CD3+CD4+ T cells.

A study was conducted to compare the pharmacokinetic profile of hys103 (anti-human CD19×anti-mouse CD3), a hybrid mouse surrogate form of MEDI-538, following a single intravenous (IV) bolus or subcutaneous (SC) injection to huCD19 transgenic mice. Experimental animals received a single dose of 0.375 mg/kg, 0.75 mg/kg, 1.5 mg/kg or 3 mg/kg of hys103, formulated in 25 mM Citrate, 25 mM Lysine HCL, 6% Trehalose, 0.02% Polysorbate 80, pH 6.0, by both routes of administration. Serum level of hys103 was monitored by ELISA over a 24 hr period following administration. A representative sample of the data is shown in FIGS. 42A and B. Serum half-life of hys103 was approximately 8 hrs. Serum bioavailability of hys103 was approximately 18% following subcutaneous administration.

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference. In addition, U.S. Provisional Application Nos. 60/990,772, filed Nov. 28, 2007, 61/039,985, filed Mar. 27, 2008, and 61/040,384, filed Mar. 28, 2008 are hereby incorporated by reference in their entirety for all purposes.

Citation or discussion of a reference herein shall not be construed as an admission that such is prior art to the present invention.

---

What is claimed is:

1. A liquid pharmaceutical formulation comprising between about 25 µg/ml and about 250 µg/ml of a single chain bispecific antibody comprising a first and a second binding domain, wherein the first binding domain specifically binds CD3 T cell surface antigen; and wherein the formulation comprises between about 5 mM and about 125 mM citrate, between about 100 mM and about 300 mM lysine, between about 10% and about 20% trehalose, and between about 0.01% and about 1% Polysorbate 80, and has a pH of between 5.0 and about 8.0.

2. The formulation of claim 1, wherein the first binding domain comprises the amino acid sequence of residues 283-525 of SEQ ID NO:5.

3. The formulation of claim 1, wherein the second binding domain specifically binds an antigen selected from the group consisting of CD 19, CD20, CD22, EphA2, EphA4, INFR, ICOS, Ep-CAM, CEA, and IL-5 receptor.

4. The formulation of claim 3, wherein the second binding domain comprises the amino acid sequence of residues 28-277 of SEQ ID NO:5.

5. The formulation of claim 3, wherein the bispecific antibody comprises the amino acid sequence of residues 28-525 of SEQ ID NO:5.

6. A lyophilized pharmaceutical formulation comprising between about 25 µg/ml and about 250 µg/ml of a single chain bispecific antibody comprising a first and a second binding domain, wherein the first binding domain specifically binds CD3 T cell surface antigen; and wherein the formulation comprises between about 5 mM and about 125 mM citrate, between about 100 mM and about 300 mM lysine, between about 0.01% and about 1% Polysorbate 80, and has a pH of between 5.0 and about 8.0.

7. The formulation of claim 6, wherein the first binding domain comprises the amino acid sequence of residues 283-525 of SEQ ID NO:5.

8. The formulation of claim 6, wherein the second binding domain specifically binds an antigen selected from the group consisting of CD 19, CD20, CD22, EphA2, EphA4, INFR, ICOS, Ep-CAM, CEA, and IL-5 receptor.

9. The formulation of claim 8, wherein the second binding domain comprises the amino acid sequence of residues 28-277 of SEQ ID NO:5.

10. The formulation of claim 8, wherein the bispecific antibody comprises the amino acid sequence of residues 28-525 of SEQ ID NO:5.

11. A liquid reconstituted pharmaceutical formulation comprising between about 25 µg/ml and about 250 µg/ml of a single chain bispecific antibody comprising a first and a second binding domain, wherein the first binding domain specifically binds CD3 T cell surface antigen; and wherein the formulation comprises between about 5 mM and about 125 mM citrate, between about 100 mM and about 300 mM lysine, between about 10% and about 20% trehalose, and between about 0.01% and about 1% Polysorbate 80, and has a pH of between 5.0 and about 8.0.

12. The formulation of claim 11, wherein the first binding domain comprises the amino acid sequence of residues 283-525 of SEQ ID NO:5.

13. The formulation of claim 11, wherein the second binding domain specifically binds an antigen selected from the group consisting of CD 19, CD20, CD22, EphA2, EphA4, INFR, ICOS, Ep-CAM, CEA, and IL-5 receptor.

14. The formulation of claim 13, wherein the second binding domain comprises the amino acid sequence of residues 28-277 of SEQ ID NO:5.

15. The formulation of claim 13, wherein the bispecific antibody comprises the amino acid sequence of residues 28-525 of SEQ ID NO:5.

16. The formulation of claim 1, wherein the formulation comprises about 55 micrograms/ml of a single chain bispecific tandemly arranged antibody or a fragment thereof, about 25 mM citrate, about 200 mM lysine, about 15% trehalose dihydrate and about 0.1% Polysorbate 80, and has a pH of about 7.0.

17. The formulation of claim 11, wherein the formulation comprises about 55 micrograms/ml of a single chain bispecific tandemly arranged antibody, about 25 mM citrate, about 200 mM lysine, about 15% trehalose dihydrate and about 0.1% Polysorbate 80, and has a pH of about 7.0.

18. The formulation of claim 1, wherein the formulation comprises between about 10 and about 100 micrograms/ml of a single chain bispecific tandemly arranged antibody or a fragment thereof.

19. The formulation of claim 1, wherein the formulation comprises between about 50 and about 55 micrograms/ml of a single chain bispecific tandemly arranged antibody or a fragment thereof.

20. The formulation of claim 1, wherein the formulation comprises between about 10% and about 15% trehalose dihydrate.

21. The formulation of claim 1, wherein the formulation comprises between about 15% and about 20% trehalose dihydrate.

22. The formulation of claim 1, wherein the bispecific antibody is a a single chain bispecific tandemly arranged antibody or a fragment thereof.

* * * * *

SEQUENCE LISTING

```
<160> NUMBER OF SEQ ID NOS: 5

<210> SEQ ID NO 1
<211> LENGTH: 111
<212> TYPE: PRT
<213> ORGANISM: artificial
<220> FEATURE:
<223> OTHER INFORMATION: recombinant polypeptide

<400> SEQUENCE: 1
```

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
            85                  90                  95

Glu Asp Pro Trp Thr Phe Gly Gly Gly Thr Lys Leu Glu Ile Lys
        100                 105                 110
```

<210> SEQ ID NO 2
<211> LENGTH: 124
<212> TYPE: PRT
<213> ORGANISM: artificial
<220> FEATURE:
<223> OTHER INFORMATION: recombinant polypeptide

<400> SEQUENCE: 2

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
            85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 3
<211> LENGTH: 119
<212> TYPE: PRT
<213> ORGANISM: artificial
<220> FEATURE:
<223> OTHER INFORMATION: recombinant polypeptide

<400> SEQUENCE: 3

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
```

```
                65                  70                  75                  80
Met Gln Leu Ser Ser Leu Thr Ser Glu Asp Ser Ala Val Tyr Tyr Cys
                    85                  90                  95

Ala Arg Tyr Tyr Asp Asp His Tyr Cys Leu Asp Tyr Trp Gly Gln Gly
                   100                 105                 110

Thr Thr Leu Thr Val Ser Ser
            115

<210> SEQ ID NO 4
<211> LENGTH: 106
<212> TYPE: PRT
<213> ORGANISM: Artificial
<220> FEATURE:
<223> OTHER INFORMATION: recombinant polypeptide

<400> SEQUENCE: 4

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 5
<211> LENGTH: 531
<212> TYPE: PRT
<213> ORGANISM: Artificial
<220> FEATURE:
<223> OTHER INFORMATION: recombinant polypeptide

<400> SEQUENCE: 5

Met Gly Trp Ser Cys Ile Ile Leu Phe Leu Val Ala Thr Ala Thr Gly
1               5                   10                  15

Val His Ser Asp Tyr Lys Asp Asp Asp Lys Asp Ile Gln Leu Thr
            20                  25                  30

Gln Ser Pro Ala Ser Leu Ala Val Ser Leu Gly Gln Arg Ala Thr Ile
        35                  40                  45

Ser Cys Lys Ala Ser Gln Ser Val Asp Tyr Asp Gly Asp Ser Tyr Leu
    50                  55                  60

Asn Trp Tyr Gln Gln Ile Pro Gly Gln Pro Pro Lys Leu Leu Ile Tyr
65                  70                  75                  80

Asp Ala Ser Asn Leu Val Ser Gly Ile Pro Pro Arg Phe Ser Gly Ser
                85                  90                  95

Gly Ser Gly Thr Asp Phe Thr Leu Asn Ile His Pro Val Glu Lys Val
            100                 105                 110

Asp Ala Ala Thr Tyr His Cys Gln Gln Ser Thr Glu Asp Pro Trp Thr
        115                 120                 125

Phe Gly Gly Gly Thr Lys Leu Glu Ile Lys Gly Gly Gly Gly Ser Gly
    130                 135                 140
```

```
Gly Gly Gly Ser Gly Gly Gly Ser Gln Val Gln Leu Gln Gln Ser
145                 150                 155                 160
Gly Ala Glu Leu Val Arg Pro Gly Ser Ser Val Lys Ile Ser Cys Lys
                165                 170                 175
Ala Ser Gly Tyr Ala Phe Ser Ser Tyr Trp Met Asn Trp Val Lys Gln
            180                 185                 190
Arg Pro Gly Gln Gly Leu Glu Trp Ile Gly Gln Ile Trp Pro Gly Asp
        195                 200                 205
Gly Asp Thr Asn Tyr Asn Gly Lys Phe Lys Gly Lys Ala Thr Leu Thr
    210                 215                 220
Ala Asp Glu Ser Ser Ser Thr Ala Tyr Met Gln Leu Ser Ser Leu Ala
225                 230                 235                 240
Ser Glu Asp Ser Ala Val Tyr Phe Cys Ala Arg Arg Glu Thr Thr Thr
                245                 250                 255
Val Gly Arg Tyr Tyr Tyr Ala Met Asp Tyr Trp Gly Gln Gly Thr Thr
            260                 265                 270
Val Thr Val Ser Ser Gly Gly Gly Ser Asp Ile Lys Leu Gln Gln
        275                 280                 285
Ser Gly Ala Glu Leu Ala Arg Pro Gly Ala Ser Val Lys Met Ser Cys
    290                 295                 300
Lys Thr Ser Gly Tyr Thr Phe Thr Arg Tyr Thr Met His Trp Val Lys
305                 310                 315                 320
Gln Arg Pro Gly Gln Gly Leu Glu Trp Ile Gly Tyr Ile Asn Pro Ser
                325                 330                 335
Arg Gly Tyr Thr Asn Tyr Asn Gln Lys Phe Lys Asp Lys Ala Thr Leu
            340                 345                 350
Thr Thr Asp Lys Ser Ser Ser Thr Ala Tyr Met Gln Leu Ser Ser Leu
        355                 360                 365
Thr Ser Glu Asp Ser Ala Val Tyr Tyr Cys Ala Arg Tyr Tyr Asp Asp
    370                 375                 380
His Tyr Cys Leu Asp Tyr Trp Gly Gln Gly Thr Thr Leu Thr Val Ser
385                 390                 395                 400
Ser Val Glu Gly Gly Ser Gly Gly Ser Gly Gly Ser Gly Gly Ser Gly
                405                 410                 415
Gly Val Asp Asp Ile Gln Leu Thr Gln Ser Pro Ala Ile Met Ser Ala
            420                 425                 430
Ser Pro Gly Glu Lys Val Thr Met Thr Cys Arg Ala Ser Ser Ser Val
        435                 440                 445
Ser Tyr Met Asn Trp Tyr Gln Gln Lys Ser Gly Thr Ser Pro Lys Arg
    450                 455                 460
Trp Ile Tyr Asp Thr Ser Lys Val Ala Ser Gly Val Pro Tyr Arg Phe
465                 470                 475                 480
Ser Gly Ser Gly Ser Gly Thr Ser Tyr Ser Leu Thr Ile Ser Ser Met
                485                 490                 495
Glu Ala Glu Asp Ala Ala Thr Tyr Tyr Cys Gln Gln Trp Ser Ser Asn
            500                 505                 510
Pro Leu Thr Phe Gly Ala Gly Thr Lys Leu Glu Leu Lys His His His
        515                 520                 525
His His His
530
```